United States Patent
Yamada et al.

(10) Patent No.: US 7,094,789 B2
(45) Date of Patent: Aug. 22, 2006

(54) 5-SUBSTITUTED ISOQUINOLINE DERIVATIVES

(75) Inventors: Rintaro Yamada, Fuji (JP); Minoru Seto, Fuji (JP)

(73) Assignee: Asahi Kasei Pharma Corporation, Tokyo (JP)

(*) Notice: Subject to any disclaimer, the term of this patent is extended or adjusted under 35 U.S.C. 154(b) by 128 days.

(21) Appl. No.: 10/623,751

(22) Filed: Jul. 22, 2003

(65) Prior Publication Data
US 2005/0020623 A1 Jan. 27, 2005

Related U.S. Application Data

(60) Provisional application No. 60/397,142, filed on Jul. 22, 2002, provisional application No. 60/425,742, filed on Nov. 13, 2002.

(30) Foreign Application Priority Data

Jul. 22, 2002 (JP) .............................. 2002-212053
Nov. 12, 2002 (JP) .............................. 2002-327751

(51) Int. Cl.
*C07D 217/02* (2006.01)
*A61K 31/44* (2006.01)

(52) U.S. Cl. ...................... 514/307; 514/310; 546/139; 546/143

(58) Field of Classification Search ................ 546/139, 546/143; 514/307, 310
See application file for complete search history.

(56) References Cited

U.S. PATENT DOCUMENTS

| | | | |
|---|---|---|---|
| 3,101,338 A | 8/1963 | Robinson | |
| 4,473,501 A | 9/1984 | Lowrie | |
| 4,520,025 A | 5/1985 | Campbell et al. | |
| 4,798,897 A | 1/1989 | Hidaka et al. | |
| 5,362,878 A | 11/1994 | Chang et al. | |
| 5,656,634 A | 8/1997 | Chang et al. | |
| 6,153,608 A | 11/2000 | Hidaka et al. | |
| 6,262,112 B1 | 7/2001 | Mittendorf et al. | |
| 6,281,243 B1 | 8/2001 | Leysen et al. | |
| 6,403,573 B1 | 6/2002 | Leysen et al. | |
| 2003/0004158 A1 | 1/2003 | Scarborough et al. | |

FOREIGN PATENT DOCUMENTS

| | | |
|---|---|---|
| CA | 2 350 208 A1 | 5/2000 |
| EP | 0 061 673 B1 | 10/1984 |
| EP | 0863136 A1 | 9/1998 |
| EP | 0 956 865 A1 | 11/1999 |
| EP | 0956865 A1 | 11/1999 |
| EP | 1 065 200 A1 | 1/2001 |
| EP | 1 256 574 A1 | 11/2002 |
| EP | 0 966 436 B1 | 12/2002 |
| GB | 2065121 A * | 6/1981 |
| JP | 62-103066 A | 5/1987 |
| JP | 10-87629 A | 4/1998 |
| JP | 2002-145778 A | 5/2002 |
| JP | 3408546 B2 | 3/2003 |
| WO | WO 93/15073 A1 | 8/1993 |
| WO | WO 99/20620 A1 | 4/1999 |
| WO | WO 99/43647 A1 | 9/1999 |
| WO | WO 00/27819 A2 | 3/2000 |
| WO | WO-01/56988 A1 | 8/2001 |

OTHER PUBLICATIONS

Suzuki et al., Br. J. Pharmacol. (1993), 109, 703-712.
P. H. Howe et al., Biochem J. (1988) 255, 423-429.
P. L. Mobley, Experimental Cell Research, 214, 55-66 (1994).

* cited by examiner

*Primary Examiner*—Zinna N. Davis
(74) *Attorney, Agent, or Firm*—Birch, Stewart, Kolasch & Birch, LLP

(57) ABSTRACT

A compound represented by the following formula (1) or a salt thereof:

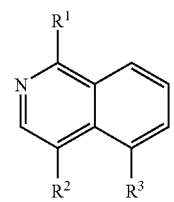

(1)

wherein $R^1$ represents hydrogen atom, a halogen atom and the like; $R^2$ represents hydrogen atom, a halogen atom, a $C_{1-6}$ alkyl group and the like; and $R^3$ represents —O—X—C($A^1$)($A^{11}$)-C($A^2$)($A^{21}$)-N($A^{31}$)($A^3$) (X represents propylene group etc., $A^{11}$ and $A^{21}$ represent hydrogen atom, or a $C_{1-6}$ alkyl group, $A^{31}$ represents a $C_{1-6}$ alkyl group substituted with hydroxyl group, or hydrogen atom, and $A^1$, $A^2$, and $A^3$ represent hydrogen atom, a $C_{1-6}$ alkyl group and the like) and the like, which has an inhibitory activity on the phosphorylation of myosin regulatory light chain, and is useful for treatment of diseases relating to contraction of various cells and the like.

50 Claims, No Drawings

5-SUBSTITUTED ISOQUINOLINE DERIVATIVES

This application claims priority on provisional Application No. 60/397,142 and 60/425,742 filed on Jul. 22, 2002 and Nov. 13, 2002, and claims priority under 35 U.S.C. § 119(a) based on Patent Application No(s). 2002-212053 and 2002-327751 filed in JAPAN on Jul. 22, 2002 and Nov. 12, 2002. The entire contents of all of these applications are hereby incorporated by reference.

TECHNICAL FIELD

The present invention relates to a novel 5-substituted isoquinoline derivative or a salt thereof, and a medicament comprising said 5-substituted isoquinoline derivative or a salt thereof as an active ingredient.

BACKGROUND ART

Movements of cells includes contraction, migration, release, aggregation and the like, and phosphorylation of the myosin regulatory light chain is important for these cell movements. The myosin regulatory light chain is a subunit having a molecular weight of 20 kDa and constituting myosin, which exists in smooth muscle cells and various non-muscle cells such as neutrophils, leukocytes, platelets and nerve cells of warm-blooded animals (Barany, K., et al., Biochemistry of Smooth Muscle Contraction, pp. 21–35, 1996). Myosin existing in smooth muscle cells and various non-muscle cells such as neutrophils, leukocytes, platelets and nerve cells of warm-blooded animals is constituted by a myosin heavy chain subunit having a molecular weight of about 200 kDa, the myosin regulatory light chain subunit having a molecular weight of about 20 kDa, and a myosin constitutive light chain subunit having a molecular weight of about 17 kDa. The myosin regulatory light chain is mainly phosphorylated by the myosin light chain kinase to increase the activity of myosin ATPase existing in the myosin heavy chain subunit (Barany, M., et al., Biochemistry of Smooth Muscle Contraction, pp. 321–339, 1996). It is known that the activated myosin having the increased ATPase activity becomes possible to interact with actin and activates movement apparatuses of cytoskeleton to activate cell movements.

That is, it is known that activation of myosin relates to cell contraction (Kamm, K., et al., Annu. Rev. Physiol., 51, pp. 299–313, 1989). It is also known that activation of myosin relates to change of cell morphology (Schmidt, J. T. et al., J, Neurobiol., 52 (3), pp. 175–188, 2002). It is known that activation of myosin relates to cell migration (Niggli, V., FEBS Lett., 445, pp. 69–72, 1999), and it is also known that activation of myosin relates to cell release (Kitani, S., et al., Biochem. Biophys. Res. Commun., 183, pp. 48–54, 1992). It is further known that activation of myosin relates to cell aggregation (Itoh, K., et al., Biochim. Biophys. Acta., 1136, pp. 52–56, 1992), and it is also known that activation of myosin relates to cell apoptosis (Mills, J. C. et al., J. Cell Biol., Vol. 140, No. 3, pp. 627–636, 1998).

Based on these findings, it is considered that an agent which inhibits the phosphorylation of the myosin regulatory light chain suppresses cell contraction, regulates change of cell morphology, suppresses cell migration, suppresses cell release, suppresses cell aggregation and suppresses cell apoptosis.

Cell contraction is deeply involved in diseases relating to contraction of various smooth muscle layers. Examples of such diseases include, for example, hypertension (A. P. Samlyo et al., Rev. Physiol. Biochem. Pharmacol., Vol. 134, pp. 209–34, 1999), angina pectoris (Shimokawa et al., Cardiovasc. Res., Vol. 43, No. 4, pp. 1029–39, 1999; Satoh, H., et al., Jpn. J. Pharmacol., 79 (suppl.), p. 211, 1999), cerebral vascular spasm (M. Satoh et al., the 57th General Meeting of Japan Neurosurgical Society, Collection of Abstracts, 153, 1998; N. Ono et al., Pharmacol. Ther., Vol. 82, No. 2–3, pp. 123–31, 1991; Shimokawa et al., Cardiovasc. Res., Vol. 43, No. 4, pp. 1029–39, 1999), erectile dysfunction (Andersson, K E. et al., World J. Vrol., 15, pp. 14–20, 1997), bronchial asthma (K. Iidzuka, Allergy, 47, 943, 1998; K. Iidzuka et al., Jpn. J. Respirology Society, 37, 196, 1999) and the like.

Change of cell morphology is deeply involved in diseases relating to morphological change of various cells. Examples of the diseases relating to change of cell morphology include, for example, various nerve dysfunctions as those relating to nerve cells. As the nerve dysfunctions, for example, neural damages caused by trauma, neurodegenerative diseases such as Alzheimer's disease, Parkinson's disease and diabetic retinopathy and the like can be exemplified (Arakawa, Y., et al., BIO Clinica, 17 (13), pp. 26–28, 2002).

Cell migration is deeply involved in diseases relating to migration of various cells. Examples of such diseases include, for example, cancer invasion and metastasis (Itoh, K. et al., Nat. Med., Vol. 5, No. 2, pp. 221–5, 1999; Keely, P. et al., Trends Cell Biol., Vol. 8, No. 3, pp. 101–6, 1998), nephritis (Fujimoto, O. et al., Journal of Japanese Society of Internal Medicine, 88 (1), pp. 148–58, 1998) and the like.

Furthermore, it is considered that cell release is deeply involved in various allergies and the like (Keane-Myers A. et al., Curr. Allergy Asthma Rep., 1(6):550–557, 2001), and cell aggregation is considered to be deeply involved in thrombosis and the like (Nakai, K. et al., Blood, Vol. 90, No. 10, pp. 3736–42, 1997). Further, it is known that cell apoptosis is involved in neurodegenerative diseases such as Alzheimer's disease and Parkinson's disease, viral diseases, hepatic diseases and the like (Thompson, C. B., Science, Vol. 267, pp. 1456–1462, 1995).

Based on these findings, it is considered that the inhibitor of the phosphorylation of myosin regulatory light chain of the present invention, which is an agent inhibiting the phosphorylation of the myosin regulatory light chain, is useful as an active ingredient of a medicament for prophylactic and/or therapeutic treatment of a disease relating to cell contraction, disease relating to change of cell morphology, disease relating to cell migration, disease relating to cell release, disease relating to cell aggregation, and/or disease relating to cell apoptosis.

It has been reported that 1-(5-isoquinolinesulfonyl)-2-methylpiperazine (H-7), which is an isoquinoline derivative, inhibits phosphorylation of the myosin regulatory light chain of mesenteric artery (Suzuki, A. et al., Br. J. Pharmacol., 109, pp. 703–712, 1993), iris smooth muscle cell (Howe, P. H. et al., Biochem J., 255, pp. 423–429, 1988), and astrocyte (Mobley P. L., et al., Exp. Cell Res., 214, pp. 55–66, 1994).

DISCLOSURE OF THE INVENTION

Conventionally, it has been desired to provide a novel compound having an action of strongly inhibiting the phosphorylation of myosin regulatory light chain.

The inventors of the present invention direct their attentions to the physiological functions of isoquinoline derivatives, and synthesized various isoquinoline derivatives and studied pharmacological actions thereof. As a result, it was found that the compounds represented by the following formula (1) and salts thereof had the desired pharmacological action, and were useful as an active ingredient of a medicament for prophylactic and/or therapeutic treatment of diseases relating to cell contraction, those relating to change of cell morphology, those relating to cell migration, those relating to cell release, those relating to cell aggregation, and those relating to cell apoptosis. The present invention was achieved on the basis of these findings.

The present invention thus provides a compound represented by the following formula (1) or a salt thereof:

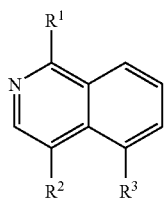

(1)

wherein $R^1$ represents hydrogen atom, a halogen atom, hydroxyl group, amino group, or a $C_{1-6}$ alkoxyl group;

$R^2$ represents hydrogen atom, a halogen atom, a $C_{1-6}$ alkyl group, —($C_{2-3}$ alkylene)O($G^1$), —($C_{2-3}$ alkylene)CO$_2$($G^1$), —N($G^2$)($G^3$), —O($C_{2-3}$ alkylene)O($G^1$), —NH($C_{2-3}$ alkylene)O($G^1$), —NH($C_{2-3}$ alkylene)N($G^2$)($G^3$), a $C_{2-3}$ alkenyl group, a $C_{2-3}$ alkynyl group, a $C_{1-6}$ alkoxyl group, —($C_{2-3}$ alkylene)SO$_2$($C_{1-6}$ alkyl), —S(O)$_p$($C_{1-6}$ alkyl), —O($C_{2-3}$ alkylene)SO$_2$($C_{1-6}$ alkyl), or cyano group;

$G^1$, $G^2$, and $G^3$ independently represent hydrogen atom, or a $C_{1-6}$ alkyl group;

p represents an integer of from 0 to 2;

$R^3$ represents a group represented by the following formula (1-1), formula (1-2), or formula (1-3);

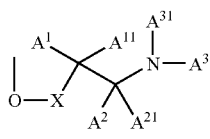

(1-1)

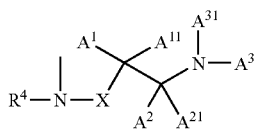

(1-2)

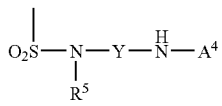

(1-3)

wherein
(i) when $R^3$ represents a group represented by the formula (1-1):

X represents propylene group, butylene group, —C($A^5$)($A^{51}$)-, —C($A^5$)($A^{51}$)-C($A^6$)($A^{61}$)-, or a single bond;

$A^{11}$, $A^{21}$, $A^{51}$, and $A^{61}$ independently represent hydrogen atom, or a $C_{1-6}$ alkyl group;

$A^{31}$ represents a $C_{1-6}$ alkyl group substituted with hydroxyl group, or hydrogen atom; and groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a 5- or 6-membered ring, provided that a group or groups among $A^1$, $A^2$, $A^3$, $A^5$, and $A^6$ not involved in the ring formation independently represent hydrogen atom, or a $C_{1-6}$ alkyl group;

(ii) when $R^3$ represents a group represented by the formula (1-2):

X represents propylene group, butylene group, —C($A^5$)($A^{51}$)-, —C($A^5$)($A^{51}$)-C($A^6$)($A^{61}$)-, or a single bond;

$A^{11}$, $A^{21}$, $A^{51}$, and $A^{61}$ independently represent hydrogen atom, or a $C_{1-6}$ alkyl group;

$A^{31}$ represents a $C_{1-6}$ alkyl group substituted with hydroxyl group, or hydrogen atom;

$R^4$ represents hydrogen atom, or a $C_{1-6}$ alkyl group; and $A^1$, $A^2$, $A^3$, $A^5$, and $A^6$ independently represent hydrogen atom, or a $C_{1-6}$ alkyl group; or groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring; or (iii) when $R^3$ represents a group represented by the formula (1-3):

Y represents a $C_{2-6}$ alkylene group, a $C_{2-6}$ alkylene group substituted with a $C_{1-6}$ alkyl group, a $C_{2-6}$ alkylene group substituted with phenyl group, a $C_{2-6}$ alkylene group substituted with benzyl group, —($C_{1-6}$ alkylene)phenylene($C_{1-6}$ alkylene)-, 1,2-cyclohexylene group, or 1,3-cyclohexylene group;

$A^4$ represents hydrogen atom, or a $C_{1-6}$ alkyl group, or may binds to any one of carbon atoms of the alkylene moiety of Y to form a 4- to 7-membered ring;

$R^5$ represents —($C_{2-6}$ alkylene)(cycloalkyl), —($C_{2-6}$ alkylene)(aryl), —($C_{2-6}$ alkylene)(heteroaryl), —($C_{2-6}$ alkylene)S(O)$_q$(cycloalkyl), —($C_{2-6}$ alkylene)S(O)$_q$(aryl), —($C_{2-6}$ alkylene)S(O)$_q$(heteroaryl), —($C_{2-6}$ alkylene)N($G^6$)(cycloalkyl), —($C_{2-6}$ alkylene)N($G^6$)(aryl), —($C_{2-6}$ alkylene)N($G^6$)(heteroaryl), —($C_{2-6}$ alkylene)CON($G^6$)(cycloalkyl), —($C_{2-6}$ alkylene)CON($G^6$)(aryl), or —($C_{2-6}$ alkylene)CON($G^6$)(heteroaryl);

$G^6$ represents hydrogen atom, or a $C_{1-6}$ alkyl group;

q represents an integer of from 0 to 2;

said "aryl" is a phenyl group which may be substituted with one or more substituents selected from the group consisting of a halogen atom, a $C_{1-6}$ alkyl group, $CF_3$ group, a $C_{1-6}$ alkoxyl group, cyano group, —N($G^7$)($G^8$), —CO$_2$($G^9$), —S(O)$_r$($G^9$), and —N($G^9$)SO$_2$($C_{1-6}$ alkyl);

$G^9$ represents hydrogen atom, or a $C_{1-6}$ alkyl group;

$G^7$ and $G^8$ independently represents hydrogen atom, or a $C_{1-6}$ alkyl group, or —N($G^7$)($G^8$) in the (aryl) as a whole may form a 4- to 7-membered ring which may contain oxygen atom, sulfur atom, or an N($G^{10}$) group, besides said nitrogen atom;

$G^{10}$ represents hydrogen atom, or a $C_{1-6}$ alkyl group;

said "heteroaryl" is selected from pyranyl, pyrazinyl, dioxolyl, furyl, thienyl, pyridyl, pyrimidyl, pyridazinyl, tetrazolyl, pyrrolyl, oxazolyl, thiazolyl, isoxazolyl, isothiazolyl, imidazolyl, pyrazolyl, oxadiazolyl, thiadiazolyl, and triazolyl, and these groups may be substituted with one or more substituents selected from the group consisting of a $C_{1-6}$ alkyl group which may optionally be substituted with a halogen atom, and a halogen atom; and r represents an integer of from 0 to 2.

The present invention also provides a compound represented by the aforementioned formula (1) or a salt thereof, wherein $R^1$ represents hydrogen atom, a halogen atom, hydroxyl group, amino group, or a $C_{1-6}$ alkoxyl group;

$R^2$ represents hydrogen atom, a halogen atom, a $C_{1-6}$ alkyl group, —($C_{2-3}$ alkylene)O($G^1$), —($C_{2-3}$ alkylene)CO$_2$($G^1$), —N($G^2$)($G^3$), —O($C_{2-3}$ alkylene)O($G^1$), —NH($C_{2-3}$ alkylene)O($G^1$), —NH($C_{2-3}$ alkylene)N($G^2$)($G^3$), a $C_{2-3}$ alkenyl group, a $C_{2-3}$ alkynyl group, a $C_{1-6}$ alkoxyl group, —($C_{2-3}$ alkylene)SO$_2$($C_{1-6}$ alkyl), —S(O)$_p$($C_{1-6}$ alkyl), or —O($C_{2-3}$ alkylene)SO$_2$($C_{1-6}$ alkyl);

$G^1$, $G^2$, and $G^3$ independently represent hydrogen atom, or a $C_{1-6}$ alkyl group;

p represents an integer of from 0 to 2;

$R^3$ represents a group represented by the formula (1-1), formula (1-2), or formula (1-3);

wherein (i) when $R^3$ represents a group represented by the formula (1-1):

X represents propylene group, butylene group, —C($A^5$)($A^{51}$)-, C($A^5$)($A^{51}$)-C($A^6$)($A^{61}$)-, or a single bond;

$A^{11}$, $A^{21}$, $A^{51}$, and $A^{61}$ independently represent hydrogen atom, or a $C_{1-6}$ alkyl group;

$A^{31}$ represents hydrogen atom; and groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a 5- or 6-membered ring, provided that a group or groups among $A^1$, $A^2$, $A^3$, $A^5$, and $A^6$ not involved in the ring formation independently represent hydrogen atom, or a $C_{1-6}$ alkyl group;

(ii) when $R^3$ represents a group represented by the formula (1-2):

X represents propylene group, butylene group, —C($A^5$)($A^{51}$)-, —C($A^5$)($A^{51}$)-C($A^6$)($A^{61}$)-, or a single bond;

$A^{11}$, $A^{21}$, $A^{51}$, and $A^{61}$ independently represent hydrogen atom, or a $C_{1-6}$ alkyl group;

$A^{31}$ represents hydrogen atom;

$R^4$ represents hydrogen atom, or a $C_{1-6}$ alkyl group; and $A^1$, $A^2$, $A^3$, $A^5$, and $A^6$ independently represent hydrogen atom, or a $C_{1-6}$ alkyl group; or groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring; or (iii) when $R^3$ represents a group represented by the formula (1-3):

Y represents a $C_{2-6}$ alkylene group, a $C_{2-6}$ alkylene group substituted with a $C_{1-6}$ alkyl group, a $C_{2-6}$ alkylene group substituted with phenyl group, a $C_{2-6}$ alkylene group substituted with benzyl group, —($C_{1-6}$ alkylene)phenylene($C_{1-6}$ alkylene)-, 1,2-cyclohexylene group, or 1,3-cyclohexylene group;

$A^4$ represents hydrogen atom, or a $C_{1-6}$ alkyl group, or may binds to any one of carbon atoms of the alkylene moiety of Y to form a 4- to 7-membered ring;

$R^5$ represents —($C_{2-6}$ alkylene)(cycloalkyl), —($C_{2-6}$ alkylene)(aryl), —($C_{2-6}$ alkylene)(heteroaryl), —($C_{2-6}$ alkylene)S(O)$_q$(cycloalkyl), —($C_{2-6}$ alkylene)S(O)$_q$(aryl), —($C_{2-6}$ alkylene)S(O)$_q$(heteroaryl), —($C_{2-6}$ alkylene)N($G^6$)(cycloalkyl), —($C_{2-6}$ alkylene)N($G^6$)(aryl), —($C_{2-6}$ alkylene)N($G^6$)(heteroaryl), —($C_{2-6}$ alkylene)CON($G^6$)(cycloalkyl), —($C_{2-6}$ alkylene)CON($G^6$)(aryl), or —($C_{2-6}$ alkylene)CON($G^6$)(heteroaryl);

$G^6$ represents hydrogen atom, or a $C_{1-6}$ alkyl group;

q represents an integer of from 0 to 2;

said "aryl" is a phenyl group which may be substituted with one or more substituents selected from the group consisting of a halogen atom, a $C_{1-6}$ alkyl group, $CF_3$ group, a $C_{1-6}$ alkoxyl group, cyano group, —N($G^7$)($G^8$), —CO$_2$($G^9$), —S(O)$_r$($G^9$), and —N($G^9$)SO$_2$($C_{1-6}$ alkyl);

$G^9$ represents hydrogen atom, or a $C_{1-6}$ alkyl group;

$G^7$ and $G^8$ independently represents hydrogen atom, or a $C_{1-6}$ alkyl group, or —N($G^7$)($G^8$) in the (aryl) as a whole may form a 4- to 7-membered ring which may contain oxygen atom, sulfur atom, or an N($G^{10}$) group, besides said nitrogen atom;

$G^{10}$ represents hydrogen atom, or a $C_{1-6}$ alkyl group;

said "heteroaryl" is selected from pyranyl, pyrazinyl, dioxolyl, furyl, thienyl, pyridyl, pyrimidyl, pyridazinyl, tetrazolyl, pyrrolyl, oxazolyl, thiazolyl, isoxazolyl, isothiazolyl, imidazolyl, pyrazolyl, oxadiazolyl, thiadiazolyl, and triazolyl, and these groups may be substituted with one or more substituents selected from the group consisting of a $C_{1-6}$ alkyl group which may optionally be substituted with a halogen atom, and a halogen atom; and r represents an integer of from 0 to 2.

The present invention further provides a compound represented by the aforementioned formula (1) or a salt thereof, wherein $R^1$ represents hydrogen atom, a halogen atom, hydroxyl group, amino group, or a $C_{1-6}$ alkoxyl group;

$R^2$ represents hydrogen atom, a halogen atom, a $C_{1-6}$ alkyl group, —($C_{2-3}$ alkylene)O($G^1$), —($C_{2-3}$ alkylene)CO$_2$($G^1$), —N($G^2$)($G^3$), —O($C_{2-3}$ alkylene)O($G^1$), —NH($C_{2-3}$ alkylene)O($G^1$), —NH($C_{2-3}$ alkylene)N($G^2$)($G^3$), a $C_{2-3}$ alkenyl group, a $C_{2-3}$ alkynyl group, a $C_{1-6}$ alkoxyl group, —($C_{2-3}$ alkylene)SO$_2$($C_{1-6}$ alkyl), —S(O)$_p$($C_{1-6}$ alkyl), or —O($C_{2-3}$ alkylene)SO$_2$($C_{1-6}$ alkyl);

$G^1$, $G^2$, and $G^3$ independently represent hydrogen atom, or a $C_{1-6}$ alkyl group;

p represents an integer of from 0 to 2;

$R^3$ represents a group represented by the formula (1-1), formula (1-2), or formula (1-3);

wherein $A^1$, $A^{11}$, $A^2$, and $A^{21}$ independently represent hydrogen atom, or a $C_{1-6}$ alkyl group;

$A^3$ represents hydrogen atom, or a $C_{1-6}$ alkyl group;

$A^{31}$ represents hydrogen atom;

X represents propylene group, butylene group, —C($A^5$)($A^{51}$)-, —C($A^5$)($A^{51}$)-C($A^6$)($A^{61}$)-, or a single bond;

$A^5$, $A^{51}$, $A^6$, and $A^{61}$ independently represent hydrogen atom, or a $C_{1-6}$ alkyl group;

alkyl groups represented by two of groups included in one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring;

$R^4$ represents hydrogen atom, or a $C_{1-6}$ alkyl group;

Y represents a $C_{2-6}$ alkylene group, a $C_{2-6}$ alkylene group substituted with a $C_{1-6}$ alkyl group, a $C_{2-6}$ alkylene group substituted with phenyl group, a $C_{2-6}$ alkylene group substituted with benzyl group, —($C_{1-6}$ alkylene)phenylene($C_{1-6}$ alkylene)-, 1,2-cyclohexylene group, or 1,3-cyclohexylene group;

A⁴ represents hydrogen atom, or a $C_{1-6}$ alkyl group, or may binds to any one of carbon atoms of the alkylene moiety of Y to form a 4- to 7-membered ring;

R⁵ represents —($C_{2-6}$ alkylene)(cycloalkyl), —($C_{2-6}$ alkylene)(aryl), —($C_{2-6}$ alkylene)(heteroaryl), —($C_{2-6}$ alkylene)S(O)$_q$(cycloalkyl), —($C_{2-6}$ alkylene)S(O)$_q$(aryl), —($C_{2-6}$ alkylene)S(O)$_q$(heteroaryl), —($C_{2-6}$ alkylene)N(G⁶)(cycloalkyl), —($C_{2-6}$ alkylene)N(G⁶)(aryl), —($C_{2-6}$ alkylene)N(G⁶)(heteroaryl), —($C_{2-6}$ alkylene)CON(G⁶)(cycloalkyl), —($C_{2-6}$ alkylene)CON(G⁶)(aryl), or —($C_{2-6}$ alkylene)CON(G⁶)(heteroaryl);

G⁶ represents hydrogen atom, or a $C_{1-6}$ alkyl group;

q represents an integer of from 0 to 2;

said "aryl" is a phenyl group which may be substituted with one or more substituents selected from the group consisting of a halogen atom, a $C_{1-6}$ alkyl group, $CF_3$ group, a $C_{1-6}$ alkoxyl group, cyano group, —N(G⁷)(G⁸), —$CO_2$(G⁹), —S(O)$_r$(G⁹), and —N(G⁹)SO₂($C_{1-6}$ alkyl);

G⁹ represents hydrogen atom, or a $C_{1-6}$ alkyl group;

G⁷ and G⁸ independently represents hydrogen atom, or a $C_{1-6}$ alkyl group, or —N(G⁷)(G⁸) in said "aryl" as a whole may form a 4- to 7-membered ring which may contain oxygen atom, sulfur atom, or an N(G¹⁰) group, besides said nitrogen atom;

G¹⁰ represents hydrogen atom, or a $C_{1-6}$ alkyl group;

said "heteroaryl" is selected from pyranyl, pyrazinyl, dioxolyl, furyl, thienyl, pyridyl, pyrimidyl, pyridazinyl, tetrazolyl, pyrrolyl, oxazolyl, thiazolyl, isoxazolyl, isothiazolyl, imidazolyl, pyrazolyl, oxadiazolyl, thiadiazolyl, and triazolyl, and these groups may optionally be substituted with one or more substituents selected from the group consisting of a $C_{1-6}$ alkyl group which may be substituted with a halogen atom, and a halogen atom; and r represents an integer of from 0 to 2, provided that, when R¹ and R² are hydrogen atoms, and R³ is a group represented by the formula (1-1), A³ is not hydrogen atom or a $C_{1-6}$ alkyl group, and the alkyl groups represented by two of groups included in one or more combinations selected from the group consisting of combinations of A³ and A², A³ and A¹, A³ and A⁵, and A³ and A⁶ bind to each other to form a 5- or 6-membered ring.

From another aspect, the present invention provides a medicament containing a compound represented by the aforementioned formula (1) or a physiologically acceptable salt thereof as an active ingredient. The aforementioned medicament has an inhibitory action on phosphorylation of myosin regulatory light chain, and is useful as a medicament for prophylactic and/or therapeutic treatment of, for example, a disease relating to cell contraction, disease relating to change of cell morphology, disease relating to cell migration, disease relating to cell release, disease relating to cell aggregation, and/or disease relating to cell apoptosis, and the like.

More specifically, there are provided a medicament for decreasing phosphorylation amount of myosin regulatory light chain in a cell, which comprises a compound represented by the aforementioned formula (1) or a physiologically acceptable salt thereof as an active ingredient, a medicament having a cell contraction inhibitory action, which comprises a compound represented by the aforementioned formula (1) or a physiologically acceptable salt thereof as an active ingredient, a medicament having an action to regulate change of cell morphology, which comprises a compound represented by the aforementioned formula (1) or a physiologically acceptable salt thereof as an active ingredient, a medicament having a cell migration inhibitory action, which comprises a compound represented by the aforementioned formula (1) or a physiologically acceptable salt thereof as an active ingredient, a medicament having a cell release inhibitory action, which comprises a compound represented by the aforementioned formula (1) or a physiologically acceptable salt thereof as an active ingredient, a medicament having a cell aggregation inhibitory action, which comprises a compound represented by the aforementioned formula (1) or a physiologically acceptable salt thereof as an active ingredient, a medicament having a cell apoptosis inhibitory action, which comprises a compound represented by the aforementioned formula (1) or a physiologically acceptable salt thereof as an active ingredient, and a medicament for inhibiting the Rho/Rho kinase pathway, which comprises a compound represented by the aforementioned formula (1) or a physiologically acceptable salt thereof as an active ingredient.

The present invention also provides an inhibitor of the phosphorylation of myosin regulatory light chain containing a compound represented by the aforementioned formula (1) or a physiologically acceptable salt thereof, and an inhibitor of the Rho/Rho kinase pathway comprising a compound represented by the aforementioned formula (1) or a physiologically acceptable salt thereof.

From another aspect, the present invention provides use of a compound represented by the aforementioned formula (1) or a physiologically acceptable salt thereof for manufacture of the aforementioned medicaments. The present invention also provides a method for prophylactic and/or therapeutic treatment of a disease relating to cell contraction, disease relating to change of cell morphology, disease relating to cell migration, disease relating to cell release, disease relating to cell aggregation, and/or disease relating to cell apoptosis and the like, which comprises the step of administrating a prophylactically and/or therapeutically effective amount of a compound represented by the aforementioned formula (1) or a physiologically acceptable salt thereof to a mammal including human, a method for decreasing phosphorylation amount of myosin regulatory light chain in a cell, which comprises the step of administrating an effective amount of a compound represented by the aforementioned formula (1) or a physiologically acceptable salt thereof to a mammal including human, a method for inhibiting cell contraction, which comprises the step of administrating an effective amount of a compound represented by the aforementioned formula (1) or a physiologically acceptable salt thereof to a mammal including human, a method for regulating change of cell morphology, which comprises the step of administrating an effective amount of a compound represented by the aforementioned formula (1) or a physiologically acceptable salt thereof to a mammal including human, a method for inhibiting cell migration, which comprises the step of administrating an effective amount of a compound represented by the aforementioned formula (1) or a physiologically acceptable salt thereof to a mammal including human, a method for inhibiting cell release, which comprises the step of administrating an effective amount of a compound represented by the aforementioned formula (1) or a physiologically acceptable salt thereof to a mammal including human, a method for inhibiting cell aggregation, which comprises the step of administrating an effective amount of a compound represented by the aforementioned formula (1) or a physiologically acceptable salt thereof to a mammal including human, a method for inhibiting cell apoptosis, which comprises the step of administrating an effective amount of a compound represented by the aforementioned formula (1) or a physiologically acceptable salt thereof to a mammal including human, and a method for inhibiting the Rho/Rho kinase pathway, which comprises the step of administrating an effective amount of a compound represented by the aforementioned formula (1) or a physiologically acceptable salt thereof to a mammal including human.

BEST MODE FOR CARRYING OUT THE INVENTION

The alkyl mentioned in this specification may be a linear or branched alkyl, and for example, a $C_{1-6}$ alkyl include linear and branched alkyls having 1 to 6 carbon atoms. Specific examples include methyl, ethyl, propyl, isopropyl, butyl, secondary butyl, tertiary butyl, pentyl, 2-methylbutyl, hexyl and the like. The $C_{1-6}$ alkyl groups as $R^2$, $A^3$, $A^4$, and $R^4$ are independently and preferably methyl group or ethyl group. As $R^2$, methyl group is particularly preferred.

The halogen may be any of fluorine atom, chlorine atom, bromine atom, and iodine atom. In particular, the halogen atom as $R^1$ is preferably chlorine atom, and the halogen atom as $R^2$ is preferably fluorine atom, or bromine atom, most preferably fluorine atom.

The alkoxyl group is not particularly limited. For example, a $C_{1-6}$ alkoxyl group includes linear and branched alkoxyl groups having 1 to 6 carbon atoms. Specific examples include methoxy group, ethoxy group, propoxy group, isopropoxy group and the like. Preferred examples of the alkoxyl group as $R^1$ and $R^2$ include methoxy group and ethoxy group, and methoxy group is a particularly preferred example.

$R^1$ is preferably hydrogen atom, hydroxyl group, or amino group. As $R^1$, any one, two or more kinds of these groups may be preferably chosen. $R^1$ is preferably hydrogen atom, or hydroxyl group, most preferably hydrogen atom.

$R^2$ is preferably hydrogen atom, a halogen atom, a $C_{1-6}$ alkyl group, $-N(G^2)(G^3)$, a $C_{2-3}$ alkenyl group, a $C_{2-3}$ alkynyl group, a $C_{1-6}$ alkoxyl group, or $-S(O)_p(C_{1-6}$ alkyl). Cyano group is also preferred.

$R^2$ is still more preferably hydrogen atom, a halogen atom, a $C_{1-6}$ alkyl group, $-N(G^2)(G^3)$, or a $C_{1-6}$ alkoxyl group.

Further, other preferred examples are as follows.

$R^2$ is preferably hydrogen atom, a halogen atom, a $C_{1-6}$ alkyl group, a $C_{2-3}$ alkenyl group, a $C_{2-3}$ alkynyl group, or a $C_{1-6}$ alkoxyl group.

$R^2$ is preferably hydrogen atom, a halogen atom, a $C_{1-6}$ alkyl group, a $C_{1-6}$ alkoxyl group, or $-S(O)_p(C_{1-6}$ alkyl).

$R^2$ is preferably hydrogen atom, a halogen atom, or a $C_{1-6}$ alkyl group, and among these, a combination of hydrogen atom and a halogen atom, and a combination of hydrogen atom and a $C_{1-6}$ alkyl group are preferred examples.

$R^2$ is preferably a $C_{1-6}$ alkyl group, $-(C_{2-3}$ alkylene)O $(G^1)$, a $C_{2-3}$ alkenyl group, $-S(O)_p(C_{1-6}$ alkyl), or cyano group. Among these groups, preferred examples are combinations of a $C_{1-6}$ alkyl group, a $C_{2-3}$ alkenyl group, or cyano group, and combinations of a $C_{1-6}$ alkyl group, $-(C_{2-3}$ alkylene)O($G^1$), a $C_{2-3}$ alkenyl group, or $-S(O)_p(C_{1-6}$ alkyl).

Further, $R^2$ is preferably a $C_{1-6}$ alkyl group, a $C_{2-3}$ alkenyl group, or cyano group. Preferred examples of the $C_{1-6}$ alkyl group include methyl group, preferred examples of the $C_{2-3}$ alkenyl group include vinyl group, and any one, two or more of them are also preferably chosen.

$R^2$ is preferably $-(C_{2-3}$ alkylene)O($G^1$), and more specifically, preferred examples include hydroxymethyl group, 2-hydroxyethyl group, 3-hydroxypropyl group, 2-methoxyethyl group, and 3-methoxypropyl group, and hydroxymethyl group is particularly preferred.

$R^2$ is preferably $-(C_{2-3}$ alkylene)$CO_2(G^1)$, and more specifically, preferred examples include 2-carboxyethyl group, 3-carboxypropyl group, 2-methoxycarbonylethyl group, and 3-methoxycarbonylpropyl group.

$R^2$ is preferably $-N(G^2)(G^3)$, and more specifically, preferred examples include amino group, methylamino group, and dimethylamino group.

$R^2$ is preferably $-O(C_{2-3}$ alkylene)O($G^1$), and more specifically, preferred examples include 2-hydroxyethoxy group, 3-hydroxypropyloxy group, 2-methoxyethoxy group, and 3-methoxypropyloxy group.

$R^2$ is preferably $-NH(C_{2-3}$ alkylene)O($G^1$), and more specifically, preferred examples include 2-(hydroxyethyl)amino group, 3-(hydroxypropyl)amino group, 2-(methoxyethyl)amino group, and 3-(methoxypropyl)amino group.

$R^2$ is preferably $-NH(C_{2-3}$ alkylene)$N(G^2)(G^3)$, and more specifically, preferred examples include 2-aminoethylamino group, 3-aminopropylamino group, 2-(methylamino)ethylamino group, 3-(methylamino)propylamino group, 2-(dimethylamino)ethylamino group, and 3-(dimethylamino)propylamino group.

$R^2$ is preferably a $C_{2-3}$ alkenyl group, and more specifically, preferred examples include ethenyl group and 2-propenyl group.

$R^2$ is preferably a $C_{2-3}$ alkynyl group, and more specifically, preferred examples include ethynyl group and 2-propynyl group.

$R^2$ is preferably a $C_{1-6}$ alkoxyl group. More specifically, preferred examples include methoxy group, ethoxy group, propoxy group, and isopropoxy group, and methoxy group is a particularly preferred example.

$R^2$ is preferably $-(C_{2-3}$ alkylene)$SO_2(C_{1-6}$ alkyl), and more specifically, preferred examples include 2-(methanesulfonyl)ethyl group, 3-(methanesulfonyl)propyl group, 2-(ethanesulfonyl)ethyl group, and 3-(ethanesulfonyl)propyl group.

$R^2$ is preferably $-S(O)_p(C_{1-6}$ alkyl). That is, $R^2$ is preferably $-S(C_{1-6}$ alkyl), $-SO(C_{1-6}$ alkyl), or $-SO_2(C_{1-6}$ alkyl). More specifically, $-S(C_{1-6}$ alkyl) is preferably methylthio group or ethylthio group, $-SO(C_{1-6}$ alkyl) is preferably methylsulfinyl group or ethylsulfinyl group, and preferred examples of $-SO_2(C_{1-6}$ alkyl) include methanesulfonyl group and ethanesulfonyl group.

$R^2$ is preferably $-O(C_{2-3}$ alkylene)$SO_2$ ($C_{1-6}$ alkyl), and more specifically, preferred examples include 2-(methanesulfonyl)ethoxy group, 3-(methanesulfonyl)propoxy group, 2-(ethanesulfonyl)ethoxy group, and 3-(ethanesulfonyl)propoxy group.

$R^3$ is preferably a group represented by the formula (1-1), formula (1-2), or formula (1-3). Each of these and combinations of two of these are also preferred examples. That is, a group represented by the formula (1-1), and group represented by the formula (1-2) are preferred examples.

$A^{11}$, $A^{21}$, $A^{51}$, and $A^{61}$ may be the same or different, and they preferably represent hydrogen atom or a $C_{1-6}$ alkyl group. Preferred examples of the $C_{1-6}$ alkyl group include methyl group and ethyl group. It is particularly preferred that all of $A^{11}$, $A^{21}$, $A^{51}$, and $A^{61}$ represent hydrogen atom, and it is also preferred that any one of $A^{11}$, $A^{21}$, $A^{51}$, and $A^{61}$ is methyl group or ethyl group, and all remaining substituents are hydrogen atoms.

$A^{31}$ is preferably hydrogen atom.

$A^{31}$ is also preferably a $C_{1-6}$ alkyl group substituted with hydroxyl group, and it is usually preferably substituted with one hydroxyl group. A particularly preferred example is a $C_{1-6}$ alkyl group of which end is substituted with hydroxyl group, and more specifically, preferred examples are 2-hydroxyethyl group and 3-hydroxypropyl group.

X is preferably propylene group, butylene group, —C($A^5$)($A^{51}$)-, or —C($A^5$)($A^{51}$)-C($A^6$)($A^{61}$)-, and propylene group, —C($A^5$)($A^{51}$)-, and —C($A^5$)($A^{51}$)-C($A^6$)($A^{61}$)- are also preferred. Further, —C($A^5$)($A^{51}$)-, and —C($A^5$)($A^{51}$)-C($A^6$)($A^{61}$)- are particularly preferred. Examples of —C($A^5$)($A^{51}$)- include methylene group, and examples of —C($A^5$)($A^{51}$)-C($A^6$)($A^{61}$)- include ethylene group.

Further, in the present invention, concerning $R^3$, groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring, and a 6-membered ring is preferred. It is particularly preferred that one ring is formed. It is preferred that the ring consists of carbon atoms, or when the ring contains a nitrogen atom to which $A^3$ binds, the ring consists of carbon atoms except for the nitrogen atom. The ring is preferably a saturated ring.

Among $A^1$, $A^2$, $A^3$, $A^5$, and $A^6$, the group or groups not involved in the ring formation independently represent hydrogen atom, or a $C_{1-6}$ alkyl group, and preferred examples of the $C_{1-6}$ alkyl group include methyl group and ethyl group. It is particularly preferred that all of $A^1$, $A^2$, $A^3$, $A^5$, and $A^6$ represent hydrogen atom, and it is also preferred that any one of $A^1$, $A^2$, $A^3$, $A^5$, and $A^6$ is methyl group or ethyl group, and all remaining substituents are hydrogen atoms.

Further, when a ring is formed by any of combinations of $A^1$ and $A^3$, $A^2$ and $A^3$, $A^3$ and $A^5$, and $A^2$ and $A^5$, $A^{11}$, $A^2$, and $A^{21}$ most preferably represent hydrogen atom.

Specifically, examples of the whole structure of the group represented by the formula (1-1), in which a ring is formed by any of the aforementioned combinations, include the following rings.

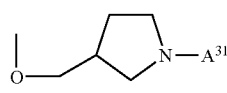
(1-1-1)

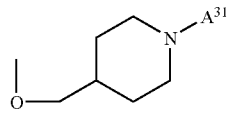
(1-1-2)

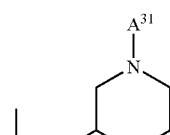
(1-1-3)

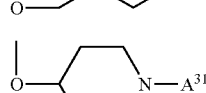
(1-1-4)

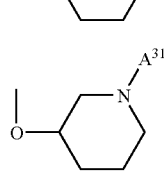
(1-1-5)

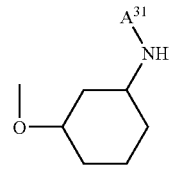
(1-1-6)

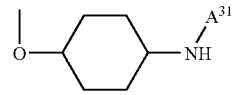
(1-1-7)

Among them, groups represented by the formula (1-1-4), formula (1-1-5), formula (1-1-6), and formula (1-1-7) are preferred, and groups represented by the formula (1-1-4), and formula (1-1-7) are more preferred. Further, groups represented by the formula (1-1-7) are mentioned as preferred examples.

Further, examples of the whole structure of the group represented by the formula (1-2), in which a ring is formed by any of the aforementioned combinations, include the following rings.

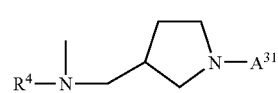
(1-2-1)

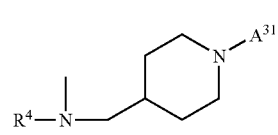
(1-2-2)

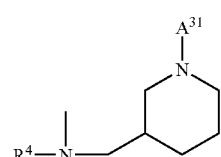
(1-2-3)

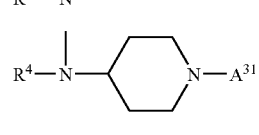
(1-2-4)

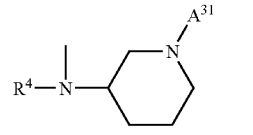
(1-2-5)

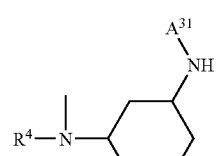
(1-2-6)

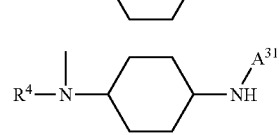
(1-2-7)

Among them, groups represented by the formula (1-2-4), formula (1-2-5), formula (1-2-6), and formula (1-2-7) are preferred, and groups represented by the formula (1-2-4), and formula (1-2-7) are more preferred. Further, groups represented by the formula (1-2-7) are mentioned as preferred examples.

$R^4$ is preferably hydrogen atom, or a $C_{1-6}$ alkyl group, and hydrogen atom is more preferred.

Y is preferably a $C_{2-6}$ alkylene group, or a $C_{2-6}$ alkylene group substituted with a $C_{1-6}$ alkyl group. Preferred examples of the $C_{2-6}$ alkylene group include ethylene group, 1,3-propylene group, and 1,4-butylene group. Preferred examples of the $C_{2-6}$ alkylene group substituted with a $C_{1-6}$ alkyl group include 1,2-propylene group, and 1,3-butylene group.

Examples of the $C_{2-6}$ alkylene group substituted with phenyl group as Y include 1-(phenyl)ethylene, and 2-(phenyl)propylene.

Preferred examples of the $C_{2-6}$ alkylene group substituted with benzyl group as Y include 1-(benzyl)ethylene, and 2-(benzyl)propylene.

—($C_{1-6}$ alkylene)phenylene($C_{1-6}$ alkylene)- as Y is preferably 1,3-xylylene group, or 1,4-xylylene group.

Y is preferably 1,3-cyclohexylene.

$A^4$ is preferably hydrogen atom, or a $C_{1-6}$ alkyl group. Preferred examples of the $C_{1-6}$ alkyl group include methyl group, and ethyl group. A particularly preferred example of $A^4$ is hydrogen atom.

Besides the above, $A^4$ may bind to any carbon in the alkylene moiety of Y to form a 4- to 7-membered ring. Specifically, examples of the whole structure of the group represented by the formula (1-3) in which a ring is formed by any of the aforementioned combinations include the following rings.

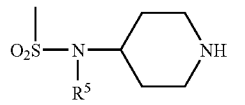
(1-3-1)

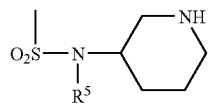
(1-3-2)

Among them, a group represented by the formula (1-3-1) is preferred.

$R^5$ is preferably —($C_{2-6}$ alkylene)(cycloalkyl), —($C_{2-6}$ alkylene)(aryl), —($C_{2-6}$ alkylene)(heteroaryl), —($C_{2-6}$ alkylene)S(O)$_p$(cycloalkyl), —($C_{2-6}$ alkylene)S(O)$_p$(aryl), or —($C_{2-6}$ alkylene)S(O)$_p$(heteroaryl).

$R^5$ is preferably —($C_{2-6}$ alkylene)(aryl), —($C_{2-6}$ alkylene)(heteroaryl), —($C_{2-6}$ alkylene)S(O)$_p$(aryl), or —($C_{2-6}$ alkylene)S(O)$_p$(heteroaryl).

$R^5$ is preferably —($C_{2-4}$ alkylene)(aryl), —($C_{2-4}$ alkylene)(heteroaryl), —($C_{2-4}$ alkylene)S(O)$_p$(aryl), or —($C_{2-4}$ alkylene)S(O)$_p$(heteroaryl).

$R^5$ is preferably —($C_{2-4}$ alkylene)(aryl), or —($C_{2-4}$ alkylene)S(O)$_p$(aryl).

$R^5$ is preferably —($C_{2-4}$ alkylene)(aryl), —($C_{2-4}$ alkylene)(heteroaryl), —($C_{2-4}$ alkylene)S(aryl), —($C_{2-4}$ alkylene)S(heteroaryl), —($C_{2-4}$ alkylene)SO$_2$(aryl), or —($C_{2-4}$ alkylene)SO$_2$(heteroaryl).

$R^5$ is preferably —($C_{2-4}$ alkylene)(aryl), —($C_{2-4}$ alkylene)S(aryl), or —($C_{2-4}$ alkylene)SO$_2$(aryl).

—($C_{2-6}$ alkylene)(cycloalkyl) as $R^5$ is preferably 2-(cyclopentyl)ethyl group, 3-(cyclopentyl)propyl group, 2-(cyclohexyl)ethyl group, or 3-(cyclohexyl)propyl group.

—($C_{2-6}$ alkylene)(aryl) as $R^5$ is preferably a 2-(aryl)ethyl group, a 3-(aryl)propyl group, or a 4-(aryl)butyl group. The aryl has the meaning as described below.

—($C_{2-6}$ alkylene)(heteroaryl) as $R^5$ is preferably a 2-(heteroaryl)ethyl group, a 3-(heteroaryl)propyl group, or a 4-(heteroaryl)butyl group. The heteroaryl has the meaning as described below.

Preferred examples of —($C_{2-6}$ alkylene)S(O)$_p$(cycloalkyl) as $R^5$ include 2-(cyclopentylthio)ethyl group, a 2-(cyclohexylthio)ethyl group, 2-(cyclopentylsulfonyl)ethyl group, and 2-(cyclohexylsulfonyl)ethyl group. The cycloalkyl has the meaning as described below.

—($C_{2-6}$ alkylene)S(O)$_p$(aryl) as $R^5$ is preferably a 2-(arylthio)ethyl group, or a 2-(arylsulfonyl)ethyl group.

—($C_{2-6}$ alkylene)S(O)$_p$(heteroaryl) as $R^5$ is preferably 2-(heteroarylthio)ethyl group or a 2-(heteroarylsulfonyl) ethyl group.

$R^5$ is preferably —($C_{2-6}$ alkylene)N($G^6$)(cycloalkyl), —($C_{2-6}$ alkylene)N($G^6$)(aryl), or —($C_{2-6}$ alkylene)N($G^6$)(heteroaryl).

$R^5$ is preferably —($C_{2-6}$ alkylene)N($G^6$)(cycloalkyl), and more specifically, preferred examples include 2-(cyclopentylamino)ethyl group, 2-(cyclohexylamino)ethyl group, 2-(N-cyclopentyl-N-methylamino)ethyl group, and 2-(N-cyclohexyl-N-methylamino)ethyl group.

$R^5$ is preferably —($C_{2-6}$ alkylene)N($G^6$)(aryl), and more specifically, preferred examples include a 2-(arylamino) ethyl group and a 2-(N-aryl-N-methylamino)ethyl group.

$R^5$ is preferably —($C_{2-6}$ alkylene)N($G^6$)(heteroaryl), and more specifically, preferred examples include a 2-(heteroarylamino)ethyl group and a 2-(N-heteroaryl-N-methylamino)ethyl group.

$R^5$ is preferably —($C_{2-6}$ alkylene)CON($G^6$)(cycloalkyl), —($C_{2-6}$ alkylene)CON($G^6$)(aryl), or —($C_{2-6}$ alkylene)CON($G^6$)(heteroaryl).

$R^5$ is preferably —($C_{2-6}$ alkylene)CON($G^6$)(cycloalkyl), and more specifically, preferred examples include 2-(cyclopentylaminocarbonyl)ethyl group, 2-(cyclohexylaminocarbonyl)ethyl group, 2-(N-cyclopentyl-N-methylaminocarbonyl)ethyl group, and 2-(N-cyclohexyl-N-methylaminocarbonyl)ethyl group.

$R^5$ is preferably —($C_{2-6}$ alkylene)CON($G^6$)(aryl), and more specifically, preferred examples include a 2-(arylaminocarbonyl)ethyl group, and a 2-(N-aryl-N-methylaminocarbonyl)ethyl group.

$R^5$ is preferably —($C_{2-6}$ alkylene)CON($G^6$)(heteroaryl), and more specifically, preferred examples include a 2-(heteroarylaminocarbonyl)ethyl group, and a 2-(N-heteroaryl-N-methylaminocarbonyl)ethyl group.

The aryl as $R^5$ is preferably phenyl group, and a substituted phenyl group is also preferred.

The substituted phenyl group is preferably a phenyl group substituted with one or more substituents, most preferably one substituent, selected from the group consisting a halogen atom, a $C_{1-6}$ alkyl group, $CF_3$ group, a $C_{1-6}$ alkoxyl group, cyano group, —N($G^7$)($G^8$), —$CO_2$($G^9$), —S(O)$_r$($G^9$), and —N($G^9$)S(O)$_2$($C_{1-6}$ alkyl).

The substituted phenyl group is preferably a phenyl group substituted with one or more substituents, most preferably one substituent, selected from the group consisting a halogen atom, a $C_{1-6}$ alkyl group, $CF_3$ group, a $C_{1-6}$ alkoxyl group, and cyano group.

The substituted phenyl group is preferably a phenyl group substituted with one or more substituents, most preferably one substituent, selected from the group consisting —N($G^7$)($G^8$), —$CO_2$($G^9$), —S(O)$_r$($G^9$), and —N($G^9$)S(O)$_2$($C_{1-6}$ alkyl).

The substituted phenyl group is preferably a phenyl group substituted with one or more halogen atoms, most preferably one halogen atom, and the halogen atoms most preferably consist of fluorine atom, chlorine atom, or bromine atom.

The substituted phenyl group is preferably a phenyl group substituted with one or more $C_{1-6}$ alkyl groups, most preferably one $C_{1-6}$ alkyl group, and the $C_{1-6}$ alkyl group is most preferably methyl group, ethyl group, propyl group, or isopropyl group.

The substituted phenyl group is preferably a phenyl group substituted with one or more $CF_3$ groups, most preferably one $CF_3$ group.

The substituted phenyl group is preferably a phenyl group substituted with one or more $C_{1-6}$ alkoxyl groups, most preferably one $C_{1-6}$ alkoxyl group. The $C_{1-6}$ alkoxyl groups are most preferably consists of methoxy group or ethoxy group.

The substituted phenyl group is preferably a phenyl group substituted with one or more cyano groups, most preferably one cyano group.

The substituted phenyl group is preferably a phenyl group substituted with one or more of —N($G^7$)($G^8$), most preferably one of —N($G^7$)($G^8$). —N($G^7$)($G^8$) most preferably consists of amino group, methylamino group, dimethylamino group, or ethylamino group.

The substituted phenyl group is preferably a phenyl group substituted with one or more of —$CO_2$($G^9$), most preferably one of —$CO_2$($G^9$). —$CO_2$($G^9$) most preferably consists of carboxyl group, methoxycarbonyl group, or ethoxycarbonyl group.

The substituted phenyl group is preferably a phenyl group substituted with one or more of —S(O)$_r$($G^9$), most preferably one of —S(O)$_r$($G^9$). —S(O)$_r$($G^9$) most preferably consists of methylthio group, ethylthio group, methylsulfinyl group, ethylsulfinyl group, methanesulfonyl group, or ethanesulfonyl group.

The substituted phenyl group is preferably a phenyl group substituted with one or more of —S($G^9$). —S($G^9$) most preferably consists of methylthio group, or ethylthio group.

The substituted phenyl group is preferably a phenyl group substituted with one or more of —SO($G^9$). —SO($G^9$) most preferably consists of methylsulfinyl group, or ethylsulfinyl group.

The substituted phenyl group is preferably a phenyl group substituted with one or more of —$SO_2$($G^9$). —$SO_2$($G^9$) is most preferably methylsulfonyl group, or ethylsulfonyl group.

The substituted phenyl group is preferably a phenyl group substituted with one or more of —N($G^9$)$SO_2$($C_{1-6}$ alkyl). —N(G⁹)$SO_2$($C_{1-6}$ alkyl) most preferably consists of methanesulfonylamino group, or ethanesulfonylamino group.

Preferred examples of the heteroaryl as $R^5$ include the followings: pyranyl group; pyrazinyl group; dioxolyl group; furyl group; thienyl group; pyridyl group; pyrimidyl group; pyridazinyl group; tetrazolyl group; pyrrolyl group; oxazolyl group; thiazolyl group; isoxazolyl group; isothiazolyl group; imidazolyl group; pyrazolyl group; oxadiazolyl group; thiadiazolyl group; and triazolyl group; and particularly preferred are 2-thienyl group and 3-thienyl group. Unsubstituted groups and substituted groups of the aforementioned groups are both preferred. Among the substituted groups, those substituted with one or more substituents selected from the group consisting of a $C_{1-6}$ alkyl group which may be substituted with a halogen atom, and a halogen atom are preferred.

The cycloalkyl means a monocyclic alkyl, and it preferably contains, for example, a 3- to 7-membered ring.

Examples of the cycloalkyl include, for example, cyclopropyl, cyclobutyl, cyclopentyl, cyclohexyl, cycloheptyl and the like, and more preferred are cyclopentyl and cyclohexyl.

Preferred examples of the compounds represented by the formula (1) are mentioned below.

Compounds wherein $R^1$ is hydrogen atom, a halogen atom, hydroxyl group, or amino group, and $R^3$ is a group represented by the formula (1-1);

compounds wherein $R^1$ is hydrogen atom, hydroxyl group, or amino group, and $R^3$ is a group represented by the formula (1-1);

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1);

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1-4), or formula (1-1-7);

compounds wherein $R^1$ is hydrogen atom, hydroxyl group, or amino group, $R^2$ is a $C_{1-6}$ alkyl group, a $C_{2-3}$ alkenyl group, or cyano group, and $R^3$ is a group represented by the formula (1-1-4), or formula (1-1-7);

compounds wherein $R^1$ is hydrogen atom, hydroxyl group, or amino group, $R^2$ is methyl group, ethyl group, vinyl group, or cyano group, and $R^3$ is a group represented by the formula (1-1-4), or formula (1-1-7);

compounds wherein $R^1$ is hydrogen atom, hydroxyl group, or amino group, $R^2$ is methyl group, ethyl group, vinyl group, or cyano group, $R^3$ is a group represented by the formula (1-1-4), or formula (1-1-7), and $A^{31}$ is hydrogen atom;

compounds wherein $R^1$ is hydrogen atom, hydroxyl group, or amino group, $R^2$ is methyl group, ethyl group, vinyl group, or cyano group, $R^3$ is a group represented by the formula (1-1-4), or formula (1-1-7), and $A^{31}$ is a $C_{1-6}$ alkyl group substituted with hydroxyl group;

compounds wherein $R^1$ is hydrogen atom, or amino group, and $R^3$ is a group represented by the formula (1-1);

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1);

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1-4), or formula (1-1-7);

compounds wherein $R^1$ is hydrogen atom, or amino group, $R^2$ is a $C_{1-6}$ alkyl group, a $C_{2-3}$ alkenyl group, or cyano group, and $R^3$ is a group represented by the formula (1-1-4), or formula (1-1-7);

compounds wherein $R^1$ is hydrogen atom, or amino group, $R^2$ is methyl group, ethyl group, vinyl group, or cyano group, and $R^3$ is a group represented by the formula (1-1-4), or formula (1-1-7);

compounds wherein $R^1$ is hydrogen atom, or amino group, $R^2$ is methyl group, ethyl group, vinyl group, or cyano group, $R^3$ is a group represented by the formula (1-1-4), or formula (1-1-7), and $A^{31}$ is hydrogen atom;

compounds wherein $R^1$ is hydrogen atom, or amino group, $R^2$ is methyl group, ethyl group, vinyl group, or cyano group, $R^3$ is a group represented by the formula (1-1-4), or formula (1-1-7), and $A^{31}$ is a $C_{1-6}$ alkyl group substituted with hydroxyl group;

compounds wherein $R^1$ is hydrogen atom, or hydroxyl group, and $R^3$ is a group represented by the formula (1-1);

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, and $R^3$ is a group represented by the formula (1-1);

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom;

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, or hydroxyl group, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, and $R^3$ is a group represented by the formula (1-1-4), or formula (1-1-7);

compounds wherein $R^1$ is hydrogen atom, or hydroxyl group, $R^2$ is a $C_{1-6}$ alkyl group, a $C_{2-3}$ alkenyl group, or cyano group, and $R^3$ is a group represented by the formula (1-1-4), or formula (1-1-7);

compounds wherein $R^1$ is hydrogen atom, or hydroxyl group, $R^2$ is methyl group, ethyl group, vinyl group, or cyano group, and $R^3$ is a group represented by the formula (1-1-4), or formula (1-1-7);

compounds wherein $R^1$ is hydrogen atom, or hydroxyl group, $R^2$ is methyl group, ethyl group, vinyl group, or cyano group, $R^3$ is a group represented by the formula (1-1-4), or formula (1-1-7), and $A^{31}$ is hydrogen atom;

compounds wherein $R^1$ is hydrogen atom, or hydroxyl group, $R^2$ is methyl group, ethyl group, vinyl group, or cyano group, $R^3$ is a group represented by the formula (1-1-4), or formula (1-1-7), and $A^{31}$ is a $C_{1-6}$ alkyl group substituted with hydroxyl group;

compounds wherein $R^1$ is hydrogen atom, and $R^3$ is a group represented by the formula (1-1);

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, and $R^3$ is a group represented by the formula (1-1);

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is a $C_{1-6}$ alkyl group, —($C_{2-3}$ alkylene)O($G^1$), a $C_{2-3}$ alkenyl group, —$S(O)_p$($C_{1-6}$ alkyl), or cyano group, and $R^3$ is a group represented by the formula (1-1-4), or formula (1-1-7);

compounds wherein $R^1$ is hydrogen atom, $R^2$ is a $C_{1-6}$ alkyl group, a $C_{2-3}$ alkenyl group, or cyano group, and $R^3$ is a group represented by the formula (1-1-4), or formula (1-1-7);

compounds wherein $R^1$ is hydrogen atom, $R^2$ is methyl group, ethyl group, vinyl group, or cyano group, and $R^3$ is a group represented by the formula (1-1-4), or formula (1-1-7);

compounds wherein $R^1$ is hydrogen atom, $R^2$ is methyl group, ethyl group, vinyl group, or cyano group, $R^3$ is a group represented by the formula (1-1-7), and $A^{31}$ is hydrogen atom (those compounds wherein $R^3$ is a group represented by the formula (1-1-4) are also preferred);

compounds wherein $R^1$ is hydrogen atom, $R^2$ is methyl group, ethyl group, vinyl group, or cyano group, $R^3$ is a group represented by the formula (1-1-7), and $A^{31}$ is a $C_{1-6}$ alkyl group substituted with hydroxyl group (those compounds wherein $R^3$ is a group represented by the formula (1-1-4) are also preferred);

compounds wherein $R^1$ is hydrogen atom, $R^2$ is hydrogen atom, a halogen atom, or a $C_{1-6}$ alkyl group, and $R^3$ is a group represented by the formula (1-1);

compounds wherein $R^1$ is hydrogen atom, $R^2$ is hydrogen atom, a halogen atom, or a $C_{1-6}$ alkyl group, $R^3$ is a group represented by the formula (1-1), and $R^{31}$ is hydrogen atom;

compounds wherein $R^1$ is hydrogen atom, $R^2$ is hydrogen atom, a halogen atom, or a $C_{1-6}$ alkyl group, $R^3$ is a group represented by the formula (1-1), and $R^{31}$ is a $C_{1-6}$ alkyl group substituted with hydroxyl group;

compounds wherein $R^1$ and $R^2$ are hydrogen atoms, and $R^3$ is a group represented by the formula (1-1);

compounds wherein $R^1$ and $R^2$ are hydrogen atoms, $R^3$ is a group represented by the formula (1-1), and $R^{31}$ is hydrogen atom;

compounds wherein $R^1$ and $R^2$ are hydrogen atoms, $R^3$ is a group represented by the formula (1-1), and $R^{31}$ is a $C_{1-6}$ alkyl group substituted with hydroxyl group;

compounds wherein $R^1$ and $R^2$ are hydrogen atoms, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is a $C_{1-6}$ alkyl group substituted with hydroxyl group, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$, are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is hydrogen atom, X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is a $C_{1-6}$ alkyl group substituted with hydroxyl group, X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is a $C_{1-6}$ alkyl group substituted with hydroxyl group, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), X is —$C(A^5)(A^{51})$-, or —$C(A^5)(A^{51})$-$C(A^6)(A^{61})$-, $A^{11}$, $A^{21}$, $A^{51}$, $A^6$, $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is hydrogen atom, X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-1), $R^{31}$ is a $C_{1-6}$ alkyl group substituted with hydroxyl group, X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is a halogen atom, and $R^3$ is a group represented by the formula (1-1);

compounds wherein $R^1$ is hydrogen atom, $R^2$ is a halogen atom, $R^3$ is a group represented by the formula (1-1), and $R^{31}$ is hydrogen atom;

compounds wherein $R^1$ is hydrogen atom, $R^2$ is a halogen atom, $R^3$ is a group represented by the formula (1-1), and $R^{31}$ is a $C_{1-6}$ alkyl group substituted with hydroxyl group;

compounds wherein $R^1$ is hydrogen atom, $R^2$ is fluorine atom, or bromine atom, $R^3$ is a group represented by the formula (1-1), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is a $C_{1-6}$ alkyl group substituted with hydroxyl group, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), X is —$C(A^5)(A^{51})$-, or —$C(A^5)(A^{51})$-$C(A^6)$ ($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is a $C_{1-6}$ alkyl group substituted with hydroxyl group, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is fluorine atom, or bromine atom, $R^3$ is a group represented by the formula (1-1-1), formula (1-1-2), formula (1-1-3), formula (1-1-4), formula (1-1-5), formula (1-1-6), or formula (1-1-7), and $A^{31}$ is hydrogen atom;

compounds wherein $R^1$ is hydrogen atom, $R^2$ is fluorine atom, or bromine atom, $R^3$ is a group represented by the formula (1-1-1), formula (1-1-2), formula (1-1-3), formula (1-1-4), formula (1-1-5), formula (1-1-6), or formula (1-1-7), and $A^{31}$ is a $C_{1-6}$ alkyl group substituted with hydroxyl group;

compounds wherein $R^1$ is hydrogen atom, $R^2$ is fluorine atom, or bromine atom, and $R^3$ is a group represented by the formula (1-1-4), or formula (1-1-7);

compounds wherein $R^1$ is hydrogen atom, $R^2$ is fluorine atom, or bromine atom, $R^3$ is a group represented by the formula (1-1-4), or formula (1-1-7), and $A^{31}$ is hydrogen atom;

compounds wherein $R^1$ is hydrogen atom, $R^2$ is fluorine atom, or bromine atom, $R^3$ is a group represented by the formula (1-1-4), or formula (1-1-7), and $A^{31}$ is a $C_{1-6}$ alkyl group substituted with hydroxyl group;

compounds wherein $R^1$ is hydrogen atom, $R^2$ is a $C_{1-6}$ alkyl group, and $R^3$ is a group represented by the formula (1-1);

compounds wherein $R^1$ is hydrogen atom, $R^2$ is a $C_{1-6}$ alkyl group, $R^3$ is a group represented by the formula (1-1), and $R^{31}$ is hydrogen atom;

compounds wherein $R^1$ is hydrogen atom, $R^2$ is a $C_{1-6}$ alkyl group, $R^3$ is a group represented by the formula (1-1), and $R^{31}$ is a $C_{1-6}$ alkyl group substituted with hydroxyl group;

compounds wherein $R^1$ is hydrogen atom, $R^2$ is methyl group, or ethyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, or ethyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring preferably consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, or ethyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, or ethyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, or ethyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is methyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is methyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is methyl group, and $R^3$ is a group represented by the formula (1-1-4), or formula (1-1-7);

compounds wherein $R^1$ is hydrogen atom, $R^2$ is methyl group, $R^3$ is a group represented by the formula (1-1-4), or formula (1-1-7), and $R^{31}$ is hydrogen atom;

compounds wherein $R^1$ is hydrogen atom, $R^2$ is methyl group, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is cyano group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is cyano group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is cyano group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is cyano group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is cyano group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is cyano group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is cyano group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is cyano group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is cyano group, $R^3$ is a group represented by the formula (1-1), $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is cyano group, $R^3$ is a group represented by the formula (1-1), $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is cyano group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is cyano group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is cyano group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is cyano group, and $R^3$ is a group represented by the formula (1-1-4), or formula (1-1-7);

compounds wherein $R^1$ is hydrogen atom, $R^2$ is cyano group, $R^3$ is a group represented by the formula (1-1-7), and $R^{31}$ is hydrogen atom (those compounds wherein $R^3$ is a group represented by the formula (1-1-4) are also preferred);

compounds wherein $R^1$ is hydrogen atom, $R^2$ is cyano group, $R^3$ is a group represented by the formula (1-1-7), and $R^{31}$ is a $C_{1-6}$ alkyl group substituted with hydroxyl group (those compounds wherein $R^3$ is a group represented by the formula (1-1-4) are also preferred);

compounds wherein $R^1$ is hydrogen atom, $R^2$ is hydroxymethyl group, $R^3$ is a group represented by the formula (1-1), and $R^4$ is hydrogen atom;

compounds wherein $R^1$ is hydrogen atom, $R^2$ is hydroxymethyl group, $R^3$ is a group represented by the formula (1-1), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is hydroxymethyl group, $R^4$ is hydrogen atom, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is hydroxymethyl group, $R^4$ is hydrogen atom, $R^3$ is a group represented by the formula (1-1-1), formula (1-1-2), formula (1-1-3), formula (1-1-4), formula (1-1-5), formula (1-1-6), or formula (1-1-7); and $R^{31}$ is hydrogen atom;

compounds wherein $R^1$ is hydrogen atom, $R^2$ is hydroxymethyl group, $R^4$ is hydrogen atom, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is hydroxymethyl group, $R^4$ is hydrogen atom, and $R^3$ is a group represented by the formula (1-1-4), or formula (1-1-7);

compounds wherein $R^1$ is hydrogen atom, $R^2$ is hydroxymethyl group, $R^4$ is hydrogen atom, $R^3$ is a group represented by the formula (1-1-4), or formula (1-1-7), and $R^{31}$ is hydrogen atom;

compounds wherein $R^1$ is hydrogen atom, $R^2$ is hydroxymethyl group, $R^4$ is hydrogen atom, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is 2-hydroxyethyl group, 2-methoxyethyl group, 3-hydroxypropyl group, or 3-methoxypropyl group, and $R^3$ is a group represented by the formula (1-1);

compounds wherein $R^1$ is hydrogen atom, $R^2$ is 2-hydroxyethyl group, or 2-methoxyethyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-hydroxyethyl-group, or 2-methoxyethyl-group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is 2-hydroxyethyl group, or 2-methoxyethyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is 2-hydroxyethyl group, or 2-methoxyethyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is 2-hydroxyethyl group, or 2-methoxyethyl group, and $R^3$ is a group represented by the formula (1-1-4), or formula (1-1-7);

compounds wherein $R^1$ is hydrogen atom, $R^2$ is 2-hydroxyethyl group, or 2-methoxyethyl group, $R^3$ is a group represented by the formula (1-1-4), or formula (1-1-7), and $R^{31}$ is hydrogen atom;

compounds wherein $R^1$ is hydrogen atom, $R^2$ is 2-hydroxyethyl group, or 2-methoxyethyl group, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is 2-carboxyethyl group, 2-(methoxycarbonyl)ethyl group, 3-carboxypropyl group, or 3-(methoxycarbonyl)propyl group, and $R^3$ is a group represented by the formula (1-1);

compounds wherein $R^1$ is hydrogen atom, $R^2$ is 2-carboxyethyl group, or 2-(methoxycarbonyl)ethyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-carboxyethyl group, or 2-(methoxycarbonyl)ethyl group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is 2-carboxyethyl group, or 2-(methoxycarbonyl)ethyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is 2-carboxyethyl group, or 2-(methoxycarbonyl)ethyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is 2-carboxyethyl group, or 2-(methoxycarbonyl)ethyl group, and $R^3$ is a group represented by the formula (1-1-4), or formula (1-1-7);

compounds wherein $R^1$ is hydrogen atom, $R^2$ is 2-carboxyethyl group, or 2-(methoxycarbonyl)ethyl group, $R^3$ is a group represented by the formula (1-1-4), or formula (1-1-7), and $R^{31}$ is hydrogen atom;

compounds wherein $R^1$ is hydrogen atom, $R^2$ is 2-carboxyethyl group, or 2-(methoxycarbonyl)ethyl group, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is amino group, methylamino group, or dimethylamino group, and $R^3$ is a group represented by the formula (1-1);

compounds wherein $R^1$ is hydrogen atom, $R^2$ is amino group, methylamino group, or dimethylamino group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is amino group, methylamino group, or dimethylamino group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is amino group, methylamino group, or dimethylamino group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is amino group, methylamino group, or dimethylamino group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is amino group, methylamino group, or dimethylamino group, and $R^3$ is a group represented by the formula (1-1-4), or formula (1-1-7);

compounds wherein $R^1$ is hydrogen atom, $R^2$ is amino group, methylamino group, or dimethylamino group, $R^3$ is a group represented by the formula (1-1-4), or formula (1-1-7), and $R^{31}$ is hydrogen atom;

compounds wherein $R^1$ is hydrogen atom, $R^2$ is amino group, methylamino group, or dimethylamino group, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is 2-hydroxyethoxy group, 2-methoxyethoxy group, 3-hydroxypropoxy group, or 3-methoxypropoxy group, and $R^3$ is a group represented by the formula (1-1);

compounds wherein $R^1$ is hydrogen atom, $R^2$ is 2-hydroxyethoxy group, or 2-methoxyethoxy group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-(hydroxyethyl)amino group, 3-(hydroxypropyl)amino group, 2-(methoxyethyl)amino group, or 3-(methoxypropyl)amino group, and $R^3$ is a group represented by the formula (1-1);

compounds wherein $R^1$ is hydrogen atom, $R^2$ is 2-(hydroxyethyl)amino group, or 2-(methoxyethyl)amino group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-aminoethylamino group, 3-aminopropylamino group, 2-(methylamino)ethylamino group, 3-(methylamino)propylamino group, 2-(dimethylamino)ethylamino group, or 3-(dimethylamino)propylamino group, and $R^3$ is a group represented by the formula (1-1);

compounds wherein $R^1$ is hydrogen atom, $R^2$ is 2-aminoethylamino group, 2-(methylamino)ethylamino group, or 2-(dimethylamino)ethylamino group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, or 2-propenyl group, and $R^3$ is a group represented by the formula (1-1);

compounds wherein $R^1$ is hydrogen atom, $R^2$ is ethenyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, and $R^3$ is a group represented by the formula (1-1-1), formula (1-1-2), formula (1-1-3), formula (1-1-4), formula (1-1-5), formula (1-1-6), or formula (1-1-7);

compounds wherein $R^1$ is hydrogen atom, $R^2$ is ethenyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is hydrogen atom;

compounds wherein $R^1$ is hydrogen atom, $R^2$ is ethenyl group, $R^3$ is a group represented by the formula (1-1-1), formula (1-1-2), formula (1-1-3), formula (1-1-4), formula (1-1-5), formula (1-1-6), or formula (1-1-7), and $R^{31}$ is a $C_{1-6}$ alkyl group substituted with hydroxyl group;

compounds wherein $R^1$ is hydrogen atom, $R^2$ is ethenyl group, and $R^3$ is a group represented by the formula (1-1-4), or formula (1-1-7);

compounds wherein $R^1$ is hydrogen atom, $R^2$ is ethenyl group, $R^3$ is a group represented by the formula (1-1-4), or formula (1-1-7), and $R^{31}$ is hydrogen atom;

compounds wherein $R^1$ is hydrogen atom, $R^2$ is ethenyl group, $R^3$ is a group represented by the formula (1-1-4), or formula (1-1-7), and $R^{31}$ is a $C_{1-6}$ alkyl group substituted with hydroxyl group;

compounds wherein $R^1$ is hydrogen atom, $R^2$ is ethynyl group, or 2-propynyl group, and $R^3$ is a group represented by the formula (1-1);

compounds wherein $R^1$ is hydrogen atom, $R^2$ is ethynyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methoxy group, ethoxy group, propoxy group, or isopropoxy group, and $R^3$ is a group represented by the formula (1-1);

compounds wherein $R^1$ is hydrogen atom, $R^2$ is methoxy group, or ethoxy group, $R^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is hydrogen atom, R$^2$ is 2-(methanesulfonyl)ethyl group, 3-(methanesulfonyl)propyl group, 2-(ethanesulfonyl)ethyl group, or 3-(ethanesulfonyl)propyl group, and R$^3$ is a group represented by the formula (1-1);

compounds wherein R$^1$ is hydrogen atom, R$^2$ is 2-(methanesulfonyl)ethyl group, or 2-(ethanesulfonyl)ethyl group, R$^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is hydrogen atom, R$^2$ is methylthio group, ethylthio group, methylsulfinyl group, ethylsulfinyl group, methanesulfonyl group, or ethanesulfonyl group, and R$^3$ is a group represented by the formula (1-1);

compounds wherein R$^1$ is hydrogen atom, R$^2$ is methylthio group, methylsulfinyl group, or methanesulfonyl group, R$^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is hydrogen atom, R$^2$ is 2-(methanesulfonyl)ethoxy group, 3-(methanesulfonyl)propoxy group, 2-(ethanesulfonyl)ethoxy group, or 3-(methanesulfonyl)propoxy group, and R$^3$ is a group represented by the formula (1-1);

compounds wherein R$^1$ is hydrogen atom, R$^2$ is 2-(methanesulfonyl)ethoxy group, or 2-(ethanesulfonyl)ethoxy group, R$^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is a halogen atom, and R$^3$ is a group represented by the formula (1-1);

compounds wherein R$^1$ is chlorine atom, and R$^3$ is a group represented by the formula (1-1);

compounds wherein R$^1$ is chlorine atom, R$^2$ is hydrogen atom, a halogen atom, or a C$_{1-6}$ alkyl group, and R$^3$ is a group represented by the formula (1-1);

compounds wherein R$^1$ is chlorine atom, R$^2$ is hydrogen atom, and R$^3$ is a group represented by the formula (1-1);

compounds wherein R$^1$ is chlorine atom, R$^2$ is hydrogen atom, R$^3$ is a group represented by the formula (1-1), X is —C(A$^5$)(A$^{51}$)-, —C(A$^5$)(A$^{51}$)-C(A$^6$)(A$^{61}$)-, or a single bond, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is chlorine atom, R$^2$ is hydrogen atom, R$^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is chlorine atom, R$^2$ is hydrogen atom, R$^3$ is a group represented by the formula (1-1), X is —C(A$^5$)(A$^{51}$)-, —C(A$^5$)(A$^{51}$)-C(A$^6$)(A$^{61}$)-, or a single bond, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is chlorine atom, R$^2$ is hydrogen atom, R$^3$ is a group represented by the formula (1-1), X is —C(A$^5$)(A$^{51}$)-, or —C(A$^5$)(A$^{51}$)-C(A$^6$)(A$^{61}$)-, A$^{11}$, A$^{21}$A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 6-membered ring, the ring consists of carbon atoms, or when the ring contains a nitrogen atom to which A$^3$ binds, the ring consists of carbon atoms except for the nitrogen atom, and the ring is a saturated ring;

compounds wherein R$^1$ is hydroxyl group, and R$^3$ is a group represented by the formula (1-1);

compounds wherein R$^1$ is hydroxyl group, R$^2$ is hydrogen atom, a halogen atom, or a C$_{1-6}$ alkyl group, and R$^3$ is a group represented by the formula (1-1);

compounds wherein R$^1$ is hydroxyl group, R$^2$ is hydrogen atom, and R$^3$ is a group represented by the formula (1-1);

compounds wherein R$^1$ is hydroxyl group, R$^2$ is hydrogen atom, R$^3$ is a group represented by the formula (1-1), X is —C(A$^5$)(A$^{51}$)-, —C(A$^5$)(A$^{51}$)-C(A$^6$)(A$^{61}$)-, or a single bond, A$^{11}$, A$^{21}$, A$^{51}$, A$^6$, and A$^{61}$ are hydrogen atoms, A$^1$, A$^2$, A$^3$, and A$^5$ are hydrogen atoms, or groups in each of one or more combinations selected from the group consisting of combinations of A$^1$ and A$^3$, A$^2$ and A$^3$, A$^2$ and A$^5$, and A$^3$ and A$^5$ bind to each other to form a 5- or 6-membered ring, the ring consists of carbon atoms, or when the ring contains a nitrogen atom to which A$^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, and $R^3$ is a group represented by the formula (1-1);

compounds wherein $R^1$ is amino group, $R^2$ is hydrogen atom, and $R^3$ is a group represented by the formula (1-1);

compounds wherein $R^1$ is amino group, $R^2$ is hydrogen atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is a halogen atom, and $R^3$ is a group represented by the formula (1-1);

compounds wherein $R^1$ is amino group, $R^2$ is fluorine atom, or bromine atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is fluorine atom, or bromine atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is fluorine atom, or bromine atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is fluorine atom, or bromine atom, $R^3$ is a group represented by the formula (1-1), X is —C($A^5$)($A^{51}$)-, or —C($A^5$)($A^{51}$)-C($A^6$)($A^{61}$)-, $A^1$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is a $C_{1-6}$ alkyl group, and $R^3$ is a group represented by the formula (1-1);

compounds wherein $R^1$ is amino group, $R^2$ is methyl group, or ethyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, or ethyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is a $C_{1-6}$ alkoxy group, and $R^3$ is a group represented by the formula (1-1);

compounds wherein $R^1$ is a $C_{1-6}$ alkoxy group, $R^2$ is hydrogen atom, and $R^3$ is a group represented by the formula (1-1);

compounds wherein $R^1$ is methoxy group, $R^2$ is hydrogen atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-1), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-1), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, a halogen atom, hydroxyl group, or amino group, and $R^3$ is a group represented by the formula (1-2);

compounds wherein $R^1$ is hydrogen atom, a halogen atom, hydroxyl group, or amino group, $R^3$ is a group represented by the formula (1-2), and $R^4$ is hydrogen atom;

compounds wherein $R^1$ is hydrogen atom, hydroxyl group, or amino group, and $R^3$ is a group represented by the formula (1-2);

compounds wherein $R^1$ is hydrogen atom, hydroxyl group, or amino group, $R^3$ is a group represented by the formula (1-2), and $R^4$ is hydrogen atom;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-2), and $R^4$ is hydrogen atom;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group, $R^3$ is a group represented by the formula (1-2), $R^4$ is hydrogen atom, X is —C($A^5$)($A^{51}$)-, —C($A^5$)

$(A^{51})$-C$(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, hydroxyl group, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2), $R^4$ is hydrogen atom, X is —C$(A^5)(A^{51})$-, —C$(A^5)(A^{51})$-C$(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, hydroxyl group, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2-1), formula (1-2-2), formula (1-2-3), formula (1-2-4), formula (1-2-5), formula (1-2-6), or formula (1-2-7), and $R^4$ is hydrogen atom;

compounds wherein $R^1$ is hydrogen atom, hydroxyl group, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2-4), or formula (1-2-7), and $R^4$ is hydrogen atom;

compounds wherein $R^1$ is hydrogen atom, hydroxyl group, or amino group, $R^2$ is a $C_{1-6}$ alkyl group, —$(C_{2-3}$ alkylene)O$(G^1)$, a $C_{2-3}$ alkenyl group, or —S(O)$_p$($C_{1-6}$ alkyl), $R^3$ is a group represented by the formula (1-2-4), or formula (1-2-7), and $R^4$ is hydrogen atom;

compounds wherein $R^1$ is hydrogen atom, hydroxyl group, or amino group, $R^2$ is methyl group, ethyl group, vinyl group, hydroxyethyl, or methylthio group, $R^3$ is a group represented by the formula (1-2-4), or formula (1-2-7), and $R^4$ is hydrogen atom;

compounds wherein $R^1$ is hydrogen atom, hydroxyl group, or amino group, $R^2$ is methyl group, ethyl group, vinyl group, or cyano group, $R^3$ is a group represented by the formula (1-2-4), or formula (1-2-7), $R^4$ is hydrogen atom, and $A^{31}$ is hydrogen atom;

compounds wherein $R^1$ is hydrogen atom, hydroxyl group, or amino group, $R^2$ is methyl group, ethyl group, vinyl group, hydroxyethyl, or methylthio group, $R^3$ is a group represented by the formula (1-2-4), or formula (1-2-7), $R^4$ is hydrogen atom, and $A^{31}$ is a $C_{1-6}$ alkyl group substituted with hydroxyl group;

compounds wherein $R^1$ is hydrogen atom, or amino group, and $R^3$ is a group represented by the formula (1-2);

compounds wherein $R^1$ is hydrogen atom, or amino group, $R^3$ is a group represented by the formula (1-2), and $R^4$ is hydrogen atom;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2), and $R^4$ is hydrogen atom;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2), $R^4$ is hydrogen atom, X is —C$(A^5)(A^{51})$-, —C$(A^5)(A^{51})$-C$(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2), $R^4$ is hydrogen atom, X is —C$(A^5)(A^{51})$-, —C$(A^5)(A^{51})$-C$(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2), $R^4$ is hydrogen atom, X is —C$(A^5)(A^{51})$-, —C$(A^5)(A^{51})$-C$(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2-1), formula (1-2-2), formula (1-2-3), formula (1-2-4), formula (1-2-5), formula (1-2-6), or formula (1-2-7), and $R^4$ is hydrogen atom;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, —S(O)$_p$($C_{1-6}$ alkyl), or cyano group, $R^3$ is a group represented by the formula (1-2-4), or formula (1-2-7), and $R^4$ is hydrogen atom;

compounds wherein $R^1$ is hydrogen atom, or amino group, $R^2$ is a $C_{1-6}$ alkyl group, —$(C_{2-3}$ alkylene)O$(G^1)$, a $C_{2-3}$ alkenyl group, or —S(O)$_p$($C_{1-6}$ alkyl), $R^3$ is a group represented by the formula (1-2-4), or formula (1-2-7), and $R^4$ is hydrogen atom;

compounds wherein $R^1$ is hydrogen atom, or amino group, $R^2$ is methyl group, ethyl group, vinyl group, hydroxyethyl, or methylthio group, $R^3$ is a group represented by the formula (1-2-4), or formula (1-2-7), and $R^4$ is hydrogen atom;

compounds wherein $R^1$ is hydrogen atom, or amino group, $R^2$ is methyl group, ethyl group, vinyl group, or cyano group, $R^3$ is a group represented by the formula (1-2-4), or formula (1-2-7), $R^4$ is hydrogen atom, and $A^{31}$ is hydrogen atom;

compounds wherein $R^1$ is hydrogen atom, or amino group, $R^2$ is methyl group, ethyl group, vinyl group, hydroxyethyl, or methylthio group, $R^3$ is a group represented by the formula (1-2-4), or formula (1-2-7), $R^4$ is hydrogen atom, and $A^{31}$ is a $C_{1-6}$ alkyl group substituted with hydroxyl group;

compounds wherein $R^1$ is hydrogen atom, or hydroxyl group, and $R^3$ is a group represented by the formula (1-2);

compounds wherein $R^1$ is hydrogen atom, or hydroxyl group, $R^3$ is a group represented-by the formula (1-2), and $R^4$ is hydrogen atom;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2), and $R^4$ is hydrogen atom;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2), $R^4$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2), $R^4$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2), $R^4$ is hydrogen atom, X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2-1), formula (1-2-2), formula (1-2-3), formula (1-2-4), formula (1-2-5), formula (1-2-6), or formula (1-2-7), and $R^4$ is hydrogen atom;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, —$S(O)_p(C_{1-6}$ alkyl), or cyano group, $R^3$ is a group represented by the formula (1-2-4), or formula (1-2-7), and $R^4$ is hydrogen atom;

compounds wherein $R^1$ is hydrogen atom, or hydroxyl group, $R^2$ is a $C_{1-6}$ alkyl group, —$(C_{2-3}$ alkylene)$O(G^1)$, a $C_{2-3}$ alkenyl group, or —$S(O)_p(C_{1-6}$ alkyl), $R^3$ is a group represented by the formula (1-2-4), or formula (1-2-7), and $R^4$ is hydrogen atom;

compounds wherein $R^1$ is hydrogen atom, or hydroxyl group, $R^2$ is methyl group, ethyl group, vinyl group, hydroxyethyl, or methylthio group, $R^3$ is a group represented by the formula (1-2-4), or formula (1-2-7), and $R^4$ is hydrogen atom;

compounds wherein $R^1$ is hydrogen atom, or hydroxyl group, $R^2$ is methyl group, ethyl group, vinyl group, or cyano group, $R^3$ is a group represented by the formula (1-2-4), or formula (1-2-7), $R^4$ is hydrogen atom, and $A^{31}$ is hydrogen atom;

compounds wherein $R^1$ is hydrogen atom, or hydroxyl group, $R^2$ is methyl group, ethyl group, vinyl group, hydroxyethyl, or methylthio group, $R^3$ is a group represented by the formula (1-2-4), or formula (1-2-7), $R^4$ is hydrogen atom, and $A^{31}$ is a $C_{1-6}$ alkyl group substituted with hydroxyl group;

compounds wherein $R^1$ is hydrogen atom, and $R^3$ is a group represented by the formula (1-2);

compounds wherein $R^1$ is hydrogen atom, $R^3$ is a group represented by the formula (1-2), and $R^4$ is hydrogen atom;

compounds wherein $R^1$ is hydrogen atom, $R^2$ is hydrogen atom, a halogen atom, or a $C_{1-6}$ alkyl group, and $R^3$ is a group represented by the formula (1-2);

compounds wherein $R^1$ is hydrogen atom, $R^2$ is hydrogen atom, a halogen atom, or a $C_{1-6}$ alkyl group, $R^3$ is a group represented by the formula (1-2), and $R^4$ is hydrogen atom;

compounds wherein $R^1$ is hydrogen atom, $R^2$ is hydrogen atom, a halogen atom, or a $C_{1-6}$ alkyl group, $R^3$ is a group represented by the formula (1-2), $R^4$ is hydrogen atom, and $R^{31}$ is hydrogen atom;

compounds wherein $R^1$ is hydrogen atom, $R^2$ is hydrogen atom, a halogen atom, or a $C_{1-6}$ alkyl group, $R^3$ is a group represented by the formula (1-2), $R^4$ is hydrogen atom, and $R^{31}$ is a $C_{1-6}$ alkyl group substituted with hydroxyl group;

compounds wherein $R^1$ and $R^2$ are hydrogen atoms, and $R^3$ is a group represented by the formula (1-2);

compounds wherein $R^1$ and $R^2$ are hydrogen atoms, $R^3$ is a group represented by the formula (1-2), and $R^4$ is hydrogen atom;

compounds wherein $R^1$ and $R^2$ are hydrogen atoms, $R^3$ is a group represented by the formula (1-2), $R^4$ is hydrogen atom, and $R^{31}$ is hydrogen atom;

compounds wherein $R^1$ and $R^2$ are hydrogen atoms, $R^3$ is a group represented by the formula (1-2), $R^4$ is hydrogen atom, and $R^{31}$ is a $C_{1-6}$ alkyl group substituted with hydroxyl group;

compounds wherein $R^1$ and $R^2$ are hydrogen atoms, $R^3$ is a group represented by the formula (1-2), X is —$C(A^5)(A^{51})$-, —$C(A^5)(A^{51})$-$C(A^6)(A^{61})$-, or a single bond, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-2), $R^4$ is hydrogen atom, X is —$C(A^5)(A^{51})$-, or —$C(A^5)(A^{51})$-$C(A^6)(A^{61})$-, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ and $R^2$ are hydrogen atoms, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring;

compounds wherein $R^1$ and $R^2$ are hydrogen atoms, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring;

compounds wherein $R^1$ is hydrogen atom, hydroxyl group, or amino group, $R^2$ is a halogen atom, and $R^3$ is a group represented by the formula (1-2);

compounds wherein $R^1$ is hydrogen atom, hydroxyl group, or amino group, $R^2$ is a halogen atom, $R^3$ is a group represented by the formula (1-2), and $R^4$ is hydrogen atom;

compounds wherein $R^1$ is hydrogen atom, $R^2$ is a halogen atom, and $R^3$ is a group represented by the formula (1-2);

compounds wherein $R^1$ is hydrogen atom, $R^2$ is a halogen atom, $R^3$ is a group represented by the formula (1-2), and $R^4$ is hydrogen atom;

compounds wherein $R^1$ is hydrogen atom, $R^2$ is fluorine atom, or bromine atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is fluorine atom, or bromine atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is fluorine atom, or bromine atom, $R^4$ is hydrogen atom, and $R^3$ is a group represented by the formula (1-2-1), formula (1-2-2), formula (1-2-3), formula (1-2-4), formula (1-2-5), formula (1-2-6), or formula (1-2-7);

compounds wherein $R^1$ is hydrogen atom, $R^2$ is fluorine atom, or bromine atom, $R^4$ is-hydrogen atom, $R^3$ is a group represented by the formula (1-2-1), formula (1-2-2), formula (1-2-3), formula (1-2-4), formula (1-2-5), formula (1-2-6), or formula (1-2-7), and $A^{31}$ is hydrogen atom;

compounds wherein $R^1$ is hydrogen atom, $R^2$ is fluorine atom, or bromine atom, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $A^{31}$ is a $C_{1-6}$ alkyl group substituted with hydroxyl group;

compounds wherein $R^1$ is hydrogen atom, $R^2$ is fluorine atom, or bromine atom, $R^4$ is hydrogen atom, and $R^3$ is a group represented by the formula (1-2-4), or formula (1-2-7);

compounds wherein $R^1$ is hydrogen atom, $R^2$ is fluorine atom, or bromine atom, $R^4$ is hydrogen atom, $R^3$ is a group represented by the formula (1-2-4), or formula (1-2-7), and $A^{31}$ is hydrogen atom;

compounds wherein $R^1$ is hydrogen atom, $R^2$ is fluorine atom, or bromine atom, $R^4$ is hydrogen atom, $R^3$ is a group represented by the formula (1-2-4), or formula (1-2-7), and $A^{31}$ is a $C_{1-6}$ alkyl group substituted with hydroxyl group;

compounds wherein $R^1$ is hydrogen atom, $R^2$ is a $C_{1-6}$ alkyl group, and $R^3$ is a group represented by the formula (1-2);

compounds wherein $R^1$ is hydrogen atom, $R^2$ is a $C_{1-6}$ alkyl group, $R^3$ is a group represented by the formula (1-2), and $R^4$ is hydrogen atom;

compounds wherein $R^1$ is hydrogen atom, $R^2$ is methyl group, or ethyl group, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, or ethyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$, which may be identical or different, represent hydrogen atom, or a $C_{1-6}$ alkyl group, and $A^1$, $A^2$, $A^3$, and $A^5$, which may be identical or different, represent hydrogen atom, or a $C_{1-6}$ alkyl group, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, or ethyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, or ethyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-2), $R^4$ is hydrogen atom, $R^{31}$ is hydrogen atom, X is —C($A^5$)($A^{51}$)-; or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, and $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-2), $R^4$ is hydrogen atom, $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, and the ring consists of carbon atoms, or when the ring contains a nitrogen atom to which $A^3$ binds, the ring consists of carbon atoms except for the nitrogen atom;

compounds wherein $R^1$ is hydrogen atom, $R^2$ is methyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-2), $R^4$ is hydrogen atom, $R^{31}$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^3$ is a group represented by the formula (1-2), $R^4$ is hydrogen atom, $R^{31}$ is a $C_{1-6}$ alkyl group substituted with hydroxyl group, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methyl group, $R^4$ is hydrogen atom, and $R^3$ is a group represented by the formula (1-2-1), formula (1-2-2), formula (1-2-3), formula (1-2-4), formula (1-2-5), formula (1-2-6), or formula (1-2-7);

compounds wherein $R^1$ is hydrogen atom, $R^2$ is methyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), hydrogen atom;

compounds wherein $R^1$ is hydrogen atom, $R^2$ is methyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), alkyl group substituted with hydroxyl group;

compounds wherein $R^1$ is hydrogen atom, $R^2$ is methyl group, $R^4$ is hydrogen atom, and $R^3$ is a group represented by the formula (1-2-4), or formula (1-2-7);

compounds wherein $R^1$ is hydrogen atom, $R^2$ is methyl group, $R^4$ is hydrogen atom, $R^3$ is a group represented by the formula (1-2-4), or formula (1-2-7), and $R^{31}$ is hydrogen atom;

compounds wherein $R^1$ is hydrogen atom, $R^2$ is methyl group, $R^4$ is hydrogen atom, $R^3$ is a group represented by the formula (1-2-7), and $R^{31}$ is hydrogen atom;

compounds wherein $R^1$ is hydrogen atom, $R^2$ is methyl group, $R^4$ is hydrogen atom, $R^3$ is a group represented by the formula (1-2-4), or formula (1-2-7), and $R^{31}$ is a $C_{1-6}$ alkyl group substituted with hydroxyl group;

compounds wherein $R^1$ is hydrogen atom, $R^2$ is hydroxymethyl group, $R^3$ is a group represented by the formula (1-2), and $R^4$ is hydrogen atom;

compounds wherein $R^1$ is hydrogen atom, $R^2$ is hydroxymethyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is hydroxymethyl group, $R^4$ is hydrogen atom, and $R^3$ is a group represented by the formula (1-2-1), formula (1-2-2), formula (1-2-3), formula (1-2-4), formula (1-2-5), formula (1-2-6), or formula (1-2-7);

compounds wherein $R^1$ is hydrogen atom, $R^2$ is hydroxymethyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is hydrogen atom;

compounds wherein $R^1$ is hydrogen atom, $R^2$ is hydroxymethyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is a $C_{1-6}$ alkyl group substituted with hydroxyl group;

compounds wherein $R^1$ is hydrogen atom, $R^2$ is hydroxymethyl group, $R^4$ is hydrogen atom, and $R^3$ is a group represented by the formula (1-2-4), or formula (1-2-7);

compounds wherein $R^1$ is hydrogen atom, $R^2$ is hydroxymethyl group, $R^4$ is hydrogen atom, $R^3$ is a group represented by the formula (1-2-4), or formula (1-2-7), and $R^{31}$ is hydrogen atom;

compounds wherein $R^1$ is hydrogen atom, $R^2$ is hydroxymethyl group, $R^4$ is hydrogen atom, $R^3$ is a group represented by the formula (1-2-4), or formula (1-2-7), and $R^{31}$ is a $C_{1-6}$ alkyl group substituted with hydroxyl group;

compounds wherein $R^1$ is hydrogen atom, $R^2$ is 2-hydroxyethyl group, 2-methoxyethyl group, 3-hydroxypropyl group, or 3-methoxypropyl group, $R^3$ is a group represented by the formula (1-2), and $R^4$ is hydrogen atom;

compounds wherein $R^1$ is hydrogen atom, $R^2$ is 2-hydroxyethyl group, or 2-methoxyethyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-carboxyethyl group, 2-(methoxycarbonyl)ethyl group, 3-carboxypropyl group, or 3-(methoxycarbonyl)propyl group, $R^3$ is a group represented by the formula (1-2), and $R^4$ is hydrogen atom;

compounds wherein $R^1$ is hydrogen atom, $R^2$ is 2-carboxyethyl group, or 2-(methoxycarbonyl)ethyl group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is amino group, methylamino group, or dimethylamino group, $R^3$ is a group represented by the formula (1-2), and $R^4$ is hydrogen atom;

compounds wherein $R^1$ is hydrogen atom, $R^2$ is amino group, methylamino group, or dimethylamino group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-hydroxyethoxy group, 2-methoxyethoxy group, 3-hydroxypropoxy group, or 3-methoxypropoxy group, $R^3$ is a group represented by the formula (1-2), and $R^4$ is hydrogen atom;

compounds wherein $R^1$ is hydrogen atom, $R^2$ is 2-hydroxyethoxy group, or 2-methoxyethoxy group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-(hydroxyethyl)amino group, 3-(hydroxypropyl)amino group, 2-(methoxyethyl)amino group, or 3-(methoxypropyl)amino group, $R^3$ is a group represented by the formula (1-2), and $R^4$ is hydrogen atom;

compounds wherein $R^1$ is hydrogen atom, $R^2$ is 2-(hydroxyethyl)amino group, or 2-(methoxyethyl)amino group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-aminoethylamino group, 3-aminopropylamino group, 2-(methylamino)ethylamino group, 3-(methylamino)propylamino group, 2-(dimethylamino)ethylamino group, or 3-(dimethylamino)propylamino group, $R^3$ is a group represented by the formula (1-2), and $R^4$ is hydrogen atom;

compounds wherein $R^1$ is hydrogen atom, $R^2$ is 2-aminoethylamino group, 2-(methylamino)ethylamino group, or 2-(dimethylamino)ethylamino group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, or 2-propenyl group, $R^3$ is a group represented by the formula (1-2), and $R^4$ is hydrogen atom;

compounds wherein $R^1$ is hydrogen atom, $R^2$ is ethenyl group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, $R^3$ is a group represented by the formula (1-2), $R^4$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, $R^3$ is a group represented by the formula (1-2), $R^4$ is hydrogen atom, $R^{31}$ is hydrogen atom, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, $R^3$ is a group represented by the formula (1-2), $R^4$ is hydrogen atom, $R^{31}$ is a $C_{1-6}$ alkyl group substituted with hydroxyl group, X is $—C(A^5)(A^{51})-$, or $—C(A^5)(A^{51})-C(A^6)(A^{61})-$, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is ethenyl group, $R^4$ is hydrogen atom, and $R^3$ is a group represented by the formula (1-2-1), formula (1-2-2), formula (1-2-3), formula (1-2-4), formula (1-2-5), formula (1-2-6), or formula (1-2-7);

compounds wherein $R^1$ is hydrogen atom, $R^2$ is ethenyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is hydrogen atom;

compounds wherein $R^1$ is hydrogen atom, $R^2$ is ethenyl group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is a $C_{1-6}$ alkyl group substituted with hydroxyl group;

compounds wherein $R^1$ is hydrogen atom, $R^2$ is ethenyl group, $R^4$ is hydrogen atom, and $R^3$ is a group represented by the formula (1-2-4), or formula (1-2-7);

compounds wherein $R^1$ is hydrogen atom, $R^2$ is ethenyl group, $R^4$ is hydrogen atom, $R^3$ is a group represented by the formula (1-2-4), or formula (1-2-7), and $R^{31}$ is hydrogen atom;

compounds wherein $R^1$ is hydrogen atom, $R^2$ is ethenyl group, $R^4$ is hydrogen atom, $R^3$ is a group represented by the formula (1-2-4), or formula (1-2-7), and $R^{31}$ is a $C_{1-6}$ alkyl group substituted with hydroxyl group;

compounds wherein $R^1$ is hydrogen atom, $R^2$ is ethynyl group, or 2-propynyl group, $R^3$ is a group represented by the formula (1-2), and $R^4$ is hydrogen atom;

compounds wherein $R^1$ is hydrogen atom, $R^2$ is ethynyl group, $R^3$ is a group represented by the formula (1-2), $R^4$ is hydrogen atom, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methoxy group, ethoxy group, propoxy group, or isopropoxy group, $R^3$ is a group represented by the formula (1-2), and $R^4$ is hydrogen atom;

compounds wherein $R^1$ is hydrogen atom, $R^2$ is methoxy group, or ethoxy group, $R^3$ is a group represented by the formula (1-2), $R^4$ is hydrogen atom, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is 2-(methanesulfonyl)ethyl group, 3-(methanesulfonyl)propyl group, 2-(ethanesulfonyl)ethyl group, or 3-(ethanesulfonyl)propyl group, $R^3$ is a group represented by the formula (1-2), and $R^4$ is hydrogen atom;

compounds wherein $R^1$ is hydrogen atom, $R^2$ is 2-(methanesulfonyl)ethyl group, or 2-(ethanesulfonyl)ethyl group, $R^3$ is a group represented by the formula (1-2), $R^4$ is hydrogen atom, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methylthio group, ethylthio group, methylsulfinyl group, ethylsulfinyl group, methanesulfonyl group, or ethanesulfonyl group, $R^3$ is a group represented by the formula (1-2), and $R^4$ is hydrogen atom;

compounds wherein $R^1$ is hydrogen atom, $R^2$ is methylthio group, methylsulfinyl group, or methanesulfonyl group, $R^3$ is a group represented by the formula (1-2), $R^4$ is hydrogen atom, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methylthio group, methylsulfinyl group, or methanesulfonyl group, $R^3$ is a group represented by the formula (1-2), $R^4$ is hydrogen atom, $R^{31}$ is hydrogen atom, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methylthio group, methylsulfinyl group, or methanesulfonyl group, $R^3$ is a group represented by the formula (1-2), $R^4$ is hydrogen atom, $R^{31}$ is a $C_{1-6}$ alkyl group substituted with hydroxyl group, X is —$C(A^5)(A^{51})$-, or —$C(A^5)(A^{51})$-C$(A^6)(A^{61})$-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, $R^2$ is methylthio group, $R^4$ is hydrogen atom, and $R^3$ is a group represented by the formula (1-2-1), formula (1-2-2), formula (1-2-3), formula (1-2-4), formula (1-2-5), formula (1-2-6), or formula (1-2-7);

compounds wherein $R^1$ is hydrogen atom, $R^2$ is methylthio group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is hydrogen atom;

compounds wherein $R^1$ is hydrogen atom, $R^2$ is methylthio group, $R^4$ is hydrogen atom, $R^3$ is a group represented by the formula (1-2-1), formula (1-2-2), formula (1-2-3), formula (1-2-4), formula (1-2-5), formula (1-2-6), or formula (1-2-7), and $R^{31}$ is a $C_{1-6}$ alkyl group substituted with hydroxyl group;

compounds wherein $R^1$ is hydrogen atom, $R^2$ is methylthio group, $R^4$ is hydrogen atom, and $R^3$ is a group represented by the formula (1-2-4), or formula (1-2-7);

compounds wherein $R^1$ is hydrogen atom, $R^2$ is methylthio group, $R^4$ is hydrogen atom, $R^3$ is a group represented by the formula (1-2-4), or formula (1-2-7), and $R^{31}$ is hydrogen atom;

compounds wherein $R^1$ is hydrogen atom, $R^2$ is methylthio group, $R^4$ is hydrogen atom, $R^3$ is a group represented by the formula (1-2-4), or formula (1-2-7), and $R^{31}$ is a $C_{1-6}$ alkyl group substituted with hydroxyl group;

compounds wherein $R^1$ is hydrogen atom, $R^2$ is 2-(methanesulfonyl)ethoxy group, 3-(methanesulfonyl)propoxy group, 2-(ethanesulfonyl)ethoxy group, or 3-(methanesulfonyl)propoxy group, $R^3$ is a group represented by the formula (1-2), and $R^4$ is hydrogen atom;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-2), $R^4$ is hydrogen atom, X is —$C(A^5)(A^{51})$-, or —$C(A^5)(A^{51})$-$C(A^6)(A^{61})$-, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is chlorine atom, and $R^3$ is a group represented by the formula (1-2);

compounds wherein $R^1$ is chlorine atom, $R^2$ is hydrogen atom, and $R^3$ is a group represented by the formula (1-2);

compounds wherein $R^1$ is chlorine atom, $R^2$ is hydrogen atom, $R^3$ is a group represented by the formula (1-2), and $R^4$ is hydrogen atom;

compounds wherein $R^1$ is chlorine atom, $R^2$ is hydrogen atom, $R^3$ is a group represented by the formula (1-2), X is —$C(A^5)(A^{51})$-, —$C(A^5)(A^{51})$-$C(A^6)(A^{61})$-, or a single bond, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is chlorine atom, $R^2$ is hydrogen atom, $R^3$ is a group represented by the formula (1-2), X is —$C(A^5)(A^{51})$-, —$C(A^5)(A^{51})$-$C(A^6)(A^{61})$-, or a single bond, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is chlorine atom, $R^2$ is hydrogen atom, $R^3$ is a group represented by the formula (1-2), $R^4$ is hydrogen atom, X is —$C(A^5)(A^{51})$-, or —$C(A^5)(A^{51})$-$C(A^6)(A^{61})$-, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, and $R^3$ is a group represented by the formula (1-2);

compounds wherein $R^1$ is hydroxyl group, $R^2$ is hydrogen atom, and $R^3$ is a group represented by the formula (1-2);

compounds wherein $R^1$ is hydroxyl group, $R^2$ is hydrogen atom, $R^3$ is a group represented by the formula (1-2), and $R^4$ is hydrogen atom;

compounds wherein $R^1$ is hydroxyl group, $R^2$ is hydrogen atom, $R^3$ is a group represented by the formula (1-2), X is —$C(A^5)(A^{51})$-, —$C(A^5)(A^{51})$-$C(A^6)(A^{61})$-, or a single bond, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-2), X is —$C(A^5)(A^{51})$-, or —$C(A^5)(A^{51})$-$C(A^6)(A^{61})$-, $A^{11}, A^{21} A^{51}, A^6$, and $A^{61}$ are hydrogen atoms, $A^1, A^2, A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-2), X is —$C(A^5)(A^{51})$-, —$C(A^5)(A^{51})$-$C(A^6)(A^{61})$-, or a single bond, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydroxyl group, $R^2$ is hydrogen atom, $R^3$ is a group represented by the formula (1-2), $R^4$ is hydrogen atom, X is —$C(A^5)(A^{51})$-, or —$C(A^5)(A^{51})$-$C(A^6)(A^{61})$-, $A^{11}, A^{21}, A^{51}, A^6$, and $A^{61}$ are hydrogen atoms, $A^1, A^2, A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, and $R^3$ is a group represented by the formula (1-2);

compounds wherein $R^1$ is amino group, $R^2$ is hydrogen atom, and $R^3$ is a group represented by the formula (1-2);

compounds wherein $R^1$ is amino group, $R^2$ is hydrogen atom, $R^3$ is a group represented by the formula (1-2), and $R^4$ is hydrogen atom;

compounds wherein $R^1$ is amino group, $R^2$ is hydrogen atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-2), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is hydrogen atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is a halogen atom, and $R^3$ is a group represented by the formula (1-2);

compounds wherein $R^1$ is amino group, $R^2$ is a halogen atom, $R^3$ is a group represented by the formula (1-2), and $R^4$ is hydrogen atom;

compounds wherein $R^1$ is amino group, $R^2$ is fluorine atom, or bromine atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is fluorine atom, or bromine atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is fluorine atom, or bromine atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is a $C_{1-6}$ alkyl group, and $R^3$ is a group represented by the formula (1-2);

compounds wherein $R^1$ is amino group, $R^2$ is a $C_{1-6}$ alkyl group, $R^3$ is a group represented by the formula (1-2), and $R^4$ is hydrogen atom;

compounds wherein $R^1$ is amino group, $R^2$ is methyl group, or ethyl group, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, or ethyl group, $R^3$ is a group represented by the formula (1-2), X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, $R^3$ is a group represented by the formula (1-2), $R^4$ is hydrogen atom, X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is amino group, $R^2$ is methyl group, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is a $C_{1-6}$ alkoxy group, and $R^3$ is a group represented by the formula (1-2);

compounds wherein $R^1$ is a $C_{1-6}$ alkoxy group, $R^2$ is hydrogen atom, and $R^3$ is a group represented by the formula (1-2);

compounds wherein $R^1$ is a $C_{1-6}$ alkoxy group, $R^2$ is hydrogen atom, $R^3$ is a group represented by the formula (1-2), and $R^4$ is hydrogen atom;

compounds wherein $R^1$ is methoxy group, $R^2$ is hydrogen atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 5- or 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-2), X is —C($A^5$)($A^{51}$)-, —C($A^5$)($A^{51}$)-C($A^6$)($A^{61}$)-, or a single bond, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^1$ and $A^3$, $A^2$ and $A^3$, $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is methoxy group, $R^2$ is hydrogen atom, $R^3$ is a group represented by the formula (1-2), $R^4$ is hydrogen atom, X is —C($A^5$)($A^{51}$)-, or —C($A^5$)($A^{51}$)-C($A^6$)($A^{61}$)-, $A^{11}$, $A^{21}$, $A^{51}$, $A^6$, and $A^{61}$ are hydrogen atoms, $A^1$, $A^2$, $A^3$, and $A^5$ are hydrogen atoms, or groups in each of one or more combinations selected from the group consisting of combinations of $A^2$ and $A^5$, and $A^3$ and $A^5$ bind to each other to form a 6-membered ring, the ring consists of carbon atoms, or when the ring contains a nitrogen atom to which $A^3$ binds, the ring consists of carbon atoms except for the nitrogen atom, and the ring is a saturated ring;

compounds wherein $R^1$ is hydrogen atom, a halogen atom, hydroxyl group, or amino group, and $R^3$ is a group represented by the formula (1-3);

compounds wherein $R^1$ is hydrogen atom, hydroxyl group, or amino group, and $R^3$ is a group represented by the formula (1-3);

compounds wherein $R^1$ is hydrogen atom, or amino group, and $R^3$ is a group represented by the formula (1-3);

compounds wherein $R^1$ is hydrogen atom, or hydroxyl group, and $R^3$ is a group represented by the formula (1-3);

compounds wherein $R^1$ is hydrogen atom, and $R^3$ is a group represented by the formula (1-3);

compounds wherein $R^1$ is hydrogen atom, $R^2$ is hydrogen atom, a halogen atom, or a $C_{1-6}$ alkyl group, and $R^3$ is a group represented by the formula (1-3);

compounds wherein $R^1$ and $R^2$ are hydrogen atoms, and $R^3$ is a group represented by the formula (1-3);

compounds wherein $R^1$ and $R^2$ are hydrogen atoms, $R^3$ is a group represented by the formula (1-3), and Y is a $C_{2-6}$ alkylene group;

compounds wherein $R^1$ and $R^2$ are hydrogen atoms, $R^3$ is a group represented by the formula (1-3), and Y is a $C_{2-4}$ alkylene group;

compounds wherein $R^1$ and $R^2$ are hydrogen atoms, $R^3$ is a group represented by the formula (1-3), and Y is ethylene group, or 1,3-propylene group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(heteroaryl)ethyl group, a (heteroaryl)propyl group, a 2-(arylthio)ethyl group, an (arylthio)propyl group, a 2-(heteroarylthio)ethyl group, a (heteroarylthio)propyl group, a 2-(arylsulfinyl)ethyl group, an (arylsulfinyl)propyl, a 2-(heteroarylsulfinyl)ethyl group, a (heteroarylsulfinyl)propyl group, a 2-(arylsulfonyl)ethyl group, an (arylsulfonyl)propyl group, a 2-(heteroarylsulfonyl)ethyl group, or a (heteroarylsulfonyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(heteroaryl)ethyl group, a (heteroaryl)propyl group, a 2-(arylthio)ethyl group, an (arylthio)propyl group, a 2-(heteroarylthio)ethyl group, a (heteroarylthio)propyl group, a 2-(arylsulfinyl)ethyl group, an (arylsulfinyl)propyl, a 2-(heteroarylsulfinyl)ethyl group, a (heteroarylsulfinyl)propyl group, a 2-(arylsulfonyl)ethyl group, an (arylsulfonyl)propyl group, a 2-(heteroarylsulfonyl)ethyl group, or a (heteroarylsulfonyl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(arylthio)ethyl group, an (arylthio)propyl group, a 2-(arylsulfinyl)ethyl group, an (arylsulfinyl)propyl, a 2-(arylsulfonyl)ethyl group, or an (arylsulfonyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(arylthio)ethyl group, an (arylthio)propyl group, a 2-(arylsulfinyl)ethyl group, an (arylsulfinyl)propyl, a 2-(arylsulfonyl)ethyl group, or an (arylsulfonyl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(arylthio)ethyl group, a 2-(arylsulfinyl)ethyl group, or a 2-(arylsulfonyl)ethyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(aryl)ethyl group, an (aryl)propyl group, a 2-(arylthio)ethyl group, a 2-(arylsulfinyl)ethyl group, or a 2-(arylsulfonyl)ethyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, hydroxyl group, or amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ and $R^2$ are hydrogen atoms, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, hydroxyl group, or amino group, $R^2$ is a $C_{1-6}$ alkyl group, and $R^3$ is a group represented by the formula (1-3);

compounds wherein $R^1$ is hydrogen atom, hydroxyl group, or amino group, $R^2$ is a $C_{1-6}$ alkyl group, $R^3$ is a group represented by the formula (1-3), and Y is a $C_{2-6}$ alkylene group;

compounds wherein $R^1$ is hydrogen atom, hydroxyl group, or amino group, $R^2$ is methyl group, or ethyl group, $R^3$ is a group represented by the formula (1-3), and Y is ethylene group, or 1,3-propylene group;

compounds wherein $R^1$ is hydrogen atom, hydroxyl group, or amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, hydroxyl group, or amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(arylthio)ethyl group, or an (arylthio)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(heteroarylthio)ethyl group, or a (heteroarylthio)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(arylsulfinyl)ethyl group, or an (arylsulfinyl)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(heteroarylsulfinyl)ethyl group, or a (heteroarylsulfinyl)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(arylsulfonyl)ethyl group, or an (arylsulfonyl)propyl group;

compounds wherein R¹ is hydrogen atom, hydroxyl group, or amino group, R² is methyl group, or ethyl group, R³ is a group represented by the formula (1-3), Y is ethylene group, or 1,3-propylene group, A⁴ is hydrogen atom, or methyl group, and R⁵ is a 2-(heteroarylsulfonyl)ethyl group, or a (heteroarylsulfonyl)propyl group;

compounds wherein R¹ is hydrogen atom, hydroxyl group, or amino group, R² is a halogen atom, and R³ is a group represented by the formula (1-3);

compounds wherein R¹ is hydrogen atom, hydroxyl group, or amino group, R² is a halogen atom, R³ is a group represented by the formula (1-3), and Y is a $C_{2-6}$ alkylene group;

compounds wherein R¹ is hydrogen atom, hydroxyl group, or amino group, R² is fluorine atom, or bromine atom, R³ is a group represented by the formula (1-3), and Y is ethylene group, or 1,3-propylene group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(aryl)ethyl group, or an (aryl)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(heteroaryl)ethyl group, or a (heteroaryl)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(arylthio)ethyl group, or an (arylthio)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(heteroarylthio)ethyl group, or a (heteroarylthio)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(arylsulfinyl)ethyl group, or an (arylsulfinyl)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(heteroarylsulfinyl)ethyl group, or a (heteroarylsulfinyl)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(arylsulfonyl)ethyl group, or an (arylsulfonyl)propyl group;

compounds wherein R¹ is hydrogen atom, hydroxyl group, or amino group, R² is fluorine atom, or bromine atom, R³ is a group represented by the formula (1-3), Y is ethylene group, or 1,3-propylene group, A⁴ is hydrogen atom, or methyl group, and R⁵ is a 2-(heteroarylsulfonyl)ethyl group, or a (heteroarylsulfonyl)propyl group;

compounds wherein R¹ is hydrogen atom, R² is 2-hydroxyethyl group, 2-methoxyethyl group, 3-hydroxypropyl group, or 3-methoxypropyl group, and R³ is a group represented by the formula (1-3);

compounds wherein R¹ is hydrogen atom, R² is 2-hydroxyethyl group, 2-methoxyethyl group, 3-hydroxypropyl group, or 3-methoxypropyl group, R³ is a group represented by the formula (1-3), and Y is a $C_{2-6}$ alkylene group;

compounds wherein R¹ is hydrogen atom, R² is 2-hydroxyethyl group, or 2-methoxyethyl group, R³ is a group represented by the formula (1-3), and Y is ethylene group, or 1,3-propylene group;

compounds wherein R¹ is hydrogen atom, R² is 2-hydroxyethyl group, or 2-methoxyethyl group, R³ is a group represented by the formula (1-3), Y is ethylene group, or 1,3-propylene group, A⁴ is hydrogen atom, or methyl group, and R⁵ is a 2-(aryl)ethyl group, or an (aryl)propyl group;

compounds wherein R¹ is hydrogen atom, R² is 2-hydroxyethyl group, or 2-methoxyethyl group, R³ is a group represented by the formula (1-3), Y is ethylene group, or 1,3-propylene group, A⁴ is hydrogen atom, or methyl group, and R⁵ is a 2-(heteroaryl)ethyl group, or a (heteroaryl)propyl group;

compounds wherein R¹ is hydrogen atom, R² is 2-hydroxyethyl group, or 2-methoxyethyl group, R³ is a group represented by the formula (1-3), Y is ethylene group, or 1,3-propylene group, A⁴ is hydrogen atom, or methyl group, and R⁵ is a 2-(arylthio)ethyl group, or an (arylthio)propyl group;

compounds wherein R¹ is hydrogen atom, R² is 2-hydroxyethyl group, or 2-methoxyethyl group, R³ is a group represented by the formula (1-3), Y is ethylene group, or 1,3-propylene group, A⁴ is hydrogen atom, or methyl group, and R⁵ is a 2-(heteroarylthio)ethyl group, or a (heteroarylthio)propyl group;

compounds wherein R¹ is hydrogen atom, R² is 2-hydroxyethyl group, or 2-methoxyethyl group, R³ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-hydroxyethyl group, or 2-methoxyethyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-hydroxyethyl group, or 2-methoxyethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-hydroxyethyl group, or 2-methoxyethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is 2-carboxyethyl group, 2-(methoxycarbonyl)ethyl group, 3-carboxypropyl group, or 3-(methoxycarbonyl)propyl group, $R^3$ is a group represented by the formula (1-3);

compounds wherein $R^1$ is hydrogen atom, $R^2$ is 2-carboxyethyl group, 2-(methoxycarbonyl)ethyl group, 3-carboxypropyl group, or 3-(methoxycarbonyl)propyl group, $R^3$ is a group represented by the formula (1-3), and Y is a $C_{2-6}$ alkylene group;

compounds wherein $R^1$ is hydrogen atom, $R^2$ is 2-carboxyethyl group, or 2-(methoxycarbonyl)ethyl group, $R^3$ is a group represented by the formula (1-3), and Y is ethylene group, or 1,3-propylene group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-carboxyethyl group, or 2-(methoxycarbonyl)ethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is amino group, methylamino group, or dimethylamino group, and $R^3$ is a group represented by the formula (1-3);

compounds wherein $R^1$ is hydrogen atom, $R^2$ is amino group, methylamino group, or dimethylamino group, $R^3$ is a group represented by the formula (1-3), and Y is a $C_{2-6}$ alkylene group;

compounds wherein $R^1$ is hydrogen atom, $R^2$ is amino group, methylamino group, or dimethylamino group, $R^3$ is a group represented by the formula (1-3), and Y is ethylene group, or 1,3-propylene group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is amino group, methylamino group, or dimethylamino group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is 2-hydroxyethoxy group, 2-methoxyethoxy group, 3-hydroxypropoxy group, or 3-methoxypropoxy group, and $R^3$ is a group represented by the formula (1-3);

compounds wherein $R^1$ is hydrogen atom, $R^2$ is 2-hydroxyethoxy group, 2-methoxyethoxy group, 3-hydroxypropoxy group, or 3-methoxypropoxy group, $R^3$ is a group represented by the formula (1-3), and Y is a $C_{2-6}$ alkylene group;

compounds wherein $R^1$ is hydrogen atom, $R^2$ is 2-hydroxyethoxy group, 2-methoxyethoxy group, 3-hydroxypropoxy group, or 3-methoxypropoxy group, $R^3$ is a group represented by the formula (1-3), and Y is ethylene group, or 1,3-propylene group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-hydroxyethoxy group, or 2-methoxyethoxy group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is 2-(hydroxyethyl)amino group, 2-(methoxyethyl)amino group, 3-(hydroxypropyl)amino group, or 3-(methoxypropyl)amino group, and $R^3$ is a group represented by the formula (1-3);

compounds wherein $R^1$ is hydrogen atom, $R^2$ is 2-(hydroxyethyl)amino group, 2-(methoxyethyl)amino group, 3-(hydroxypropyl)amino group, or 3-(methoxypropyl)amino group, $R^3$ is a group represented by the formula (1-3), and Y is a $C_{2-6}$ alkylene group;

compounds wherein $R^1$ is hydrogen atom, $R^2$ is 2-(hydroxyethyl)amino group, 2-(methoxyethyl)amino group, 3-(hydroxypropyl)amino group, or 3-(methoxypropyl)amino group, $R^3$ is a group represented by the formula (1-3), and Y is ethylene group, or 1,3-propylene group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-(hydroxyethyl)amino group, or 2-(methoxyethyl)amino group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein R¹ is hydrogen atom, R² is 2-aminoethylamino group, 3-aminopropylamino group, 2-(methylamino)ethylamino group, 3-(methylamino)propylamino group, 2-(dimethylamino)ethylamino group, or 3-(dimethylamino)propylamino group, and R³ is a group represented by the formula (1-3);

compounds wherein R¹ is hydrogen atom, R² is 2-aminoethylamino group, 3-aminopropylamino group, 2-(methylamino)ethylamino group, 3-(methylamino)propylamino group, 2-(dimethylamino)ethylamino group, or 3-(dimethylamino)propylamino group, R³ is a group represented by the formula (1-3), and Y is a $C_{2-6}$ alkylene group; 3-aminopropylamino group, 2-(methylamino)ethylamino group, 3-(methylamino)propylamino group, 2-(dimethylamino)ethylamino group, or 3-(dimethylamino)propylamino group, R³ is a group represented by the formula (1-3), and Y is ethylene group, or 1,3-propylene group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(aryl)ethyl group, or an (aryl)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(heteroaryl)ethyl group, or a (heteroaryl)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(arylthio)ethyl group, or an (arylthio)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(heteroarylthio)ethyl group, or a (heteroarylthio)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(arylsulfinyl)ethyl group, or an (arylsulfinyl)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(heteroarylsulfinyl)ethyl group, or a (heteroarylsulfinyl)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(arylsulfonyl)ethyl group, or an (arylsulfonyl)propyl group;

compounds wherein R¹ is hydrogen atom, R² is 2-aminoethylamino group, 2-(methylamino)ethylamino group, or 2-(dimethylamino)ethylamino group, R³ is a group represented by the formula (1-3), Y is ethylene group, or 1,3-propylene group, A⁴ is hydrogen atom, or methyl group, and R⁵ is a 2-(heteroarylsulfonyl)ethyl group, or a (heteroarylsulfonyl)propyl group;

compounds wherein R¹ is hydrogen atom, R² is a $C_{2-3}$ alkenyl group, and R³ is a group represented by the formula (1-3);

compounds wherein R¹ is hydrogen atom, R² is a $C_{2-3}$ alkenyl group, R³ is a group represented by the formula (1-3), and Y is a $C_{2-6}$ alkylene group;

compounds wherein R¹ is hydrogen atom, R² is a $C_{2-3}$ alkenyl group, R³ is a group represented by the formula (1-3), and Y is ethylene group, or 1,3-propylene group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(aryl)ethyl group, or an (aryl)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(heteroaryl)ethyl group, or a (heteroaryl)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(arylthio)ethyl group, or an (arylthio)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(heteroarylthio)ethyl group, or a (heteroarylthio)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(arylsulfinyl)ethyl group, or an (arylsulfinyl)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(heteroarylsulfinyl)ethyl group, or a (heteroarylsulfinyl)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(arylsulfonyl)ethyl group, or an (arylsulfonyl)propyl group;

compounds wherein R¹ is hydrogen atom, R² is ethenyl group, or 2-propenyl group, R³ is a group represented by the formula (1-3), Y is ethylene group, or 1,3-propylene group, A⁴ is hydrogen atom, or methyl group, and R⁵ is a 2-(heteroarylsulfonyl)ethyl group, or a (heteroarylsulfonyl)propyl group;

compounds wherein R¹ is hydrogen atom, R² is a $C_{2-3}$ alkynyl group, and R³ is a group represented by the formula (1-3);

compounds wherein R¹ is hydrogen atom, R² is a $C_{2-3}$ alkynyl group, R³ is a group represented by the formula (1-3), and Y is a $C_{2-6}$ alkylene group;

compounds wherein R¹ is hydrogen atom, R² is a $C_{2-3}$ alkynyl group, R³ is a group represented by the formula (1-3), and Y is ethylene group, or 1,3-propylene group;

compounds wherein R¹ is hydrogen atom, R² is ethynyl group, or 2-propynyl group, R³ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is ethynyl group, or 2-propynyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is a $C_{1-6}$ alkoxyl group, and $R^3$ is a group represented by the formula (1-3);

compounds wherein $R^1$ is hydrogen atom, $R^2$ is a $C_{1-6}$ alkoxyl group, $R^3$ is a group represented by the formula (1-3), and Y is a $C_{2-6}$ alkylene group;

compounds wherein $R^1$ is hydrogen atom, $R^2$ is a $C_{1-6}$ alkoxyl group, $R^3$ is a group represented by the formula (1-3), and Y is ethylene group, or 1,3-propylene group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is methoxy group, or ethoxy group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is 2-(methanesulfonyl)ethyl group, 3-(methanesulfonyl)propyl group, 2-(ethanesulfonyl)ethyl group, or 3-(ethanesulfonyl)propyl group, and $R^3$ is a group represented by the formula (1-3);

compounds wherein $R^1$ is hydrogen atom, $R^2$ is 2-(methanesulfonyl)ethyl group, 3-(methanesulfonyl)propyl group, 2-(ethanesulfonyl)ethyl group, or 3-(ethanesulfonyl)propyl group, $R^3$ is a group represented by the formula (1-3), and Y is a $C_{2-6}$ alkylene group;

compounds wherein $R^1$ is hydrogen atom, $R^2$ is 2-(methanesulfonyl)ethyl group, 3-(methanesulfonyl)propyl group, 2-(ethanesulfonyl)ethyl group, or 3-(ethanesulfonyl)propyl group, $R^3$ is a group represented by the formula (1-3), and Y is ethylene group, or 1,3-propylene group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-(methanesulfonyl)ethyl group, or 2-(ethanesulfonyl)ethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is methylthio group, ethylthio group, methylsulfinyl group, ethylsulfinyl group, methanesulfonyl group, or ethanesulfonyl group, and $R^3$ is a group represented by the formula (1-3);

compounds wherein $R^1$ is hydrogen atom, $R^2$ is methylthio group, ethylthio group, methylsulfinyl group, ethylsulfinyl group, methanesulfonyl group, or ethanesulfonyl group, $R^3$ is a group represented by the formula (1-3), and Y is a $C_{2-6}$ alkylene group;

compounds wherein $R^1$ is hydrogen atom, $R^2$ is methylthio group, ethylthio group, methylsulfinyl group, ethylsulfinyl group, methanesulfonyl group, or ethanesulfonyl group, $R^3$ is a group represented by the formula (1-3), and Y is ethylene group, or 1,3-propylene group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is methylthio group, methylsulfinyl group, or methanesulfonyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydrogen atom, $R^2$ is 2-(methanesulfonyl)ethoxy group, 3-(methanesulfonyl)propoxy group, 2-(ethanesulfonyl)ethoxy group, or 3-(methanesulfonyl)propoxy group, and $R^3$ is a group represented by the formula (1-3);

compounds wherein $R^1$ is hydrogen atom, $R^2$ is 2-(methanesulfonyl)ethoxy group, 3-(methanesulfonyl)propoxy group, 2-(ethanesulfonyl)ethoxy group, or 3-(methanesulfonyl)propoxy group, $R^3$ is a group represented by the formula (1-3), and Y is a $C_{2-6}$ alkylene group;

compounds wherein $R^1$ is hydrogen atom, $R^2$ is 2-(methanesulfonyl)ethoxy group, 3-(methanesulfonyl)propoxy group, 2-(ethanesulfonyl)ethoxy group, or 3-(methanesulfonyl)propoxy group, $R^3$ is a group represented by the formula (1-3), and Y is ethylene group, or 1,3-propylene group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydrogen atom, $R^2$ is 2-(methanesulfonyl)ethoxy group, or 2-(ethanesulfonyl)ethoxy group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is chlorine atom, and $R^3$ is a group represented by the formula (1-3);

compounds wherein $R^1$ is chlorine atom, $R^2$ is hydrogen atom, and $R^3$ is a group represented by the formula (1-3);

compounds wherein $R^1$ is chlorine atom, $R^2$ is hydrogen atom, $R^3$ is a group represented by the formula (1-3), and Y is a $C_{2-6}$ alkylene group;

compounds wherein $R^1$ is chlorine atom, $R^2$ is hydrogen atom, $R^3$ is a group represented by the formula (1-3), and Y is ethylene group, or 1,3-propylene group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is chlorine atom, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is chlorine atom, $R^2$ is a $C_{1-6}$ alkyl group, and $R^3$ is a group represented by the formula (1-3);

compounds wherein $R^1$ is chlorine atom, $R^2$ is a $C_{1-6}$ alkyl group, $R^3$ is a group represented by the formula (1-3), and Y is a $C_{2-6}$ alkylene group;

compounds wherein $R^1$ is chlorine atom, $R^2$ is methyl group, or ethyl group, $R^3$ is a group represented by the formula (1-3), and Y is ethylene group, or 1,3-propylene group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is chlorine atom, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is chlorine atom, $R^2$ is a halogen atom, and $R^3$ is a group represented by the formula (1-3);

compounds wherein $R^1$ is chlorine atom, $R^2$ is a halogen atom, $R^3$ is a group represented by the formula (1-3), and Y is a $C_{2-6}$ alkylene group;

compounds wherein $R^1$ is chlorine atom, $R^2$ is fluorine atom, or bromine atom, $R^3$ is a group represented by the formula (1-3), and Y is ethylene group, or 1,3-propylene group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is chlorine atom, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydroxyl group, and $R^3$ is a group represented by the formula (1-3);

compounds wherein $R^1$ is hydroxyl group, $R^2$ is hydrogen atom, and $R^3$ is a group represented by the formula (1-3);

compounds wherein $R^1$ is hydroxyl group, $R^2$ is hydrogen atom, $R^3$ is a group represented by the formula (1-3), and Y is a $C_{2-6}$ alkylene group;

compounds wherein $R^1$ is hydroxyl group, $R^2$ is hydrogen atom, $R^3$ is a group represented by the formula (1-3), and Y is ethylene group, or 1,3-propylene group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydroxyl group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydroxyl group, $R^2$ is a $C_{1-6}$ alkyl group, and $R^3$ is a group represented by the formula (1-3);

compounds wherein $R^1$ is hydroxyl group, $R^2$ is a $C_{1-6}$ alkyl group, $R^3$ is a group represented by the formula (1-3), and Y is a $C_{2-6}$ alkylene group;

compounds wherein $R^1$ is hydroxyl group, $R^2$ is methyl group, or ethyl group, $R^3$ is a group represented by the formula (1-3), and Y is ethylene group, or 1,3-propylene group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydroxyl group, $R^2$ is methyl group, or ethyl group, $R^3$ is a group represented by the formula (1-3), Y is ethylene group, or 1;3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydroxyl group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is hydroxyl group, $R^2$ is a halogen atom, and $R^3$ is a group represented by the formula (1-3);

compounds wherein $R^1$ is hydroxyl group, $R^2$ is a halogen atom, $R^3$ is a group represented by the formula (1-3), and Y is a $C_{2-6}$ alkylene group;

compounds wherein $R^1$ is hydroxyl group, $R^2$ is fluorine atom, or bromine atom, $R^3$ is a group represented by the formula (1-3), and Y is ethylene group, or 1,3-propylene group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is hydroxyl group, $R^2$ is fluorine atom, or bromine atom, $R^3$ is a group represented by the formula (1-3), Y is ethylene group, or 1,3-propylene. group, $A^4$ is hydrogen atom, or methyl group, and $R^5$ is a 2-(heteroaryl)ethyl group, or a (heteroaryl)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is hydroxyl group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is amino group, and $R^3$ is a group represented by the formula (1-3);

compounds wherein $R^1$ is amino group, $R^2$ is hydrogen atom, and $R^3$ is a group represented by the formula (1-3);

compounds wherein $R^1$ is amino group, $R^2$ is hydrogen atom, $R^3$ is a group represented by the formula (1-3), and Y is a $C_{2-6}$ alkylene group;

compounds wherein $R^1$ is amino group, $R^2$ is hydrogen atom, $R^3$ is a group represented by the formula (1-3), and Y is ethylene group, or 1,3-propylene group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is amino group, $R^2$ is hydrogen atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is amino group, $R^2$ is a $C_{1-6}$ alkyl group, and $R^3$ is a group represented by the formula (1-3);

compounds wherein $R^1$ is amino group, $R^2$ is a $C_{1-6}$ alkyl group, $R^3$ is a group represented by the formula (1-3), and Y is a $C_{2-6}$ alkylene group;

compounds wherein $R^1$ is amino group, $R^2$ is methyl group, or ethyl group, $R^3$ is a group represented by the formula (1-3), and Y is ethylene group, or 1,3-propylene group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group;

compounds wherein $R^1$ is amino group, $R^2$ is methyl group, or ethyl group, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group;

compounds wherein $R^1$ is amino group, $R^2$ is a halogen atom, and $R^3$ is a group represented by the formula (1-3);

compounds wherein $R^1$ is amino group, $R^2$ is a halogen atom, $R^3$ is a group represented by the formula (1-3), and Y is a $C_{2-6}$ alkylene group;

compounds wherein $R^1$ is amino group, $R^2$ is fluorine atom, or bromine atom, $R^3$ is a group represented by the formula (1-3), and Y is ethylene group, or 1,3-propylene group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(aryl)ethyl group, or an (aryl)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroaryl)ethyl group, or a (heteroaryl)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylthio)ethyl group, or an (arylthio)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylthio)ethyl group, or a (heteroarylthio)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfinyl)ethyl group, or an (arylsulfinyl)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfinyl)ethyl group, or a (heteroarylsulfinyl)propyl group;

compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(arylsulfonyl)ethyl group, or an (arylsulfonyl)propyl group; and compounds wherein $R^1$ is amino group, $R^2$ is fluorine atom, or bromine atom, $R^3$ is a group represented by the formula (1-3), Y is ethylene group, or 1,3-propylene group, $A^4$ is hydrogen atom, or methyl group, and $R^5$ is a 2-(heteroarylsulfonyl)ethyl group, or a (heteroarylsulfonyl)propyl group.

Further, specific examples of the compounds of the present invention represented by the formula (1) include, for example, the compounds listed in Tables 1 to 3 mentioned below. The compounds listed in Table 1 are compounds having a structure of the formula (1-11), the compounds listed in Table 2 are compounds having the structure of the formula (1-21), and the compounds listed in Table 3 are compounds having the structure of the formula (1-31). However, the scope of the present invention is not limited to these compounds.

TABLE 1

(1-11)

$$\begin{array}{c} Q^1 \\ | \\ O\!-\!Q^2 \end{array}$$

| Compound No. | Q1 Substituent No. | Q2 Substituent No. |
|---|---|---|
| 1-1 | a-1 | b-3 |
| 1-2 | a-1 | b-4 |
| 1-3 | a-1 | b-5 |
| 1-4 | a-1 | b-6 |
| 1-5 | a-1 | b-7 |
| 1-6 | a-1 | b-8 |
| 1-7 | a-1 | b-9 |
| 1-8 | a-1 | b-10 |
| 1-9 | a-3 | b-1 |
| 1-10 | a-3 | b-2 |
| 1-11 | a-3 | b-3 |
| 1-12 | a-3 | b-4 |
| 1-13 | a-3 | b-5 |
| 1-14 | a-3 | b-6 |
| 1-15 | a-3 | b-10 |
| 1-16 | a-4 | b-1 |
| 1-17 | a-4 | b-2 |
| 1-18 | a-4 | b-3 |
| 1-19 | a-4 | b-4 |
| 1-20 | a-4 | b-5 |
| 1-21 | a-4 | b-6 |
| 1-22 | a-4 | b-10 |
| 1-23 | a-5 | b-1 |
| 1-24 | a-5 | b-2 |
| 1-25 | a-5 | b-3 |
| 1-26 | a-5 | b-4 |
| 1-27 | a-5 | b-5 |
| 1-28 | a-5 | b-6 |
| 1-29 | a-5 | b-10 |

TABLE 1-continued (1-11)

Q¹
|
O—Q²

| Compound No. | Q1 Substituent No. | Q2 Substituent No. |
|---|---|---|
| 1-30 | a-6 | b-1 |
| 1-31 | a-6 | b-2 |
| 1-32 | a-6 | b-3 |
| 1-33 | a-6 | b-4 |
| 1-34 | a-6 | b-5 |
| 1-35 | a-6 | b-6 |
| 1-36 | a-6 | b-10 |
| 1-37 | a-7 | b-1 |
| 1-38 | a-7 | b-2 |
| 1-39 | a-7 | b-3 |
| 1-40 | a-7 | b-4 |
| 1-41 | a-7 | b-5 |
| 1-42 | a-7 | b-6 |
| 1-43 | a-8 | b-1 |
| 1-44 | a-8 | b-2 |
| 1-45 | a-8 | b-3 |
| 1-46 | a-8 | b-4 |
| 1-47 | a-8 | b-5 |
| 1-48 | a-8 | b-6 |
| 1-49 | a-9 | b-1 |
| 1-50 | a-9 | b-2 |
| 1-51 | a-9 | b-3 |
| 1-52 | a-9 | b-4 |
| 1-53 | a-9 | b-5 |
| 1-54 | a-9 | b-6 |
| 1-55 | a-3 | b-7 |
| 1-56 | a-3 | b-8 |
| 1-57 | a-3 | b-9 |
| 1-58 | a-10 | b-1 |
| 1-59 | a-10 | b-2 |
| 1-60 | a-10 | b-3 |
| 1-61 | a-10 | b-4 |
| 1-62 | a-10 | b-5 |
| 1-63 | a-10 | b-6 |
| 1-64 | a-10 | b-7 |
| 1-65 | a-10 | b-8 |
| 1-66 | a-10 | b-9 |
| 1-67 | a-10 | b-10 |
| 1-68 | a-10 | b-11 |

Among the compounds listed in Table 1, preferred are the compounds of the exemplary compound numbers of 1-1, 1-2, 1-3, 1-4, 1-8, 1-9, 1-10, 1-11, 1-12, 1-13, 1-14, 1-15, 1-16, 1-17, 1-18, 1-19, 1-20, 1-21, 1-22, 1-55, 1-56, 1-57, 1-58, 1-59, 1-60, 1-61, 1-62, 1-63, 1-64, 1-65, 1-66, 1-67, and 1-68.

More preferred compounds are the compounds of the exemplary compound numbers of 1-2, i.e., 4-[(5-isoquinolyl)oxy]piperidine; 1-9, i.e., 3-[(1-amino-5-isoquinolyl)oxy]propylamine; and 1-11, i.e., 3-[(1-amino-5-isoquinolyl)oxy]methylpiperidine.

Still more preferred compounds are the compounds of the exemplary compound numbers of 1-21, i.e., trans-4-[(4-methyl-5-isoquinolyl)oxy]cyclohexylamine; and 1-63, i.e., trans-4-[(4-bromo-5-isoquinolyl)oxy]cyclohexylamine.

Further, preferred compounds also include trans-4-[(4-cyano-5-isoquinolyl)oxy]cyclohexylamine, 4-[(4-cyano-5-isoquinolyl)oxy]piperidine, trans-1-[(4-cyano-5-isoquinolyl)oxy]-4-[(2-hydroxyethyl)amino]cyclohexane, 1-(2-hydroxyethyl)-4-[(4-cyano-5-isoquinolyl)oxy]piperidine, and 1-(3-hydroxypropyl)-4-[(4-cyano-5-isoquinolyl)oxy]piperidine.

TABLE 2

(1-21)

Q¹
|
N—Q²
/
Q³

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 2-1 | a-1 | b-1 | c-1 | 2-56 | a-2 | b-1 | c-1 |
| 2-2 | a-1 | b-2 | c-1 | 2-57 | a-2 | b-2 | c-1 |
| 2-3 | a-1 | b-3 | c-1 | 2-58 | a-2 | b-3 | c-1 |
| 2-4 | a-1 | b-4 | c-1 | 2-59 | a-2 | b-4 | c-1 |
| 2-5 | a-1 | b-5 | c-1 | 2-60 | a-2 | b-5 | c-1 |
| 2-6 | a-1 | b-6 | c-1 | 2-61 | a-2 | b-6 | c-1 |
| 2-7 | a-1 | b-7 | c-1 | 2-62 | a-2 | b-7 | c-1 |
| 2-8 | a-1 | b-8 | c-1 | 2-63 | a-2 | b-8 | c-1 |
| 2-9 | a-1 | b-9 | c-1 | 2-64 | a-2 | b-9 | c-1 |
| 2-10 | a-1 | b-10 | c-1 | 2-65 | a-2 | b-10 | c-1 |
| 2-11 | a-1 | b-11 | c-1 | 2-66 | a-2 | b-11 | c-1 |
| 2-12 | a-3 | b-1 | c-1 | 2-67 | a-4 | b-1 | c-1 |
| 2-13 | a-3 | b-2 | c-1 | 2-68 | a-4 | b-2 | c-1 |
| 2-14 | a-3 | b-3 | c-1 | 2-69 | a-4 | b-3 | c-1 |
| 2-15 | a-3 | b-4 | c-1 | 2-70 | a-4 | b-4 | c-1 |
| 2-16 | a-3 | b-5 | c-1 | 2-71 | a-4 | b-5 | c-1 |
| 2-17 | a-3 | b-6 | c-1 | 2-72 | a-4 | b-6 | c-1 |
| 2-18 | a-3 | b-7 | c-1 | 2-73 | a-4 | b-7 | c-1 |

TABLE 2-continued (1-21)

$$Q^1\!-\!\underset{\underset{Q^3}{|}}{N}\!-\!Q^2$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 2-19 | a-3 | b-8 | c-1 | 2-74 | a-4 | b-8 | c-1 |
| 2-20 | a-3 | b-9 | c-1 | 2-75 | a-4 | b-9 | c-1 |
| 2-21 | a-3 | b-10 | c-1 | 2-76 | a-4 | b-10 | c-1 |
| 2-22 | a-3 | b-11 | c-1 | 2-77 | a-4 | b-11 | c-1 |
| 2-23 | a-5 | b-1 | c-1 | 2-78 | a-6 | b-1 | c-1 |
| 2-24 | a-5 | b-2 | c-1 | 2-79 | a-6 | b-2 | c-1 |
| 2-25 | a-5 | b-3 | c-1 | 2-80 | a-6 | b-3 | c-1 |
| 2-26 | a-5 | b-4 | c-1 | 2-81 | a-6 | b-4 | c-1 |
| 2-27 | a-5 | b-5 | c-1 | 2-82 | a-6 | b-5 | c-1 |
| 2-28 | a-5 | b-6 | c-1 | 2-83 | a-6 | b-6 | c-1 |
| 2-29 | a-5 | b-7 | c-1 | 2-84 | a-6 | b-7 | c-1 |
| 2-30 | a-5 | b-8 | c-1 | 2-85 | a-6 | b-8 | c-1 |
| 2-31 | a-5 | b-9 | c-1 | 2-86 | a-6 | b-9 | c-1 |
| 2-32 | a-5 | b-10 | c-1 | 2-87 | a-6 | b-10 | c-1 |
| 2-33 | a-5 | b-11 | c-1 | 2-88 | a-6 | b-11 | c-1 |
| 2-34 | a-7 | b-1 | c-1 | 2-89 | a-8 | b-1 | c-1 |
| 2-35 | a-7 | b-2 | c-1 | 2-90 | a-8 | b-2 | c-1 |
| 2-36 | a-7 | b-3 | c-1 | 2-91 | a-8 | b-3 | c-1 |
| 2-37 | a-7 | b-4 | c-1 | 2-92 | a-8 | b-4 | c-1 |
| 2-38 | a-7 | b-5 | c-1 | 2-93 | a-8 | b-5 | c-1 |
| 2-39 | a-7 | b-6 | c-1 | 2-94 | a-8 | b-6 | c-1 |
| 2-40 | a-7 | b-7 | c-1 | 2-95 | a-8 | b-7 | c-1 |
| 2-41 | a-7 | b-8 | c-1 | 2-96 | a-8 | b-8 | c-1 |
| 2-42 | a-7 | b-9 | c-1 | 2-97 | a-8 | b-9 | c-1 |
| 2-43 | a-7 | b-10 | c-1 | 2-98 | a-8 | b-10 | c-1 |
| 2-44 | a-7 | b-11 | c-1 | 2-99 | a-8 | b-11 | c-1 |
| 2-45 | a-9 | b-1 | c-1 | 2-100 | a-10 | b-1 | c-1 |
| 2-46 | a-9 | b-2 | c-1 | 2-101 | a-10 | b-2 | c-1 |
| 2-47 | a-9 | b-3 | c-1 | 2-102 | a-10 | b-3 | c-1 |
| 2-48 | a-9 | b-4 | c-1 | 2-103 | a-10 | b-4 | c-1 |
| 2-49 | a-9 | b-5 | c-1 | 2-104 | a-10 | b-5 | c-1 |
| 2-50 | a-9 | b-6 | c-1 | 2-105 | a-10 | b-6 | c-1 |
| 2-51 | a-9 | b-7 | c-1 | 2-106 | a-10 | b-7 | c-1 |
| 2-52 | a-9 | b-8 | c-1 | 2-107 | a-10 | b-8 | c-1 |
| 2-53 | a-9 | b-9 | c-1 | 2-108 | a-10 | b-9 | c-1 |
| 2-54 | a-9 | b-10 | c-1 | 2-109 | a-10 | b-10 | c-1 |
| 2-55 | a-9 | b-11 | c-1 | 2-110 | a-10 | b-11 | c-1 |
| 2-111 | a-1 | b-1 | c-2 | 2-144 | a-2 | b-1 | c-2 |
| 2-112 | a-1 | b-2 | c-2 | 2-145 | a-2 | b-2 | c-2 |
| 2-113 | a-1 | b-3 | c-2 | 2-146 | a-2 | b-3 | c-2 |
| 2-114 | a-1 | b-4 | c-2 | 2-147 | a-2 | b-4 | c-2 |
| 2-115 | a-1 | b-5 | c-2 | 2-148 | a-2 | b-5 | c-2 |
| 2-116 | a-1 | b-6 | c-2 | 2-149 | a-2 | b-6 | c-2 |
| 2-117 | a-1 | b-7 | c-2 | 2-150 | a-2 | b-7 | c-2 |
| 2-118 | a-1 | b-8 | c-2 | 2-151 | a-2 | b-8 | c-2 |
| 2-119 | a-1 | b-9 | c-2 | 2-152 | a-2 | b-9 | c-2 |
| 2-120 | a-1 | b-10 | c-2 | 2-153 | a-2 | b-10 | c-2 |
| 2-121 | a-1 | b-11 | c-2 | 2-154 | a-2 | b-11 | c-2 |
| 2-122 | a-3 | b-1 | c-2 | 2-155 | a-4 | b-1 | c-2 |
| 2-123 | a-3 | b-2 | c-2 | 2-156 | a-4 | b-2 | c-2 |
| 2-124 | a-3 | b-3 | c-2 | 2-157 | a-4 | b-3 | c-2 |
| 2-125 | a-3 | b-4 | c-2 | 2-158 | a-4 | b-4 | c-2 |
| 2-126 | a-3 | b-5 | c-2 | 2-159 | a-4 | b-5 | c-2 |
| 2-127 | a-3 | b-6 | c-2 | 2-160 | a-4 | b-6 | c-2 |
| 2-128 | a-3 | b-7 | c-2 | 2-161 | a-4 | b-7 | c-2 |
| 2-129 | a-3 | b-8 | c-2 | 2-162 | a-4 | b-8 | c-2 |
| 2-130 | a-3 | b-9 | c-2 | 2-163 | a-4 | b-9 | c-2 |
| 2-131 | a-3 | b-10 | c-2 | 2-164 | a-4 | b-10 | c-2 |
| 2-132 | a-3 | b-11 | c-2 | 2-165 | a-4 | b-11 | c-2 |
| 2-133 | a-5 | b-1 | c-2 | 2-166 | a-1 | b-4 | c-3 |
| 2-134 | a-5 | b-2 | c-2 | 2-167 | a-1 | b-5 | c-3 |
| 2-135 | a-5 | b-3 | c-2 | 2-168 | a-1 | b-6 | c-3 |
| 2-136 | a-5 | b-4 | c-2 | 2-169 | a-1 | b-10 | c-3 |
| 2-137 | a-5 | b-5 | c-2 | 2-170 | a-2 | b-4 | c-3 |
| 2-138 | a-5 | b-6 | c-2 | 2-171 | a-2 | b-5 | c-3 |
| 2-139 | a-5 | b-7 | c-2 | 2-172 | a-2 | b-6 | c-3 |
| 2-140 | a-5 | b-8 | c-2 | 2-173 | a-2 | b-10 | c-3 |

TABLE 2-continued (1-21)

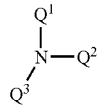

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 2-141 | a-5 | b-9 | c-2 | 2-174 | a-3 | b-4 | c-3 |
| 2-142 | a-5 | b-10 | c-2 | 2-175 | a-3 | b-5 | c-3 |
| 2-143 | a-5 | b-11 | c-2 | 2-176 | a-3 | b-6 | c-3 |
| 2-178 | a-11 | b-1 | c-1 | 2-177 | a-3 | b-10 | c-3 |
| 2-179 | a-11 | b-2 | c-1 | 2-189 | a-12 | b-1 | c-1 |
| 2-180 | a-11 | b-3 | c-1 | 2-190 | a-12 | b-2 | c-1 |
| 2-181 | a-11 | b-4 | c-1 | 2-191 | a-12 | b-3 | c-1 |
| 2-182 | a-11 | b-5 | c-1 | 2-192 | a-12 | b-4 | c-1 |
| 2-183 | a-11 | b-6 | c-1 | 2-193 | a-12 | b-5 | c-1 |
| 2-184 | a-11 | b-7 | c-1 | 2-194 | a-12 | b-6 | c-1 |
| 2-185 | a-11 | b-8 | c-1 | 2-195 | a-12 | b-7 | c-1 |
| 2-186 | a-11 | b-9 | c-1 | 2-196 | a-12 | b-8 | c-1 |
| 2-187 | a-11 | b-10 | c-1 | 2-197 | a-12 | b-9 | c-1 |
| 2-188 | a-11 | b-11 | c-1 | 2-198 | a-12 | b-10 | c-1 |
| 2-200 | a-13 | b-1 | c-1 | 2-199 | a-12 | b-11 | c-1 |
| 2-201 | a-13 | b-2 | c-1 | 2-206 | a-13 | b-7 | c-1 |
| 2-202 | a-13 | b-3 | c-1 | 2-207 | a-13 | b-8 | c-1 |
| 2-203 | a-13 | b-4 | c-1 | 2-208 | a-13 | b-9 | c-1 |
| 2-204 | a-13 | b-5 | c-1 | 2-209 | a-13 | b-10 | c-1 |
| 2-205 | a-13 | b-6 | c-1 | 2-210 | a-13 | b-11 | c-1 |

Among the compounds listed in Tables 2 and 3, preferred are compounds of the exemplary compound numbers of 2-2 to 2-22, 2-24 to 2-30, 2-32, 2-33, 2-35 to 2-41, 2-43 to 2-47, 2-57 to 2-77, 2-79 to 2-85, 2-87 to 2-91, 2-99, 2-101 to 2-110, 2-114, 2-181 to 2-183, 2-189 to 2-199 and 2-203 to 2-205.

More preferred compounds are the compounds of the exemplary compound numbers of 2-4, i.e., 4-(5-isoquinolyl)aminopiperidine; 2-6, i.e., trans-N-(5-isoquinolyl)-1,4-cyclohexanediamine; 2-70, i.e., 4-(4-methyl-5-isoquinolyl)aminopiperidine; 2-72, i.e., trans-N-(4-methyl-5-isoquinolyl)-1,4-cyclohexanediamine; 2-103, i.e., 4-(4-fluoro-5-isoquinolyl)aminopiperidine; 2-104, i.e., cis-N-(4-fluoro-5-isoquinolyl)-1,4-cyclohexanediamine; 2-105, i.e., trans-N-(4-fluoro-5-isoquinolyl)-1,4-cyclohexanediamine; 2-181, i.e., 4-(4-bromo-5-isoquinolyl)aminopiperidine; 2-182, i.e., cis-N-(4-bromo-5-isoquinolyl)-1,4-cyclohexanediamine; 2-183, i.e., trans-N-(4-bromo-5-isoquinolyl)-1,4-cyclohexanediamine; 2-192, i.e., 4-(4-ethyl-5-isoquinolyl)aminopiperidine; 2-193, i.e., cis-N-(4-ethyl-5-isoquinolyl)-1,4-cyclohexanediamine; and 2-194, i.e., trans-N-(4-ethyl-5-isoquinolyl)-1,4-cyclohexanediamine.

Further, trans-N-(1-hydroxy-4-methyl-5-isoquinolyl)-1,4-cyclohexanediamine is also a preferred compound.

TABLE 3

(1-31)

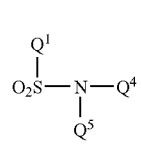

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-1 | a-1 | d-1 | e-1 | 3-35 | a-1 | d-2 | e-1 |
| 3-2 | a-1 | d-1 | e-2 | 3-36 | a-1 | d-2 | e-2 |
| 3-3 | a-1 | d-1 | e-3 | 3-37 | a-1 | d-2 | e-3 |
| 3-4 | a-1 | d-1 | e-4 | 3-38 | a-1 | d-2 | e-4 |
| 3-5 | a-1 | d-1 | e-5 | 3-39 | a-1 | d-2 | e-5 |
| 3-6 | a-1 | d-1 | e-6 | 3-40 | a-1 | d-2 | e-6 |
| 3-7 | a-1 | d-1 | e-7 | 3-41 | a-1 | d-2 | e-7 |
| 3-8 | a-1 | d-1 | e-8 | 3-42 | a-1 | d-2 | e-8 |
| 3-9 | a-1 | d-1 | e-9 | 3-43 | a-1 | d-2 | e-9 |
| 3-10 | a-1 | d-1 | e-10 | 3-44 | a-1 | d-2 | e-10 |
| 3-11 | a-1 | d-1 | e-11 | 3-45 | a-1 | d-2 | e-11 |
| 3-12 | a-1 | d-1 | e-12 | 3-46 | a-1 | d-2 | e-12 |
| 3-13 | a-1 | d-1 | e-13 | 3-47 | a-1 | d-2 | e-13 |
| 3-14 | a-1 | d-1 | e-14 | 3-48 | a-1 | d-2 | e-14 |

TABLE 3-continued (1-31)

$$O_2S\underset{\underset{Q^5}{|}}{\overset{\overset{Q^1}{|}}{-}}N-Q^4$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-15 | a-1 | d-1 | e-15 | 3-49 | a-1 | d-2 | e-15 |
| 3-16 | a-1 | d-1 | e-16 | 3-50 | a-1 | d-2 | e-16 |
| 3-17 | a-1 | d-1 | e-17 | 3-51 | a-1 | d-Z | e-17 |
| 3-18 | a-1 | d-1 | e-18 | 3-52 | a-1 | d-2 | e-18 |
| 3-19 | a-1 | d-1 | e-19 | 3-53 | a-1 | d-2 | e-19 |
| 3-20 | a-1 | d-1 | e-20 | 3-54 | a-1 | d-2 | e-20 |
| 3-21 | a-1 | d-1 | e-21 | 3-55 | a-1 | d-2 | e-21 |
| 3-22 | a-1 | d-1 | e-22 | 3-56 | a-1 | d-2 | e-22 |
| 3-23 | a-1 | d-1 | e-23 | 3-57 | a-1 | d-2 | e-23 |
| 3-24 | a-1 | d-1 | e-24 | 3-58 | a-1 | d-2 | e-24 |
| 3-25 | a-1 | d-1 | e-25 | 3-59 | a-1 | d-2 | e-25 |
| 3-26 | a-1 | d-1 | e-26 | 3-60 | a-1 | d-2 | e-26 |
| 3-27 | a-1 | d-1 | e-27 | 3-61 | a-1 | d-2 | e-27 |
| 3-28 | a-1 | d-1 | e-28 | 3-62 | a-1 | d-2 | e-28 |
| 3-29 | a-1 | d-1 | e-29 | 3-63 | a-1 | d-2 | e-29 |
| 3-30 | a-1 | d-1 | e-30 | 3-64 | a-1 | d-2 | e-30 |
| 3-31 | a-1 | d-1 | e-31 | 3-65 | a-1 | d-2 | e-31 |
| 3-32 | a-1 | d-1 | e-32 | 3-66 | a-1 | d-2 | e-32 |
| 3-33 | a-1 | d-1 | e-33 | 3-67 | a-1 | d-2 | e-33 |
| 3-34 | a-1 | d-1 | e-34 | 3-68 | a-1 | d-2 | e-34 |
| 3-69 | a-1 | d-3 | e-1 | 3-103 | a-1 | d-4 | e-1 |
| 3-70 | a-1 | d-3 | e-2 | 3-104 | a-1 | d-4 | e-2 |
| 3-71 | a-1 | d-3 | e-3 | 3-105 | a-1 | d-4 | e-3 |
| 3-72 | a-1 | d-3 | e-4 | 3-106 | a-1 | d-4 | e-4 |
| 3-73 | a-1 | d-3 | e-5 | 3-107 | a-1 | d-4 | e-5 |
| 3-74 | a-1 | d-3 | e-6 | 3-108 | a-1 | d-4 | e-6 |
| 3-75 | a-1 | d-3 | e-7 | 3-109 | a-1 | d-4 | e-7 |
| 3-76 | a-1 | d-3 | e-8 | 3-110 | a-1 | d-4 | e-8 |
| 3-77 | a-1 | d-3 | e-9 | 3-111 | a-1 | d-4 | e-9 |
| 3-78 | a-1 | d-3 | e-10 | 3-112 | a-1 | d-4 | e-10 |
| 3-79 | a-1 | d-3 | e-11 | 3-113 | a-1 | d-4 | e-11 |
| 3-80 | a-1 | d-3 | e-12 | 3-114 | a-1 | d-4 | e-12 |
| 3-81 | a-1 | d-3 | e-13 | 3-115 | a-1 | d-4 | e-13 |
| 3-82 | a-1 | d-3 | e-14 | 3-116 | a-1 | d-4 | e-14 |
| 3-83 | a-1 | d-3 | e-15 | 3-117 | a-1 | d-4 | e-15 |
| 3-84 | a-1 | d-3 | e-16 | 3-118 | a-1 | d-4 | e-16 |
| 3-85 | a-1 | d-3 | e-17 | 3-119 | a-1 | d-4 | e-17 |
| 3-86 | a-1 | d-3 | e-18 | 3-120 | a-1 | d-4 | e-18 |
| 3-87 | a-1 | d-3 | e-19 | 3-121 | a-1 | d-4 | e-19 |
| 3-88 | a-1 | d-3 | e-20 | 3-122 | a-1 | d-4 | e-20 |
| 3-89 | a-1 | d-3 | e-21 | 3-123 | a-1 | d-4 | e-21 |
| 3-90 | a-1 | d-3 | e-22 | 3-124 | a-1 | d-4 | e-22 |
| 3-91 | a-1 | d-3 | e-23 | 3-125 | a-1 | d-4 | e-23 |
| 3-92 | a-1 | d-3 | e-24 | 3-126 | a-1 | d-4 | e-24 |
| 3-93 | a-1 | d-3 | e-25 | 3-127 | a-1 | d-4 | e-25 |
| 3-94 | a-1 | d-3 | e-26 | 3-128 | a-1 | d-4 | e-26 |
| 3-95 | a-1 | d-3 | e-27 | 3-129 | a-1 | d-4 | e-27 |
| 3-96 | a-1 | d-3 | e-28 | 3-130 | a-1 | d-4 | e-28 |
| 3-97 | a-1 | d-3 | e-29 | 3-131 | a-1 | d-4 | e-29 |
| 3-98 | a-1 | d-3 | e-30 | 3-132 | a-1 | d-4 | e-30 |
| 3-99 | a-1 | d-3 | e-31 | 3-133 | a-1 | d-4 | e-31 |
| 3-100 | a-1 | d-3 | e-32 | 3-134 | a-1 | d-4 | e-32 |
| 3-101 | a-1 | d-3 | e-33 | 3-135 | a-1 | d-4 | e-33 |
| 3-102 | a-1 | d-3 | e-34 | 3-136 | a-1 | d-4 | e-34 |
| 3-137 | a-1 | d-5 | e-1 | 3-171 | a-1 | d-6 | e-1 |
| 3-138 | a-1 | d-5 | e-2 | 3-172 | a-1 | d-6 | e-2 |
| 3-139 | a-1 | d-5 | e-3 | 3-173 | a-1 | d-6 | e-3 |
| 3-140 | a-1 | d-5 | e-4 | 3-174 | a-1 | d-6 | e-4 |
| 3-141 | a-1 | d-5 | e-5 | 3-175 | a-1 | d-6 | e-5 |
| 3-142 | a-1 | d-5 | e-6 | 3-176 | a-1 | d-6 | e-6 |
| 3-143 | a-1 | d-5 | e-7 | 3-177 | a-1 | d-6 | e-7 |
| 3-144 | a-1 | d-5 | e-8 | 3-178 | a-1 | d-6 | e-8 |
| 3-145 | a-1 | d-5 | e-9 | 3-179 | a-1 | d-6 | e-9 |
| 3-146 | a-1 | d-5 | e-10 | 3-180 | a-1 | d-6 | e-10 |
| 3-147 | a-1 | d-5 | e-11 | 3-181 | a-1 | d-6 | e-11 |
| 3-148 | a-1 | d-5 | e-12 | 3-182 | a-1 | d-6 | e-12 |
| 3-149 | a-1 | d-5 | e-13 | 3-183 | a-1 | d-6 | e-13 |

TABLE 3-continued (1-31)

$$O_2S\overset{Q^1}{\underset{Q^5}{-}}N-Q^4$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-150 | a-1 | d-5 | e-14 | 3-184 | a-1 | d-6 | e-14 |
| 3-151 | a-1 | d-5 | e-15 | 3-185 | a-1 | d-6 | e-15 |
| 3-152 | a-1 | d-5 | e-16 | 3-186 | a-1 | d-6 | e-16 |
| 3-153 | a-1 | d-5 | e-17 | 3-187 | a-1 | d-6 | e-17 |
| 3-154 | a-1 | d-5 | e-18 | 3-188 | a-1 | d-6 | e-18 |
| 3-155 | a-1 | d-5 | e-19 | 3-189 | a-1 | d-6 | e-19 |
| 3-156 | a-1 | d-5 | e-20 | 3-190 | a-1 | d-6 | e-20 |
| 3-157 | a-1 | d-5 | e-21 | 3-191 | a-1 | d-6 | e-21 |
| 3-158 | a-1 | d-5 | e-22 | 3-192 | a-1 | d-6 | e-22 |
| 3-159 | a-1 | d-5 | e-23 | 3-193 | a-1 | d-6 | e-23 |
| 3-160 | a-1 | d-5 | e-24 | 3-194 | a-1 | d-6 | e-24 |
| 3-161 | a-1 | d-5 | e-25 | 3-195 | a-1 | d-6 | e-25 |
| 3-162 | a-1 | d-5 | e-26 | 3-196 | a-1 | d-6 | e-26 |
| 3-163 | a-1 | d-5 | e-27 | 3-197 | a-1 | d-6 | e-27 |
| 3-164 | a-1 | d-5 | e-28 | 3-198 | a-1 | d-6 | e-28 |
| 3-165 | a-1 | d-5 | e-29 | 3-199 | a-1 | d-6 | e-29 |
| 3-166 | a-1 | d-5 | e-30 | 3-200 | a-1 | d-6 | e-30 |
| 3-167 | a-1 | d-5 | e-31 | 3-201 | a-1 | d-6 | e-31 |
| 3-168 | a-1 | d-5 | e-32 | 3-202 | a-1 | d-6 | e-32 |
| 3-169 | a-1 | d-5 | e-33 | 3-203 | a-1 | d-6 | e-33 |
| 3-170 | a-1 | d-5 | e-34 | 3-204 | a-1 | d-6 | e-34 |
| 3-205 | a-1 | d-7 | e-1 | 3-239 | a-1 | d-8 | e-1 |
| 3-206 | a-1 | d-7 | e-2 | 3-240 | a-1 | d-8 | e-2 |
| 3-207 | a-1 | d-7 | e-3 | 3-241 | a-1 | d-8 | e-3 |
| 3-208 | a-1 | d-7 | e-4 | 3-242 | a-1 | d-8 | e-4 |
| 3-209 | a-1 | d-7 | e-5 | 3-243 | a-1 | d-8 | e-5 |
| 3-210 | a-1 | d-7 | e-6 | 3-244 | a-1 | d-8 | e-6 |
| 3-211 | a-1 | d-7 | e-7 | 3-245 | a-1 | d-8 | e-7 |
| 3-212 | a-1 | d-7 | e-8 | 3-246 | a-1 | d-8 | e-8 |
| 3-213 | a-1 | d-7 | e-9 | 3-247 | a-1 | d-8 | e-9 |
| 3-214 | a-1 | d-7 | e-10 | 3-248 | a-1 | d-8 | e-10 |
| 3-215 | a-1 | d-7 | e-11 | 3-249 | a-1 | d-8 | e-11 |
| 3-216 | a-1 | d-7 | e-12 | 3-250 | a-1 | d-8 | e-12 |
| 3-217 | a-1 | d-7 | e-13 | 3-251 | a-1 | d-8 | e-13 |
| 3-218 | a-1 | d-7 | e-14 | 3-252 | a-1 | d-8 | e-14 |
| 3-219 | a-1 | d-7 | e-15 | 3-253 | a-1 | d-8 | e-15 |
| 3-220 | a-1 | d-7 | e-16 | 3-254 | a-1 | d-8 | e-16 |
| 3-221 | a-1 | d-7 | e-17 | 3-255 | a-1 | d-8 | e-17 |
| 3-222 | a-1 | d-7 | e-18 | 3-256 | a-1 | d-8 | e-18 |
| 3-223 | a-1 | d-7 | e-19 | 3-257 | a-1 | d-8 | e-19 |
| 3-224 | a-1 | d-7 | e-20 | 3-258 | a-1 | d-8 | e-20 |
| 3-225 | a-1 | d-7 | e-21 | 3-259 | a-1 | d-8 | e-21 |
| 3-226 | a-1 | d-7 | e-22 | 3-260 | a-1 | d-8 | e-22 |
| 3-227 | a-1 | d-7 | e-23 | 3-261 | a-1 | d-8 | e-23 |
| 3-228 | a-1 | d-7 | e-24 | 3-262 | a-1 | d-8 | e-24 |
| 3-229 | a-1 | d-7 | e-25 | 3-263 | a-1 | d-8 | e-25 |
| 3-230 | a-1 | d-7 | e-26 | 3-264 | a-1 | d-8 | e-26 |
| 3-231 | a-1 | d-7 | e-27 | 3-265 | a-1 | d-8 | e-27 |
| 3-232 | a-1 | d-7 | e-28 | 3-266 | a-1 | d-8 | e-28 |
| 3-233 | a-1 | d-7 | e-29 | 3-267 | a-1 | d-8 | e-29 |
| 3-234 | a-1 | d-7 | e-30 | 3-268 | a-1 | d-8 | e-30 |
| 3-235 | a-1 | d-7 | e-31 | 3-269 | a-1 | d-8 | e-31 |
| 3-236 | a-1 | d-7 | e-32 | 3-270 | a-1 | d-8 | e-32 |
| 3-237 | a-1 | d-7 | e-33 | 3-271 | a-1 | d-8 | e-33 |
| 3-238 | a-1 | d-7 | e-34 | 3-272 | a-1 | d-8 | e-34 |
| 3-273 | a-1 | d-9 | e-1 | 3-307 | a-2 | d-1 | e-1 |
| 3-274 | a-1 | d-9 | e-2 | 3-308 | a-2 | d-1 | e-2 |
| 3-275 | a-1 | d-9 | e-3 | 3-309 | a-2 | d-1 | e-3 |
| 3-276 | a-1 | d-9 | e-4 | 3-310 | a-2 | d-1 | e-4 |
| 3-277 | a-1 | d-9 | e-5 | 3-311 | a-2 | d-1 | e-5 |
| 3-278 | a-1 | d-9 | e-6 | 3-312 | a-2 | d-1 | e-6 |
| 3-279 | a-1 | d-9 | e-7 | 3-313 | a-2 | d-1 | e-7 |
| 3-280 | a-1 | d-9 | e-8 | 3-314 | a-2 | d-1 | e-8 |
| 3-281 | a-1 | d-9 | e-9 | 3-315 | a-2 | d-1 | e-9 |
| 3-282 | a-1 | d-9 | e-10 | 3-316 | a-2 | d-1 | e-10 |
| 3-283 | a-1 | d-9 | e-11 | 3-317 | a-2 | d-1 | e-11 |
| 3-284 | a-1 | d-9 | e-12 | 3-318 | a-2 | d-1 | e-12 |

TABLE 3-continued (1-31)

$$O_2S-N-Q^4$$ with $Q^1$ above S and $Q^5$ below N

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-285 | a-1 | d-9 | e-13 | 3-319 | a-2 | d-1 | e-13 |
| 3-286 | a-1 | d-9 | e-14 | 3-320 | a-2 | d-1 | e-14 |
| 3-287 | a-1 | d-9 | e-15 | 3-321 | a-2 | d-1 | e-15 |
| 3-288 | a-1 | d-9 | e-16 | 3-322 | a-2 | d-1 | e-16 |
| 3-289 | a-1 | d-9 | e-17 | 3-323 | a-2 | d-1 | e-17 |
| 3-290 | a-1 | d-9 | e-18 | 3-324 | a-2 | d-1 | e-18 |
| 3-291 | a-1 | d-9 | e-19 | 3-325 | a-2 | d-1 | e-19 |
| 3-292 | a-1 | d-9 | e-20 | 3-326 | a-2 | d-1 | e-20 |
| 3-293 | a-1 | d-9 | e-21 | 3-327 | a-2 | d-1 | e-21 |
| 3-294 | a-1 | d-9 | e-22 | 3-328 | a-2 | d-1 | e-22 |
| 3-295 | a-1 | d-9 | e-23 | 3-329 | a-2 | d-1 | e-23 |
| 3-296 | a-1 | d-9 | e-24 | 3-330 | a-2 | d-1 | e-24 |
| 3-297 | a-1 | d-9 | e-25 | 3-331 | a-2 | d-1 | e-25 |
| 3-298 | a-1 | d-9 | e-26 | 3-332 | a-2 | d-1 | e-26 |
| 3-299 | a-1 | d-9 | e-27 | 3-333 | a-2 | d-1 | e-27 |
| 3-300 | a-1 | d-9 | e-28 | 3-334 | a-2 | d-1 | e-28 |
| 3-301 | a-1 | d-9 | e-29 | 3-335 | a-2 | d-1 | e-29 |
| 3-302 | a-1 | d-9 | e-30 | 3-336 | a-2 | d-1 | e-30 |
| 3-303 | a-1 | d-9 | e-31 | 3-337 | a-2 | d-1 | e-31 |
| 3-304 | a-1 | d-9 | e-32 | 3-338 | a-2 | d-1 | e-32 |
| 3-305 | a-1 | d-9 | e-33 | 3-339 | a-2 | d-1 | e-33 |
| 3-306 | a-1 | d-9 | e-34 | 3-340 | a-2 | d-1 | e-34 |
| 3-341 | a-2 | d-2 | e-1 | 3-375 | a-2 | d-3 | e-1 |
| 3-342 | a-2 | d-2 | e-2 | 3-376 | a-2 | d-3 | e-2 |
| 3-343 | a-2 | d-2 | e-3 | 3-377 | a-2 | d-3 | e-3 |
| 3-344 | a-2 | d-2 | e-4 | 3-378 | a-2 | d-3 | e-4 |
| 3-345 | a-2 | d-2 | e-5 | 3-379 | a-2 | d-3 | e-5 |
| 3-346 | a-2 | d-2 | e-6 | 3-380 | a-2 | d-3 | e-6 |
| 3-347 | a-2 | d-2 | e-7 | 3-381 | a-2 | d-3 | e-7 |
| 3-348 | a-2 | d-2 | e-8 | 3-382 | a-2 | d-3 | e-8 |
| 3-349 | a-2 | d-2 | e-9 | 3-383 | a-2 | d-3 | e-9 |
| 3-350 | a-2 | d-2 | e-10 | 3-384 | a-2 | d-3 | e-10 |
| 3-351 | a-2 | d-2 | e-11 | 3-385 | a-2 | d-3 | e-11 |
| 3-352 | a-2 | d-2 | e-12 | 3-386 | a-2 | d-3 | e-12 |
| 3-353 | a-2 | d-2 | e-13 | 3-387 | a-2 | d-3 | e-13 |
| 3-354 | a-2 | d-2 | e-14 | 3-388 | a-2 | d-3 | e-14 |
| 3-355 | a-2 | d-2 | e-15 | 3-389 | a-2 | d-3 | e-15 |
| 3-356 | a-2 | d-2 | e-16 | 3-390 | a-2 | d-3 | e-16 |
| 3-357 | a-2 | d-2 | e-17 | 3-391 | a-2 | d-3 | e-17 |
| 3-358 | a-2 | d-2 | e-18 | 3-392 | a-2 | d-3 | e-18 |
| 3-359 | a-2 | d-2 | e-19 | 3-393 | a-2 | d-3 | e-19 |
| 3-360 | a-2 | d-2 | e-20 | 3-394 | a-2 | d-3 | e-20 |
| 3-361 | a-2 | d-2 | e-21 | 3-395 | a-2 | d-3 | e-21 |
| 3-362 | a-2 | d-2 | e-22 | 3-396 | a-2 | d-3 | e-22 |
| 3-363 | a-2 | d-2 | e-23 | 3-397 | a-2 | d-3 | e-23 |
| 3-364 | a-2 | d-2 | e-24 | 3-398 | a-2 | d-3 | e-24 |
| 3-365 | a-2 | d-2 | e-25 | 3-399 | a-2 | d-3 | e-25 |
| 3-366 | a-2 | d-2 | e-26 | 3-400 | a-2 | d-3 | e-26 |
| 3-367 | a-2 | d-2 | e-27 | 3-401 | a-2 | d-3 | e-27 |
| 3-368 | a-2 | d-2 | e-28 | 3-402 | a-2 | d-3 | e-28 |
| 3-369 | a-2 | d-2 | e-29 | 3-403 | a-2 | d-3 | e-29 |
| 3-370 | a-2 | d-2 | e-30 | 3-404 | a-2 | d-3 | e-30 |
| 3-371 | a-2 | d-2 | e-31 | 3-405 | a-2 | d-3 | e-31 |
| 3-372 | a-2 | d-2 | e-32 | 3-406 | a-2 | d-3 | e-32 |
| 3-373 | a-2 | d-2 | e-33 | 3-407 | a-2 | d-3 | e-33 |
| 3-374 | a-2 | d-2 | e-34 | 3-408 | a-2 | d-3 | e-34 |
| 3-409 | a-2 | d-4 | e-1 | 3-443 | a-2 | d-5 | e-1 |
| 3-410 | a-2 | d-4 | e-2 | 3-444 | a-2 | d-5 | e-2 |
| 3-411 | a-2 | d-4 | e-3 | 3-445 | a-2 | d-5 | e-3 |
| 3-412 | a-2 | d-4 | e-4 | 3-446 | a-2 | d-5 | e-4 |
| 3-413 | a-2 | d-4 | e-5 | 3-447 | a-2 | d-5 | e-5 |
| 3-414 | a-2 | d-4 | e-6 | 3-448 | a-2 | d-5 | e-6 |
| 3-415 | a-2 | d-4 | e-7 | 3-449 | a-2 | d-5 | e-7 |
| 3-416 | a-2 | d-4 | e-8 | 3-450 | a-2 | d-5 | e-8 |
| 3-417 | a-2 | d-4 | e-9 | 3-451 | a-2 | d-5 | e-9 |
| 3-418 | a-2 | d-4 | e-10 | 3-452 | a-2 | d-5 | e-10 |
| 3-419 | a-2 | d-4 | e-11 | 3-453 | a-2 | d-5 | e-11 |

TABLE 3-continued (1-31)

$$O_2S(Q^1)-N(Q^5)-Q^4$$

| Compound No. | Q2 Substituent No. | Q3 Substituent No. | Q1 Substituent No. | Compound No. | Q2 Substituent No. | Q3 Substituent No. | Q1 Substituent No. |
|---|---|---|---|---|---|---|---|
| 3-420 | a-2 | d-4 | e-12 | 3-454 | a-2 | d-5 | e-12 |
| 3-421 | a-2 | d-4 | e-13 | 3-455 | a-2 | d-5 | e-13 |
| 3-422 | a-2 | d-4 | e-14 | 3-456 | a-2 | d-5 | e-14 |
| 3-423 | a-2 | d-4 | e-15 | 3-457 | a-2 | d-5 | e-15 |
| 3-424 | a-2 | d-4 | e-16 | 3-458 | a-2 | d-5 | e-16 |
| 3-425 | a-2 | d-4 | e-17 | 3-459 | a-2 | d-5 | e-17 |
| 3-426 | a-2 | d-4 | e-18 | 3-460 | a-2 | d-5 | e-18 |
| 3-427 | a-2 | d-4 | e-19 | 3-461 | a-2 | d-5 | e-19 |
| 3-428 | a-2 | d-4 | e-20 | 3-462 | a-2 | d-5 | e-20 |
| 3-429 | a-2 | d-4 | e-21 | 3-463 | a-2 | d-5 | e-21 |
| 3-430 | a-2 | d-4 | e-22 | 3-464 | a-2 | d-5 | e-22 |
| 3-431 | a-2 | d-4 | e-23 | 3-465 | a-2 | d-5 | e-23 |
| 3-432 | a-2 | d-4 | e-24 | 3-466 | a-2 | d-5 | e-24 |
| 3-433 | a-2 | d-4 | e-25 | 3-467 | a-2 | d-5 | e-25 |
| 3-434 | a-2 | d-4 | e-26 | 3-468 | a-2 | d-5 | e-26 |
| 3-435 | a-2 | d-4 | e-27 | 3-469 | a-2 | d-5 | e-27 |
| 3-436 | a-2 | d-4 | e-28 | 3-470 | a-2 | d-5 | e-28 |
| 3-437 | a-2 | d-4 | e-29 | 3-471 | a-2 | d-5 | e-29 |
| 3-438 | a-2 | d-4 | e-30 | 3-472 | a-2 | d-5 | e-30 |
| 3-439 | a-2 | d-4 | e-31 | 3-473 | a-2 | d-5 | e-31 |
| 3-440 | a-2 | d-4 | e-32 | 3-474 | a-2 | d-5 | e-32 |
| 3-441 | a-2 | d-4 | e-33 | 3-475 | a-2 | d-5 | e-33 |
| 3-442 | a-2 | d-4 | e-34 | 3-476 | a-2 | d-5 | e-34 |
| 3-477 | a-2 | d-6 | e-1 | 3-511 | a-2 | d-7 | e-1 |
| 3-478 | a-2 | d-6 | e-2 | 3-512 | a-2 | d-7 | e-2 |
| 3-479 | a-2 | d-6 | e-3 | 3-513 | a-2 | d-7 | e-3 |
| 3-480 | a-2 | d-6 | e-4 | 3-514 | a-2 | d-7 | e-4 |
| 3-481 | a-2 | d-6 | e-5 | 3-515 | a-2 | d-7 | e-5 |
| 3-482 | a-2 | d-6 | e-6 | 3-516 | a-2 | d-7 | e-6 |
| 3-483 | a-2 | d-6 | e-7 | 3-517 | a-2 | d-7 | e-7 |
| 3-484 | a-2 | d-6 | e-8 | 3-518 | a-2 | d-7 | e-8 |
| 3-485 | a-2 | d-6 | e-9 | 3-519 | a-2 | d-7 | e-9 |
| 3-486 | a-2 | d-6 | e-10 | 3-520 | a-2 | d-7 | e-10 |
| 3-487 | a-2 | d-6 | e-11 | 3-521 | a-2 | d-7 | e-11 |
| 3-488 | a-2 | d-6 | e-12 | 3-522 | a-2 | d-7 | e-12 |
| 3-489 | a-2 | d-6 | e-13 | 3-523 | a-2 | d-7 | e-13 |
| 3-490 | a-2 | d-6 | e-14 | 3-524 | a-2 | d-7 | e-14 |
| 3-491 | a-2 | d-6 | e-15 | 3-525 | a-2 | d-7 | e-15 |
| 3-492 | a-2 | d-6 | e-16 | 3-526 | a-2 | d-7 | e-16 |
| 3-493 | a-2 | d-6 | e-17 | 3-527 | a-2 | d-7 | e-17 |
| 3-494 | a-2 | d-6 | e-18 | 3-528 | a-2 | d-7 | e-18 |
| 3-495 | a-2 | d-6 | e-19 | 3-529 | a-2 | d-7 | e-19 |
| 3-496 | a-2 | d-6 | e-20 | 3-530 | a-2 | d-7 | e-20 |
| 3-497 | a-2 | d-6 | e-21 | 3-531 | a-2 | d-7 | e-21 |
| 3-498 | a-2 | d-6 | e-22 | 3-532 | a-2 | d-7 | e-22 |
| 3-499 | a-2 | d-6 | e-23 | 3-533 | a-2 | d-7 | e-23 |
| 3-500 | a-2 | d-6 | e-24 | 3-534 | a-2 | d-7 | e-24 |
| 3-501 | a-2 | d-6 | e-25 | 3-535 | a-2 | d-7 | e-25 |
| 3-502 | a-2 | d-6 | e-26 | 3-536 | a-2 | d-7 | e-26 |
| 3-503 | a-2 | d-6 | e-27 | 3-537 | a-2 | d-7 | e-27 |
| 3-504 | a-2 | d-6 | e-28 | 3-538 | a-2 | d-7 | e-28 |
| 3-505 | a-2 | d-6 | e-29 | 3-539 | a-2 | d-7 | e-29 |
| 3-506 | a-2 | d-6 | e-30 | 3-540 | a-2 | d-7 | e-30 |
| 3-507 | a-2 | d-6 | e-31 | 3-541 | a-2 | d-7 | e-31 |
| 3-508 | a-2 | d-6 | e-32 | 3-542 | a-2 | d-7 | e-32 |
| 3-509 | a-2 | d-6 | e-33 | 3-543 | a-2 | d-7 | e-33 |
| 3-510 | a-2 | d-6 | e-34 | 3-544 | a-2 | d-7 | e-34 |
| 3-545 | a-2 | d-8 | e-1 | 3-579 | a-2 | d-9 | e-1 |
| 3-546 | a-2 | d-8 | e-2 | 3-580 | a-2 | d-9 | e-2 |
| 3-547 | a-2 | d-8 | e-3 | 3-581 | a-2 | d-9 | e-3 |
| 3-548 | a-2 | d-8 | e-4 | 3-582 | a-2 | d-9 | e-4 |
| 3-549 | a-2 | d-8 | e-5 | 3-583 | a-2 | d-9 | e-5 |
| 3-550 | a-2 | d-8 | e-6 | 3-584 | a-2 | d-9 | e-6 |
| 3-551 | a-2 | d-8 | e-7 | 3-585 | a-2 | d-9 | e-7 |
| 3-552 | a-2 | d-8 | e-8 | 3-586 | a-2 | d-9 | e-8 |
| 3-553 | a-2 | d-8 | e-9 | 3-587 | a-2 | d-9 | e-9 |
| 3-554 | a-2 | d-8 | e-10 | 3-588 | a-2 | d-9 | e-10 |

TABLE 3-continued (1-31)

$$O_2S \overset{Q^1}{\underset{Q^5}{-}} N - Q^4$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-555 | a-2 | d-8 | e-11 | 3-589 | a-2 | d-9 | e-11 |
| 3-556 | a-2 | d-8 | e-12 | 3-590 | a-2 | d-9 | e-12 |
| 3-557 | a-2 | d-8 | e-13 | 3-591 | a-2 | d-9 | e-13 |
| 3-558 | a-2 | d-8 | e-14 | 3-592 | a-2 | d-9 | e-14 |
| 3-559 | a-2 | d-8 | e-15 | 3-593 | a-2 | d-9 | e-15 |
| 3-560 | a-2 | d-8 | e-16 | 3-594 | a-2 | d-9 | e-16 |
| 3-561 | a-2 | d-8 | e-17 | 3-595 | a-2 | d-9 | e-17 |
| 3-562 | a-2 | d-8 | e-18 | 3-596 | a-2 | d-9 | e-18 |
| 3-563 | a-2 | d-8 | e-19 | 3-597 | a-2 | d-9 | e-19 |
| 3-564 | a-2 | d-8 | e-20 | 3-598 | a-2 | d-9 | e-20 |
| 3-565 | a-2 | d-8 | e-21 | 3-599 | a-2 | d-9 | e-21 |
| 3-566 | a-2 | d-8 | e-22 | 3-600 | a-2 | d-9 | e-22 |
| 3-567 | a-2 | d-8 | e-23 | 3-601 | a-2 | d-9 | e-23 |
| 3-568 | a-2 | d-8 | e-24 | 3-602 | a-2 | d-9 | e-24 |
| 3-569 | a-2 | d-8 | e-25 | 3-603 | a-2 | d-9 | e-25 |
| 3-570 | a-2 | d-8 | e-26 | 3-604 | a-2 | d-9 | e-26 |
| 3-571 | a-2 | d-8 | e-27 | 3-605 | a-2 | d-9 | e-27 |
| 3-572 | a-2 | d-8 | e-28 | 3-606 | a-2 | d-9 | e-28 |
| 3-573 | a-2 | d-8 | e-29 | 3-607 | a-2 | d-9 | e-29 |
| 3-574 | a-2 | d-8 | e-30 | 3-608 | a-2 | d-9 | e-30 |
| 3-575 | a-2 | d-8 | e-31 | 3-609 | a-2 | d-9 | e-31 |
| 3-576 | a-2 | d-8 | e-32 | 3-610 | a-2 | d-9 | e-32 |
| 3-577 | a-2 | d-8 | e-33 | 3-611 | a-2 | d-9 | e-33 |
| 3-578 | a-2 | d-8 | e-34 | 3-612 | a-2 | d-9 | e-34 |
| 3-613 | a-3 | d-1 | e-1 | 3-647 | a-3 | d-2 | e-1 |
| 3-614 | a-3 | d-1 | e-2 | 3-648 | a-3 | d-2 | e-2 |
| 3-615 | a-3 | d-1 | e-3 | 3-649 | a-3 | d-2 | e-3 |
| 3-616 | a-3 | d-1 | e-4 | 3-650 | a-3 | d-2 | e-4 |
| 3-617 | a-3 | d-1 | e-5 | 3-651 | a-3 | d-2 | e-5 |
| 3-618 | a-3 | d-1 | e-6 | 3-652 | a-3 | d-2 | e-6 |
| 3-619 | a-3 | d-1 | e-7 | 3-653 | a-3 | d-2 | e-7 |
| 3-620 | a-3 | d-1 | e-8 | 3-654 | a-3 | d-2 | e-8 |
| 3-621 | a-3 | d-1 | e-9 | 3-655 | a-3 | d-2 | e-9 |
| 3-622 | a-3 | d-1 | e-10 | 3-656 | a-3 | d-2 | e-10 |
| 3-623 | a-3 | d-1 | e-11 | 3-657 | a-3 | d-2 | e-11 |
| 3-624 | a-3 | d-1 | e-12 | 3-658 | a-3 | d-2 | e-12 |
| 3-625 | a-3 | d-1 | e-13 | 3-659 | a-3 | d-2 | e-13 |
| 3-626 | a-3 | d-1 | e-14 | 3-660 | a-3 | d-2 | e-14 |
| 3-627 | a-3 | d-1 | e-15 | 3-661 | a-3 | d-2 | e-15 |
| 3-628 | a-3 | d-1 | e-16 | 3-662 | a-3 | d-2 | e-16 |
| 3-629 | a-3 | d-1 | e-17 | 3-663 | a-3 | d-2 | e-17 |
| 3-630 | a-3 | d-1 | e-18 | 3-664 | a-3 | d-2 | e-18 |
| 3-631 | a-3 | d-1 | e-19 | 3-665 | a-3 | d-2 | e-19 |
| 3-632 | a-3 | d-1 | e-20 | 3-666 | a-3 | d-2 | e-20 |
| 3-633 | a-3 | d-1 | e-21 | 3-667 | a-3 | d-2 | e-21 |
| 3-634 | a-3 | d-1 | e-22 | 3-668 | a-3 | d-2 | e-22 |
| 3-635 | a-3 | d-1 | e-23 | 3-669 | a-3 | d-2 | e-23 |
| 3-636 | a-3 | d-1 | e-24 | 3-670 | a-3 | d-2 | e-24 |
| 3-637 | a-3 | d-1 | e-25 | 3-671 | a-3 | d-2 | e-25 |
| 3-638 | a-3 | d-1 | e-26 | 3-672 | a-3 | d-2 | e-26 |
| 3-639 | a-3 | d-1 | e-27 | 3-673 | a-3 | d-2 | e-27 |
| 3-640 | a-3 | d-1 | e-28 | 3-674 | a-3 | d-2 | e-28 |
| 3-641 | a-3 | d-1 | e-29 | 3-675 | a-3 | d-2 | e-29 |
| 3-642 | a-3 | d-1 | e-30 | 3-676 | a-3 | d-2 | e-30 |
| 3-643 | a-3 | d-1 | e-31 | 3-677 | a-3 | d-2 | e-31 |
| 3-644 | a-3 | d-1 | e-32 | 3-678 | a-3 | d-2 | e-32 |
| 3-645 | a-3 | d-1 | e-33 | 3-679 | a-3 | d-2 | e-33 |
| 3-646 | a-3 | d-1 | e-34 | 3-680 | a-3 | d-2 | e-34 |
| 3-681 | a-4 | d-1 | e-1 | 3-715 | a-4 | d-2 | e-1 |
| 3-682 | a-4 | d-1 | e-2 | 3-716 | a-4 | d-2 | e-2 |
| 3-683 | a-4 | d-1 | e-3 | 3-717 | a-4 | d-2 | e-3 |
| 3-684 | a-4 | d-1 | e-4 | 3-718 | a-4 | d-2 | e-4 |
| 3-685 | a-4 | d-1 | e-5 | 3-719 | a-4 | d-2 | e-5 |
| 3-686 | a-4 | d-1 | e-6 | 3-720 | a-4 | d-2 | e-6 |
| 3-687 | a-4 | d-1 | e-7 | 3-721 | a-4 | d-2 | e-7 |
| 3-688 | a-4 | d-1 | e-8 | 3-722 | a-4 | d-2 | e-8 |
| 3-689 | a-4 | d-1 | e-9 | 3-723 | a-4 | d-2 | e-9 |

TABLE 3-continued (1-31)

$$O_2S\overset{Q^1}{\underset{Q^5}{|}}N-Q^4$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-690 | a-4 | d-1 | e-10 | 3-724 | a-4 | d-2 | e-10 |
| 3-691 | a-4 | d-1 | e-11 | 3-725 | a-4 | d-2 | e-11 |
| 3-692 | a-4 | d-1 | e-12 | 3-726 | a-4 | d-2 | e-12 |
| 3-693 | a-4 | d-1 | e-13 | 3-727 | a-4 | d-2 | e-13 |
| 3-694 | a-4 | d-1 | e-14 | 3-728 | a-4 | d-2 | e-14 |
| 3-695 | a-4 | d-1 | e-15 | 3-729 | a-4 | d-2 | e-15 |
| 3-696 | a-4 | d-1 | e-16 | 3-730 | a-4 | d-2 | e-16 |
| 3-697 | a-4 | d-1 | e-17 | 3-731 | a-4 | d-2 | e-17 |
| 3-698 | a-4 | d-1 | e-18 | 3-732 | a-4 | d-2 | e-18 |
| 3-699 | a-4 | d-1 | e-19 | 3-733 | a-4 | d-2 | e-19 |
| 3-700 | a-4 | d-1 | e-20 | 3-734 | a-4 | d-2 | e-20 |
| 3-701 | a-4 | d-1 | e-21 | 3-735 | a-4 | d-2 | e-21 |
| 3-702 | a-4 | d-1 | e-22 | 3-736 | a-4 | d-2 | e-22 |
| 3-703 | a-4 | d-1 | e-23 | 3-737 | a-4 | d-2 | e-23 |
| 3-704 | a-4 | d-1 | e-24 | 3-738 | a-4 | d-2 | e-24 |
| 3-705 | a-4 | d-1 | e-25 | 3-739 | a-4 | d-2 | e-25 |
| 3-706 | a-4 | d-1 | e-26 | 3-740 | a-4 | d-2 | e-26 |
| 3-707 | a-4 | d-1 | e-27 | 3-741 | a-4 | d-2 | e-27 |
| 3-708 | a-4 | d-1 | e-28 | 3-742 | a-4 | d-2 | e-28 |
| 3-709 | a-4 | d-1 | e-29 | 3-743 | a-4 | d-2 | e-29 |
| 3-710 | a-4 | d-1 | e-30 | 3-744 | a-4 | d-2 | e-30 |
| 3-711 | a-4 | d-1 | e-31 | 3-745 | a-4 | d-2 | e-31 |
| 3-712 | a-4 | d-1 | e-32 | 3-746 | a-4 | d-2 | e-32 |
| 3-713 | a-4 | d-1 | e-33 | 3-747 | a-4 | d-2 | e-33 |
| 3-714 | a-4 | d-1 | e-34 | 3-748 | a-4 | d-2 | e-34 |
| 3-749 | a-5 | d-1 | e-1 | 3-783 | a-5 | d-2 | e-1 |
| 3-750 | a-5 | d-1 | e-2 | 3-784 | a-5 | d-2 | e-2 |
| 3-7S1 | a-5 | d-1 | e-3 | 3-785 | a-5 | d-2 | e-3 |
| 3-752 | a-5 | d-1 | e-4 | 3-786 | a-5 | d-2 | e-4 |
| 3-753 | a-5 | d-1 | e-5 | 3-787 | a-5 | d-2 | e-5 |
| 3-7S4 | a-5 | d-1 | e-6 | 3-788 | a-5 | d-2 | e-6 |
| 3-7S5 | a-5 | d-1 | e-7 | 3-789 | a-5 | d-2 | e-7 |
| 3-756 | a-5 | d-1 | e-8 | 3-790 | a-5 | d-2 | e-8 |
| 3-757 | a-5 | d-1 | e-9 | 3-791 | a-5 | d-2 | e-9 |
| 3-758 | a-5 | d-1 | e-10 | 3-792 | a-5 | d-2 | e-10 |
| 3-759 | a-5 | d-1 | e-11 | 3-793 | a-5 | d-2 | e-11 |
| 3-760 | a-5 | d-1 | e-12 | 3-794 | a-5 | d-2 | e-12 |
| 3-761 | a-5 | d-1 | e-13 | 3-795 | a-5 | d-2 | e-13 |
| 3-762 | a-5 | d-1 | e-14 | 3-796 | a-5 | d-2 | e-14 |
| 3-763 | a-5 | d-1 | e-15 | 3-797 | a-5 | d-2 | e-15 |
| 3-764 | a-5 | d-1 | e-16 | 3-798 | a-5 | d-2 | e-16 |
| 3-765 | a-5 | d-1 | e-17 | 3-799 | a-5 | d-2 | e-17 |
| 3-766 | a-5 | d-1 | e-18 | 3-800 | a-5 | d-2 | e-18 |
| 3-767 | a-5 | d-1 | e-19 | 3-801 | a-5 | d-2 | e-19 |
| 3-768 | a-5 | d-1 | e-20 | 3-802 | a-5 | d-2 | e-20 |
| 3-769 | a-5 | d-1 | e-21 | 3-803 | a-5 | d-2 | e-21 |
| 3-770 | a-5 | d-1 | e-22 | 3-804 | a-5 | d-2 | e-22 |
| 3-771 | a-5 | d-1 | e-23 | 3-805 | a-5 | d-2 | e-23 |
| 3-772 | a-5 | d-1 | e-24 | 3-806 | a-5 | d-2 | e-24 |
| 3-773 | a-5 | d-1 | e-25 | 3-807 | a-5 | d-2 | e-25 |
| 3-774 | a-5 | d-1 | e-26 | 3-808 | a-5 | d-2 | e-26 |
| 3-775 | a-5 | d-1 | e-27 | 3-809 | a-5 | d-2 | e-27 |
| 3-776 | a-5 | d-1 | e-28 | 3-810 | a-5 | d-2 | e-28 |
| 3-777 | a-5 | d-1 | e-29 | 3-811 | a-5 | d-2 | e-29 |
| 3-778 | a-5 | d-1 | e-30 | 3-812 | a-5 | d-2 | e-30 |
| 3-779 | a-5 | d-1 | e-31 | 3-813 | a-5 | d-2 | e-31 |
| 3-780 | a-5 | d-1 | e-32 | 3-814 | a-5 | d-2 | e-32 |
| 3-781 | a-5 | d-1 | e-33 | 3-815 | a-5 | d-2 | e-33 |
| 3-782 | a-5 | d-1 | e-34 | 3-816 | a-5 | d-2 | e-34 |
| 3-817 | a-6 | d-1 | e-1 | 3-851 | a-6 | d-2 | e-1 |
| 3-818 | a-6 | d-1 | e-2 | 3-852 | a-6 | d-2 | e-2 |
| 3-819 | a-6 | d-1 | e-3 | 3-853 | a-6 | d-2 | e-3 |
| 3-820 | a-6 | d-1 | e-4 | 3-854 | a-6 | d-2 | e-4 |
| 3-821 | a-6 | d-1 | e-5 | 3-855 | a-6 | d-2 | e-5 |
| 3-822 | a-6 | d-1 | e-6 | 3-856 | a-6 | d-2 | e-6 |
| 3-823 | a-6 | d-1 | e-7 | 3-857 | a-6 | d-2 | e-7 |
| 3-824 | a-6 | d-1 | e-8 | 3-858 | a-6 | d-2 | e-8 |

TABLE 3-continued (1-31)

$$O_2S{-}N{-}Q^4$$ with $Q^1$ above S and $Q^5$ below N

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-825 | a-6 | d-1 | e-9 | 3-859 | a-6 | d-2 | e-9 |
| 3-826 | a-6 | d-1 | e-10 | 3-860 | a-6 | d-2 | e-10 |
| 3-827 | a-6 | d-1 | e-11 | 3-861 | a-6 | d-2 | e-11 |
| 3-828 | a-6 | d-1 | e-12 | 3-862 | a-6 | d-2 | e-12 |
| 3-829 | a-6 | d-1 | e-13 | 3-863 | a-6 | d-2 | e-13 |
| 3-830 | a-6 | d-1 | e-14 | 3-864 | a-6 | d-2 | e-14 |
| 3-831 | a-6 | d-1 | e-15 | 3-865 | a-6 | d-2 | e-15 |
| 3-832 | a-6 | d-1 | e-16 | 3-866 | a-6 | d-2 | e-16 |
| 3-833 | a-6 | d-1 | e-17 | 3-867 | a-6 | d-2 | e-11 |
| 3-834 | a-6 | d-1 | e-18 | 3-868 | a-6 | d-2 | e-18 |
| 3-835 | a-6 | d-1 | e-19 | 3-869 | a-6 | d-2 | e-19 |
| 3-836 | a-6 | d-1 | e-20 | 3-870 | a-6 | d-2 | e-20 |
| 3-837 | a-6 | d-1 | e-21 | 3-871 | a-6 | d-2 | e-21 |
| 3-838 | a-6 | d-1 | e-22 | 3-872 | a-6 | d-2 | e-22 |
| 3-839 | a-6 | d-1 | e-23 | 3-873 | a-6 | d-2 | e-23 |
| 3-840 | a-6 | d-1 | e-24 | 3-874 | a-6 | d-2 | e-24 |
| 3-841 | a-6 | d-1 | e-25 | 3-875 | a-6 | d-2 | e-25 |
| 3-842 | a-6 | d-1 | e-26 | 3-876 | a-6 | d-2 | e-26 |
| 3-843 | a-6 | d-1 | e-27 | 3-877 | a-6 | d-2 | e-27 |
| 3-844 | a-6 | d-1 | e-28 | 3-878 | a-6 | d-2 | e-28 |
| 3-845 | a-6 | d-1 | e-29 | 3-879 | a-6 | d-2 | e-29 |
| 3-846 | a-6 | d-1 | e-30 | 3-880 | a-6 | d-2 | e-30 |
| 3-847 | a-6 | d-1 | e-31 | 3-881 | a-6 | d-2 | e-31 |
| 3-848 | a-6 | d-1 | e-32 | 3-882 | a-6 | d-2 | e-32 |
| 3-849 | a-6 | d-1 | e-33 | 3-883 | a-6 | d-2 | e-33 |
| 3-850 | a-6 | d-1 | e-34 | 3-884 | a-6 | d-2 | e-34 |
| 3-885 | a-7 | d-1 | e-1 | 3-919 | a-7 | d-2 | e-1 |
| 3-886 | a-7 | d-1 | e-2 | 3-920 | a-7 | d-2 | e-2 |
| 3-887 | a-7 | d-1 | e-3 | 3-921 | a-7 | d-2 | e-3 |
| 3-888 | a-7 | d-1 | e-4 | 3-922 | a-7 | d-2 | e-4 |
| 3-889 | a-7 | d-1 | e-5 | 3-923 | a-7 | d-2 | e-5 |
| 3-890 | a-7 | d-1 | e-6 | 3-924 | a-7 | d-2 | e-6 |
| 3-891 | a-7 | d-1 | e-7 | 3-925 | a-1 | d-2 | e-7 |
| 3-892 | a-7 | d-1 | e-8 | 3-926 | a-7 | d-2 | e-8 |
| 3-893 | a-7 | d-1 | e-9 | 3-927 | a-7 | d-2 | e-9 |
| 3-894 | a-7 | d-1 | e-10 | 3-928 | a-7 | d-2 | e-10 |
| 3-895 | a-7 | d-1 | e-11 | 3-929 | a-7 | d-2 | e-11 |
| 3-896 | a-7 | d-1 | e-12 | 3-930 | a-1 | d-2 | e-12 |
| 3-897 | a-7 | d-1 | e-13 | 3-931 | a-1 | d-2 | e-13 |
| 3-898 | a-7 | d-1 | e-14 | 3-932 | a-1 | d-2 | e-14 |
| 3-899 | a-7 | d-1 | e-15 | 3-933 | a-1 | d-2 | e-15 |
| 3-900 | a-1 | d-1 | e-16 | 3-934 | a-1 | d-2 | e-16 |
| 3-901 | a-1 | d-1 | e-11 | 3-935 | a-1 | d-2 | e-17 |
| 3-902 | a-1 | d-1 | e-18 | 3-936 | a-1 | d-2 | e-18 |
| 3-903 | a-1 | d-1 | e-19 | 3-937 | a-1 | d-2 | e-19 |
| 3-904 | a-1 | d-1 | e-20 | 3-938 | a-1 | d-2 | e-20 |
| 3-905 | a-1 | d-1 | e-21 | 3-939 | a-1 | d-2 | e-21 |
| 3-906 | a-1 | d-1 | e-22 | 3-940 | a-1 | d-2 | e-22 |
| 3-907 | a-1 | d-1 | e-23 | 3-941 | a-1 | d-2 | e-23 |
| 3-908 | a-1 | d-1 | e-24 | 3-942 | a-1 | d-2 | e-24 |
| 3-909 | a-1 | d-1 | e-25 | 3-943 | a-1 | d-2 | e-25 |
| 3-910 | a-1 | d-1 | e-26 | 3-944 | a-1 | d-2 | e-26 |
| 3-911 | a-1 | d-1 | e-27 | 3-945 | a-1 | d-2 | e-27 |
| 3-912 | a-1 | d-1 | e-28 | 3-946 | a-1 | d-2 | e-28 |
| 3-913 | a-1 | d-1 | e-29 | 3-947 | a-1 | d-2 | e-29 |
| 3-914 | a-1 | d-1 | e-30 | 3-948 | a-1 | d-2 | e-30 |
| 3-915 | a-1 | d-1 | e-31 | 3-949 | a-1 | d-2 | e-31 |
| 3-916 | a-1 | d-1 | e-32 | 3-950 | a-1 | d-2 | e-32 |
| 3-917 | a-1 | d-1 | e-33 | 3-951 | a-1 | d-2 | e-33 |
| 3-918 | a-7 | d-1 | e-34 | 3-952 | a-7 | d-2 | e-34 |
| 3-953 | a-8 | d-1 | e-1 | 3-987 | a-8 | d-2 | e-1 |
| 3-954 | a-8 | d-1 | e-2 | 3-988 | a-8 | d-2 | e-2 |
| 3-955 | a-8 | d-1 | e-3 | 3-989 | a-8 | d-2 | e-3 |
| 3-956 | a-8 | d-1 | e-4 | 3-990 | a-8 | d-2 | e-4 |
| 3-957 | a-8 | d-1 | e-5 | 3-991 | a-8 | d-2 | e-5 |
| 3-958 | a-8 | d-1 | e-6 | 3-992 | a-8 | d-2 | e-6 |
| 3-959 | a-8 | d-1 | e-7 | 3-993 | a-8 | d-2 | e-7 |

TABLE 3-continued (1-31)

$$O_2S\overset{Q^1}{\underset{Q^5}{-}}N-Q^4$$

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-960 | a-8 | d-1 | e-8 | 3-994 | a-8 | d-2 | e-8 |
| 3-961 | a-8 | d-1 | e-9 | 3-995 | a-8 | d-2 | e-9 |
| 3-962 | a-8 | d-1 | e-10 | 3-996 | a-8 | d-2 | e-10 |
| 3-963 | a-8 | d-1 | e-11 | 3-997 | a-8 | d-2 | e-11 |
| 3-964 | a-8 | d-1 | e-12 | 3-998 | a-8 | d-2 | e-12 |
| 3-965 | a-8 | d-1 | e-13 | 3-999 | a-8 | d-2 | e-13 |
| 3-966 | a-8 | d-1 | e-14 | 3-1000 | a-8 | d-2 | e-14 |
| 3-967 | a-8 | d-1 | e-15 | 3-1001 | a-8 | d-2 | e-15 |
| 3-968 | a-8 | d-1 | e-16 | 3-1002 | a-8 | d-2 | e-16 |
| 3-969 | a-8 | d-1 | e-17 | 3-1003 | a-8 | d-2 | e-17 |
| 3-970 | a-8 | d-1 | e-18 | 3-1004 | a-8 | d-2 | e-18 |
| 3-971 | a-8 | d-1 | e-19 | 3-1005 | a-8 | d-2 | e-19 |
| 3-972 | a-8 | d-1 | e-20 | 3-1006 | a-8 | d-2 | e-20 |
| 3-973 | a-8 | d-1 | e-21 | 3-1007 | a-8 | d-2 | e-21 |
| 3-974 | a-8 | d-1 | e-22 | 3-1008 | a-8 | d-2 | e-22 |
| 3-975 | a-8 | d-1 | e-23 | 3-1009 | a-8 | d-2 | e-23 |
| 3-976 | a-8 | d-1 | e-24 | 3-1010 | a-8 | d-2 | e-24 |
| 3-977 | a-8 | d-1 | e-25 | 3-1011 | a-8 | d-2 | e-25 |
| 3-978 | a-8 | d-1 | e-26 | 3-1012 | a-8 | d-2 | e-26 |
| 3-979 | a-8 | d-1 | e-27 | 3-1013 | a-8 | d-2 | e-27 |
| 3-980 | a-8 | d-1 | e-28 | 3-1014 | a-8 | d-2 | e-28 |
| 3-981 | a-8 | d-1 | e-29 | 3-1015 | a-8 | d-2 | e-29 |
| 3-982 | a-8 | d-1 | e-30 | 3-1016 | a-8 | d-2 | e-30 |
| 3-983 | a-8 | d-1 | e-31 | 3-1017 | a-8 | d-2 | e-31 |
| 3-984 | a-8 | d-1 | e-32 | 3-1018 | a-8 | d-2 | e-32 |
| 3-985 | a-8 | d-1 | e-33 | 3-1019 | a-8 | d-2 | e-33 |
| 3-986 | a-8 | d-1 | e-34 | 3-1020 | a-8 | d-2 | e-34 |
| 3-1021 | a-9 | d-1 | e-1 | 3-1055 | a-9 | d-2 | e-1 |
| 3-1022 | a-9 | d-1 | e-2 | 3-1056 | a-9 | d-2 | e-2 |
| 3-1023 | a-9 | d-1 | e-3 | 3-1057 | a-9 | d-2 | e-3 |
| 3-1024 | a-9 | d-1 | e-4 | 3-1058 | a-9 | d-2 | e-4 |
| 3-1025 | a-9 | d-1 | e-5 | 3-1059 | a-9 | d-2 | e-5 |
| 3-1026 | a-9 | d-1 | e-6 | 3-1060 | a-9 | d-2 | e-6 |
| 3-1027 | a-9 | d-1 | e-7 | 3-1061 | a-9 | d-2 | e-7 |
| 3-1028 | a-9 | d-1 | e-8 | 3-1062 | a-9 | d-2 | e-8 |
| 3-1029 | a-9 | d-1 | e-9 | 3-1063 | a-9 | d-2 | e-9 |
| 3-1030 | a-9 | d-1 | e-10 | 3-1064 | a-9 | d-2 | e-10 |
| 3-1031 | a-9 | d-1 | e-11 | 3-1065 | a-9 | d-2 | e-11 |
| 3-1032 | a-9 | d-1 | e-12 | 3-1066 | a-9 | d-2 | e-12 |
| 3-1033 | a-9 | d-1 | e-13 | 3-1067 | a-9 | d-2 | e-13 |
| 3-1034 | a-9 | d-1 | e-14 | 3-1068 | a-9 | d-2 | e-14 |
| 3-1035 | a-9 | d-1 | e-15 | 3-1069 | a-9 | d-2 | e-15 |
| 3-1036 | a-9 | d-1 | e-16 | 3-1070 | a-9 | d-2 | e-16 |
| 3-1037 | a-9 | d-1 | e-17 | 3-1071 | a-9 | d-2 | e-17 |
| 3-1038 | a-9 | d-1 | e-18 | 3-1072 | a-9 | d-2 | e-18 |
| 3-1039 | a-9 | d-1 | e-19 | 3-1073 | a-9 | d-2 | e-19 |
| 3-1040 | a-9 | d-1 | e-20 | 3-1074 | a-9 | d-2 | e-20 |
| 3-1041 | a-9 | d-1 | e-21 | 3-1075 | a-9 | d-2 | e-21 |
| 3-1042 | a-9 | d-1 | e-22 | 3-1076 | a-9 | d-2 | e-22 |
| 3-1043 | a-9 | d-1 | e-23 | 3-1077 | a-9 | d-2 | e-23 |
| 3-1044 | a-9 | d-1 | e-24 | 3-1078 | a-9 | d-2 | e-24 |
| 3-1045 | a-9 | d-1 | e-25 | 3-1079 | a-9 | d-2 | e-25 |
| 3-1046 | a-9 | d-1 | e-26 | 3-1080 | a-9 | d-2 | e-26 |
| 3-1047 | a-9 | d-1 | e-27 | 3-1081 | a-9 | d-2 | e-27 |
| 3-1048 | a-9 | d-1 | e-28 | 3-1082 | a-9 | d-2 | e-28 |
| 3-1049 | a-9 | d-1 | e-29 | 3-1083 | a-9 | d-2 | e-29 |
| 3-1050 | a-9 | d-1 | e-30 | 3-1084 | a-9 | d-2 | e-30 |
| 3-1051 | a-9 | d-1 | e-31 | 3-1085 | a-9 | d-2 | e-31 |
| 3-1052 | a-9 | d-1 | e-32 | 3-1086 | a-9 | d-2 | e-32 |
| 3-1053 | a-9 | d-1 | e-33 | 3-1087 | a-9 | d-2 | e-33 |
| 3-1054 | a-9 | d-1 | e-34 | 3-1088 | a-9 | d-2 | e-34 |
| 3-1089 | a-10 | d-1 | e-1 | 3-1123 | a-10 | d-2 | e-1 |
| 3-1090 | a-10 | d-1 | e-2 | 3-1124 | a-10 | d-2 | e-2 |
| 3-1091 | a-10 | d-1 | e-3 | 3-1125 | a-10 | d-2 | e-3 |
| 3-1092 | a-10 | d-1 | e-4 | 3-1126 | a-10 | d-2 | e-4 |
| 3-1093 | a-10 | d-1 | e-5 | 3-1127 | a-10 | d-2 | e-5 |
| 3-1094 | a-10 | d-1 | e-6 | 3-1128 | a-10 | d-2 | e-6 |

TABLE 3-continued (1-31)

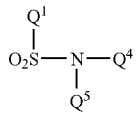

| Compound No. | Q1 Substituent No. | Q2 Substituent No. | Q3 Substituent No. | Compound No. | Q1 Substituent No. | Q2 Substituent No. | Q3 Substituent No. |
|---|---|---|---|---|---|---|---|
| 3-1095 | a-10 | d-1 | e-7 | 3-1129 | a-10 | d-2 | e-7 |
| 3-1096 | a-10 | d-1 | e-8 | 3-1130 | a-10 | d-2 | e-8 |
| 3-1097 | a-10 | d-1 | e-9 | 3-1131 | a-10 | d-2 | e-9 |
| 3-1098 | a-10 | d-1 | e-10 | 3-1132 | a-10 | d-2 | e-10 |
| 3-1099 | a-10 | d-1 | e-11 | 3-1133 | a-10 | d-2 | e-11 |
| 3-1100 | a-10 | d-1 | e-12 | 3-1134 | a-10 | d-2 | e-12 |
| 3-1101 | a-10 | d-1 | e-13 | 3-1135 | a-10 | d-2 | e-13 |
| 3-1102 | a-10 | d-1 | e-14 | 3-1136 | a-10 | d-2 | e-14 |
| 3-1103 | a-10 | d-1 | e-15 | 3-1137 | a-10 | d-2 | e-15 |
| 3-1104 | a-10 | d-1 | e-16 | 3-1138 | a-10 | d-2 | e-16 |
| 3-1105 | a-10 | d-1 | e-17 | 3-1139 | a-10 | d-2 | e-17 |
| 3-1106 | a-10 | d-1 | e-18 | 3-1140 | a-10 | d-2 | e-18 |
| 3-1107 | a-10 | d-1 | e-19 | 3-1141 | a-10 | d-2 | e-19 |
| 3-1108 | a-10 | d-1 | e-20 | 3-1142 | a-10 | d-2 | e-20 |
| 3-1109 | a-10 | d-1 | e-21 | 3-1143 | a-10 | d-2 | e-21 |
| 3-1110 | a-10 | d-1 | e-22 | 3-1144 | a-10 | d-2 | e-22 |
| 3-1111 | a-10 | d-1 | e-23 | 3-1145 | a-10 | d-2 | e-23 |
| 3-1112 | a-10 | d-1 | e-24 | 3-1146 | a-10 | d-2 | e-24 |
| 3-1113 | a-10 | d-1 | e-25 | 3-1147 | a-10 | d-2 | e-25 |
| 3-1114 | a-10 | d-1 | e-26 | 3-1148 | a-10 | d-2 | e-26 |
| 3-1115 | a-10 | d-1 | e-27 | 3-1149 | a-10 | d-2 | e-27 |
| 3-1116 | a-10 | d-1 | e-28 | 3-1150 | a-10 | d-2 | e-28 |
| 3-1117 | a-10 | d-1 | e-29 | 3-1151 | a-10 | d-2 | e-29 |
| 3-1118 | a-10 | d-1 | e-30 | 3-1152 | a-10 | d-2 | e-30 |
| 3-1119 | a-10 | d-1 | e-31 | 3-1153 | a-10 | d-2 | e-31 |
| 3-1120 | a-10 | d-1 | e-32 | 3-1154 | a-10 | d-2 | e-32 |
| 3-1121 | a-10 | d-1 | e-33 | 3-1155 | a-10 | d-2 | e-33 |
| 3-1122 | a-10 | d-1 | e-34 | 3-1156 | a-10 | d-2 | e-34 |

Among the compounds listed in Table 3, preferred are the compounds of the exemplary compound numbers of 3-1 to 3-12, 3-35 to 3-46, 2-307 to 2-318, 3-341 to 3-352, 3-613 to 3-624, 3-647 to 3-658, 3-681 to 3-692, and 3-715 to 3-726.

More preferred compounds are the compounds of the exemplary compound numbers of 3-1, i.e., N-[(5-isoquinolyl)sulfonyl]-N-(3-phenylpropyl)ethylenediamine; 3-12, i.e., N-[(5-isoquinolyl)sulfonyl]-N-[2-(phenylsulfonyl)ethyl]ethylenediamine; 3-35, i.e., N-[(5-isoquinolyl)sulfonyl]-N-(3-phenylpropyl)-1,3-propylenediamine; 3-37, i.e., N-[(5-isoquinolyl)sulfonyl]-N-[2-(2-thienyl)ethyl]-1,3-propylenediamine; 3-46, i.e., N-[(5-isoquinolyl)sulfonyl]-N-[2-(phenylsulfonyl)ethyl]-1,3-propylenediamine; 3-47, i.e., N-[(5-isoquinolyl)sulfonyl]-N-(4-phenylbutyl)-1,3-propylenediamine; 3-205, i.e., 4-{N-[(5-isoquinolyl)sulfonyl]-N-(3-phenylpropyl)}aminopiperidine; 3-318, i.e., N-[(1-hydroxy-5-isoquinolyl)sulfonyl]-N-[2-(phenylsulfonyl)ethyl]ethylenediamine; 3-341, i.e., N-[(1-hydroxy-5-isoquinolyl)sulfonyl]-N-(3-phenylpropyl)-1,3-propylenediamine; 3-352, i.e., N-[(1-hydroxy-5-isoquinolyl)sulfonyl]-N-[2-(phenylsulfonyl)ethyl]-1,3-propylenediamine; 3-624, i.e., N-[(1-amino-5-isoquinolyl)sulfonyl]-N-[2-(phenylsulfonyl)ethyl]ethylenediamine; 3-647, i.e., N-[(1-amino-5-isoquinolyl)sulfonyl]-N-(3-phenylpropyl)-1,3-propylenediamine; and 3-715, i.e., N-[(4-methyl-5-isoquinolyl)sulfonyl]-N-(3-phenylpropyl)-1,3-propylenediamine.

In the formulas (1-11), (1-21), and (1-31), the substituent of $Q^1$ is any of the following groups.

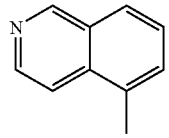

a-1

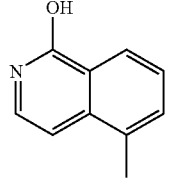

a-2

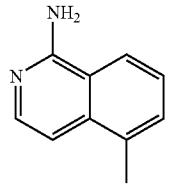

a-3

-continued
 a-4
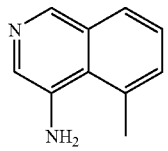 a-5
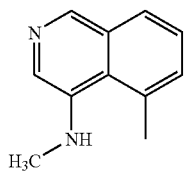 a-6
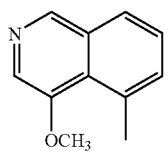 a-7
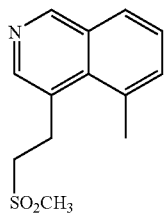 a-8
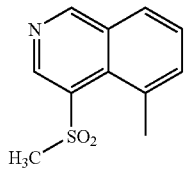 a-9
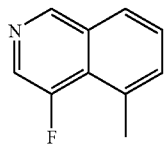 a-10
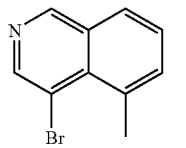 a-11
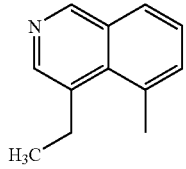 a-12
-continued
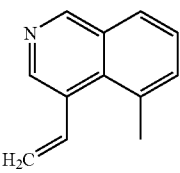 a-13
In the formulas (1-11) and (1-21), the substituent of $Q^2$ is any of the following groups.
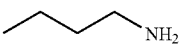 b-1
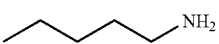 b-2
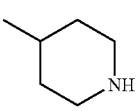 b-3
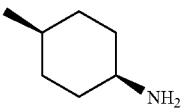 b-4
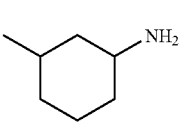 b-5
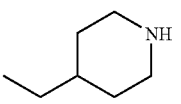 b-6
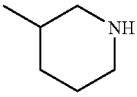 b-7
b-8
b-9
b-10
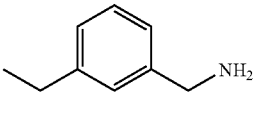 b-11

In the formula (1-21), the substituent of $Q^3$ is any of the following groups.
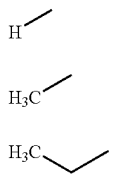
c-1
c-2
c-3
In the formula (1-31), the substituent of $Q^4$ is any of the following groups.
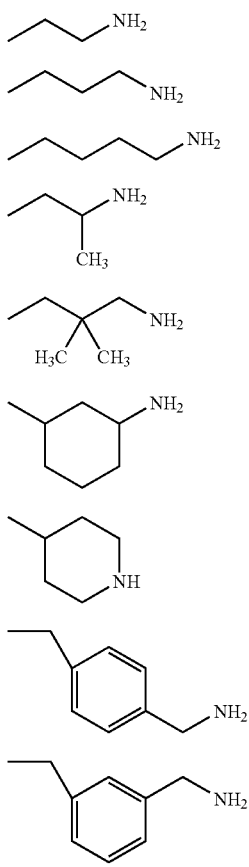
d-1
d-2
d-3
d-4
d-5
d-6
d-7
d-8
d-9
In the formula (1-31), the substituent of $Q^5$ is any of the following groups.
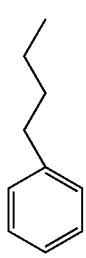
e-1
-continued
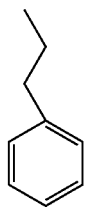
e-2
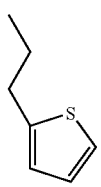
e-3
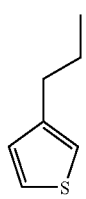
e-4
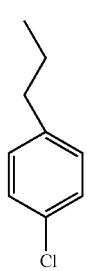
e-5
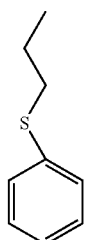
e-6
e-7
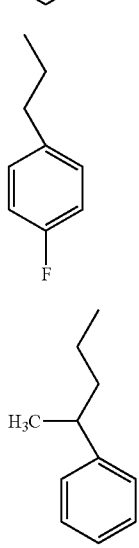
e-8

-continued
e-9
e-10
e-11
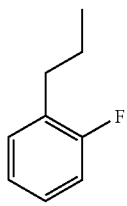
e-12
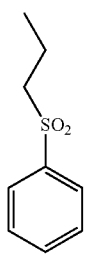
e-13
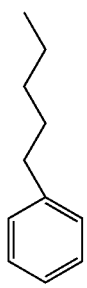
e-14
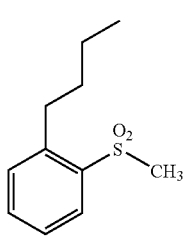
-continued
e-15
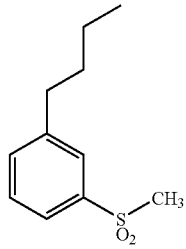
e-16
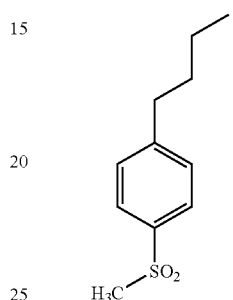
e-17
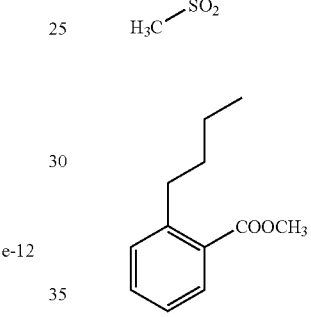
e-18
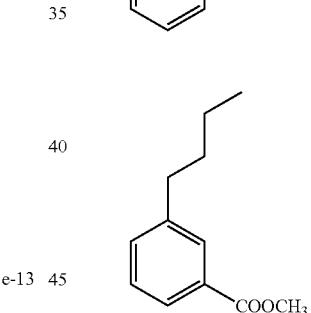
e-19
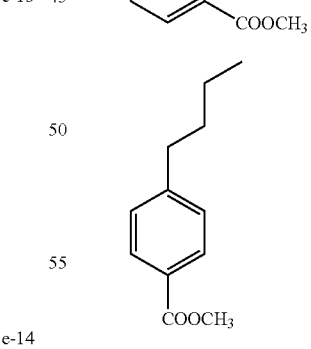
e-20
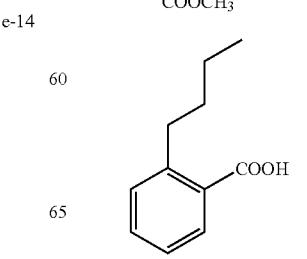

-continued e-21 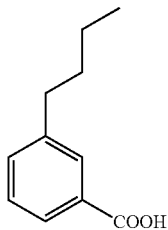

e-22 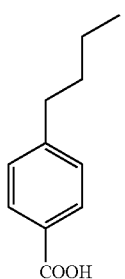

e-23 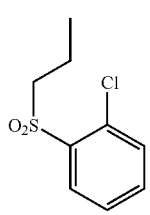

e-24 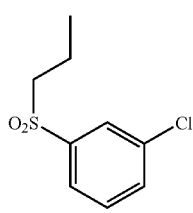

e-25 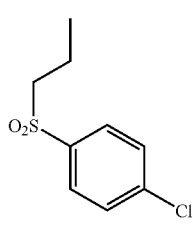

e-26 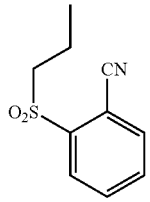

e-27 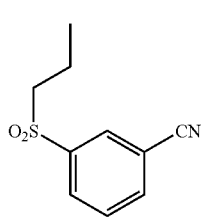

-continued e-28 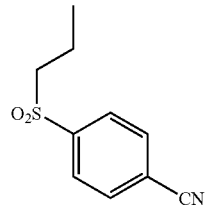

e-29 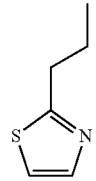

e-30 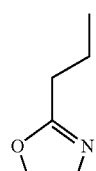

e-31 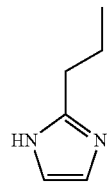

e-32 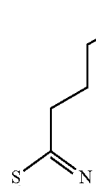

e-33 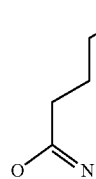

e-34 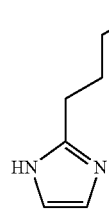

The compounds of the present invention represented by the formula (1) may have one or more asymmetric carbons, and stereoisomers based on such asymmetric carbons such as optical antipodes and diastereoisomer may exist. The stereoisomers in pure forms, any mixtures, racemates and the like of the stereoisomers all fall within the scope of the present invention. Further, when the compounds of the present invention have an olefinic double bond or a cyclic structure, two or more kinds of stereoisomers may exist, and such stereoisomers in pure forms, any mixtures, racemates and the like of such stereoisomers all fall within the scope of the present invention. Furthermore, the compounds of the present invention represented by the formula (1) may exist as tautomers. Existence of such tautomers is apparent to those skilled in the art, and such tautomers all fall within the scope of the present invention.

The compounds of the present invention may also exist as salts. Forms of the salts are not particularly limited. Acid addition salts are generally formed, or base addition salts may be formed depending on the types of substituents. The types of physiologically acceptable salts are well known to those skilled in the art, and examples include, for example, those described by Berge et al. in J. Pharm. Sci., 66, 1–19 (1977). Examples of the acid addition salts include, for example, mineral acid salts such as hydrochlorides, hydrobromides, hydroiodides, nitrates, sulfates, and hydrogensulfates, phosphates, hydrogenphosphates, organic acid salts such as acetates, trifluoroacetates, gluconates, lactates, salicylates, citrates, tartrates, ascorbates, succinates, maleates, fumarates, formates, benzoates, methanesulfonates, ethanesulfonates, benzenesulfonates and p-toluenesulfonates. Where one or more substituents contain an acidic moiety, examples of suitable pharmacologically acceptable base addition salts include, for example, metal salts such as sodium salts, potassium salts, magnesium salts, lithium salts, calcium salts, aluminum salts and zinc salts, and salts of organic amines such as ethanolamine.

Methods for preparation of the compounds represented by the formula (1) are not particularly limited. For example, they can be prepared according to the methods described below.

That is, the compounds represented by the formula (1) wherein $A^{31}$ is hydrogen atom can be prepared by removing a protective group (PG) of an amino group of a compound represented by the following formula (A):

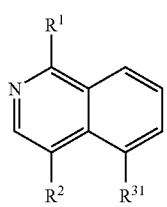

(A)

wherein $R^1$ and $R^2$ have the same meanings as those defined above; and $R^{31}$ represent a group represented by the following formula (a-1), (a-2), or (a-3):

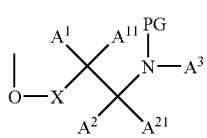

(a-1)

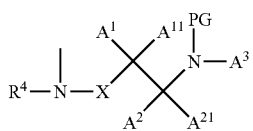

(a-2)

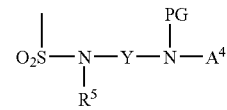

(a-3)

wherein $A^1$, $A^{11}$, $A^2$, $A^{21}$, $A^3$, $A^4$, X, Y, $R^4$ and $R^5$ have the same meanings as those defined above, and PG represents a protective group for the amino group. The PG group used herein is not particularly limited so long as it can protect the amino group, does not react in reactions other than the deprotection step in this preparation process, and can be easily removed. Preferred examples include t-butoxycarbonyl group (Boc group) and benzyloxycarbonyl group (Cbz group), and a particularly preferred example is Boc group.

For example, when PG is Boc group, the Boc group can be removed from a compound of the formula (A) to prepare a compound of the formula (1) by using known acidic conditions. Examples of the solvent used for the reaction include, for example, water, alcohols, ether solvents such as 1,4-dioxane and a mixed solvent thereof. As the acid, a mineral acid can be used. Specific examples include hydrochloric acid, sulfuric acid, nitric acid, and phosphoric acid, and hydrochloric acid is preferred. As for the amount of the acid used, it is preferable to use 1 to 100 moles based on the compound of the formula (A). The reaction is preferably performed in the temperature range of from room temperature to the reflux temperature of the solvent.

Alternatively, the deprotection can be performed by using trifluoroacetic acid. Examples of the method include a method of using trifluoroacetic acid alone, and a method of using trifluoroacetic acid as a mixed solvent system with water or dichloromethane. The reaction is performed, for example, in the temperature range of from 0 to 100° C., preferably from room temperature to 50° C. As for the amount of trifluoroacetic acid, 1 to 100 moles are preferably used based on the compound of the formula (A).

Further, when PG is Cbz group, a method for removing the Cbz group from the compound of the formula (A) to prepare a compound (1) can be carried out by using a condition of known hydrogenation reduction. Examples of the method include a method of performing the hydrogenation in an alcohol, ethyl acetate, an ether solvent such as 1,4-dioxane, or a mixed solvent thereof, and examples of the catalyst include, for example, palladium carbon. The reaction can be performed at a temperature of, for example, from 0 to 80° C., preferably from 10 to 40° C.

By referring to prior art described in, for example, Greene, T. W. and Wuts, P. G. M. "Protective Groups in Organic Synthesis", John Wiley and Sons Inc. (3rd edition) and Kocienski, P. J., "Protecting Groups", Georg Thieme Verlag (1994), it will be apparent to those skilled in the art that a particular functional group can be protected by an appropriate protective group, and then deprotected in the synthesis examples shown in this specification.

The compounds represented by the formula (1) wherein $A^{31}$ is a $C_{1-6}$ alkyl group substituted with hydroxyl group can be prepared by subjecting a compound of the formula (1) wherein $A^{31}$ is hydrogen atom to a substitution reaction using a $C_{1-6}$ alkylating agent substituted with hydroxyl group. Examples of the alkylating agent include alkyl halides, alkyl tosylates, and alkyl mesylates. The reaction is usually performed in the presence of a base. An inorganic base is preferred, and examples include potassium carbonate, sodium hydrogencarbonate, potassium hydride, and sodium hydride.

The alkylating agent is preferably used in an amount of 1 to 10 moles. The reaction is preferably performed at a temperature of from −10 to 80° C., and the reaction time is preferably from 0.5 to 48 hours.

Examples of the reaction solvent include alcoholic solvents such as methanol and ethanol, and inert solvents such as dimethylformamide, dimethylacetamide, tetrahydrofuran, 1,4-dioxane, acetone, dimethyl sulfoxide, and acetonitrile.

Moreover, as for the introduction of the $C_{1-6}$ alkyl group substituted with hydroxyl group, it may be preferable to perform the substitution reaction with a $C_{1-6}$ alkylating agent substituted with a protected hydroxyl group and then deprotect the hydroxyl group. Examples of the protective group of hydroxyl group include a trialkylsilyl group such as tert-butyldimethylsilyl group (TBDMS group), an acyl group such as acetyl group, benzyl group (Bn group), and tetrahydropyranyl (THP) group, and preferred examples include tetrahydropyranyl (THP) group. For example, the objective compounds can be prepared by subjecting a compound of the formula (1) wherein $A^{31}$ is hydrogen atom to a substitution reaction using an alkylating agent substituted with hydroxyl group protected with tetrahydropyranyl (THP) group, and then performing deprotection for the THP group under a known acidic condition. As for the removal of THP, examples of the solvent used for the reaction include water, alcohols, ether solvents such as 1,4-dioxane and mixed solvents of these. As the acid, mineral acids can be used, and specific examples are hydrochloric acid, sulfuric acid, nitric acid, and phosphoric acid. The acid is preferably used in an amount of 1 to 100 moles. The reaction is preferably performed in the temperature range of from room temperature to the reflux temperature of the solvent.

The compounds of the formula (A) wherein $R^1$ is hydroxyl group, or a $C_{1-6}$ alkoxyl group can be prepared from a compound represented by the following formula (B):

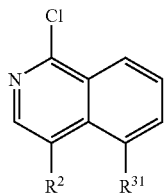

(B)

wherein $R^2$ and $R^{31}$ have the same meanings as those defined above. That is, by hydrolyzing a compound of the formula (B), a compound of the formula (A) wherein $R^1$ is hydroxyl group can be obtained. The hydrolysis is preferably carried out in a mineral acid. Examples of the mineral acid to be used include hydrochloric acid, sulfuric acid, nitric acid and the like, and particularly preferred examples are hydrochloric acid and sulfuric acid. The acid is preferably used in an amount of 1 to 100 moles based on the compound of the formula (B). The reaction is carried out at a temperature of, for example, from room temperature to 200° C. However, depending on type of the protective group of $R^{31}$ or reaction conditions, the reaction may proceed to a compound of the formula (1) wherein the PG group of $R^{31}$ is removed, not a compound of the formula (A). The reaction time is preferably from 0.1 to 48 hours.

Further, by using a desired $C_{1-6}$ alcohol instead of water as a solvent in the aforementioned reaction using the compound of the formula (B), a compound of the formula (A) wherein $R^1$ is a corresponding $C_{1-6}$ alkoxyl group can be obtained. The $C_{1-6}$ alcohol to be used is preferably used in a large excess amount. However, depending on type of the protective group of $R^{31}$ or reaction conditions, the reaction may proceed to a compound of the formula (1) wherein the PG group of $R^{31}$ is removed, not a compound of the formula (A).

The compounds of the formula (A) wherein $R^1$ is amino group can be obtained by aminating a compound of the formula (B). The reaction can be performed by, for example, using aqueous ammonia at a concentration of from 2 to 28%, and examples of the method include a method of performing the reaction in the temperature range of from room temperature to 200° C. The reaction time is preferably from 0.1 to 48 hours.

Alternatively, the compounds of the formula (A) wherein $R^1$ is amino group can be prepared by converting a compound of the formula (B) into a compound of the formula (B) in which the chlorine atom is converted into 4-methoxybenzylamino group and then removing the 4-methoxybenzyl moiety by an acidolysis reaction. That is, the conversion into 4-methoxybenzylamino group can be first carried out by using 4-methoxybenzylamine in an inert solvent in the presence of a palladium catalyst, phosphorus compound, and base (according to, for example, Buchwald, S. L., J. Org. Chem., 1158 (2000); Buchwald, S. L., Organic Letters, 1101 (2000)). Examples of the inert solvent include ether type solvents such as tetrahydrofuran, 1,4-dioxane, and 1,2-dimethoxyethane, toluene, and N,N-dimethylformamide. Examples of the palladium catalyst include tris(dibenzylideneacetone)dipalladium(0), palladium(II) acetate and the like. Examples of the phosphorus compound include 2-(di-tert-butylphosphino)biphenyl, 2-(dicyclohexylphosphino)biphenyl, 2,2'-bis(diphenylphosphino)-1,1'-binaphthyl, xantphos, and tri(tert-butyl)phosphine. Further, examples of the base include sodium tert-butoxide, cesium carbonate, potassium phosphate and the like. 4-Methoxybenzylamine is preferably used in an amount of 1 to 10 moles.

The removal of the 4-methoxybenzyl moiety is preferably performed by a decomposition reaction using an acid. Examples of the solvent used for the reaction include, for example, water, alcohols, ether type solvents such as 1,4-dioxane and mixed solvents of these. As the acid, a mineral acid can be used. Specific examples include hydrochloric acid, sulfuric acid, nitric acid, and phosphoric acid, and hydrochloric acid is a preferred example. The acid is preferably used in an amount of from 1 to 100 moles. The reaction is preferably performed in the temperature range of from room temperature to reflux temperature of the solvent. Alternatively, a method of using trifluoroacetic acid alone, or a method of using trifluoroacetic acid as a mixed solvent system with water or dichloromethane can be mentioned. The reaction is performed, for example, in the temperature range of from 0 to 100° C., preferably from room temperature to 50° C.

However, depending on type of the protective group of $R^{31}$ or reaction conditions, the reaction may proceed to a compound of the formula (1) wherein the PG group of $R^{31}$ is removed, not a compound of the formula (A).

The compounds of the formula (A) wherein $R^1$ is chlorine atom can be obtained as compounds of the formula (B), per se, as described later, and further, the compounds of the formula (A) wherein $R^1$ is a halogen atom other than chlorine atom can be prepared by a halogen exchange reaction of a compound of the formula (B). For example, by using potassium fluoride or cesium fluoride as an alkali halide, a compound of the formula (A) wherein $R^1$ is fluorine atom can be synthesized.

The compounds of the formula (A) wherein $R^1$ is chlorine atom (corresponding to the compounds of the formula (B)) can be prepared from a compound represented by the following formula (C):

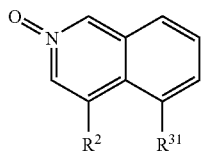

(C)

wherein $R^2$ and $R^{31}$ have the same meanings as those defined above. It is preferable to chlorinate a compound of the formula (C) with a chlorinating reagent to convert it into a compound of the formula (B). As for the solvent, the reaction can be performed, for example, without solvent or in an inert solvent. Examples of the inert solvent include dichloromethane, 1,2-dichloroethane, chloroform, and toluene. Examples of the chlorinating reagent include phosphorus trichloride, phosphorus pentachloride, and phosphorus oxychloride. The chlorinating reagent is preferably used in an amount of from 1 to 10 moles based on the compound of the formula (C). The reaction is preferably performed at a temperature of from room temperature to about 100° C. The reaction time is preferably from 0.1 to 48 hours.

Further, the compounds of the formula (C) can be prepared from a compound represented by the following formula (D):

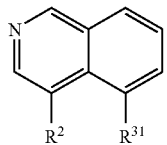

(D)

wherein $R^2$ and $R^{31}$ have the same meanings as those defined above. It is preferable to convert a compound of the formula (D) into a compound of the formula (C) by oxidization in a solvent. Examples of the solvent include acetic acid, trifluoroacetic acid, dichloromethane, 1,2-dichloroethane, chloroform, acetonitrile, acetone, trichlorofluoromethane, benzene, and 1,4-dioxane, as well as tert-butanol, water, and mixed solvents of these. Example of the oxidizing agent include hydrogen peroxide, sodium periodate, sodium perborate, 3-chloroperbenzoic acid, ruthenium trichloride, and dimethyl dioxylane, and the oxidizing agent is preferably used in an amount of 1 to 20 moles based on the compound of the formula (D). The reaction is preferably performed at a temperature of from room temperature to about 100° C. The reaction time is preferably from 0.1 to 48 hours.

The compounds of the formula (A) wherein $R^1$ is hydrogen atom correspond to the compounds of the formula (D), and can be obtained as compounds of the formula (D). Among the compounds of the formula (D), the compounds represented by the following formula (D-3):

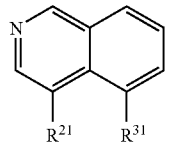

(D-3)

wherein $R^{21}$ represents any one of the atoms and groups defined for $R^2$ except for hydrogen atom and bromine atom, and $R^{31}$ has the same meaning as that defined above, can be obtained from a compound represented by the following formula (D-2):

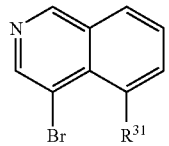

(D-2)

wherein $R^{31}$ has the same meaning as that defined above, by the following various methods.

(i) The compounds of the formula (D-3) wherein $R^{21}$ is fluorine atom can be produced from a compound of the formula (D-2). The compound of the formula (D-2) is preferably converted into a compound of the formula (D-3) wherein $R^{21}$ is fluorine atom by a halogen exchange reaction using a fluorinating agent in an inert solvent. Examples of the inert solvent include dimethylformamide, sulfolane, N,N-dimethylformamide and the like. Examples of the fluorinating agent include cesium fluoride, potassium fluoride, and tetra(n-butyl)ammonium fluoride, and cesium fluoride is preferred. The fluorinating agent is preferably used in an amount of 1 to 20 moles based on the compound of the formula (D-2). The reaction is performed at a temperature of, for example, from room temperature to 200° C., preferably 80 to 150° C. The reaction time is preferably from 0.1 to 48 hours.

(ii) The compounds of the formula (D-3) wherein $R^{21}$ is a $C_{1-6}$ alkyl group, —($C_{2-3}$ alkylene)O($G^1$), —($C_{2-3}$ alkylene)$CO_2$($G^1$), a $C_{2-3}$ alkenyl group, a $C_{2-3}$ alkynyl group, or —($C_{2-3}$ alkylene)$SO_2$($C_{1-6}$ alkyl) can be produced from a compound of the formula (D-2). That is, the compound of the formula (D-2) is preferably converted by alkylation in an inert solvent. Examples of the inert solvent include ether type solvents such as diethyl ether, tetrahydrofuran, and 1,2-dimethoxyethane, acetonitrile, N,N-dimethylformamide, water, and mixed solvents of these. The alkylation is preferably performed by a reaction with an alkylating reagent in the presence of either one of a nickel catalyst and palladium catalyst.

Examples of the nickel catalyst include dichloro(1,1'-bis(diphenylphosphino)ferrocene)nickel(II), dichloro(1,3-bis(diphenylphosphino)propane)nickel(II), and bis(acetylacetonato)nickel(II). Examples of the palladium catalyst include dichloro(1,1'-bis(bisdiphenylphosphino)ferrocene) palladium(II), tetrakis(triphenylphosphine)palladium(0), dichloro(bis(triphenylphosphine))palladium(II), and dichloro(bis(benzonitrile))palladium(II). Examples of the alkylating reagent include Grignard reagents including methyl iodide magnesium, methyl bromide magnesium and the like, organic zinc reagents including (ethoxycarbonylethyl)zinc bromide, (ethoxycarbonylmethyl)zinc bromide and the like, organic tin reagents including allyltributyltin, vinyltributyltin and the like, organic aluminum reagents including vinyldiisobutylaluminum and the like, organic boron reagents including alkylboron, alkenylboron and the like, organic lithium reagents including methyllithium, vinyllithium and the like, organic copper reagents including alkylcopper, alkenylcopper and the like, organic silicon reagents containing vinyltrimethylsilane, trimethylsilylacetylene and the like, and the like. The alkylating reagent is preferably used in an amount of 1 to 20 moles, and the catalyst is preferably used in an amount of 0.0001 to 1 mole, based on the compound of the formula (D-2).

The reaction is performed at a temperature of, for example, from 0 to 80° C., preferably from room temperature to 60° C., and the reaction time is preferably from 0.1 to 48 hours. For example, if methyl iodide magnesium or methyl bromide magnesium is used as the aforementioned alkylating reagent, a compound of the formula (D-3) wherein $R^{21}$ is methyl group can be prepared, if allyltributyltin is used, a compound of the formula (D-3) wherein $R^{21}$ is allyl group can be obtained, if (ethoxycarbonylethyl)zinc bromide is used, a compound of the formula (D-3) wherein $R^{21}$ is ethoxycarbonylethyl group can be prepared, if (ethoxycarbonylmethyl)zinc bromide is used, a compound of the formula (D-3) wherein $R^{21}$ is ethoxycarbonylmethyl group can be prepared, if vinyltributyltin is used, a compound of the formula (D-3) wherein $R^{21}$ is vinyl group can be prepared, and if an alkylboron is used, a compound of the formula (D-3) wherein $R^{21}$ is a corresponding alkyl group can be prepared.

Further, the preparation can be performed by a reaction with an alkenyl compound or alkynyl compound including acrylic esters, acrylonitrile, propargyl alcohol derivatives, end-acetylene derivatives and the like in the presence of a base and copper(I) iodide or the like. As for these reactions, Frank, W. C. et al., J. Org. Chem., 2947 (1978); Sonogashira, K. et al., Tetrahedron, 2303 (1984) and the like can be referred to. Examples of the base include triethylamine, diethylamine, diisopropylamine, sodium acetate, sodium hydroxide, lithium hydroxide, potassium carbonate, sodium tert-butoxide and the like. If protection with a protective group and subsequent deprotection are required during the aforementioned synthesis, the reactions can be properly performed by using the aforementioned methods of Greene and Wuts, and Kocienski.

(iii) The compounds of the formula (D-3) wherein $R^{21}$ is $-N(G^2)(G^3)$, $-NH(C_{2-3}$ alkylene$)O(G^1)$, or $-NH(C_{2-3}$ alkylene$)N(G^2)(G^3)$ can be prepared from a compound of the formula (D-2). Examples of the method include a method of aminating a compound of the formula (D-2) in an inert solvent. The amination herein referred to means conversion into unsubstituted $-NH_2$ and also conversion into an amino which may have one or two substituents. Examples of the inert solvent include ether type solvents such as tetrahydrofuran, 1,4-dioxane, and 1,2-dimethoxyethane, N,N-dimethylformamide, N-methylpyrrolidone, dimethyl sulfoxide, sulfolane, alcohol solvents such as methanol and ethanol, water, and mixed solvents of these. Examples of the aminating reagent include ammonia, primary amines such as monomethylamine, and secondary amines such as dimethylamine. The aminating reagent is preferably used in an amount of 1 mole to large excess amount based on the compound of the formula (D-2). The substitution reaction is preferably performed under a heating condition of from room temperature to about 200° C., and the reaction time is preferably from 0.5 to 72 hours.

Alternatively, the coupling of a compound of the formula (D-2) with the aminating agent can be carried out in an inert solvent in the presence of a palladium catalyst, phosphorus compound, and base (for example, according to Buchwald, S. L., J. Org. Chem., 1158 (2000); Buchwald, S. L., Organic Letters, 1101 (2000)). Examples of the inert solvent include ether type solvents such as tetrahydrofuran, 1,4-dioxane, and 1,2-dimethoxyethane, toluene, and N,N-dimethylformamide. Examples of the palladium catalyst include tris(dibenzylideneacetone)dipalladium(0), palladium(II) acetate and the like. Examples of the phosphorus compound include 2-(di-tert-butylphosphino)biphenyl, 2-(dicyclohexylphosphino)biphenyl, 2,2'-bis(diphenylphosphino)-1,1'-binaphthyl, xantphos, and tri(tert-butyl)phosphine. Further, examples of the base include sodium tert-butoxide, cesium carbonate, potassium phosphate and the like. Examples of the aminating agent include lithium hexamethyldisilazide, primary amines such as methylamine, and secondary amines, such as dimethylamine. In the above reaction, when lithium hexamethyldisilazide is used, a compound of the formula (D-3) introduced with amino group as $R^{21}$ can be obtained, when methylamine is used, a compound of the formula (D-3) introduced with methylamino group as $R^{21}$ can be obtained, and when dimethylamine is used, a compound of the formula (D-3) introduced with dimethylamino group as $R^{21}$ can be obtained, respectively.

(iv) The compounds of the formula (D-3) wherein $R^{21}$ is a $C_{1-6}$ alkoxyl group, $-O(C_{2-3}$ alkylene$)O(G^1)$, or $-O(C_{2-3}$ alkylene$)SO_2(C_{1-6}$ alkyl$)$ can be prepared from a compound of the formula (D-2). Preferred examples of the method include a method of etherifying a compound of the formula (D-2) in an inert solvent. Examples of the inert solvent include ether type solvents such as tetrahydrofuran, 1,4-dioxane, and 1,2-dimethoxyethane, N,N-dimethylformamide, N-methylpyrrolidone, dimethyl sulfoxide, sulfolane, water, and mixed solvents of these. Examples of the etherification reagent include metal alcoholates of lithium, sodium, potassium and the like (e.g., $C_{1-6}$ alkoxides such as methylate and ethylate, 2-hydroxyethylate, 2-methoxyethylate, 2-methanesulfonylethylate and the like are included). The reaction is preferably performed in the presence of a copper catalyst, and the reaction is preferably performed at a temperature of from room temperature to about 180° C. The etherification reagent is preferably used in an amount of from 1 to 20 moles. For example, when methylate is used as the metal alcoholate, a compound of the formula (D-3) wherein methoxy group is introduced as $R^{21}$ is obtained, when ethylate is used, a compound of the formula (D-3) wherein ethoxy group is introduced as $R^{21}$ is obtained, when 2-hydroxyethylate is used, a compound of the formula (D-3) wherein 2-hydroxyethoxy group is introduced as $R^{21}$ is obtained, when 2-methoxyethylate is used, a compound of the formula (D-3) wherein 2-methoxyethoxy group is introduced as $R^{21}$ is obtained, and when 2-methanesulfonylethylate is used, a compound of the formula (D-3) wherein 2-methanesulfonylethoxy group is introduced as $R^{21}$ is obtained, respectively. The reaction time is preferably from 0.1 to 72 hours.

Alternatively, a compound of the formula (D-3) wherein $R^{21}$ is a $C_{1-6}$ alkoxyl group, $-O(C_{2-3}$ alkylene$)O(G^1)$, or $-O(C_{2-3}$ alkylene$)SO_2(C_{1-6}$ alkyl$)$ can also be obtained by reacting a compound of the formula (D-2) with an etherification agent in the presence of a palladium catalyst, phosphorus compound, and base in an inert solvent (for example, according to Buchwald, S. L., J. Org. Chem., 1158 (2000); Buchwald, S. L., Organic Letters, 1101 (2000)). Examples of the inert solvent include ether type solvents such as tetrahydrofuran, 1,4-dioxane, and 1,2-dimethoxy ethane, and toluene. Examples of the palladium catalyst include palladium(II) acetate, tris(dibenzylideneacetone)dipalladium(0), palladium(II) acetate and the like. Examples of the phosphorus compound include 2-(di-tert-butylphosphino) biphenyl, 2-(di-tert-butylphosphino)-1,1'-binaphthyl, and 2-(di-tert-butylphosphino)-2'-dimethylamino-1,1'-binaphthyl. Further, examples of the base include sodium tert-butoxide, potassium tert-butoxide, cesium carbonate, potassium phosphate and the like. Examples of the etherification agent include, for example, alcohols such as methanol, ethanol, ethylene glycol, and methanesulfonylethanol. In the above reaction, depending on the alcohol used, a compound of the formula (D-3) in which $R^{21}$ is converted into a corresponding alkoxyl group can be obtained. When protection with a protective group and subsequent deprotection are required during the aforementioned synthesis, the reaction can be appropriately performed by using the aforementioned methods of Greene and Wuts, and Kocienski.

(v) The compounds of the formula (D-3) wherein $R^{21}$ is —S($C_{1-6}$ alkyl) can be prepared from a compound of the formula (D-2). Preferred examples of the method include a method of alkylthionating a compound of the formula (D-2) in an inert solvent. Examples of the inert solvent include, for example, tetrahydrofuran, 1,4-dioxane, 1,2-dimethoxyethane, N,N-dimethylformamide, N-methylpyrrolidone, dimethyl sulfoxide, sulfolane, methanol, ethanol, propanol, water, and a mixed solvent of these. Examples of the alkylthionating reagent include, for example, metal thiolates of lithium, sodium, potassium and the like (e.g., $C_{1-6}$ alkyl thiolates such as methyl thiolate and ethyl thiolate are included). The alkylthionating reagent is preferably used 1 to 20 moles, and the reaction is preferably performed at a temperature of from room temperature to about 180° C. The reaction time is preferably from 0.1 to 72 hours.

Further, the compounds of the formula (D-3) wherein $R^{21}$ is —SO($C_{1-6}$ alkyl) can be prepared from a compound of the formula (D-3) wherein $R^{21}$ is —S($C_{1-6}$ alkyl). Preferred examples of the method include a method of oxidizing a compound of the formula (D-3) wherein $R^{21}$ is —S($C_{1-6}$ alkyl) in an inert solvent. Examples of the inert solvent include, for example, dichloromethane, chloroform, tetrahydrofuran, 1,4-dioxane, acetonitrile, tert-butanol, acetic acid, trifluoroacetic acid, water, and mixed solvents of these. Examples of the oxidizing agent, which is used in an amount of 0.3 to 2 equivalences, include sodium metaperiodate, 3-chloroperbenzoic acid, and hydrogen peroxide. The oxidizing agent is preferably used in an amount of 0.3 to 2 moles based on the starting compound, and the reaction time is preferably from 0.1 to 48 hours.

Further, the compounds of the formula (D-3) wherein $R^{21}$ is —$SO_2$($C_{1-6}$ alkyl) can be produced from a compound of the formula (D-3) wherein $R^{21}$ is —S($C_{1-6}$ alkyl). Preferred examples of the method include a method of oxidizing a compound of the formula (D-3) wherein $R^{21}$ is —S($C_{1-6}$ alkyl) in an inert solvent. Although the reaction can be performed by using an inert solvent and oxidizing agent similar to those used in the aforementioned oxidation step, the oxidizing agent is preferably used in an amount of 2 moles or more based on the starting compound. Alternatively, the compounds of the formula (D-3) wherein $R^{21}$ is —$SO_2$($C_{1-6}$ alkyl) can be prepared from a compound of the formula (D-2). Preferred examples of the method include a method of sulfonylating a compound of the formula (D-2) in an inert solvent. Examples of the inert solvent include, for example, tetrahydrofuran, 1,4-dioxane, 1,2-dimethoxyethane, N,N-dimethylformamide, N-methylpyrrolidone, dimethyl sulfoxide, sulfolane, methanol, ethanol, propanol, water, and a mixed solvents of these. Examples of the slufonylating agent include sodium and potassium ($C_{1-6}$ alkyl)sulfinates, and by using the agent, a compound of the formula (D-2) can be converted into a compound of the formula (D-3) wherein $R^{21}$ is a corresponding $C_{1-6}$ alkyl-sulfonyl group. The reaction is preferably performed at a temperature of from room temperature to about 180° C. The reaction time is preferably from 0.1 to 48 hours. When protection with a protective group and subsequent deprotection are required during the aforementioned synthesis, reactions can be properly performed by using the aforementioned methods of Greene and Wuts, and Kocienski.

(vi) The compounds of the formula (D-3) wherein $R^{21}$ is cyano group can be produced from a compound of the formula (D-2). That is, a preferred example of the production method is a method of cyanating a compound of the formula (D-2) by using an appropriate cyanating agent in an inert solvent (e.g., according to Newman, M. S. et al., J. Org. Chem. 2525 (1961)). Examples of the inert solvent include, for example, solvents such as tetrahydrofuran, 1,4-dioxane, 1,2-dimethoxyethane, N,N-dimethylformamide, N-methylpyrrolidone, dimethyl sulfoxide, sulfolane, methanol, ethanol, and propanol, water, and mixed solvents of these. Examples of the cyanating agent include copper(I) cyanide, sodium cyanide, potassium cyanide, zinc cyanide, silver cyanide, potassium ferrocyanide (II) and the like. The cyanating agent is preferably used in an amount of 1 to 20 moles, and the reaction is preferably performed at a temperature of from room temperature to about 180° C.

Alternatively, the coupling of the compound of the formula (D-3) with the cyanating agent can be carried out in an inert solvent in the presence of a catalyst and a phosphorus compound (e.g., according to Maligres, P. E. et al., Tetrahedron Letters, 8193 (1999)). Examples of the catalyst include dichloro(1,1'-bis(diphenylphosphino)ferrocene)palladium(II), tetrakis(triphenylphosphine)palladium(0), dichloro(bis(triphenylphosphine))palladium(II), dichloro (bis(benzonitrile))palladium(II), tris(dibenzylideneacetone) dipalladium(0), palladium(II) acetate, dichloro(1,1'-bis (diphenylphosphino)ferrocene)nickel(II), dichloro (1,3-bis (diphenylphosphino)propane)nickel(II), dibromo(bis (triphenylphosphine))nickel(II), bis(acetylacetonato)nickel (II) and the like, and examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, 1,1'-bis(diphenylphosphino)ferrocene, xantphos, and tri(tert-butyl)phosphine. In the aforementioned synthesis, if protection with a protective group and subsequent deprotection are required, reactions can be properly performed by using the methods of Greene and Wuts, and Kocienski mentioned above.

The compounds of the formula (D) wherein $R^2$ is hydrogen atom, which is represented by the following formula (D-1):

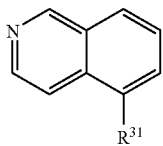
(D-1)

wherein $R^{31}$ has the same meaning as that defined above, can be produced by the following method.

The compounds represented by the following formula (D-1-1):

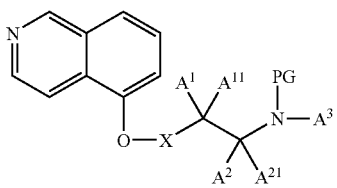
(D-1-1)

wherein $A^1$, $A^{11}$, $A^2$, $A^{21}$, $A^3$, X, and PG have the same meanings as those defined above, which correspond to the compounds of the formula (D-1) wherein $R^{31}$ is a group represented by the formula (a-1), can be prepared from commercially available 5-hydroxyisoquinoline (Aldrich) and an N-protected amino alcohol represented by the following formula (E-11):

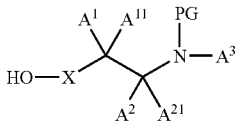
(E-11)

wherein $A^1$, $A^{11}$, $A^2$, $A^{21}$, $A^3$, X, and PG have the same meanings as those defined above, which is commercially available or can be prepared. Examples of the reaction method include a method of carrying out the reaction in an inert solvent in the presence of a phosphorus reagent, and azo compound (e.g., Tsunoda et al., Chemistry Letters, 539 (1994); Mitsunobu, O., Synthesis, 1 (1981)). Examples of the inert solvent include, for example, tetrahydrofuran, toluene, and dichloromethane. Examples of the phosphorus reagent include, for example, triphenylphosphine and tri(n-butyl)phosphine. Examples of the azo compound include, for example, diethyl azodicarboxylate, di(isopropyl) azodicarboxylate and 1,1'-azobis(N,N-dimethylformamide). The amounts of the phosphorus reagent, azo compound, and N-protected amino alcohol (E-11) may be the same or different, and they are used in amounts of 1 to 6 moles, preferably 2 to 4 moles, based on 5-hydroxyisoquinoline. The reaction temperature is about −10 to 80° C., preferably about 0 to 60° C.

The compounds represented by the following formula (D-1-2):

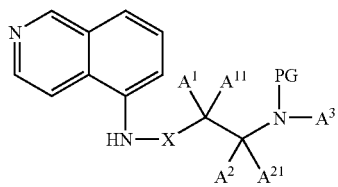
(D-1-2)

wherein $A^1$, $A^{11}$, $A^2$, $A^{21}$, $A^3$, X, and PG have the same meanings as those defined above, which correspond to the compounds represented by the formula (D-1) wherein $R^{31}$ is a group represented by the formula (a-2) provided that $R^4$ is hydrogen atom, can be prepared from commercially available 5-aminoisoquinoline (Aldrich) and an N-protected aminocarbonyl compound represented by the following formula (F-11):

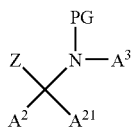
(F-11)

wherein $A^2$, $A^{21}$, $A^3$, and PG have the same meanings as those defined above, and Z represents a group represented by the following formula (F-11-1), (F-11-2), (F-11-3), or (F-11-4):

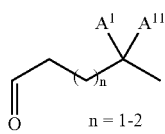
(F-11-1)

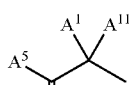
(F-11-2)

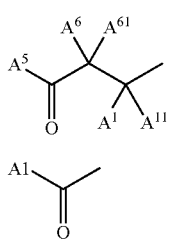
(F-11-3)

(F-11-4)

wherein $A^1$, $A^{11}$, $A^5$, $A^6$, and $A^{61}$ have the same meanings as those defined above, and n is 1 or 2, which is commercially available or can be prepared. Examples of the reaction method include a method of performing reduction amination without solvent or in an inert solvent. Examples of the inert solvent include, for example, dichloromethane, 1,2-dichloroethane, and toluene, and a dehydrating agent may be used together. Examples of the dehydrating agent include, for example, titanium isopropoxide. Preferably, dehydration condensation is performed under the aforementioned conditions to form a Schiff base, then the aforementioned inert solvent is removed, and the inert solvent is newly added to perform the reduction. Examples of the reducing agent include, for example, sodium borohydride and sodium cyanoborohydride. Examples of the inert solvent for the reduction include alcohols such as methanol. The reducing agent is preferably used in an amount of about 1 to 10 moles based on the compound of the formula (F-11). The reaction is preferably performed at 0° C. to 80° C. The reaction time is preferably from 0.1 to 72 hours.

The compounds of the formula (1) wherein $A^{31}$ is a $C_{1-6}$ alkyl group substituted with hydroxyl group can also be prepared by subjecting a compound corresponding to a compound of the formula (F-11) which is substituted with a $C_{1-6}$ alkyl group substituted with a protected hydroxyl group instead of the substitution of PG to a series of steps similar to those explained in the present specification. That is, in such a reaction route, $R^3$ in the formula (A) is a group represented by the formula (a-1) or formula (a-2), and the objective compound is prepared via a compound analogous to the corresponding compound of the formula (A), in which a $C_{1-6}$ alkyl group substituted with a protected hydroxyl group substitutes instead of the substitution of PG.

Further, the compounds represented by the following formula (D-1-3):

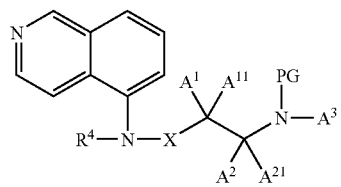

(D-1-3)

wherein $A^1$, $A^{11}$, $A^2$, $A^{21}$, $A^3$, X, $R^4$, and PG have the same meanings as those defined above, which correspond to the compounds represented by the formula (D-1) in which $R^{31}$ represents a group represented by the formula (a-2), can be prepared from commercially available 5-bromoisoquinoline and an N-protected diamine represented by the following formula (F-12):

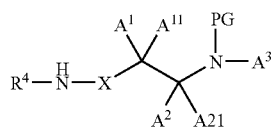

(F-12)

wherein $A^1$, $A^{11}$, $A^2$, $A^{21}$, $A^3$, X, $R^4$, and PG have the same meanings as those defined above. Examples of the reaction method include a method of carrying out the reaction in an inert solvent in the presence of a palladium catalyst, phosphorus compound, and base (for example, according to Buchwald, S. L., J. Org. Chem., 1158 (2000); Buchwald, S. L., Organic Letters, 1101 (2000)). Examples of the inert solvent include, for example, 1,4-dioxane, toluene, tetrahydrofuran, and dimethoxyethane. Examples of the palladium catalyst include, for example, tris(dibenzylideneacetone) dipalladium(0), and palladium(II) acetate. Examples of the phosphorus compound include, for example, 2-(di-tert-butylphosphino)biphenyl, 2-(dicyclohexylphosphino)biphenyl, 2,2'-bis(diphenylphosphino)-1,1'-binaphthyl, xantphos, and tri(tert-butyl)phosphine. Examples of the base include, for example, sodium tert-butoxide, cesium carbonate, and potassium phosphate. The reaction is performed at a temperature of, for example, from 20 to 120° C.

The compounds represented by the following formula (D-1-4):

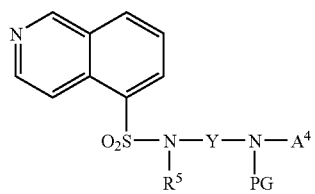

(D-1-4)

wherein $A^4$, $R^5$, Y, and PG have the same meanings as those defined above, which correspond to the compounds represented by the formula (D-1) in which $R^{31}$ is a group represented by the formula (a-3), can be prepared from a compound represented by the following formula (J-1):

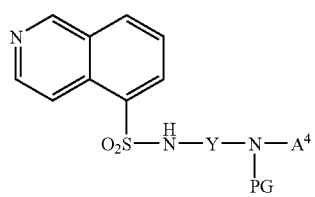

(J-1)

wherein $A^4$, Y, and PG have the same meanings as those defined above, and an alcohol represented by the following formula (H-1):

$R^5$—OH (H-1)

wherein $R^5$ has the same meanings as that defined above. Examples of the reaction method include a method of carrying out the reaction in an inert solvent in the presence of a phosphorus reagent, and azo compound (for example, Tsunoda et al., Chemistry Letters, 539 (1994) or Mitsunobu, O., Synthesis, 1 (1981)). Examples of the inert solvent include, for example, tetrahydrofuran, toluene, benzene, and dichloromethane. Examples of the phosphorus reagent include, for example, triphenylphosphine, and tributylphosphine. Examples of the azo compound include, for example, diethyl azodicarboxylate, di(isopropyl)azodicarboxylate, and 1,1'-azobis(N,N-dimethylformamide). The phosphorus reagent, the azo compound, and the alcohol of the formula (H-1) can be used in amounts of 1 to 6 moles, preferably 1 to 4 moles, based on the compound of the formula (J-1), and the reaction temperature is about −10 to 80° C., preferably about 0 to 60° C.

The compounds of the formula (J-1) can be prepared from a known compound, 5-isoquinolinesulfonyl chloride (Japanese Patent Unexamined Publication (Kokai) Nos. 57-156463, 57-200366, 58-121278, 58-121279, 59-93054, and 63-2980), which is also commercially available, and an N-protected diamine represented by the following formula (K-1):

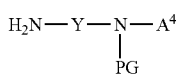

(K-1)

wherein $A^4$, Y, and PG have the same meanings as those defined above, by coupling them in an inert solvent in the presence of a base. Examples of the inert solvent include, for example, halogenated hydrocarbons such as dichloromethane, chloroform, and 1,2-dichloroethane, and acetonitrile. Examples of the base include, for example, organic bases such as triethylamine, N,N-diisopropylethylamine, and pyridine, and inorganic bases such as potassium carbonate, and sodium hydrogencarbonate. The base and the N-protected diamine of the formula (K-1) are usually used in amounts of 1 to 6 moles, preferably 1.1 to 2.2 moles, based on 5-isoquinolinesulfonyl chloride, and the reaction temperature is about −10 to 40° C., preferably about 0 to 30° C. The reaction time is preferably from 0.1 to 48 hours.

The compounds represented by the following formula (D-2-1):

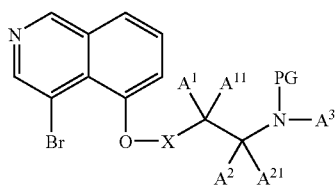

(D-2-1)

wherein $A^1$, $A^{11}$, $A^2$, $A^{21}$, $A^3$, X, and PG have the same meanings as those defined above, which correspond to the compounds of the formula (D-2) in which $R^{31}$ represents a group represented by the formula (a-1), can be prepared from 4-bromo-5-hydroxyisoquinoline represented by the following formula (E-2):

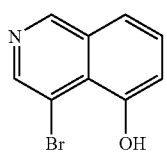

(E-2)

and an N-protected amino alcohol of the formula (E-11). The reaction can be carried out under the same conditions as those of the method of preparing the compounds of the formula (D-1-1) from 5-hydroxyisoquinoline and an N-protected amino alcohol of the formula (E-11), except that 5-hydroxyisoquinoline is changed to 4-bromo-5-hydroxyisoquinoline of the formula (E-2).

The compound represented by the formula (E-2) can be prepared from 4-bromo-5-aminoisoquinoline (Reference Example 1) represented by the following formula (F-2):

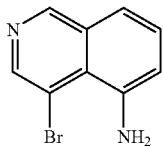

(F-2)

The compound of the formula (F-2) is reacted with sodium nitrite in hydrochloric acid, and thereby converted into a diazonium salt. Sodium nitrite is preferably used in an amount of 1 to 2 moles based on the compound of the formula (F-2). The reaction is performed at −30 to 10° C., preferably −20 to 0° C. The time for formation of the diazonium salt is preferably from 0.1 to 4 hours. Then, for example, the diazonium salt is converted into the compound of the formula (E-2) by hydroxylation in aqueous sulfuric acid. The reaction temperature in the aqueous sulfuric acid is preferably from room temperature to 100° C. The time for the hydroxylation is preferably from 2 to 48 hours.

Further, the compounds represented by the following formula (D-2-2):

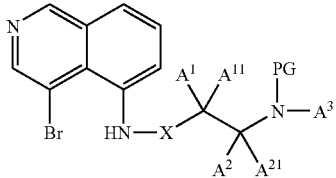

(D-2-2)

wherein $A^1$, $A^{11}$, $A^2$, $A^{21}$, $A^3$, X, and PG have the same meanings as those defined above, which correspond to the compounds represented by the formula (D-2) in which $R^{31}$ represents a group represented by the formula (a-2) provided that $R^4$ is hydrogen atom, can be prepared from 4-bromo-5-aminoisoquinoline of the formula (F-2), and an N-protected aminocarbonyl compound of the formula (F-11). The reaction can be carried out under the same conditions as those of the method of preparing the compounds of the formula (D-1-2) from 5-aminoisoquinoline, and the N-protected aminocarbonyl compound of the formula (F-11), except that 5-aminoisoquinoline is changed to 4-bromo-5-hydroxyisoquinoline of the formula (F-2).

The compounds represented by the following formula (D-2-4):

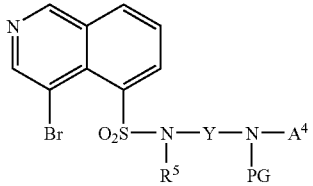

(D-2-4)

wherein $A^4$, $R^5$, Y, and PG have the same meanings as those defined above, which correspond to the compounds of the formula (D-2) in which $R^{31}$ represents a group represented by the formula (a-3), can be prepared from a compound represented by the following formula (J-2):

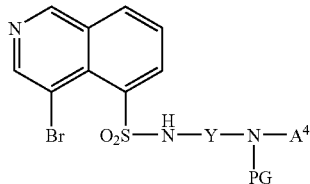

(J-2)

wherein $A^4$, Y, and PG have the same meanings as those defined above, and an alcohol of the formula (H-1). The reaction can be carried out under the same conditions as the method of preparing the compounds of the formula (D-1-4) from a compound of the formula (J-1), and an alcohol of the formula (H-1) except that the compound of the formula (J-1) is changed to a compound of the formula (J-2).

The compounds of the formula (J-2) can be produced from a known compound, 4-bromo-5-isoquinolinesulfonyl chloride (Japanese Patent No. 2763791), and an N-protected diamine of the formula (K-1), which is commercially available or can be prepared, by coupling them in an inert solvent in the presence of a base. The reaction can be carried out under the same conditions as those in the method of preparing the compounds of the formula (J-1) from 5-isoquinolinesulfonyl chloride, and an N-protected diamine of the formula (K-1) except that 5-isoquinolinesulfonyl chloride is changed to 4-bromo-5-isoquinolinesulfonyl chloride.

The compounds represented by the following formula (B-1):

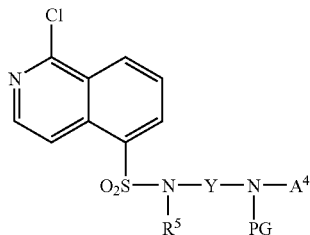

(B-1)

wherein $A^4$, $R^5$, Y, and PG have the same meanings as those defined above, which correspond to the compounds of the formula (B) in which $R^2$ is hydrogen atom, and $R^{31}$ is a group represented by the formula (a-3), can be prepared from a compound represented by the following formula (M):

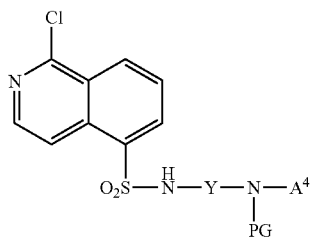

(M)

wherein $A^4$, Y, and PG have the same meanings as those defined above, and an alcohol of the formula (H-1). The reaction can be carried out under the same conditions as those in the method of preparing the compounds of the formula (D-1-4) from a compound of the formula (J-1), and an alcohol of the formula (H-1) except that the compound of the formula (J-1) is changed to a compound of the formula (M).

The compounds of the formula (M) can be produced from a known compound, 1-chloro-5-isoquinolinesulfonyl chloride (Japanese Patent Unexamined Publication (Kokai) No. 63-2980), and an N-protected diamine of the formula (K-1) by coupling them in an inert solvent in the presence of a base. The reaction can be carried out under the same conditions as those in the method of preparing the compounds of the formula (J-1) from 5-isoquinolinesulfonyl chloride, and an N-protected diamine of the formula (K-1) except that 5-isoquinolinesulfonyl chloride is changed into 1-chloro-5-isoquinolinesulfonyl chloride.

The compounds represented by the following formula (A-1):

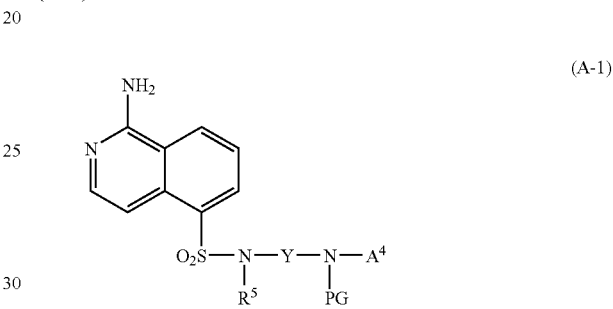

(A-1)

wherein $A^4$, $R^5$, Y, and PG have the same meanings as those defined above, which correspond to the compound of the formula (A) wherein $R^1$ is amino group, $R^2$ is hydrogen atom, and $R^{31}$ is a group represented by the formula (a-3), can be prepared from a compound represented by the following formula (P):

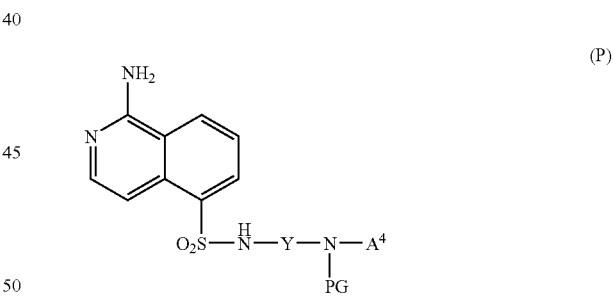

(P)

wherein $A^4$, Y, and PG have the same meanings as those defined above, and an alcohol of the formula (H-1). The reaction can be carried out under the same conditions as those in the method of preparing the compound of the formula (D-1-4) from a compound of the formula (J-1), and an alcohol of the formula (H-1) except that the compound of the formula (J-1) is changed to a compound of the formula (P).

The compounds of the formula (P) can be produced by aminating a compound of the formula (M). Examples of the reaction method include a method of attaining the conversion by adding aqueous ammonia in an inert solvent. Examples of the inert solvent include 1,4-dioxane, and tetrahydrofuran, and aqueous ammonia having a concentration of 20% or more, for example, may be used. The reaction is carried out at room temperature to 200° C., preferably 100 to 150° C. The reaction time is preferably from 0.5 to 72 hours.

The compounds of the present invention represented by the aforementioned formula (1) have cell movement inhibitory actions on the basis of inhibition against phosphorylation of the myosin regulatory light chain in the cells, and are useful as active ingredients of medicaments. Among the cell movement inhibitory actions of the compounds of the present invention, the cell contraction inhibitory action can be confirmed by measuring vasoconstriction inhibitory activity, intraocular pressure depression activity, or the like. The action to regulate change of cell morphology can be confirmed by, for example, measuring extension of neural axes of nerve cells, or the like. The inhibitory action on cell migration (the action will be abbreviated as "cell migration inhibitory action") can be confirmed by measuring neutrophil migration inhibitory activity, respiratory tract inflammation suppression activity, or the like. The cell release inhibitory action can be confirmed by measuring the chemical mediator releasing amount from neutrophils. The cell aggregation inhibitory action can be confirmed by measuring platelet aggregation inhibitory activity, or the like. Further, the apoptosis inhibitory action can be confirmed by giving stimulation to induce apoptosis to cells and then measuring viability of the cells or occurring frequencies of morphological changes characteristic to apoptosis such as nuclear condensation, nuclear fragmentation, and blebbing of cells. However, since the cell movement inhibitory actions on the basis of the inhibition of phosphorylation of the myosin regulatory light chain in the cells are known to be associated with various biological actions as described in the section of related art in the specification, the cell movement inhibitory actions must be construed in their broadest sense including the aforementioned cell contraction inhibitory action, action to regulate change of cell morphology, cell migration inhibitory action, cell release inhibitory action, cell aggregation inhibitory action, and apoptosis inhibitory action.

For example, the compounds of the present invention represented by the aforementioned formula (1) have an inhibitory activity against phosphorylation of the myosin regulatory light chain (see, Test Example 1 of the specification), vasoconstriction inhibitory activity (see, Test Example 2 in the specification), respiratory tract constriction inhibitory activity (see, Test Example 3 in the specification), intraocular pressure reducing activity (see, Test Example 4 in the specification), neutrophil migration inhibitory activity (see, Test Example 5 in the specification), and respiratory tract inflammation suppression activity (see, Test Example 6 in the specification). Further, as demonstrated by the test examples, the compounds represented by the aforementioned formula (1) have notably higher vasoconstriction inhibitory activity, respiratory tract constriction inhibitory activity, intraocular pressure reducing activity, neutrophil migration inhibitory activity, and respiratory tract inflammation suppression activity as compared with the conventional isoquinoline compounds. Therefore, the compounds represented by the aforementioned formula (1) and salts thereof are useful as active ingredients of medicaments for prophylactic and/or therapeutic treatment of diseases relating to contraction of various cells, diseases relating to morphological change of various cells, diseases relating to migration of various cells, diseases relating to release of various cells, diseases relating to aggregation of various cells, and/or diseases relating to apoptosis of various cells, and the like.

Although it is not intended to be bound by any specific theory, action mechanism of the compounds of the present invention represented by the aforementioned general formula (1) can be presumed as follows. It is known that increase of the amount of phosphorylated myosin regulatory light chain activates the actomyosin system, which is a movement apparatus of cytoskeleton, and activates cell movements. Therefore, it is considered that the phosphorylation reaction of myosin regulatory light chain is important for cell movements (Kamm, K., et al., Annu. Rev. Physiol., 51, pp. 299–313, 1989; Schmidt, J. T. et al., J. Neurobiol., 52(3), pp. 175–188, 2002; Niggli, V., FEBS Lett., 445, pp. 69–72, 1999; Itoh, K., et al., Biochim. Biophys. Acta., 1136, pp. 52–56, 1992; Kitani, S., et al., Biochem. Biophys. Res. Commun., 183, pp. 48–54, 1992; Mills, J. C., J. Cell Biol., 140(3), pp. 627–636, 1998). Measurement of the amount of phosphorylated myosin regulatory light chain in the cells revealed that the compounds represented by the aforementioned formula (1) decrease the amount of phosphorylated myosin regulatory light chain in the cells (refer to Test Example 1).

It is known that the amount of phosphorylated myosin regulatory light chain in the cells is determined by activated states of two reaction routes including Reaction route 1 and Reaction route 2 described below (Fukata, Y., et al., Trends Pharmacol. Sci., 22, pp. 32–39, 2001).

<Reaction Route 1>

Increase of intracellular calcium concentration→Activation of myosin light chain kinase→Increase of amount of phosphorylated myosin regulatory light chain <Reaction Route 2>

Activation of low molecular weight G protein Rho→Activation of Rho kinase→Phosphorylation (inactivation) of myosin phosphatase→Increase of amount of phosphorylated myosin regulatory light chain It is considered that a compound that inhibits Reaction route 1 and/or Reaction route 2 mentioned above has an activity for decreasing the amount of phosphorylated myosin regulatory light chain. In order to estimate whether either or both of Reaction route 1 and Reaction route 2 mentioned above are the target site for the compounds of the present invention represented by the aforementioned formula (1), effects of the compounds of the present invention represented by the aforementioned formula (1) on increase of intracellular calcium concentration and activity of myosin light chain kinase were examined. As a result, it was found that the compounds of the present invention gave no influence on the increase of intracellular calcium concentration (see, Test Example 7), and did not inhibit the myosin light chain kinase activity (see, Test Example 8). Therefore, it is presumed that the compounds of the formula (1) according to the present invention do not inhibit Reaction route 1 mentioned above, but inhibit Reaction route 2 mentioned above to decrease the amount of phosphorylated myosin regulatory light chain. Thus, the compounds of the present invention can be used as inhibitors of the Rho/Rho kinase pathway. The inhibition of Reaction route 2 mentioned above by the compounds of the present invention represented by the aforementioned formula (1) can be confirmed by measuring the inhibitory activity for the Rho kinase activity, or alternatively, by measuring the inhibitory activity for the phosphorylation reaction of myosin phosphatase.

The activity of Rho kinase can be measured by the method disclosed in WO01/56988. More specifically, ATP ($\gamma^{32}$P-ATP) is added to a substrate (Ribosomal S6 kinase substrate) together with a commercially available Rho kinase (Upstate)

to start the enzymatic reaction and phosphorylate the substrate. The substrate is adsorbed on filter paper, and ATP is washed off with the phosphate buffer. Then, the amount of the phosphorylated substrate is measured by using a liquid scintillation counter. The inhibitory activity of the compounds of the present invention represented by the aforementioned formula (1) for the Rho kinase activity can be determined by adding the compounds before starting the enzymatic reaction, and measuring suppression of the phosphorylation amount of the substrate. The phosphorylation reaction of myosin phosphatase can be measured by, for example, using an antibody specifically recognizing the phosphorylated myosin phosphatase (Feng, J. et al., J. Biol. Chem., 274, pp. 37385–37390, 1999). More specifically, proteins including myosin phosphatase are extracted from a tissue, subjected to electrophoresis on acrylamide gel, and transferred to a nitrocellulose membrane. The proteins are reacted with antibodies specifically recognizing phosphorylated myosin phosphatase to detect the amount of phosphorylated myosin phosphatase. The inhibitory activity on the phosphorylation reaction of myosin phosphatase can be determined by adding the compounds before starting the extraction from the tissue, and measuring suppression of the phosphorylation amount of the myosin phosphatase.

It is considered that the compounds of the present invention represented by the aforementioned formula (1) inhibit the Rho/Rho kinase pathway, which is Reaction route 2 mentioned above, and exhibit more potent cell contraction inhibitory activity and cell migration inhibitory activity compared with the conventional isoquinoline compounds. It is known that the Rho/Rho kinase route plays an important role for cell contraction and cell migration. Other than the above, it has been reported that the Rho/Rho kinase pathway controls a variety of cellular functions such as aggregation, release, production, division, and gene expression in various cell lines (Fukata, Y., et al., Trends in Pharmacological Sciences, 22, pp. 32–39, 2001; Murata T., et al., J. Hepatotol., 35, pp. 474–481, 2001; Ohnaka, K., et al., Biochem. Biophys. Res. Commun., 287, pp. 337–342, 2001; Arakawa, Y. et al., BIO Clinica, 17(13), pp. 26–28, 2002). Therefore, the compounds of the present invention which inhibit the Rho/Rho kinase pathway exhibit, based on that effect, more potent cell contraction inhibitory activity (Test Examples 2, 3, and 4), cell morphology change regulating activity, cell migration inhibitory activity (Test Examples 5, and 6), cell release inhibitory activity, cell aggregation inhibitory activity, cell apoptosis inhibitory activity, and/or activity of regulating gene expression in cells compared with the conventional isoquinoline compounds, and are useful as active ingredients of medicaments for prophylactic and/or therapeutic treatment of diseases relating to contraction of various cells, diseases relating to morphological change of various cells, diseases relating to migration of various cells, diseases relating to release from various cells, diseases relating to aggregation of various cells, diseases relating to apoptosis of various cells, and/or diseases relating to abnormal gene expression in various cells (Jikken Igaku (Experimental Medicine) Vol. 17, 7, 1999).

Examples of the diseases relating to contraction of various cells include, for example, as those relating to vascular smooth muscles, hypertension, arteriosclerosis, cerebral circulatory disturbance, brain function disorder with the aforementioned disease (mental disorder, memory disorder, dementia, delirium, poriomania, dyskinesia and the like), dizziness, cardiac diseases, pokkuri-byou (sudden death), disturbances of peripheral circulation, disturbances of retinal circulation, renal failure and the like, as those relating to airway smooth muscles, asthma, acute respiratory distress syndrome (ARDS), pulmonary emphysema, peripheral respiratory tract disease, chronic bronchitis, chronic obstructive pulmonary disease (COPD), and the like (Ueki, J. et al., Gendai Iryo (Contemporary Medical Care), Vol. 34, No. 9, pp. 87–92, 2002), as those relating to digestive tract smooth muscles, vomiting, chronic gastritis, reflux esophagitis, irritable bowel syndrome and the like, as those relating to smooth muscle cells existing in eyes, glaucoma, and the like, as those relating to smooth muscles of bladder and urethra, dysuria, pollakiuria, incontinence and the like, as those relating to smooth muscles of uterus, gestational toxicosis, threatened premature delivery, abortion and the like, and as those relating to smooth muscles of penis, erectile dysfunction is known. However, the diseases are not limited to the aforementioned examples.

More precisely, examples of hypertension include essential hypertension, renal hypertension, renovascular hypertension, hypertension during pregnancy, endocrine hypertension, cardiovascular hypertension, neurogenic hypertension, iatrogenic hypertension, pulmonary hypertension and the like, and examples of arteriosclerosis include those in which pathological change is observed in major arteries in whole body such as coronary artery, aorta abdominalis, renal artery, carotid artery, ophthalmic artery, and cerebral artery. Examples of cerebral circulatory disturbance include cerebral thrombosis, cerebral infarction, cerebral hemorrhage, transient brain ischemic attack, hypertensive encephalopathy, cerebral arteriosclerosis, subdural hemorrhage, epidural hemorrhage, subarachnoid hemorrhage, brain hypoxia, cerebral edema, encephalitis, brain tumor, head injury, mental disorder, metabolic intoxication, drug intoxication, transient aphyxia, deep anesthesia in operation and the like. The cardiac diseases include congestive heart failure, acute myocardial infarction, previous myocardial infarction, subendocardial infarction, right ventricular infarction, atypical myocardial infarction, ischemic cardiomyopathy, variant angina pectoris, stable angina, effort angina, coronary vasospasm, postinfarction angina, unstable angina pectoris, arrhythmia, and acute cardiac death.

The peripheral circulatory disturbances include aortic diseases such as Buerger's disease, arteriosclerotic obliteration, and Raynaud's syndrome, venous diseases such as venous thrombosis and thrombophlebitis, hyperviscosity syndrome, frostbite and chilblain, psychoesthesia and hypnagogic disturbance due to feeling of cold, bedsore, cleft, and alopecia. Examples of the retinal circulatory disturbances include retinal vascular obstruction caused thereby, arteriosclerotic retinopathy, vasospastic retinopathy, hypertonic fundus, hypertensive retinopathy, renal retinopathy, hypertensive neuroretinopathy, diabetic retinopathy and the like. Glaucoma includes primary glaucoma, secondary glaucoma, developmental glaucoma, childhood secondary glaucoma and the like, as well as more narrowly classified types of the foregoings, including primary open-angle glaucoma, primary angle-closure glaucoma, mixed-type glaucoma, ocular hypertension, and the like (Japanese Journal of Ophthalmology, vol. 107, No. 3, 2003). The urinary disturbances include dysuria, bladder neck contracture, bladder neck occlusion, urethral syndrome, detrusor sphincter dyssynergia, unstable bladder, chronic prostatitis, chronic cystitis, prostate pain, Hinman's syndrome, Fowler's syndrome, psychogenic dysuria, drug-induced dysuria, dysuria with aging and the like. The erectile dysfunction include organic erectile dysfunction accompanying diseases of diabetes mellitus, arteriosclerosis, hypertension, multiple-sclerotic cardiac diseases, hyperlipidemia, depression and the like, functional erectile dysfunction, erectile dysfunction with aging, and erectile dysfunction after spinal cord injury or radical prostatectomy.

Examples of the diseases relating to morphological change of various cells include, for example, various nerve dysfunctions as those relating to nerve cells. As the nerve dysfunctions, for example, neural damages caused by trauma (spinal cord injury and the like), neurodegenerative diseases such as Alzheimer's disease, Parkinson's disease and diabetic retinopathy and the like can be exemplified Examples of the diseases relating to migration of various cells include, for example, as those relating to cancer cells, infiltration and metastasis of cancer. Examples of those relating to vascular endothelial cells include angiogenesis. Examples of those relating to leukocytes include bacterial infection, allergic hypersensitive diseases (e.g., bronchial asthma, atopic dermatitis, pollinosis, anaphylactic shock and the like), collagen diseases (e.g., rheumatoid arthritis, systemic lupus erythematodes, multiple sclerosis, Sjogren's disease and the like), angiitis, inflammatory bowel diseases (e.g., ulcerative colitis, Crohn's disease and the like), ischemic reperfusion injury of visceral organs, traumatic spinal cord injury, pneumonia, hepatitis, nephritis, pancreatitis, otitis media, sinusitis, arthritis (for example, osteoarthritis, gout and the like can be exemplified), fibrosis, AIDS, adult T-cell leukemia, rejection after organ transplantation (graft versus host reaction), vascular restenosis, and endotoxin shock. Example of the cancer include myelocytic leukemia, lymphatic leukemia, gastric cancer, carcinoma of the colon and rectum, lung cancer, pancreatic carcinoma, hepatocellular carcinoma, carcinoma of the esophagus, ovarian cancer, breast cancer, skin cancer, head and neck cancer, cancer of the testicles, neuroblastoma, urinary tract epithelial cancer, multiple myeloma, carcinoma uteri, melanoma, brain tumor and the like. Examples of hepatitis include hepatitis by virus infection (e.g., hepatitis B, hepatitis C and the like), and alcoholic hepatitis. Examples of the pneumonia include chronic obstructive pulmonary disease (COPD) and interstitial pneumonia, which may shift to fibrosis. Examples of nephritis include chronic nephritic syndrome, asymptomatic proteinuria, acute nephritic syndrome, nephrotic syndrome, IgA nephropathy, pyelonephritis, glomerulonephritis and the like. Fibrosis include chronic pathological changes characterized by excess deposition of connective tissue proteins in lung, skin, heart, liver, pancreas, kidney and the like. The major pathological conditions are pulmonary fibrosis, hepatic fibrosis, and skin fibrosis. However, fibrosis is not limited to these examples. In hepatic fibrosis, viral hepatitis progresses by infection of, in particular, hepatitis B virus or hepatitis C virus, thus hepatic cells cause necrosis, and thereby fibrosis progresses, which means macronodular hepatic cirrhosis. Further, hepatic fibrosis also includes micronodular hepatic cirrhosis caused by progress of alcoholic hepatitis.

Examples of diseases relating to release of various cells include, as those relating to leukocytes, for example, allergic diseases.

Examples of the allergic diseases include asthma, atopic dermatitis, allergic conjunctivitis, allergic arthritis, allergic rhinitis, allergic pharyngitis and the like.

Examples of the diseases relating to aggregation of various cells include, as those relating to platelets, for example, thrombosis.

Thrombosis include the aforementioned circulatory disturbances of major arteries, major veins and peripheral arteries and veins in whole body, as well as shock caused by hemorrhage, drug intoxication, or endotoxin, disseminated intravascular coagulation (DIC) following it, and multiple organ failure (MOF).

Examples of the diseases relating to apoptosis of various cells include, as those relating to nerves, for example, neurodegenerative diseases such as Alzheimer's disease, Parkinson's disease, diabetic peripheral neuropathy, retinopathy, amyotrophic lateral sclerosis due to cerebral ischemia, pigmented retinitis, and cerebellar degeneration, and glaucoma. Examples of glaucoma are mentioned above. AIDS, and fulminant hepatites are examples of disease relating to viruses, chronic heart failure due to myocardial ischemia is an example of diseases relating to smooth muscles, myelodysplasia, aplastic anemia, sideroblastic anemia, and graft-versus-host disease (GVHD) after organ transplantation are examples of diseases relating to blood, arthrosteitis, and osteoporosis is an example of diseases relating to bones.

Examples of the diseases relating to abnormal gene expression of various cells include, for example, bone diseases as those relating to bone cells, AIDS as one relating to virus, and cancers as those relating to cancer cells.

Examples of the bone diseases include osteoporosis, hypercalcemia, bone Paget's disease, renal osteodystrophy, rheumatoid arthritis, osteoarthritis, osteogenesis imperfecta tarda, bone damage, periodontal bone disorder, and the like. Examples of AIDS include acquired immunodeficiency syndrome caused by human immunodeficiency virus (HIV) infection. Examples of the cancers include gastric cancer, carcinoma of the colon and rectum, hepatocellular carcinoma, pancreatic carcinoma, lung cancer, leukemia, malignant lymphoma, carcinoma uteri, ovarian cancer, breast cancer, skin cancer and the like.

Usefulness of the compounds of the present invention represented by the aforementioned formula (1) as active ingredients of medicaments for prophylactic and/or therapeutic treatment of hypertension can be confirmed by administering the compound to various hypertension model animals or the like. Examples of hypertension animal models include spontaneous hypertensive rat (SHR), renal hypertensive rat, DOCA-salt hypertensive rat and the like (Uehata, M. et al., Nature, 389, 990–994, 1997). A compound is orally, intravenously or intraperitoneally administered to a hypertension model animal at a dose of 0.1 to 1,000 mg/kg, preferably 0.1 to 100 mg/kg, and the diastolic blood pressure is measured. The usefulness as a medicament for hypertension can be confirmed based on an action of reducing the diastolic blood pressure.

Usefulness of the compounds of the present invention represented by the aforementioned formula (1) as active ingredients of medicaments for prophylactic and/or therapeutic treatment of pulmonary hypertension can be confirmed by using, for example, a rat model of pulmonary hypertension created by administering monocrotaline to a rat for 2 to 3 weeks (Ito, K. M. et al., Am. J. Physiol., 279, H1786–H1795, 2000). A compound is orally, intravenously or intraperitoneally administered to a model animal of pulmonary hypertension at a dose of 0.1 to 1,000 mg/kg, preferably 0.1 to 100 mg/kg, and the intrapulmonary pressure is measured. The usefulness as a medicament for pulmonary hypertension can be confirmed based on an action of decreasing the intrapulmonary pressure.

Usefulness of the compounds of the present invention represented by the aforementioned formula (1) as active ingredients of medicaments for prophylactic and/or therapeutic treatment of arteriosclerosis can be confirmed by using, for example, a rat model of L-NAME-induced arteriosclerosis (Cir. Res. 89(5):415–21, 2001), a rat model of balloon-induced neointimal formation (Sawada N. et al., Circulation 101 (17):2030–3, 2000) or the like. A compound is orally, intravenously or intraperitoneally administered to a model animal of arteriosclerosis at a dose of 0.1 to 1,000 mg/kg, preferably 0.1 to 100 mg/kg, and thickening of arteries is observed. The usefulness as a medicament for arteriosclerosis can be confirmed based on an action of suppressing neointimal formation in arteries.

Usefulness of the compounds of the present invention represented by the aforementioned formula (1) as active ingredients of medicaments for prophylactic and/or therapeutic treatment of cerebral circulatory dysfunction can be confirmed by using, for example, a gerbil model of hippocampal neuronal death (Kirino et al., Brain Res., 239, 57–69, 1982) or the like. A compound is orally, intravenously or intraperitoneally administered to the model animal at a dose of 0.1 to 1,000 mg/kg, preferably 0.1 to 100 mg/kg, and the amount of energy-related substances and survival period of gerbil, or inhibition of late-onset of neuronal death is measured. The usefulness as a medicament for cerebral circulatory dysfunction can be confirmed based on actions for maintaining, improving and activating cerebral metabolic ability, brain and nerve protective action, and action for suppressing formation of cerebral infarction.

Usefulness of the compounds of the present invention represented by the aforementioned formula (1) as active ingredients of medicaments for prophylactic and/or therapeutic treatment of cardiac diseases can be confirmed by using, for example, a rat model of myocardial infarction based on the ligation of artery (Xia Q. G. et al., Cardiovasc. Res., 49(1):110–7, 2001) or the like. Effectiveness as a medicament for cardiac diseases can be confirmed by orally, intravenously or intraperitoneally administering a compound to the model animal at a dose of 0.1 to 1,000 mg/kg, preferably 0.1 to 100 mg/kg, and observing a cardiac tissue fixed by formalin perfusion after ischemic reperfusion.

Usefulness of the compounds of the present invention represented by the aforementioned formula (1) as active ingredients of medicaments for prophylactic and/or therapeutic treatment of disturbances of peripheral circulation can be confirmed by using, for example, a rat model of bedsore (Pierce S. M. et al., Am. J. Physiol. Heart Circ. Physiol., 281(1):H67–74, 2001) or the like. Effectiveness as a medicament for bedsore (peripheral circulatory disturbance) can be confirmed by orally, intravenously or intraperitoneally administering a compound to the model animal at a dose of 0.1 to 1,000 mg/kg, preferably 0.1 to 100 mg/kg, compressing the hind leg skin at a pressure of 50 mmHg, and then observing a tissue of necrotic area of the lesion or measuring epithelial blood flow of the same.

Usefulness of the compounds of the present invention represented by the aforementioned formula (1) as active ingredients of medicaments for prophylactic and/or therapeutic treatment of disturbances of retinal circulation can be confirmed by using, for example, rabbit model of rose bengal-mediated argon laser retinal vein photothrombosis (Jpn. J. Ophthalmol., 45(4):359–62, 2001), or the like. Effectiveness as a medicament for retinal circulatory disturbance can be confirmed by orally, intravenously or intraperitoneally administering a compound to the model animal at a dose of 0.1 to 1,000 mg/kg, preferably 0.1 to 100 mg/kg, comparing the degree of retinal circulatory disturbance with that of a control based on count of laser spots.

Usefulness of the compounds of the present invention represented by the aforementioned formula (1) as active ingredients of medicaments for prophylactic and/or therapeutic treatment of renal failure can be confirmed by using, for example, a rat model of one-kidney, one-clip renal hypertension (Kiso to Rinsho, 30, 511–524, 1996). Effectiveness as a medicament for renal failure can be confirmed by orally, intravenously or intraperitoneally administering a compound to the model animal at a dose of 0.1 to 1,000 mg/kg, preferably 0.1 to 100 mg/kg, and measuring the diuretic effect.

Usefulness of the compounds of the present invention represented by the aforementioned formula (1) as active ingredients of medicaments for prophylactic and/or therapeutic treatment of asthma, for example, bronchial asthma, can be confirmed by using, for example, suppression of constriction of an isolated trachea, a model animal of bronchial asthma, inhibition of chemotaxis of human peripheral leucocytes (Kunihiko Iizuka, Allergy, 47:943, 1998; Kunihiko Iizuka, and Akihiro Yoshii, Jpn. J. Respirol Soc, 37:196, 1999.), or the like. The usefulness as a medicament for bronchial asthma can be confirmed by orally, intravenously or intraperitoneally administering a compound to the model animal at a dose of 0.1 to 1,000 mg/kg, preferably 0.1 to 100 mg/kg, and measuring elevation of airway resistance caused by acetylcholine inhalation, or performing histological analysis.

Usefulness of the compounds of the present invention represented by the aforementioned formula (1) as active ingredients of medicaments for prophylactic and/or therapeutic treatment of irritable bowel syndrome can be confirmed by administering the compounds to any of various stress burden model animals. The aforementioned usefulness can be confirmed by administering a compound to a stress burden model animal, for example, a rat model of arresting stress, a CRH-administered rat model (Miyata, K. et al., Am. J. Physiol., 274, G827–831, 1998), or the like. A compound is orally, intravenously or intraperitoneally administered to a stress burden model animal at a dose of 0.1 to 1,000 mg/kg, preferably 0.1 to 100 mg/kg, and counting the number of fecal pellets. The usefulness as a medicament for curative medicine of irritable bowel syndrome can be confirmed based on effect for reducing the number of fecal pellets.

Usefulness of the compounds of the present invention represented by the aforementioned formula (1) as active ingredients of medicaments for prophylactic and/or therapeutic treatment of glaucoma can be confirmed by, for example, measuring intraocular pressure of a rabbit, cat or monkey after administration of the medicaments by instillation (Surv. Ophthalmol. 41:S9–S18, 1996). The usefulness as a medicament for glaucoma can be confirmed by instilling or orally, intravenously or intraperitoneally administering a compound to a locally anesthetized rat or monkey model animal at a dose of 0.1 to 1,000 mg/kg, preferably 0.1 to 100 mg/kg, and measuring the intraocular pressure over time using an tonometer.

Usefulness of the compounds of the present invention represented by the aforementioned formula (1) as active ingredients of medicaments for prophylactic and/or therapeutic treatment of dysuria can be confirmed by using, for example, a model of rhythmic bladder contraction (Kaneko S. et al., Folia Pharmacol. Japon, Vol. 93(2), 55–60, 1989; Nomura N. et al., Folia Pharmacol. Japon, Vol. 94(3), 173-, 1989.) or the like. The usefulness as a medicament for urinary disturbance can be confirmed by orally, intravenously or intraperitoneally administering a compound to an anesthetized rat or dog at a dose of 0.1 to 1,000 mg/kg, preferably 0.1 to 100 mg/kg, and measuring the number of rhythmic contraction of filled bladder (micturition).

Usefulness of the compounds of the present invention represented by the aforementioned formula (1) as active ingredients of medicaments for prophylactic and/or therapeutic treatment of erectile dysfunction can be confirmed by a known method, for example, the method described in J. Uro., 151, 797–800, 1994. A compound is dissolved in a hydrophilic ointment, 30 mg of the ointment was applied to a rat penis, and the rat is held in an acrylic cylinder for 10 minutes so that the rat was not able to lick the penis. The rat is moved to an acrylic cage of 30 cm×30 cm, and videotaped for 60 minutes from the side and the bottom of the cage. Then, the number of erection of the penis per 30 minutes can be counted to confirm the usefulness as a medicament for erectile dysfunction.

Usefulness of the compounds of the present invention represented by the aforementioned formula (1) as active ingredients of medicaments for suppressing cancer metastasis and invasion can be confirmed by, for example, the method described in Cancer Res., 55:3551–3557 (1995). The usefulness as a medicament for cancer metastasis and invasion can be confirmed by orally, intravenously or intraperitoneally administering a compound at a dose of 0.1 to 1,000 mg/kg, preferably 0.1 to 100 mg/kg, to a nude mouse transplanted with human cancer cell suspension transplantable to immunodeficient mice at the same site (spontaneous metastasis model), and measuring the metastasized lesion.

Usefulness of the compounds of the present invention represented by the aforementioned formula (1) as active ingredients of medicaments for prophylactic and/or therapeutic treatment of collagen disease can be confirmed by using, for example, collagen-induced arthritis model of a rat or mouse (Griffith, M. M. et al., Arthritis Rheumatism, 24:781, 1981; Wooley, P. H. et al., J. Exp. Med., 154:688, 1981). The usefulness as a medicament for collagen disease can be confirmed by orally, intravenously or intraperitoneally administering a compound to the model mouse or rat at a dose of 0.1 to 1,000 mg/kg, preferably 0.1 to 100 mg/kg, and measuring footpad volume or progression of bone destruction.

Usefulness of the compounds of the present invention represented by the aforementioned formula (1) as active ingredients of medicaments for prophylactic and/or therapeutic treatment of inflammatory bowel disease can be confirmed by using a rat model of idiopathic ulcerative colitis induced by subserosal injection of acetic acid, a model of sodium dextransulfate-induced colitis, a model of trinitrobenzenesulfonic acid-induced colitis (Kojima et al., Folia. Pharmacol. Jpn., 118, 123–130, 2001), or the like. The usefulness as a medicament for inflammatory bowel disease can be confirmed by, for example, orally, intravenously or intraperitoneally administering a compound at a dose of 0.1 to 1,000 mg/kg, preferably 0.1 to 100 mg/kg, to a rat in which colitis is induced by intraintestinal injection of acetic acid, dissecting the rat after several days to two weeks, then observing and measuring the ulcer area of the intestinal epithelium, and amount of leucotriene B4 in a colon homogenate.

Usefulness of the compounds of the present invention represented by the aforementioned formula (1) as active ingredients of medicaments for prophylactic and/or therapeutic treatment of spinal cord injury can be confirmed by using, for example, a rat model of spinal cord ablation (Sayer F. T. et al., Exp. Neurol., 175(1):282–96, 2002) or the like. Effectiveness as a medicament for spinal cord injury can be confirmed by orally, intravenously or intraperitoneally administering a compound to the model animal at a dose of 0.1 to 1,000 mg/kg, preferably 0.1 to 100 mg/kg, and, after several weeks, examining a tissue of the spinal cord with a microscope to measure a degree of nerve regeneration.

Usefulness of the compounds of the present invention represented by the aforementioned formula (1) as active ingredients of medicaments for prophylactic and/or therapeutic treatment of pneumonia can be confirmed by using, for example, a mouse model of OVA-induced chronic pneumonia (Henderson W. R. et al., Am. J. Respir. Crit. Care Med., 165(1):108–16, 2002) or the like. Effectiveness as a medicament for pneumonia can be confirmed by orally, intravenously or intraperitoneally administering a compound to the model animal at a dose of 0.1 to 1,000 mg/kg, preferably 0.1 to 100 mg/kg, and counting number of eosinophils or monocytes in the pulmonary cavity.

Usefulness of the compounds of the present invention represented by the aforementioned formula (1) as active ingredients of medicaments for prophylactic and/or therapeutic treatment of hepatitis can be confirmed by using a mouse model of endotoxin-induced liver injury according to, for example, the method described in J. Immunol., 159, 3961–3967, 1997. The usefulness as a medicament for hepatitis can be confirmed by orally, intravenously or intraperitoneally administering a compound to the mouse model of endotoxin-induced liver injury at a dose of 0.1 to 1,000 mg/kg, preferably 0.1 to 100 mg/kg, and measuring the plasmic transaminase level or amount of hydroxyproline in a hepatic tissue, which are indicators of liver function, or performing histological analysis.

Usefulness of the compounds of the present invention represented by the aforementioned formula (1) as active ingredients of medicaments for prophylactic and/or therapeutic treatment of pancreatitis can be confirmed by using, for example, a mouse model of cerulein-inducted acute pancreatitis (Niedirau, C. et al., Gastroenterology 88 (5 Pt 1):1192–204, 1985) or the like. Effectiveness as a medicament for pancreatitis can be confirmed by orally, intravenously or intraperitoneally administering a compound to the model animal at a dose of 0.1 to 1,000 mg/kg, preferably 0.1 to 100 mg/kg, and measuring the serum amylase activity, or weight of pancreas.

Usefulness of the compounds of the present invention represented by the aforementioned formula (1) as active ingredients of medicaments for prophylactic. and/or therapeutic treatment of nephritis can be confirmed by using, for example, a nephritis rat model prepared by administering anti-GBM antibodies obtained by immunizing a rabbit with a GBM fraction derived from a rat to a rat (WO01/56988), or the like. A compound is orally, intravenously or intraperitoneally administered to the nephritis rat model at a dose of 0.1 to 1,000 mg/kg, preferably 0.1 to 100 mg/kg, and the urinary proteins are measured. The usefulness as a medicament for nephritis can be confirmed based on an action of reducing the urinary protein level.

Usefulness of the compounds of the present invention represented by the aforementioned formula (1) as active ingredients for suppressing allograft rejection at the time of organ transplantation can be confirmed by using, for example, a rat model of skin transplantation, rat model of heart transplantation (Ochiai T. et al., Transplant. Proc., 19, 1284–1286, 1987), or the like. Effectiveness as a medicament for suppressing rejection at the time of organ transplantation can be confirmed by orally, intravenously or intraperitoneally administering a compound to a model animal at a dose of 0.1 to 1,000 mg/kg, preferably 0.1 to 100 mg/kg, and estimating the graft survival ratio.

Usefulness of the compounds of the present invention represented by the aforementioned formula (1) as active ingredients of medicaments for prophylactic and/or therapeutic treatment of rheumatoid arthritis can be confirmed by using collagen-induced arthritis model of a rat or mouse (Griffith, M. M. et al., Arthritis Rheumatism, 24:781, 1981; Wooley, P. H. et al., J. Exp. Med., 154:688, 1981). The usefulness as a medicament for rheumatoid arthritis can be confirmed by orally, intravenously or intraperitoneally administering a compound to a model mouse or model rat at a dose of 0.1 to 1,000 mg/kg, preferably 0.1 to 100 mg/kg, and measuring footpad volume or progression of bone destruction.

Usefulness of the compounds of the present invention represented by the aforementioned formula (1) as active ingredients of medicaments for prophylactic and/or therapeutic treatment of chronic obstructive pulmonary disease (COPD) can be confirmed by using, for example, suppression of constriction of an isolated trachea, a model animal of bronchial asthma, a guinea pig model of tobacco smoke exposition (Fuchigami J. et al., 73rd Meeting of Japanese Pharmacological Society, Collection of Abstracts, 2000), inhibition of chemotaxis of human peripheral leucocytes or the like. The usefulness as a medicament for COPD can be confirmed by orally, intravenously or intraperitoneally administering a compound to a guinea pig exposed to tobacco smoke at a dose of 0.1 to 1,000 mg/kg, preferably 0.1 to 100 mg/kg, and counting the number of migrating leucocytes in a bronchoalveolar lavage fluid, or performing histological analysis.

Usefulness of the compounds of the present invention represented by the aforementioned formula (1) as active ingredients of medicaments for prophylactic and/or therapeutic treatment of hepatic fibrosis can be confirmed by using a carbon tetrachloride-induced hepatic fibrosis model according to, for example, the method described in J. Hepatol., 35(4), 474–81, 2001. The usefulness as a medicament for hepatic fibrosis can be confirmed by orally, intravenously or intraperitoneally administering a compound to the hepatic fibrosis model at a dose of 0.1 to 1,000 mg/kg, preferably 0.1 to 100 mg/kg, and measuring the plasmic transaminase level, or amount of hydroxyproline in a hepatic tissue, which are indicators of liver function, or performing histological analysis.

Usefulness of the compounds of the present invention represented by the aforementioned formula (1) as active ingredients of medicaments for prophylactic and/or therapeutic treatment of pulmonary fibrosis can be confirmed by using an animal model of Bleomycin-induced pulmonary fibrosis according to the method described in, for example, Am. J. Respir. Crit. Care Med., 163(1), pp. 210–217, 2001. The usefulness as a medicament for pulmonary fibrosis can be confirmed by orally, intravenously or intraperitoneally administering a compound to the pulmonary fibrosis mouse model at a dose of 0.1 to 1,000 mg/kg, preferably 0.1 to 100 mg/kg, and measuring respiratory function, or amount of hydroxyproline in a pulmonary tissue.

Usefulness of the compounds of the present invention represented by the aforementioned formula (1) as active ingredients of medicaments for prophylactic and/or therapeutic treatment of allergy can be confirmed by using, for example, an atopic dermatitis mouse model or the like according to the method described in, for example, Allergy, 50 (12) 1152–1162, 2001. The usefulness as a medicament for allergy can be confirmed by orally, intravenously or intraperitoneally administering a compound to an NC/Nga mouse pretreated with a surfactant or an organic solvent at a dose of 0.1 to 1,000 mg/kg, preferably 0.1 to 100 mg/kg, when eruption is induced in the mouse by using housedust mite antigens, and measuring the plasmic IgE level, number of eosinophils and the like.

Usefulness of the compounds of the present invention represented by the aforementioned formula (1) as active ingredients of medicaments for prophylactic and/or therapeutic treatment of thrombosis can be confirmed by using, for example, a rabbit model of experimentally-induced venous thrombus (Maekawa, T. et al., Trombos. Diathes. Haemorrh., 60, pp. 363–370, 1974), or the like. Effectiveness as a medicament for thrombosis can be confirmed by orally, intravenously or intraperitoneally administering a compound to the model animal at a dose of 0.1 to 1,000 mg/kg, preferably 0.1 to 100 mg/kg, and estimating the incidence of thrombus.

Usefulness of the compounds of the present invention represented by the aforementioned formula (1) as active ingredients of medicaments for prophylactic and/or therapeutic treatment of bone disease can be confirmed by using, for example, a mouse model of osteoporosis prepared by ovariectomy (OVX mouse, Golub, L. M. et al., Ann. N.Y. Acad. Sci., 878, pp. 290–310, 1999). A compound is orally, intravenously or intraperitoneally administered to the OVX mouse at a dose of 0.1 to 1,000 mg/kg, preferably 0.1 to 100 mg/kg, and deciduous dental roots are measured, or weight of skeletal bones is measured. The usefulness as a medicament for bone disease can be confirmed based on an action for suppressing periodontal breakdowns, or an action for suppressing skeletal bone weight loss.

Usefulness of the compounds of the present invention represented by the aforementioned formula (1) as active ingredients of medicaments for prophylactic and/or therapeutic treatment of AIDS can be confirmed by using, for example, a rhesus monkey model of SIV-infection (Crub S. et al., Acta Neuropathol., 101(2), pp. 85–91, 2001) or the like. Effectiveness as a medicament for AIDS can be confirmed by orally, intravenously or intraperitoneally administering a compound to the model animal at a dose of 0.1 to 1,000 mg/kg, preferably 0.1 to 100 mg/kg, and quantifying the SIV mRNA level in blood.

Usefulness of the compounds of the present invention represented by the aforementioned formula (1) as active ingredients of medicaments for prophylactic and/or therapeutic treatment of cancer can be confirmed by using, for example, a mouse model of ultraviolet ray irradiation-induced skin cancer, a nude mouse model of tumor xenograft (Orengo I. F. et al., Arch Dermatol., 138(6), pp. 823–4, 2002; Ki D. W. et al., Anticancer Res., 22(2A), pp. 777–88, 2002) or the like. Effectiveness as a medicament for cancer can be confirmed by orally, intravenously or intraperitoneally administering a compound to a model animal at a dose of 0.1 to 1,000 mg/kg, preferably 0.1 to 100 mg/kg, and observing progression or reduction of the grafted cancer tissues on the body surface.

Further, when test compounds of the compounds of the present invention or salts thereof were introduced into wells of a 96-well plate at a concentration three times higher than the $IC_{50}$ values obtained in Test Example 1, and the cell suspension prepared in Test Example 1 was added at a density of $10^6$/well, incubated for 30 minutes at room temperature and stained with trypan blue to determine the survival rates of the cells, a viability as high as 90% or more was observed in all the wells. Furthermore, when the compounds of the present invention or salts thereof were orally administered to mice every day at a dose of 30 mg/kg for 5 days, death was not observed. Therefore, the compounds of the present invention had no particular problem also in safety.

As the active ingredients of the medicaments of the present invention, the compounds represented by the aforementioned formula (1), and physiologically acceptable salts thereof can be used. The aforementioned substance, per se, may be administrated as the medicament of the present invention. A pharmaceutical composition containing one or more kinds of the aforementioned substances as the active ingredients and one or more kinds of pharmaceutical additives can be generally prepared and administrated orally or parenterally (e.g., intravenous administration, intramuscular administration, subcutaneous administration, transdermal administration, intrapulmonary administration, intranasal administration, instillation, intraurethral administration, intravaginal administration, sublingual administration, intrarectal administration, and the like) to human or an animal other than human. The aforementioned pharmaceutical composition can be prepared in a dosage form suitable for an intended administration route. More specifically, examples of the pharmaceutical composition suitable for oral administration include oral drug products (tablets, film-coated tablets, intraoral collapsing tablets, hard capsules, soft capsules, powders, fine granules, granules, dry syrups, syrups, pills, troches and the like), and examples of the pharmaceutical composition suitable for parenteral administration include injections (liquid dosage forms, lyophilized dosage forms, suspensions and the like), inhalants, suppositories, transdermally absorbed agents (e.g., tapes), ointments, ophthalmic solutions, ophthalmic ointments, ophthalmic membrane adherent agents and the like. For glaucoma, preferred examples of the dosage form include oral drug products, ophthalmic solutions, ophthalmic ointments, and ophthalmic membrane adherent agents. Further, preferred dosage forms for bronchial asthma or chronic obstructive pulmonary disease include oral drug products, inhalants (for example, a method of inhaling powder of the pharmaceutical composition or a liquid dosage form prepared by dissolving or suspending the pharmaceutical composition in a solvent as it is, or inhaling mist thereof by using a sprayer called atomizer or nebulizer), and transdermal preparations.

These pharmaceutical compositions can be prepared in a conventional manner by using pharmaceutical additives usually used in this field (e.g., excipients, disintegrants, binders, lubricants, colorants, buffering agents, coating agents, flavors, fragrances, emulsifying agents, isotonic agents, solubilizing agents, preservatives, viscosity improvers, pH adjusters and the like). Examples of the excipients include saccharides such as lactose, sucrose, and trehalose, sugar alcohols such as D-mannitol, erythritol, xylitol, and sorbitol, starches such as maize starch, crystalline cellulose, calcium phosphate and the like, examples of the disintegrants include starches, partially pregelatinized starch, carmellose and metal salts thereof, croscarmellose sodium, sodium carboxymethyl starch, agar powder, crospovidone, low substituted hydroxypropylcellulose and the like, examples of the binders include hydroxypropylmethylcellulose, hydroxypropylcellulose, polyvinyl alcohol, methylcellulose, ethylcellulose, popidone, acacia powder, pullulan, pregelatinized starch and the like, and examples of the lubricants include stearic acid and metal salts thereof, talc, silicic acid and metal salts thereof, salt-hardened oil, sucrose fatty acid esters, sodium laurylsulfate, sodium stearyl fumarate and the like When solid pharmaceutical compositions are prepared, there are used pharmaceutical additives including, for example, sucrose, lactose, glucose, fructose, trehalose, D-mannitol, sorbitol, erythritol, xylitol, maltitol, maize starch, potato starch, wheat starch, rice starch, crystalline cellulose, carmellose, carmellose calcium, low substituted hydroxypropylcellulose, croscarmellose sodium, crospovidone, dextrin, cyclodextrin, dextran, agar, xanthane gum, guar gum, rosin, acacia, hydroxypropylcellulose, hydroxypropylmethylcellulose, methylcellulose, ethylcellulose, polyvinyl alcohol, povidone, pregelatinized starch, partly pregelatinized starch, pullulan, pectin, polysorbate, polyethylene glycol, propylene glycol, glycerol, magnesium stearate, talc, light anhydrous silicic acid, hydrated silicon dioxide, kaolin, sucrose fatty acid esters, sodium laurylsulfate, silicic acid, aluminum silicate, magnesium aluminometasilicate, calcium carbonate, sodium hydrogencarbonate, sodium chloride, sodium citrate, citric acid, succinic acid, tartaric acid, hydrogenated castor oil, hydrogenated tallow, stearic acid, cetanol, olive oil, orange oil, soybean oil, cacao butter, carnauba wax, paraffin, vaseline, triacetin, triethyl citrate, iron oxide, caramel, tartrazine, vanillin, carmellose sodium, cellulose derivatives such as hydroxypropylmethylcellulose phthalate, hydroxypropylmethylcellulose acetate succinate, carboxymethylethylcellulose, carboxyvinyl polymer, cellulose acetate phthalate, cellulose acetate trimellitate, ethylcellulose, and cellulose acetate, polyethylene glycol, gelatin, shellac, methacrylic acid and derivatives thereof as well as copolymers thereof, ethylcellulose aqueous dispersion (Aquacoat), silicone oil, triacetin and the like. The tablets can be tablets having usual surfaces of the tablets as required, and examples include sugar-coated tablets, enteric coating tablets, film-coated tablets, bilayer tablets, and multilayer tablets.

When semi-solid pharmaceutical compositions are prepared, there are used pharmaceutical additives including, for example, animal fats and oils (olive oil, maize oil, castor oil and the like), mineral fats and oils (vaseline, white petrolatum, solid paraffin and the like), waxes (ojoba oil, carnauba wax, beeswax and the like), partially or totally synthesized glycerol fatty acid esters. Examples of commercial products include Witepsol (Dynamit Nobel), Pharmasol (Nippon Oil & Fats) and the like. When liquid pharmaceutical compositions are prepared, pharmaceutical additives including, for example, sodium chloride, glucose, sorbitol, glycerol, olive oil, propylene glycol, ethyl alcohol and the like can be used. When injections are prepared, sterile liquid media, for example, physiological saline, isotonic solutions, oily liquids such as sesame oil and soybean oil are used. Further, if necessary, suitable suspending agents such as carboxymethylcellulose sodium, nonionic surfactants, solubilizing agents such as benzyl benzoate and benzyl alcohol and the like may be used together. When eye drops are prepared, they can be prepared as aqueous liquids or aqueous solutions. For example, aqueous solutions can be prepared by using a sterile aqueous solution for injections. To these liquids for instillation, various additives such as buffers (borate buffers, acetate buffers, carbonate buffers and the like are preferred in view of reduction of stimulus), isotonic agents (for example, sodium chloride, potassium chloride and the like can be mentioned), preservatives (for example, methyl paraoxybenzoate, ethyl paraoxybenzoate, benzyl alcohol, chlorobutanol and the like can be mentioned), viscosity improvers (for example, methylcellulose, sodium carboxymethylcellulose and the like can be mentioned) and the like may be optionally added. As for preparation of inhalants, when the composition is inhaled as powder, for example, preparation of the aforementioned solid pharmaceutical composition can be referred to, and the obtained powder is preferably further pulverized. Further, when the composition is inhaled as a liquid, preferable methods include a method of preparing the pharmaceutical composition by referring to the aforementioned preparation of solid pharmaceutical composition to prepare a solid composition and dissolving the solid in distilled water or a suitable solvent to obtain a medicament solution upon use, or a method of preparing the pharmaceutical composition by referring to the aforementioned preparation of liquid pharmaceutical composition to obtain a medicament solution. The size of particles in the aforementioned powder or medicament solution is preferably a particle size suitable for inhalation, and the upper limit of the size is, for example, preferably 100 µm or less, more preferably 50 µm or less, particularly preferably 10 µm or less. The lower limit of the particle size is not particularly limited, and a smaller particle size is more preferred.

A content of the active ingredient in the aforementioned pharmaceutical composition can be suitably chosen depending on a dosage form. The content may be, for example, about 0.1 to 100% by weight, preferably about 1 to 50% by weight, based on the total weight of the composition. A dose of the medicament of the present invention can be suitably determined for each administration in consideration of the age, weight, sexuality of a patient, the type of a disease, the severity of pathological condition and the like. Examples of the doses include, for example, about 1 to 500 mg, preferably about 1 to 100 mg, and most preferably about 1 to 30 mg. These doses can be administered once in a day or several times a day as divided portions.

The compounds represented by the aforementioned formula (1) or physiologically acceptable salts thereof may be used optionally in combination with other one or more kinds of medicaments (a medicament used in combination with the compounds represented by the aforementioned formula (1) or physiologically acceptable salts thereof is hereinafter referred to as a "medicament for combinational use"). For that purpose, administration time of each of the compound represented by the aforementioned general formula (1) or a physiologically acceptable salt and a medicament for combinational use is not limited, and they may be simultaneously administered, or administered with an interval. Therefore, the compound represented by the aforementioned formula (1) or a physiologically acceptable salt thereof and the medicament for combinational use may be prepared in separate forms, or they may be mixed and formed in a single form. When they are mixed, mixing ratio of the compound represented by the aforementioned formula (1) or a physiologically acceptable salt thereof and the medicament for combinational use, form of the both after mixing and the like may be suitably determined depending on an object to be administered, a route of administration, a disease to be treated, symptoms, physicochemical properties, ease of administration and the like.

The dose of the medicament for combinational use can be suitably chosen on the basis of a clinically used dosage. The medicament for combinational use may be a low molecular weight compound, peptide, polymer such as protein, polypeptide, nucleic acid oligomer, peptide nucleic acid (PNA) oligomer, and antibody, vaccine or the like. For example, when the object of administration is a human, the medicament for combinational use may be used in an amount chosen from the range of from 0.01 to 100 weight parts relative to 1 weight part of the compound represented by the aforementioned formula (1) or a physiologically acceptable salt thereof, and the medicament can be used in a preferred form, for example, in the form of an oral preparation, injection (liquid dosage form, suspension and the like), drip infusion, inhalant, suppository, transdermally absorbed agent (e.g., tape), ointment, ophthalmic solution, ophthalmic ointment, ophthalmic membrane adherent agent or the like using the aforementioned pharmaceutical additives as required.

The aforementioned medicament for combinational use can be optionally chosen from various medicaments of which diseases to be applied are those relating to contraction of various cells, those relating to morphological change of various cells, those relating to migration of various cells, those relating to release of various cells, those relating to aggregation of various cells, those relating to apoptosis of various cells, and/or those relating to abnormal gene expression of various cells and the like, depending on object of administration, administration route, objective disease, symptoms and the like For example, for glaucoma, which is exemplified in this specification as a disease relating to contraction of various cells, the medicament for combinational use can be optionally chosen from non-selective β-adrenergic receptor antagonists (e.g., timolol maleate and the like), selective β-adrenergic receptor antagonists (e.g., betaxolol and the like), cholinergic receptor agonists (e.g., pilocarpine hydrochloride and the like), choline esterase inhibitors (e.g., fisostigmine and the like), carbonic anhydrase inhibitors (e.g., brinzolamide and the like), prostaglandine derivatives (e.g., latanoprost and the like), non-selective sympatholytic agents (e.g., epinephrine hydrochloride and the like), selective α1 adrenergic receptor antagonists (e.g., bunazosin hydrochloride and the like), selective α2 adrenergic receptor antagonists (e.g., brimonidin tartrate and the like), α1- and β-adrenergic receptor antagonists (e.g., nipradilol and the like), α-adrenergic receptor agonists (e.g., dipivefrin hydrochloride and the like), calcium antagonists (e.g., iganidipin and the like), and so forth (AI Report, Cima Science Journal, 2002).

For example, for bronchial asthma, which is exemplified in this specification as a disease relating to contraction of various cells or as a disease relating to migration of various cells, the medicament for combinational use can be optionally chosen from suppressants of chemical mediator release (e.g., sodium cromoglicate and the like), anti-histamic agents (e.g., epinastine hydrochloride and the like), suppressants of lipid mediator production, suppressants of Th2 cytokine production (e.g., suplatast tosilate and the like), bronchodilators, steroid agents and the like. Examples of the suppressants of chemical mediator release include thromboxane A2 receptor antagonists (e.g., seratrodast and the like), leukotriene receptor antagonists (e.g., pranlukast and the like), and the like. Examples of the bronchodilators include anticholinergic agents (e.g., ipratropium bromide and the like), xantine derivatives (e.g., theophylline and the like), β2-adrenergic receptor antagonists (e.g., formoterol and the like) and the like. Examples of the steroid agents include oral steroids (e.g., predonizolone and the like), inhalant steroids (e.g., fluticasone propionate and the like) and the like (AI Report, Cima Science Journal, 2002).

For example, for chronic obstructive pulmonary disease (COPD), which is exemplified in this specification as a disease relating to contraction of various cells or as a disease relating to migration of various cells, the medicament for combinational use can be optionally chosen from bronchodilators, steroid agents and the like. Anticholinergic agents and steroid agents that can be exemplified as the bronchodilators are the same as those explained above (AI Report, Cima Science Journal, 2002).

Those mentioned above are examples for selection of the medicament for combinational use, and the medicament for combinational use is not limited to the examples mentioned above.

EXAMPLES

The present invention will be further specifically explained with reference to examples. However, the scope of the present invention is not limited to the following examples.

For thin layer chromatography (TLC), Precoated Silica Gel 60 F254 (produced by Merck) was used. After development with chloroform:methanol (100:1 to 4:1), or ethyl acetate:n-hexane (100:1 to 1:10), spots were observed by UV irradiation (254 nm) or coloration with ninhydrine or phosphomolybdic acid. For drying organic solvent, anhydrous magnesium sulfate or anhydrous sodium sulfate was used. For flash column chromatography, Silica gel 60N (spherical shape, neutral, 40 to 100 μm, produced by Kanto Chemicals) was used. For preparative thin layer chromatography (PTLC), Precoated Silica Gel 60 F254 (20×20 cm, thickness: 2 mm, produced by Merck) was used. Elution was performed with hexane:ethyl acetate=1:0 to 0:1, or chloroform:ethanol=10:1 to 1:1. For the measurement of nuclear magnetic resonance (NMR) spectra, the measurement was performed by using Gemini-300 (FT-NMR, produced by Varian), or AL-300 (FT-NMR, produced by JOEL). As a solvent, deuterated chloroform was used, unless otherwise indicated. Chemical shifts were measured by using tetramethylsilane (TMS) as an internal standard, and indicated with δ (ppm), and binding constant was indicated with J (Hz). Mass spectrum (MS) was measured by liquid chromatography-mass spectrometry (LC-MS). Platform-LC type mass spectrometry apparatus (produced by Micromass) was used as the mass spectrometer, and the measurement was performed by the electrospray ionization (ESI) method. As the liquid chromatography apparatus, an apparatus produced by GILSON was used. As the separation column, Mightysil RP-18 GP 50-4.6 (produced by Kanto Chemicals) was used. Elution was generally performed at a flow rate of 2 ml/minute using a linear gradient of 5 to 100% (v/v) Solution B [acetonitrile containing 0.1% (v/v) acetic acid] in Solution A [water containing 0.1% (v/v) acetic acid] from 0 minute to 5 minutes as the solvent.

Example 1

N-[(5-Isoquinolyl)sulfonyl]-N-(3-phenylpropyl)-1,3-propylenediamine hydrochloride (Exemplary Compound No. 3-35)

(Step A) Synthesis of N-(tert-butoxycarbonyl)-N'-[(5-isoquinolyl)sulfonyl]-1,3-propylenediamine (Intermediate 1)

A solution of N-(tert-butoxycarbonyl)-1,3-propylenediamine (2.09 g, Tokyo Kasei Kogyo) and triethylamine (3.4 ml, Tokyo Kasei Kogyo) in dichloromethane (20 ml) was added with a solution of isoquinoline-5-sulfonyl chloride (2.73 g, prepared according to Japanese Patent Unexamined Publication (Kokai) No. 61-227581) in dichloromethane (15 ml) with stirring and ice cooling and stirred at room temperature for 14 hours and 30 minutes. The reaction mixture was washed successively with saturated aqueous sodium hydrogencarbonate and saturated brine. The organic layer was dried, and then the solvent was evaporated under reduced pressure. Then, the residue was purified by flash column chromatography (chloroform:methanol=50:1) to obtain the title compound (4 g).

(Step B) Synthesis of N-(tert-butoxycarbonyl)-N'-[(5-isoquinolyl)sulfonyl]-N'-(3-phenylpropyl)-1,3-propylenediamine (Intermediate 2)

A solution of Intermediate 1 (640 mg), 1,1'-azobis(N,N-dimethylformamide) (1200 mg, Aldrich or prepared according to Chemistry Letters, 539 (1994)) and 3-phenyl-1-propanol (710 μl, Tokyo Kasei Kogyo) in tetrahydrofuran (30 ml) was added with tri(n-butyl)phosphine (1.75 ml, Tokyo Kasei Kogyo) with stirring and ice cooling and stirred at room temperature under argon atmosphere for 13.5 hours. The precipitates in the reaction mixture were removed by filtration, and then the solvent was evaporated from the filtrate under reduced pressure. The residue was purified by flash column chromatography (hexane/ethyl acetate mixed solvent) to obtain the title compound (913 mg, mixture with a small amount of 3-phenyl-1-propanol).

(Step C) Synthesis of N-[(5-isoquinolyl)sulfonyl]-N-(3-phenylpropyl)-1,3-propylenediamine hydrochloride Intermediate 2 (913 mg) was added with 10% hydrogen chloride/methanol solution (18 ml, Tokyo Kasei Kogyo) at room temperature and stirred for 25 minutes under reflux by heating. After the reaction, the solvent was evaporated under reduced pressure, and the residue was crystallized from a mixed solvent of methanol and diethyl ether to obtain the title compound (653 mg).

$^1$H-NMR (DMSO-$d_6$) δ (ppm): 1.65–1.90 (4H, m), 2.39–2.45 (2H, m), 2.67–2.84 (2H, m), 3.21–3.34 (2H, m), 3.35–3.46 (2H, m), 7.05 (1H, d, J=6.9 Hz), 7.11–7.29 (4H, m), 7.85–8.05 (4H, m), 8.42 (1H, d, J=7.4 Hz), 8.50 (1H, d, J=6.3 Hz), 8.60 (1H, d, J=8.5 Hz), 8.75 (1H, d, J=6.3 Hz), 9.71 (1H, s)

MS (m/z): 384 (MH+)

Example 2

N-[(5-Isoquinolyl)sulfonyl]-N-[2-(2-thienyl)ethyl]-1,3-propylenediamine hydrochloride (Exemplary Compound No. 3-37)

(Step A) Synthesis of N-(tert-butoxycarbonyl)-N'-[(5-isoquinolyl)sulfonyl]-N'-[2-(2-thienyl)ethyl]-1,3-propylenediamine (Intermediate 3)

According to the method of Example 1, Step B with the modifications that the reaction was carried out for 24 hours, and the compound was purified by silica gel column chromatography (n-hexane:ethyl acetate=3:1), the title compound (333 mg) was obtained from Intermediate 1 (365 mg), tri(n-butyl)phosphine (747 μl), 2-(2-thienyl)ethanol (385 mg, Aldrich) and 1,1'-azobis(N,N-dimethylformamide) (517 mg).

(Step B) Synthesis of N-[(5-isoquinolyl)sulfonyl]-N-[2-(2-thienyl)ethyl]-1,3-propylenediamine hydrochloride According to the method of Example 1, Step C, deprotection was performed (50° C., 2 hours) by using Intermediate 3 (238 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (202 mg) as white powdery solid.

$^1$H-NMR (DMSO-$d_6$) δ (ppm): 1.82–1.96 (2H, m), 2.70–2.83 (2H, m), 2.94–3.04 (2H, m), 3.41–3.55 (4H, m), 6.70–6.80 (2H, m), 7.13–7.20 (1H, m), 7.96–8.27 (4H, m), 8.47–8.77 (4H, m), 9.76–9.86 (1H, br.s)

MS (m/z): 376 (MH+)

Example 3

4-{N-[(5-Isoquinolyl)sulfonyl]-N-(3-phenylpropyl)}aminopiperidine hydrochloride (Exemplary Compound No. 3-205)

(Step A) Synthesis of 1-(tert-butoxycarbonyl)-4-N-[(5-isoquinolyl)sulfonyl]aminopiperidine (Intermediate 4)

According to the method of Example 1, Step B, the title compound (665 mg) was obtained from (5-isoquinolyl)sulfonyl chloride (455 mg), 4-amino-1-(tert-butoxycarbonyl)piperidine (441 mg, Asta Tech) and triethylamine (335 μl).

(Step B) Synthesis of 1-(tert-butoxycarbonyl)-4-{N-[(5-isoquinolyl)sulfonyl]-N-(3-phenylpropyl)}aminopiperidine (Intermediate 5)

According to the method of Example 1, Step B with the modifications that the reaction was carried out for 24 hours, and the compound was purified by silica gel column chromatography (n-hexane:ethyl acetate=3:1), the title compound (357 mg) was obtained from Intermediate 4 (392 mg), tri(n-butyl)phosphine (747 μl), 3-phenyl-1-propanol (405 μl) and 1,1'-azobis(N,N-dimethylformamide) (517 mg).

(Step C) Synthesis of 4-{N-[(5-isoquinolyl)sulfonyl]-N-(3-phenylpropyl)}aminopiperidine hydrochloride According to the method of Example 1, Step C, deprotection was performed (50° C., 2 hours) by using Intermediate 5 (254 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (192 mg) as white powdery solid.

$^1$H-NMR (DMSO-$d_6$) δ (ppm): 1.64–1.83 (4H, m), 1.98–2.15 (2H, m), 2.88–3.03 (2H, m), 3.20–3.30 (4H, m), 3.90–4.20 (3H, m), 7.08–7.30 (5H, m), 7.91–8.00 (1H, m) 8.42–9.13 (6H, m), 9.71–9.82 (1H, br.s)

MS (m/z): 410 (MH+)

Example 4

N-[(5-Isoquinolyl)sulfonyl]-N-(4-phenylbutyl)-1,3-propylenediamine hydrochloride (Exemplary Compound No. 3-47)

(Step A) Synthesis of N-(tert-butoxycarbonyl)-N'-[(5-isoquinolyl)sulfonyl]-N'-(4-phenylbutyl)-1,3-propylenediamine (Intermediate 6)

According to the method of Example 1, Step B with the modifications that the reaction was carried out for 24 hours, and the compound was purified by silica gel column chromatography (n-hexane:ethyl acetate=3:1), the title compound (348 mg) was obtained from Intermediate 1 (365 mg), tri(n-butyl)phosphine (747 μl), 4-phenyl-1-butanol (462 μl, Tokyo Kasei Kogyo) and 1,1'-azobis(N,N-dimethylformamide) (517 mg).

(Step B) Synthesis of N-[(5-isoquinolyl)sulfonyl]-N-(4-phenylbutyl)-1,3-propylenediamine hydrochloride According to the method of Example 1, Step C, deprotection was performed (50° C., 2 hours) by using Intermediate 6 (249 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (188 mg) as white powdery solid.

$^1$H-NMR (DMSO-$d_6$) δ (ppm): 1.28–1.48 (4H, m), 1.77–1.87 (2H, m), 2.40–2.46 (2H, m), 2.67–2.78 (2H, m), 3.25–3.31 (2H, m), 3.36–3.41 (2H, m), 7.01–7.05 (2H, m), 7.13–7.27 (3H, m), 7.94–8.12 (4H, m), 8.47–8.65 (3H, m), 8.76 (1H, dd, J=3, 6.6 Hz), 9.72–9.70 (1H, br.s)

MS (m/z): 398 (MH+)

Example 5

N-[(4-Methyl-5-isoquinolyl)sulfonyl]-N-(3-phenylpropyl)-1,3-propylenediamine hydrochloride (Exemplary Compound No. 3-715)

(Step A) Synthesis of N-(tert-butoxycarbonyl)-N'-[(4-bromo-5-isoquinolyl)sulfonyl]-1,3-propylenediamine (Intermediate 7)

According to the method of Example 1, Step A, a solution of N-(3-aminopropyl)carbamic acid tert-butyl ester (383 mg) and triethylamine (335 μl) in dichloromethane (3 ml) was added with a solution of (4-bromo-5-isoquinolyl)sulfonyl chloride (483 mg, prepared from 4-bromo-5-aminoisoquinoline obtained in Reference Example 1 according to the method described in Japanese Patent No. 2763791) in dichloromethane (3 ml) with stirring and ice cooling and stirred at room temperature for 20 hours. The reaction mixture was successively washed with saturated aqueous sodium hydrogencarbonate twice and with saturated brine, and the organic layer was dried over anhydrous sodium sulfate (Wako Pure Chemical Industries). Then, the solvent was evaporated under reduced pressure to obtain a residue (711 mg). Subsequently, according to the method of Example 1, Step B with the modifications that the reaction was carried out for 24 hours, and the compound was purified by silica gel column chromatography (n-hexane:ethyl acetate=3:1), the title compound (540 mg) was obtained from the aforementioned residue, tri(n-butyl)phosphine (747 µl), 3-phenyl-1-propanol (405 µl) and 1,1'-azobis(N,N-dimethylformamide) (517 mg).

(Step B) Synthesis of N-(tert-butoxycarbonyl)-N'-[(4-methyl-5-isoquinolyl)sulfonyl]-N'-(3-phenylpropyl)-1,3-propylenediamine (Intermediate 8)

Under nitrogen atmosphere, a suspension of Intermediate 7 (540 mg) and dichloro(1,3-bis(diphenylphosphino)propane)nickel(II) (5.2 mg, Tokyo Kasei Kogyo) in tetrahydrofuran (5 ml) was added dropwise with a solution of methyl iodide magnesium in diethyl ether (0.84 M, 1.3 ml, Kanto Chemicals) and stirred with heating at 50° C. for 15 hours. The reaction mixture was returned to room temperature and slowly added with water (2.5 ml) and then 2 N aqueous sodium hydroxide (10 ml). The insoluble matters were removed by filtration, and then the target compound was extracted three times with ethyl acetate (30 ml for each time). The combined organic layer was washed once with saturated brine (30 ml) and dried over anhydrous magnesium sulfate. The solvent was evaporated under reduced pressure, and the residue was purified by silica gel column chromatography (n-hexane:ethyl acetate=2:1) to obtain the title compound (143 mg).

(Step C) Synthesis of N-[(4-methyl-5-isoquinolyl)sulfonyl]-N-(3-phenylpropyl)-1,3-propylenediamine hydrochloride According to the method of Example 1, Step C, deprotection was performed (5° C., 2 hours) by using Intermediate 8 (87 mg) and 10% hydrogen chloride/methanol solution (5 ml). The reaction mixture was cooled to room temperature, and the solvent was evaporated under reduced pressure. The residue was added with methanol (1 ml) and diethyl ether (3 ml). The deposited precipitates were collected by filtration and washed with diethyl ether to obtain the title compound (70 mg) as white powdery solid.

$^1$H-NMR (DMSO-$d_6$) δ (ppm): 1.97–2.08 (4H, m), 2.58–2.63 (2H, m), 2.79–2.87 (2H, m), 3.03 (3H, d, J=2.1 Hz), 3.44–3.57 (4H, m), 7.16–7.30 (5H, m), 7.90–8.19 (5H, m), 8.58–8.68 (2H, m), 9.58–9.65 (1H, br.s)

MS (m/z): 398 (MH+)

Example 6

N-[(5-Isoquinolyl)sulfonyl]-N-[2-(phenylsulfonyl)ethyl]-1,3-propylenediamine hydrochloride (Exemplary Compound No. 3-46)

(Step A) Synthesis of N-(tert-butoxycarbonyl)-N'-[(5-isoquinolyl)sulfonyl]-N'-[2-(phenylsulfonyl)ethyl]-1,3-propylenediamine (Intermediate 9)

According to the method of Example 1, Step B with the modifications that the reaction was carried out for 24 hours, and the compound was purified by silica gel column chromatography (n-hexane:ethyl acetate=3:1), the title compound (346 mg) was obtained from Intermediate 1 (365 mg), tri(n-butyl)phosphine (747 µl), 2-(phenylsulfonyl)ethanol (359 µl, Aldrich) and 1,1'-azobis(N,N-dimethylformamide) (517 mg).

(Step B) Synthesis of N-[(5-isoquinolyl)sulfonyl]-N-[2-(phenylsulfonyl)ethyl]-1,3-propylenediamine hydrochloride According to the method of Example 1, Step C, deprotection was performed (50° C., 2 hours) by using Intermediate 9 (266 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (203 mg) as white powdery solid.

$^1$H-NMR (DMSO-$d_6$) δ (ppm): 1.72–1.83 (2H, m), 2.70–2.81 (2H, m), 3.33–3.69 (6H, m), 7.66–8.00 (9H, m), 8.23–8.32 (2H, m), 8.55–8.75 (2H, m), 9.71 (1H, s)

MS (m/z): 434 (MH+)

Example 7

N-[(5-Isoquinolyl)sulfonyl]-N-[2-(phenylsulfonyl)ethyl]ethylenediamine hydrochloride (Exemplary Compound No. 3-12)

(Step A) Synthesis of N-(tert-butoxycarbonyl)-N'-[(5-isoquinolyl)sulfonyl]ethylenediamine (Intermediate 10)

According to the method of Example 1, Step A, the title compound (246 mg) was obtained from (5-isoquinolyl)sulfonyl chloride (455 mg), N-(2-aminoethyl)carbamic acid tert-butyl ester (353 mg, Tokyo Kasei Kogyo) and triethylamine (335 µl).

(Step B) Synthesis of N-(tert-butoxycarbonyl)-N'-[(5-isoquinolyl)sulfonyl]-N'-[2-(phenylsulfonyl)ethyl]ethylenediamine (Intermediate 11)

According to the method of Example 1, Step B with the modifications that the reaction was carried out for 24 hours, and the compound was purified by silica gel column chromatography (n-hexane:ethyl acetate=3:1), the title compound (337 mg) was obtained from Intermediate 10 (352 mg), tri(n-butyl)phosphine (747 µl), 2-(phenylsulfonyl)ethanol (359 µl) and 1,1'-azobis(N,N-dimethylformamide) (517 mg).

(Step C) Synthesis of N-[(5-isoquinolyl)sulfonyl]-N-[2-(phenylsulfonyl)ethyl]ethylenediamine hydrochloride According to the method of Example 1, Step C, deprotection was performed (50° C., 2 hours) by using Intermediate 11 (260 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (197 mg) as white powdery solid.

$^1$H-NMR (DMSO-$d_6$) δ (ppm): 2.85–2.96 (2H, m), 3.51–3.61 (4H, m), 3.72–3.78 (2H, m), 7.66–7.71 (2H, m), 7.78–7.83 (1H, m), 7.87–7.90 (2H, m), 7.95–8.01 (1H, m), 8.17 (3H, br.s), 8.40–8.43 (1H, m), 8.50–8.54 (1H, m), 8.68 (1H, d, J=8.1 Hz), 8.77 (1H, d, J=6.6 Hz), 9.79 (1H, s)

MS (m/z): 420 (MH+)

Example 8

N-[(1-Amino-5-isoquinolyl)sulfonyl]-N-(3-phenyl-propyl)-1,3-propylenediamine hydrochloride (Exemplary Compound No. 3-647)

(Step A) Synthesis of N-(tert-butoxycarbonyl)-N'-[(1-chloro-5-isoquinolyl)sulfonyl]-1,3-propylenediamine (Intermediate 12)

According to the method of Example 1, Step A, a solution of N-(3-aminopropyl)carbamic acid tert-butyl ester (383 mg) and triethylamine (335 µl) in dichloromethane (3 ml) was added with a solution of (1-chloro-5-isoquinolyl)sulfonyl chloride (524 mg, prepared from (1-chloro-5-isoquinolyl)sulfonyl chloride hydrochloride according to the method of Japanese Patent Unexamined Publication (Kokai) No. 63-2980) in dichloromethane (3 ml) with stirring and ice cooling and stirred at room temperature for 20 hours. The reaction mixture was successively washed with saturated aqueous sodium hydrogencarbonate twice and with saturated brine. The organic layer was dried over anhydrous sodium sulfate (Wako Pure Chemical Industries), and then the solvent was evaporated under reduced pressure. Then, the residue was purified by silica gel column chromatography (n-hexane:ethyl acetate=2:1) to obtain the title compound (640 mg).

(Step B) Synthesis of N-[(i-amino-5-isoquinolyl)sulfonyl]-N'-(tert-butoxycarbonyl)-1,3-propylenediamine (Intermediate 13)

A solution of Intermediate 12 (400 mg) in 1,4-dioxane (2 ml, Wako Pure Chemical Industries) was added with 28% aqueous ammonia (2 ml, Wako Pure Chemical Industries) and stirred in a sealed tube with heating at 130° C. for 24 hours. The reaction mixture was cooled to room temperature, then added with saturated aqueous sodium hydrogencarbonate and extracted three times with dichloromethane (30 ml for each time). The combined organic layer was dried over anhydrous sodium sulfate, and then the solvent was evaporated under reduced pressure. The obtained light yellow solid was recrystallized from methanol to obtain the title compound (228 mg) as white powdery solid.

(Step C) Synthesis of N-[(1-amino-5-isoquinolyl)sulfonyl]-N'-(tert-butoxycarbonyl)-N-(3-phenylpropyl)-1,3-propylenediamine (Intermediate 14)

According to the method of Example 1, Step B with the modifications that the reaction was carried out for 24 hours, and the compound was purified by silica gel column chromatography (ethyl acetate:methanol=30:1), the title compound (150 mg) was obtained from Intermediate 13 (190 mg), tri(n-butyl)phosphine (374 µl), 3-phenyl-1-propanol (203 µl) and 1,1'-azobis(N,N-dimethylformamide) (259 mg).

(Step D) Synthesis of N-[(1-amino-5-isoquinolyl)sulfonyl]-N-(3-phenylpropyl)-1,3-propylenediamine hydrochloride According to the method of Example 1, Step C, deprotection was performed (5° C., 2 hours) by using Intermediate 14 (125 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (90 mg) as white powdery solid.

$^1$H-NMR (DMSO-$d_6$) δ (ppm): 1.67–1.86 (4H, m), 2.39–2.49 (2H, m), 2.65–2.74 (2H, m), 3.15–3.70 (4H, m), 7.04–7.28 (5H, m), 7.61 (1H, d, J=7.5 Hz), 7.80–7.91 (2H, m), 8.05 (3H, br.s), 8.38 (1H, d, J=7.5 Hz), 8.95 (1H, d, J=8.1 Hz), 9.52 (1.5H, br.s), 13.90 (0.5H, br.s)

MS (m/z): 399 (MH+)

Example 9

N-[(1-Amino-5-isoquinolyl)sulfonyl]-N-[2-(phenylsulfonyl)ethyl]ethylenediamine hydrochloride (Exemplary Compound No. 3-624)

(Step A) Synthesis of N-(tert-butoxycarbonyl)-N'-[(1-chloro-5-isoquinolyl)sulfonyl]ethylenediamine (Intermediate 15)

According to the method of Example 1, Step A, the title compound (617 mg) was obtained from (1-chloro-5-isoquinolyl)sulfonyl chloride (524 mg), N-(2-aminoethyl)carbamic acid tert-butyl ester (353 mg) and triethylamine (335 µl).

(Step B) Synthesis of N-[(1-amino-5-isoquinolyl)sulfonyl]-N'-(tert-butoxycarbonyl)ethylenediamine (Intermediate 16)

According to the method of Example 8, Step B, the title compound (220 mg) was obtained from Intermediate 15 (386 mg) as white powdery solid.

(Step C) Synthesis of N-[(1-amino-5-isoquinolyl)sulfonyl]-N'-(tert-butoxycarbonyl)-N-[2-(phenylsulfonyl)ethyl]ethylenediamine (Intermediate 17)

According to the method of Example 1, Step B with the modifications that the reaction was carried out for 24 hours, and the compound was purified by silica gel column chromatography (ethyl acetate:methanol=20:1), the title compound (134 mg) was obtained from Intermediate 16 (183 mg), tri(n-butyl)phosphine (374 µl), 2-(phenylsulfonyl)ethanol (180 µl) and 1,1'-azobis(N,N-dimethylformamide) (259 mg).

(Step D) Synthesis of N-[(1-amino-5-isoquinolyl)sulfonyl]-N-[2-(phenylsulfonyl)ethyl]ethylenediamine hydrochloride According to the method of Example 1, Step C, deprotection was performed (50° C., 2 hours) by using Intermediate 17 (134 mg) and 10% hydrogen chloride/methanol solution (2.5 ml). The reaction mixture was cooled to room temperature and then added with diethyl ether (2.5 ml). The deposited precipitates were collected by filtration and washed with diethyl ether to obtain the title compound (100 mg) as white powdery solid.

$^1$H-NMR (DMSO-$d_6$) δ (ppm): 2.90–3.00 (2H, m), 3.49–3.59 (4H, m), 3.72–3.78 (2H, m), 7.56 (1H, d, J=7.2 Hz), 7.66–7.72 (2H, m), 7.78–7.92 (5H, m), 8.15 (3H, br.s), 8.33 (1H, d, J=6.9 Hz), 8.98 (1H, d, J=8.1 Hz), 9.55 (1.5H, br.s), 13.90 (0.5H, br.s)

MS (m/z): 435 (MH+)

Example 10

3-[(1-Amino-5-isoquinolyl)oxy]propylamine hydrochloride (Exemplary Compound No. 1-9)

(Step A) Synthesis of N-(tert-butoxycarbonyl)-3-[(1-chloro-5-isoquinolyl)oxy]propylamine (Intermediate 18)

A suspension of 1-chloro-5-hydroxyisoquinoline (539 mg, synthesized according to the method described in a reference (Georgian, V. et al., J. Org. Chem., 27, 4571 (1962))), (3-hydroxypropyl)carbamic acid tert-butyl ester (1.58 g, Tokyo Kasei Kogyo) and 1,1'-azobis(N,N-dimethylformamide) (1.55 g) in tetrahydrofuran (8 ml) was added with tri(n-butyl)phosphine (2.24 ml) with ice cooling and stirred at room temperature for 24 hours. The deposited solid was removed by filtration, and the solvent was evaporated under reduced pressure. Then, the residue was purified by silica gel column chromatography (n-hexane:ethyl acetate=3:1) to obtain the title compound (860 mg) as white powdery solid.

(Step B) Synthesis of N-(tert-butoxycarbonyl)-3-[1-(4-methoxybenzyl)amino-5-isoquinolyl]oxy]propylamine (Intermediate 19)

The title compound was synthesized from Intermediate 18 according to the method described in a reference (Buchwald, S. L., J. Org. Chem., 65, 1158 (2000)). That is, a suspension of Intermediate 18 (674 mg), tris (dibenzylideneacetone)dipalladium(0) (92 mg, Aldrich), 2-(di-tert-butylphosphino)biphenyl (119 mg, Strem Chemicals), 4-methoxybenzylamine (329 mg, Tokyo Kasei Kogyo) and sodium tert-butoxide (269 mg, Tokyo Kasei Kogyo) in toluene (5 ml) was stirred with heating at 80° C. under nitrogen atmosphere for 2 hours. The reaction mixture was cooled to room temperature and added with ethyl acetate (5 ml). The insoluble matters were removed by filtration through Celite. The solvent was evaporated under reduced pressure, and the residue was purified by silica gel column chromatography (n-hexane:ethyl acetate=1:1) to obtain the title compound (525 mg).

(Step C) Synthesis of N-(tert-butoxycarbonyl)-3-[(1-amino-5-isoquinolyl)oxy]propylamine (Intermediate 20)

Intermediate 19 (438 mg) was dissolved in 95% trifluoroacetic acid (5 ml) and stirred with heating at 50° C. for 20 hours. The reaction mixture was returned to room temperature, and the solvent was evaporated under reduced pressure. The residue was dissolved in methanol (5 ml), added with triethylamine (558 μl) and di-tert-butyl dicarbonate (437 mg, Wako Pure Chemical Industries) and stirred at room temperature for 2 hours. The solvent was evaporated under reduced pressure, and the residue was purified by silica gel column chromatography (n-hexane:ethyl acetate=1:3) to obtain the title compound (222 mg).

(Step D) Synthesis of 3-[(1-amino-5-isoquinolyl)oxy]propylamine hydrochloride

According to the method of Example 1, Step C, deprotection was performed (50° C., 2 hours) by using Intermediate 20 (159 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (116 mg) as white powdery solid.

$^1$H-NMR (DMSO-$d_6$) δ (ppm): 1.91–2.22 (2H, m), 3.00–3.06 (2H, m), 4.29 (2H, t, J=5.9 Hz), 7.37 (1H, dd, J=2.4, 7.2 Hz), 7.48 (1H, d, J=8.1 Hz), 7.68–7.74 (2H, m), 8.10–8.30 (4H, m), 9.22 (1.4H, br.s), 13.70 (0.6H, br.s)
MS (m/z): 218 (MH+)

Example 11

3-[(1-Amino-5-isoquinolyl)oxy]methylpiperidine hydrochloride (Exemplary Compound No. 1-11)

(Step A) Synthesis of 1-(tert-butoxycarbonyl)-3-[(1-chloro-5-isoquinolyl)oxy]methylpiperidine (Intermediate 21)

According to the method of Example 10, Step A, the title compound (960 mg) was obtained from 1-chloro-5-hydroxyisoquinoline (539 mg), (3-hydroxymethylpiperidine) carbamic acid tert-butyl ester (1.94 g, Murphy, Larry), tri(n-butyl)phosphine (2.24 ml) and 1,1'-azobis(N,N-dimethylformamide) (1.55 g).

(Step B) Synthesis of 1-(tert-butoxycarbonyl)-3-[1-(4-methoxybenzyl)amino-5-isoquinolyl]oxy]methylpiperidine (Intermediate 22)

According to the method of Example 10, Step B, the title compound (573 mg) was obtained from Intermediate 21 (754 mg), tris(dibenzylideneacetone)dipalladium(0) (92 mg), 2-(di-tert-butylphosphino)biphenyl (119 mg), 4-methoxybenzylamine (329 mg) and sodium tert-butoxide (269 mg).

(Step C) Synthesis of 1-(tert-butoxycarbonyl)-3-[(1-amino-5-isoquinolyl)oxy]methylpiperidine (Intermediate 23)

According to the method of Example 10, Step C, the title compound (250 mg) was obtained from Intermediate 22 (478 mg), 95% trifluoroacetic acid (5 ml), triethylamine (558 μl) and di-tert-butyl dicarbonate (437 mg).

(Step D) Synthesis of 3-[(1-amino-5-isoquinolyl)oxy]methylpiperidine hydrochloride According to the method of Example 1, Step C, deprotection was performed (50° C., 2 hours) by using Intermediate 23 (179 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (132 mg) as white powdery solid.

$^1$H-NMR (DMSO-$d_6$) δ (ppm): 1.42–1.55 (1H, m), 1.73–1.93 (3H, m), 2.30–2.43 (1H, m), 2.80–2.92 (2H, m), 3.21–3.44 (4H, m), 4.07–4.20 (2H, m), 7.38 (1H, dd, J=1.8, 6.9 Hz), 7.48 (1H, d, J=8.1 Hz), 7.68–7.74 (2H, m), 8.17 (1H, d, J=8.1 Hz), 9.10–9.50 (3.4H, m), 13.68 (0.6H, br.s)
MS (m/z): 258 (MH+)

Example 12

N-[(1-Hydroxy-5-isoquinolyl)sulfonyl]-N-[2-(phenylsulfonyl)ethyl]ethylenediamine hydrochloride (Exemplary Compound No. 3-318)

(Step A) Synthesis of N-[(1-chloro-5-isoquinolyl)sulfonyl]-N'-(tert-butoxycarbonyl)-N-[2-(phenylsulfonyl)ethyl]ethylenediamine (Intermediate 24)

According to the method of Example 1, Step B with the modifications that the reaction was carried out for 24 hours, and the compound was purified by silica gel column chromatography (n-hexane:ethyl acetate=2:1), the title compound (416 mg) was obtained from Intermediate 15 (386 mg), tri(n-butyl)phosphine (747 μl), 2-(phenylsulfonyl)ethanol (359 μl) and 1,1'-azobis(N,N-dimethylformamide) (517 mg).

(Step B) Synthesis of N-[(1-hydroxy-5-isoquinolyl)sulfonyl]-N-[2-(phenylsulfonyl)ethyl]ethylenediamine hydrochloride Intermediate 24 (277 mg) was added with concentrated hydrochloric acid (5 ml) and stirred with heating at 90° C. for 48 hours. The reaction mixture was cooled to room temperature. The deposited precipitates were collected by filtration and washed with ethanol to obtain the title compound (200 mg) as white powdery solid.

$^1$H-NMR (DMSO-$d_6$) δ (ppm): 2.90–2.94 (2H, m), 3.42–3.47 (2H, m), 3.50–3.57 (2H, m), 3.66–3.72 (2H, m), 6.98 (1H, d, J=7.5 Hz), 7.37 (1H, t, J=6.9 Hz), 7.60 (1H, t, J=7.8 Hz), 7.66–7.72 (2H, m), 7.78–7.83 (1H, m), 7.88 (2H, d, J=7.8 Hz), 7.94 (3H, br.s), 8.07 (1H, d, J=7.2 Hz), 8.51 (1H, d, J=8.1 Hz), 11.73 (1H, d, J=5.4 Hz)

MS (m/z): 436 (MH+)

Example 13

N-[(1-Hydroxy-5-isoquinolyl)sulfonyl]-N-[2-(phenylsulfonyl)ethyl]-1,3-propylenediamine hydrochloride (Exemplary Compound No. 3-352)

(Step A) Synthesis of N-[(1-chloro-5-isoquinolyl)sulfonyl]-N'-(tert-butoxycarbonyl)-N-[2-(phenylsulfonyl)ethyl]propylenediamine (Intermediate 25)

According to the method of Example 1, Step B with the modifications that the reaction was carried out for 24 hours, and the compound was purified by silica gel column chromatography (n-hexane:ethyl acetate=2:1), the title compound (426 mg) was obtained from Intermediate 12 (400 mg), tri(n-butyl)phosphine (747 μl), 2-(phenylsulfonyl)ethanol (359 μl) and 1,1'-azobis(N,N-dimethylformamide) (517 mg).

(Step B) Synthesis of N-[(1-hydroxy-5-isoquinolyl)sulfonyl]-N-[2-(phenylsulfonyl)ethyl]propylenediamine hydrochloride Intermediate 25 (284 mg) was added with concentrated hydrochloric acid (5 ml) and stirred with heating at 90° C. for 48 hours. The reaction mixture was cooled to room temperature, and then the solvent was evaporated under reduced pressure. The residue was added with ethanol (4 ml). The deposited precipitates were collected by filtration and washed with ethanol to obtain the title compound (206 mg) as white powdery solid.

$^1$H-NMR (DMSO-$d_6$) δ (ppm): 1.69–1.79 (2H, m), 2.67–2.75 (2H, m), 3.30–3.48 (4H, m), 3.56–3.62 (2H, m), 6.92 (1H, d, J=7.5 Hz), 7.35 (1H, dd, J=6.0, 7.5 Hz), 7.57 (1H, t, J=7.5 Hz), 7.65–7.72 (1H, m), 7.78–7.90 (6H, m), 8.01 (1H, d, J=7.8 Hz), 8.49 (1H, d, J=7.8 Hz), 11.71 (1H, d, J=5.7 Hz)

MS (m/z): 450 (MH+)

Example 14

N-[(1-Hydroxy-5-isoquinolyl)sulfonyl]-N-(3-phenylpropyl)-1,3-propylenediamine hydrochloride (Exemplary Compound No. 3-341)

(Step A) Synthesis of N-[(1-chloro-5-isoquinolyl)sulfonyl]-N'-(tert-butoxycarbonyl)-N-(3-phenylpropyl)-1,3-propylenediamine (Intermediate 26)

According to the method of Example 1, Step B with the modifications that the reaction was carried out for 24 hours, and the compound was purified by silica gel column chromatography (n-hexane:ethyl acetate=3:1), the title compound (414 mg) was obtained from Intermediate 12 (400 mg), tri(n-butyl)phosphine (747 μl), 3-phenyl-1-propanol (405 μl) and 1,1'-azobis(N,N-dimethylformamide) (517 mg).

(Step B) Synthesis of N-[(1-hydroxy-5-isoquinolyl)sulfonyl]-N-(3-phenylpropyl)-1,3-propylenediamine hydrochloride According to the method of Example 13, Step B, the title compound (185 mg) was obtained from Intermediate 26 (259 mg) as white powdery solid.

$^1$H-NMR (DMSO-$d_6$) δ (ppm): 1.66–1.88 (4H, m), 2.40–2.46 (2H, m), 2.71–2.77 (2H, m), 3.19–3.25 (2H, m), 3.20–3.38 (2H, m), 7.03–7.27 (6H, m), 7.36–7.40 (1H, m), 7.61 (1H, t, J=7.8 Hz), 7.94 (3H, bs.s), 8.16 (1H, dd, J=0.9, 7.8 Hz), 8.49 (1H, d, J=8.1 Hz), 11.69 (1H, br.s)

MS (m/z): 400 (MH+)

Example 15

N-(5-Isoquinolyl)ethylenediamine hydrochloride (Step A) Synthesis of N-(tert-butoxycarbonyl)-N'-(5-isoquinolyl)ethylenediamine (Intermediate 27)

Under nitrogen atmosphere, a suspension of 5-bromoisoquinoline (416 mg, Spex), tris(dibenzylideneacetone)dipalladium(0) (92 mg), 2-(di-tert-butylphosphino)biphenyl (119 mg), N-(2-aminoethyl)carbamic acid tert-butyl ester (385 mg) and sodium tert-butoxide (269 mg) in toluene (5 ml) was stirred with heating at 80° C. for 2 hours. The reaction mixture was cooled to room temperature and added with ethyl acetate (5 ml). The insoluble matters were removed by filtration through Celite. The solvent was evaporated under reduced pressure, and the residue was purified by silica gel column chromatography (n-hexane:ethyl acetate=2:1) to obtain the title compound (402 mg).

(Step B) Synthesis of N-(5-isoquinolyl)ethylenediamine hydrochloride

According to the method of Example 1, Step C, deprotection was performed (50° C., 2 hours) by using Intermediate 27 (287 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (252 mg) as light yellow powdery solid.

$^1$H-NMR (DMSO-$d_6$) δ (ppm): 3.12–3.21 (2H, m), 3.55–3.60 (2H, m), 7.17 (1H, d, J=7.8 Hz), 7.27 (1H, br.s), 7.68 (1H, d, J=8.1 Hz), 7.79 (1H, dd, J=7.8, 8.1 Hz), 8.30 (3H, br.s), 8.62 (1H, d, J=6.6 Hz), 8.84 (1H, d, J=6.6 Hz), 9.69 (1H, s)

MS (m/z): 188 (MH+)

Example 16

N-(5-Isoquinolyl)-1,3-propylenediamine hydrochloride (Exemplary Compound No. 2-1)

(Step A) Synthesis of N-(tert-butoxycarbonyl)-N'-(5-isoquinolyl)-1,3-propylenediamine (Intermediate 28)

According to the method of Example 15, Step A, the title compound (422 mg) was obtained from 5-bromoisoquinoline (416 mg), tris(dibenzylideneacetone)dipalladium(0) (92 mg), 2-(di-tert-butylphosphino)biphenyl (119 mg), N-(3-aminopropyl)carbamic acid tert-butyl ester (418 mg) and sodium tert-butoxide (269 mg).

(Step B) Synthesis of N-(5-isoquinolyl)-1,3-propylenediamine hydrochloride

According to the method of Example 1, Step C, deprotection was performed (50° C., 2 hours) by using Intermediate 28 (301 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (264 mg) as light yellow powdery solid.

$^1$H-NMR (DMSO-$d_6$) δ (ppm): 1.96–2.05 (2H, m), 2.90–3.00 (2H, m), 3.37–3.45 (2H, m), 7.12 (1H, d, J=8.1 Hz), 7.27 (1H, br.s), 7.64 (1H, d, J=7.8 Hz), 7.78 (1H, dd, J=7.8, 8.1 Hz), 8.17 (3H, br.s), 8.59 (1H, d, J=6.9 Hz), 8.81 (1H, d, J=6.9 Hz), 9.69 (1H, s)

MS (m/z): 202 (MH+)

Example 17

N-(5-Isoquinolyl)-N'-methyl-1,3-propylenediamine hydrochloride (Step A) Synthesis of N-(tert-butoxycarbonyl)-N-methyl-N'-(5-isoquinolyl)-1,3-propylenediamine (Intermediate 29)

Under nitrogen atmosphere, a suspension of 5-bromoisoquinoline (252 mg), tris(dibenzylideneacetone)palladium(0) (59 mg), 2-(di-tert-butylphosphino)biphenyl (74 mg), (3-aminopropyl)methylcarbamic acid tert-butyl ester (274 mg, Asta Tech), and sodium tert-butoxide (163 mg) in toluene was stirred with heating at 70° C. for 3 hours. The reaction mixture was returned to room temperature and purified by silica gel column chromatography (n-hexane: ethyl acetate=1:1) to obtain the title compound (325 mg).

(Step B) Synthesis of N-(5-isoquinolyl)-N'-methyl-1,3-propylenediamine hydrochloride According to the method of Example 1, Step C, deprotection was performed (room temperature, 31 hours) by using Intermediate 29 (325 mg) and 10% hydrogen chloride/methanol solution (5 ml). The solvent was evaporated under reduced pressure, and the residue was added with methanol (1 ml) and diethyl ether (3 ml). The deposited precipitates were collected by filtration and washed with diethyl ether to obtain the title compound (273 mg) as light yellow powdery solid.

$^1$H-NMR (DMSO-$d_6$) δ (ppm): 2.00–2.05 (2H, m), 2.47–2.51 (3H, m), 2.95–2.99 (2H, m), 3.35–3.40 (2H, m), 7.10 (1H, d, J=7.5 Hz), 7.63 (1H, d, J=8.1 Hz), 7.75 (1H, t, J=8.1 Hz), 8.56 (1H, d, J=6.6 Hz), 8.84 (1H, d, J=6.6 Hz), 9.20 (1.5H, br.s), 9.69 (1H, s)

MS (m/z): 216 (MH+)

Example 18

N-(5-Isoquinolyl)-1,4-butylenediamine hydrochloride (Exemplary Compound No. 2-2)

(Step A) Synthesis of N-(tert-butoxycarbonyl)-N'-(5-isoquinolyl)-1,4-butylenediamine (Intermediate 30)

According to the method of Example 15, Step A, the title compound (442 mg) was obtained from 5-bromoisoquinoline (416 mg), tris(dibenzylideneacetone)dipalladium(0) (92 mg), 2-(di-tert-butylphosphino)biphenyl (119 mg), N-(4-aminobutyl)carbamic acid tert-butyl ester (452 mg, Tokyo Kasei Kogyo) and sodium tert-butoxide (269 mg).

(Step B) Synthesis of N-(5-isoquinolyl)-1,4-butylenediamine hydrochloride

According to the method of Example 1, Step C, deprotection was performed (50° C., 2 hours) by using Intermediate 30 (316 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (276 mg) as light yellow powdery solid.

$^1$H-NMR (DMSO-$d_6$) δ (ppm): 1.72–1.80 (4H, m), 2.80–2.90 (2H, m), 3.27–3.35 (2H, m), 7.11 (1H, d, J=7.8 Hz), 7.65 (1H, d, J=7.8 Hz), 7.78 (1H, t, J=7.8 Hz), 8.20 (3H, br.s), 8.59 (1H, d, J=6.9 Hz), 8.91 (1H, d, J=6.9 Hz), 9.73 (1H, s)

MS (m/z): 216 (MH+)

Example 19

N-(5-Isoquinolyl)-pentamethylenediamine hydrochloride (Step A) Synthesis of N-(tert-butoxycarbonyl)-N'-(5-isoquinolyl)-pentamethylenediamine (Intermediate 31)

Under nitrogen atmosphere, a suspension of 5-bromoisoquinoline (245 mg), tris(dibenzylideneacetone)palladium(0) (56 mg), 2-(di-tert-butylphosphino)biphenyl (69 mg), N-(5-aminopentyl)carbamic acid tert-butyl ester (282 mg, Tokyo Kasei Kogyo) and sodium tert-butoxide (160 mg) in toluene was stirred with heating at 70° C. for 4.5 hours. The reaction mixture was cooled to room temperature and purified by silica gel column chromatography (n-hexane:ethyl acetate=1:1) to obtain the title compound (327 mg).

(Step B) Synthesis of N-(5-isoquinolyl)pentamethylenediamine hydrochloride

According to the method of the above Example, deprotection was performed (room temperature, 31 hours) by using Intermediate 31 (327 mg) and 10% hydrogen chloride/methanol solution (5 ml). The solvent was evaporated under reduced pressure, and the residue was added with methanol (1 ml) and diethyl ether (3 ml). The deposited precipitates were collected by filtration and washed with diethyl ether to obtain the title compound (262 mg) as light yellow powdery solid.

$^1$H-NMR (DMSO-$d_6$) δ (ppm): 1.41–1.51 (2H, m), 1.59–1.75 (4H, m), 2.72–2.79 (2H, m), 7.07 (1H, d, J=7.8 Hz), 7.62 (1H, d, J=8.1 Hz), 7.75 (1H, t, J=8.1 Hz), 8.18 (3H, br.s), 8.55 (1H, d, J=6.6 Hz), 8.88 (1H, d, J=6.6 Hz), 9.70 (1H, s)

MS (m/z): 230 (MH+)

Example 20

4-(5-Isoquinolyl)aminopiperidine hydrochloride (Exemplary Compound No. 2-4)

(Step A) Synthesis of 4-(5-isoquinolyl)amino-1-(tert-butoxycarbonyl)piperidine (Intermediate 32)

According to the method of Example 15, Step A, the title compound (327 mg) was obtained from 5-bromoisoquinoline (416 mg), tris(dibenzylideneacetone)dipalladium(0) (92 mg), 2-(di-tert-butylphosphino)biphenyl (119 mg), 4-amino-1-(tert-butoxycarbonyl)piperidine (481 mg, Asta Tech) and sodium tert-butoxide (269 mg).

(Step B) Synthesis of 4-(5-isoquinolyl)aminopiperidine hydrochloride

According to the method of Example 1, Step C, deprotection was performed (50° C., 2 hours) by using Intermediate 32 (327 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (286 mg) as light yellow powdery solid.

$^1$H-NMR (DMSO-$d_6$) δ (ppm): 1.83–1.96 (2H, m), 2.10–2.20 (2H, m), 2.99–3.11 (2H, m), 3.30–3.41 (2H, m), 3.82–3.91 (1H, m), 7.28 (1H, d, J=8.1 Hz), 7.70 (1H, d, J=8.1 Hz), 7.80 (1H, t, J=8.1 Hz), 8.60 (1H, d, J=6.9 Hz), 8.92 (1H, d, J=6.9 Hz), 9.32 (2H, br.s), 9.74 (1H, s)

MS (m/z): 228 (MH+)

Example 21

4-(5-Isbquinolyl)aminomethylpiperidine hydrochloride (Exemplary Compound No. 2-8)

(Step A) Synthesis of 1-(tert-butoxycarbonyl)-4-(5-isoquinolyl)aminomethylpiperidine (Intermediate 33)

According to the method of Example 15, Step A, the title compound (260 mg) was obtained from 5-bromoisoquinoline (416 mg), tris(dibenzylideneacetone)dipalladium(0) (92 mg), 2-(di-tert-butylphosphino)biphenyl (119 mg), 4-aminomethyl-1-(tert-butoxycarbonyl)piperidine (514 mg, Asta Tech) and sodium tert-butoxide (269 mg).

(Step B) Synthesis of 4-(5-isoquinolyl)aminomethylpiperidine hydrochloride

According to the method of Example 1, Step C, deprotection was performed (50° C., 2 hours) by using Intermediate 33 (171 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (149 mg) as light yellow powdery solid.

$^1$H-NMR (DMSO-$d_6$) δ (ppm): 1.40–1.53 (2H, m), 1.92–2.11 (3H, m), 2.76–2.88 (2H, m), 3.19–3.30 (4H, m), 7.12 (1H, d, J=7.8 Hz), 7.23 (1H, br.s), 7.62 (1H, d, J=8.1 Hz), 7.76 (1H, dd, J=7.8, 8.1 Hz), 8.59 (1H, d, J=6.6 Hz), 8.79 (1H, d, J=6.6 Hz), 8.83–9.16 (3H, br.s), 9.68 (1H, s)

MS (m/z): 242 (MH+)

Example 22

3-(5-Isoquinolyl)aminomethylpiperidine hydrochloride (Exemplary Compound No. 2-3)

(Step A) Synthesis of 1-(tert-butoxycarbonyl)-3-(5-isoquinolyl)aminomethylpiperidine (Intermediate 34)

According to the method of Example 15, Step A, the title compound (249 mg) was obtained from 5-bromoisoquinoline (416 mg), tris(dibenzylideneacetone)dipalladium(0) (92 mg), 2-(di-tert-butylphosphino)biphenyl (119 mg), 4-aminomethyl-1-(tert-butoxycarbonyl)piperidine (514 mg, Asta Tech) and sodium tert-butoxide (269 mg).

(Step B) Synthesis of 3-(5-isoquinolyl)aminomethylpiperidine hydrochloride

According to the method of Example 1, Step C, deprotection was performed (50° C., 2 hours) by using Intermediate 34 (171 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (139 mg) as light yellow powdery solid.

$^1$H-NMR (DMSO-$d_6$) δ (ppm): 1.23–1.36 (1H, m), 1.63–1.96 (3H, m), 2.21–3.30 (1H, m), 2.64–2.83 (2H, m), 3.15–3.36 (4H, m), 7.12 (1H, d, J=7.9 Hz), 7.26 (1H, br.s), 7.64 (1H, d, J=7.9 Hz), 7.76 (1H, t, J=7.9 Hz), 8.59 (1H, d, J=6.7 Hz), 8.81 (1H, d, J=6.7 Hz), 8.98 (1H, br.s), 9.32 (1H, br.s), 9.69 (1H, s)

MS (m/z): 242 (MH+)

Example 23

Cis-N-(5-Isoquinolyl)-1,4-cyclohexanediamine hydrochloride (Exemplary Compound No. 2-5)

(Step A) Synthesis of trans-4-(N-tert-butoxycarbonylamino)cyclohexanol (Intermediate 35)

A solution of trans-4-aminocyclohexanol (50 g, Tokyo Kasei Kogyo) and 2 N aqueous sodium hydroxide (200 ml) in 2-propanol (200 ml) was added with di-t-butyl dicarbonate (94.8 g, Wako Pure Chemical Industries) with stirring and ice cooling and stirred at room temperature for 4.5 hours. The reaction mixture was cooled again on ice and stirred for 1 hour. Then, the deposited crystals were collected by filtration, washed with water and then dried at 40° C. under reduced pressure to obtain the title compound (90.3 g).

(Step B) Synthesis of trans-N-(tert-butoxycarbonyl)-N-(4-methanesulfonyloxycyclohexyl)amine (Intermediate 36)

A solution of Intermediate 35 (90.3 g) in pyridine (415 ml) was added dropwise with methanesulfonyl chloride (42.4 ml) with stirring and ice cooling over 15 minutes and stirred with ice cooling for 30 minutes and at room temperature for 20 minutes. The reaction mixture was added with methanol (54.2 ml) to terminate the reaction, stirred at room temperature for 2.5 hours, further added with water (540 ml) and stirred at room temperature for 1 hour and with ice cooling for 1 hour. The deposited precipitates were collected by filtration, washed with water and then dried at 40° C. under reduced pressure to obtain the title compound (105 g).

(Step C) Synthesis of cis-4-(N-tert-butoxycarbonylamino)cyclohexyl azide (Intermediate 37)

A solution of Intermediate 36 (196 g) and trimethylsilyl azide (283 ml, Tokyo Kasei Kogyo) in dimethylformamide (667 ml) was added with cesium fluoride (305 g, Wako Pure Chemical Industries) with stirring and stirred at 70° C. for 4 days. The reaction mixture was cooled to room temperature and then added twice with water in a volume of 2.75 l in total. This reaction mixture was stirred with ice cooling for 2 hours, and the deposited precipitates were collected by filtration. Then, the precipitates were washed with water to obtain a roughly purified product of the title compound (142 g).

(Step D) Synthesis of cis-4-(N-tert-butoxycarbonylamino)cyclohexylamine (Intermediate 38)

The roughly purified product of Intermediate 37 (142 g) was reduced by hydrogenation at room temperature for 9 hours by using 10% Pd/C (7.1 g) and ethyl acetate solution (1.42 l) under hydrogen atmosphere of 1 atm. The palladium catalyst was removed by filtration, and the solvent was evaporated under reduced pressure. Then, the residue was purified by flash column chromatography (chloroform:methanol:triethylamine=100:20:10) to obtain the title compound (45.8 g).

(Step E) Synthesis of cis-N-(tert-butoxycarbonyl)-N'-(5-isoquinolyl)-1,4-cyclohexanediamine (Intermediate 39)

Under nitrogen atmosphere, a suspension of 5-bromoisoquinoline (253 mg), tris(dibenzylideneacetone)palladium(0) (58 mg), 2-(di-tert-butylphosphino)biphenyl (74 mg), Intermediate 38 (311 mg) and sodium tert-butoxide (165 mg) in toluene was stirred with heating at 70° C. for 3 hours. The reaction mixture was cooled to room temperature and purified by silica gel column chromatography (n-hexane:ethyl acetate=1:1) to obtain the title compound (320 mg).

(Step F) Synthesis of cis-N-(5-isoquinolyl)-1,4-cyclohexanediamine hydrochloride According to the method of Example 1, Step C, deprotection was performed (room temperature, 31 hours) by using Intermediate 39 (214 mg) and 10% hydrogen chloride/methanol solution (5 ml). The solvent was evaporated under reduced pressure, and the residue was added with methanol (1 ml) and diethyl ether (3 ml). The deposited precipitates were collected by filtration and washed with diethyl ether to obtain the title compound (215 mg) as light yellow powdery solid.

$^1$H-NMR (DMSO-$d_6$) δ (ppm): 1.60–2.05 (8H, m), 2.49 (2H, s), 3.05–3.23 (1H, m), 3.70–3.80 (1H, m), 7.15 (1H, d, J=7.8 Hz), 7.67 (1H, d, J=7.8 Hz), 7.78 (1H, t, J=7.8 Hz), 8.18 (2H, br.s), 8.60 (1H, d, J=6.6 Hz), 8.90 (1H, d, J=6.9 Hz), 9.71 (1H, s)

MS (m/z): 242 (MH+)

Example 24

Trans-N-(5-isoquinolyl)-1,4-cyclohexanediamine hydrochloride (Exemplary Compound No. 2-6)

(Step A) Synthesis of trans-4-(N-tert-butoxycarbonylamino)cyclohexylamine (Intermediate 40)

A solution of trans-1,4-cyclohexanediamine (25 g, Tokyo Kasei Kogyo) in a mixed solvent of water (437 ml) and t-butyl alcohol (512 ml) was added with 2.5 N aqueous sodium hydroxide (30 ml), added dropwise with di-t-butyl dicarbonate (23.9 g) with ice cooling and stirred at room temperature for 15 hours. The reaction mixture was concentrated under reduced pressure, added with water and extracted with dichloromethane, and the organic layer was dried over anhydrous magnesium sulfate, and then the solvent was evaporated under reduced pressure. The residue was purified by silica gel column chromatography (ethyl acetate:methanol=10:1) to obtain the title compound (12.9 g).

(Step B) Synthesis of trans-N-(tert-butoxycarbonyl)-N'-(5-isoquinolyl)-1,4-cyclohexanediamine (Intermediate 41)

Under nitrogen atmosphere, a suspension of 5-bromoisoquinoline (100 mg), tris(dibenzylideneacetone)palladium(0) (23 mg), 2-(di-tert-butylphosphino)biphenyl (29 mg), Intermediate 40 (122 mg) and sodium tert-butoxide (66 mg) in toluene was stirred with heating at 70° C. for 3.5 hours. The reaction mixture was cooled to room temperature and purified by silica gel column chromatography (n-hexane:ethyl acetate=1:1) to obtain the title compound (69 mg).

(Step C) Synthesis of trans-N-(5-isoquinolyl)-1,4-cyclohexanediamine hydrochloride According to the method of Example 1, Step C, deprotection was performed (50° C., 1 hour) by using Intermediate 41 (69 mg) and 10% hydrogen chloride/methanol solution (4 ml). The solvent was evaporated under reduced pressure, and the residue was added with methanol (0.5 ml) and diethyl ether (2 ml). The deposited precipitates were collected by filtration and washed with diethyl ether to obtain the title compound (58.7 mg) as light yellow powdery solid.

$^1$H-NMR (DMSO-$d_6$) δ (ppm): 1.35–1.62 (4H, m), 1.95–2.20 (4H, m), 2.49 (1H, t, J=1.8 Hz), 2.90–3.10 (1H, m), 3.40–3.52 (1H, m), 7.21 (1H, d, J=8.1 Hz), 7.63 (1H, d, J=8.1 Hz), 7.75 (1H, t, J=8.1 Hz), 8.31 (2H, br.s), 8.56 (1H, d, J=6.6 Hz), 8.84 (1H, d, J=6.9 Hz), 9.70 (1H, s)

MS (m/z): 242 (MH+)

Example 25

N-(5-Isoquinolyl)-1,3-cyclohexanediamine hydrochloride (Exemplary Compound No. 2-7)

(Step A) Synthesis of N-(tert-butoxycarbonyl)-1,3-cyclohexanediamine (Intermediate 42)

According to the method of Example 24, Step A, the title compound (3.8 g) was obtained from 1,3-cyclohexanediamine (11.4 g, Tokyo Kasei Kogyo) and di-tert-butyl dicarbonate (10.9 g).

(Step B) Synthesis of N-(tert-butoxycarbonyl)-N'-(5-isoquinolyl)-1,3-cyclohexanediamine (Intermediate 43)

According to the method of Example 15, Step A, the title compound (273 mg) was obtained from 5-bromoisoquinoline (416 mg), tris(dibenzylideneacetone)dipalladium(0) (92 mg), 2-(di-tert-butylphosphino)biphenyl (119 mg), Intermediate 42 (514 mg, synthesized according to Example 24, Step A) and sodium tert-butoxide (269 mg).

(Step C) Synthesis of N-(5-isoquinolyl)-1,3-cyclohexanediamine hydrochloride According to the method of Example 1, Step C, deprotection was performed (50° C., 2 hours) by using Intermediate 43 (171 mg) and 10% hydrogen chloride/methanol solution (2.5 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (149 mg) as light yellow powdery solid.

$^1$H-NMR (DMSO-$d_6$) δ (ppm): 1.24–2.40 (8H, m), 3.15–4.15 (2H, m), 7.25 (1H, d, J=7.8 Hz), 7.68 (1H, m), 7.81 (1H, m), 8.22 (1H, br.s), 8.58 (1H, d, J=6.9 Hz), 8.84 (1H, m), 9.72 (1H, s)

MS (m/z): 242 (MH+)

Example 26

N-(5-Isoquinolyl)-1,3-xylylenediamine hydrochloride (Exemplary Compound No. 2-11)

(Step A) Synthesis of N-(tert-butoxycarbonyl)-N'-(5-isoquinolyl)-1,3-xylylenediamine (Intermediate 44)

According to the method of Example 15, Step A, the title compound (508 mg) was obtained under nitrogen atmosphere from 5-bromoisoquinoline (416 mg), tris(dibenzylideneacetone)dipalladium(0) (92 mg), 2-(di-tert-butylphosphino)biphenyl (119 mg), N-(tert-butoxycarbonyl)-1,3-xylylenediamine (567 mg, Asta Tech) and sodium tert-butoxide (269 mg).

(Step B) Synthesis of N-(5-isoquinolyl)-1,3-xylylenediamine hydrochloride

According to the method of Example 1, Step C, deprotection was performed (50° C., 2 hours) by using Intermediate 44 (364 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (316 mg) as light yellow powdery solid.

$^1$H-NMR (DMSO-$d_6$) δ (ppm): 3.96–4.01 (2H, m), 4.57 (2H, s), 6.91 (1H, dd, J=1.5, 7.8 Hz), 7.34–7.44 (3H, m), 7.57–7.69 (3H, m), 7.95 (1H, br.s), 8.51 (3H, br.s), 8.63 (1H, d, J=6.9 Hz), 8.85 (1H, d, J=6.9 Hz), 9.69 (1H, s)

MS (m/z): 264 (MH+)

Example 27

4-[(5-Isoquinolyl)oxy]piperidine hydrochloride (Exemplary Compound No. 1-2)

(Step A) Synthesis of 1-(tert-butoxycarbonyl)-4-[(5-isoquinolyl)oxy]piperidine (Intermediate 45)

According to the method of Example 10, Step A with the modifications that the reaction was carried out for 48 hours, and the compound was purified by silica gel column chromatography (n-hexane:ethyl acetate=3:1), the title compound (213 mg) was obtained from 5-hydroxyisoquinoline (145 mg, Aldrich), tri(n-butyl)phosphine (747 µl), 1-(tert-butoxycarbonyl)-4-hydroxypiperidine (604 mg, Aldrich) and 1,1'-azobis(N,N-dimethylformamide) (517 mg).

(Step B) Synthesis of
4-[(5-isoquinolyl)oxy]piperidine hydrochloride

According to the method of Example 1, Step C, deprotection was performed (50° C., 2 hours) by using Intermediate 45 (164 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (128 mg) as white powdery solid.

$^1$H-NMR (DMSO-$d_6$) δ (ppm): 2.00–2.13 (2H, m), 2.19–2.32 (2H, m), 3.08–3.21 (2H, m), 3.25–3.39 (2H, m), 5.03–5.11 (1H, m), 7.77 (1H, d, J=7.5 Hz), 7.93 (1H, t, J=8.1 Hz), 8.08 (1H, d, J=8.4 Hz), 8.58 (1H, d, J=6.6 Hz), 8.65 (1H, d, J=6.6 Hz), 9.44 (2H, br.s), 9.86 (1H, s)

MS (m/z): 229 (MH+)

Example 28

4-[N-(5-Isoquinolyl)-N-methyl]aminopiperidine hydrochloride (Exemplary Compound No. 2-114)

(Step A) Synthesis of
4-aminomethyl-1-(tert-butoxycarbonyl)piperidine
(Intermediate 46)

A solution of methylamine hydrochloride (1.01 g, Wako Pure Chemical Industries) and 1-(tert-butoxycarbonyl)-4-oxopiperidine (1.99 g, Aldrich) in methanol (13 ml) was stirred in the presence of platinum oxide (69 mg, Wako Pure Chemical Industries) at room temperature for 3 hours under hydrogen atmosphere of ordinary pressure. The hydrogen was purged with a nitrogen gas, and the platinum catalyst was removed by filtration. Then, the reaction mixture was adjusted to pH of from 10 to 11 with 1 N aqueous sodium hydroxide. The reaction mixture was added with water (10 ml), and the product was extracted three times with ethyl acetate (15 ml for each time). The organic layer was dried over anhydrous sodium sulfate, and then the solvent was evaporated under reduced pressure. The residue was purified by silica gel column chromatography (ethyl acetate:methanol=20:1) to obtain the title compound (2.01 g).

(Step B) Synthesis of 1-(tert-butoxycarbonyl)-4-[N-(5-isoquinolyl)-N-methyl]aminopiperidine (Intermediate 47)

According to the method of Example 15, Step A, the title compound (88 mg) was obtained from 5-bromoisoquinoline (416 mg), tris(dibenzylideneacetone)dipalladium(0) (92 mg), 2-(di-tert-butylphosphino)biphenyl (119 mg), Intermediate 46 (515 mg) and sodium tert-butoxide (269 mg).

(Step C)
4-[N-(5-isoquinolyl)-N-methyl]aminopiperidine
hydrochloride

According to the method of Example 1, Step C, deprotection was performed (50° C., 2 hours) by using Intermediate 47 (68 mg) and 10% hydrogen chloride/methanol solution (2 ml). The reaction mixture was cooled to room temperature, and then the solvent was evaporated under reduced pressure. The residue was added with methanol (0.5 ml) and diethyl ether (1.5 ml). The deposited precipitates were collected by filtration and washed with diethyl ether to obtain the title compound (56 mg) as light yellow powdery solid.

MS (m/z): 242 (MH+)

Example 29

3-N-(5-Isoquinolyl)aminopiperidine hydrochloride
(Exemplary Compound No. 2-10)

(Step A) Synthesis of 1-N-(tert-butoxycarbonyl)-3-N'-(5-isoquinolyl)aminopiperidine (Intermediate 48)

According to the method of Example 15, Step A, the title compound (437 mg) was obtained under nitrogen atmosphere from 5-bromoisoquinoline (300 mg), tris(dibenzylideneacetone)dipalladium(0) (69 mg), 2-(di-tert-butylphosphino)biphenyl (86 mg), (+/−)-3-amino-1-N-(tert-butoxycarbonyl)piperidine (341 mg, Asta Tech) and sodium tert-butoxide (197 mg).

(Step B) Synthesis of
3-N-(5-isoquinolyl)aminopiperidine hydrochloride

According to the method of Example 1, Step C, deprotection was performed (room temperature, 3 hours) by using Intermediate 48 (195 mg) and 10% hydrogen chloride/methanol solution (4 ml). The solvent was evaporated under reduced pressure, and the residue was added with methanol (1 ml) and diethyl ether (3 ml). The deposited precipitates were collected by filtration and washed with diethyl ether to obtain the title compound (131 mg) as light yellow powdery solid.

$^1$H-NMR (DMSO-$d_6$) δ (ppm): 1.68–1.93 (1H, m), 1.95–2.02 (2H, m), 2.06–2.20 (1H, m), 3.16–3.26 (2H, m), 3.65 (2H, d, J=6.0 Hz), 3.87–3.91 (1H, m), 7.23 (1H, d, J=7.5 Hz), 7.49 (1H, br.s), 7.69 (1H, d, J=8.1 Hz), 7.78 (1H, dd, 7.8 Hz), 8.62 (1H, d, J=6.6 Hz), 8.91 (1H, d, J=6.9 Hz), 9.44 (1H, br.s), 9.71 (1H, s), 9.78 (1H, s)

MS (m/z): 228 (MH+)

Examples 30 to 102

According to the method of Example 1, Step B, Intermediates 64 to 70 (amines) obtained in Reference Examples 9 to 15 were used to perform the Mitsunobu reaction with an alcohol suitably selected from alcohols (al-1) to (al-11). The obtained crowns were allowed to act on a mixed solvent of trifluoroacetic acid and dichloromethane (1/1) and thereby obtained the compounds of Examples 30 to 102 listed in Table 4 shown below. The compound of each example showed a peak of MH+ in the mass spectrum as expected. The compounds listed in Table 4 are represented by the following formula (1a). In the formula (1a), substituents are as shown in the following tables.

TABLE 4

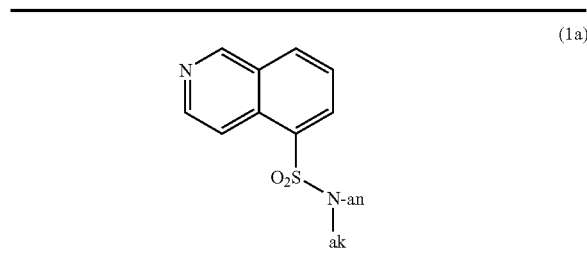
(1a)

| Example No. | Reagent Alcohol | Reagent Amine | Compound of Example —ak | Compound of Example -an | Exemplary Compound No. |
|---|---|---|---|---|---|
| 30 | al-1 | am-1 | ak-1 | an-1 | 3-1 |
| 31 | al-2 | am-1 | ak-2 | an-1 | 3-2 |
| 32 | al-3 | am-1 | ak-3 | an-1 | 3-3 |
| 33 | al-4 | am-1 | ak-4 | an-1 | 3-4 |
| 34 | al-5 | am-1 | ak-5 | an-1 | 3-5 |
| 35 | al-6 | am-1 | ak-6 | an-1 | 3-6 |
| 36 | al-7 | am-1 | ak-7 | an-1 | 3-7 |
| 37 | al-8 | am-1 | ak-8 | an-1 | 3-8 |
| 38 | al-9 | am-1 | ak-9 | an-1 | 3-9 |
| 39 | al-10 | am-1 | ak-10 | an-1 | 3-11 |
| 40 | al-2 | am-2 | ak-2 | an-2 | 3-36 |
| 41 | al-4 | am-2 | ak-4 | an-2 | 3-38 |
| 42 | al-5 | am-2 | ak-5 | an-2 | 3-39 |
| 43 | al-6 | am-2 | ak-6 | an-2 | 3-40 |
| 44 | al-7 | am-2 | ak-7 | an-2 | 3-41 |
| 45 | al-8 | am-2 | ak-8 | an-2 | 3-42 |
| 46 | al-9 | am-2 | ak-9 | an-2 | 3-43 |
| 47 | al-10 | am-2 | ak-10 | an-2 | 3-45 |
| 48 | al-1 | am-3 | ak-1 | an-3 | 3-69 |
| 49 | al-2 | am-3 | ak-2 | an-3 | 3-70 |
| 50 | al-3 | am-3 | ak-3 | an-3 | 3-71 |
| 51 | al-4 | am-3 | ak-4 | an-3 | 3-72 |
| 52 | al-5 | am-3 | ak-5 | an-3 | 3-73 |
| 53 | al-6 | am-3 | ak-6 | an-3 | 3-74 |
| 54 | al-7 | am-3 | ak-7 | an-3 | 3-75 |
| SS | al-8 | am-3 | ak-8 | an-3 | 3-76 |
| 56 | al-9 | am-3 | ak-9 | an-3 | 3-77 |
| 57 | al-10 | am-3 | ak-10 | an-3 | 3-79 |
| 58 | al-11 | am-3 | ak-11 | an-3 | 3-80 |
| 59 | al-1 | am-4 | ak-1 | an-4 | 3-137 |
| 60 | al-2 | am-4 | ak-2 | an-4 | 3-138 |
| 61 | al-3 | am-4 | ak-3 | an-4 | 3-139 |
| 62 | al-4 | am-4 | ak-4 | an-4 | 3-140 |
| 63 | al-5 | am-4 | ak-5 | an-4 | 3-141 |
| 64 | al-6 | am-4 | ak-6 | an-4 | 3-142 |
| 65 | al-7 | am-4 | ak-7 | an-4 | 3-143 |
| 66 | al-8 | am-4 | ak-8 | an-4 | 3-144 |
| 67 | al-9 | am-4 | ak-9 | an-4 | 3-145 |
| 68 | al-10 | am-4 | ak-10 | an-4 | 3-147 |
| 69 | al-11 | am-4 | ak-11 | an-4 | 3-148 |
| 70 | al-1 | am-5 | ak-1 | an-5 | 3-171 |
| 71 | al-2 | am-5 | ak-2 | an-5 | 3-172 |
| 72 | al-3 | am-5 | ak-3 | an-5 | 3-173 |
| 73 | al-5 | am-5 | ak-4 | an-5 | 3-174 |
| 74 | al-5 | am-5 | ak-5 | an-5 | 3-175 |
| 7S | al-6 | am-5 | ak-6 | an-5 | 3-176 |
| 76 | al-7 | am-5 | ak-7 | an-5 | 3-177 |
| 77 | al-8 | am-5 | ak-8 | an-5 | 3-178 |
| 78 | al-9 | am-5 | ak-9 | an-5 | 3-179 |
| 79 | al-10 | am-5 | ak-10 | an-5 | 3-181 |
| 80 | al-11 | am-5 | ak-11 | an-5 | 3-182 |
| 81 | al-1 | am-6 | ak-1 | an-6 | 3-239 |
| 82 | al-2 | am-6 | ak-2 | an-6 | 3-240 |
| 83 | al-3 | am-6 | ak-3 | an-6 | 3-241 |
| 84 | al-4 | am-6 | ak-4 | an-6 | 3-242 |
| 85 | al-5 | am-6 | ak-5 | an-6 | 3-243 |
| 86 | al-6 | am-6 | ak-6 | an-6 | 3-244 |
| 87 | al-7 | am-6 | ak-7 | an-6 | 3-245 |
| 88 | al-8 | am-6 | ak-8 | an-6 | 3-246 |
| 89 | al-9 | am-6 | ak-9 | an-6 | 3-247 |
| 90 | al-10 | am-6 | ak-10 | an-6 | 3-249 |
| 91 | al-11 | am-6 | ak-11 | an-6 | 3-250 |
| 92 | al-1 | am-7 | ak-1 | an-7 | 3-273 |
| 93 | al-2 | am-7 | ak-2 | an-7 | 3-274 |
| 94 | aI-3 | am-7 | ak-3 | an-7 | 3-275 |
| 95 | aI-4 | am-7 | ak-4 | an-7 | 3-276 |
| 96 | al-5 | am-7 | ak-5 | an-7 | 3-277 |
| 97 | al-6 | am-7 | ak-6 | an-7 | 3-278 |
| 98 | al-7 | am-7 | ak-7 | an-7 | 3-279 |
| 99 | al-B | am-7 | ak-8 | an-7 | 3-280 |
| 100 | al-9 | am-7 | ak-9 | an-7 | 3-281 |
| 101 | al-10 | am-7 | ak-10 | an-7 | 3-283 |
| 102 | al-11 | am-7 | ak-11 | an-7 | 3-284 |

Table 4 mentioned above, an-1 to an-7 are the following groups.

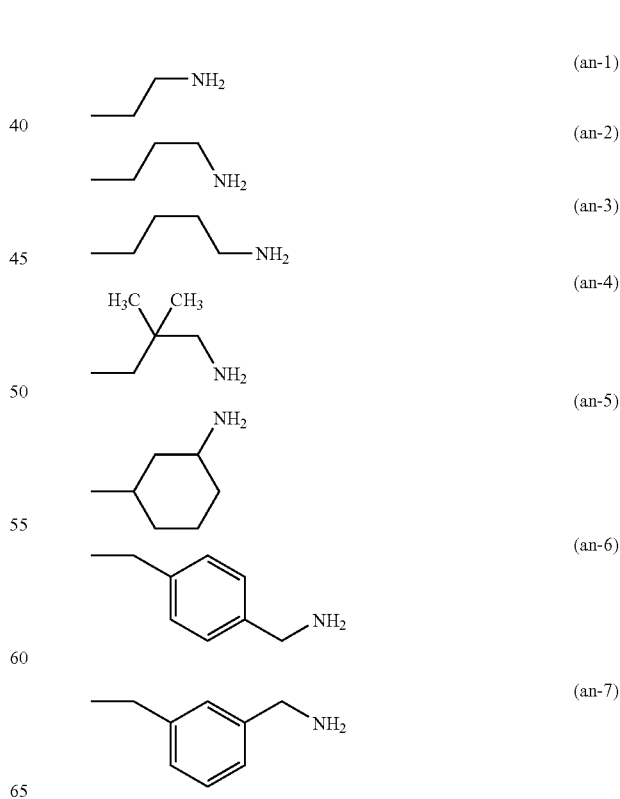

Tables 15 and 16 mentioned above, ak-1 to ak-11 are the following groups.

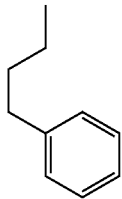 (ak-1)

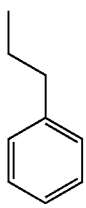 (ak-2)

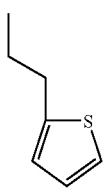 (ak-3)

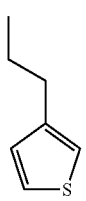 (ak-4)

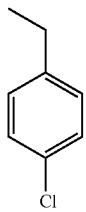 (ak-5)

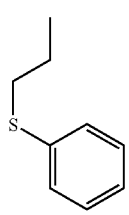 (ak-6)

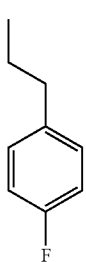 (ak-7)

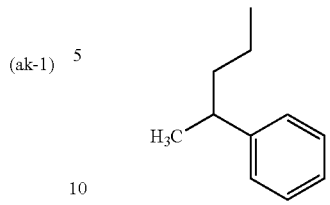 (ak-8)

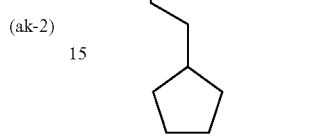 (ak-9)

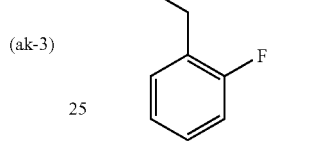 (ak-10)

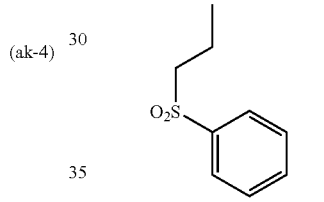 (ak-11)

The alcohols (al-1) to (al-11) used in Examples 30 to 102 were as follows.

al-1 is 3-phenyl-1-propanol (Tokyo Kasei Kogyo), al-2 is phenethyl alcohol (Tokyo Kasei Kogyo), al-3 is 2-(2-thienyl)ethanol (Aldrich), al-4 is 2-(3-thienyl)ethanol (Aldrich), al-5 is 4-chlorophenethyl alcohol (Tokyo Kasei Kogyo), al-6 is 2-(phenylthio)ethanol (Aldrich), al-7 is 4-fluorophenethyl alcohol (Aldrich), al-8 is 3-phenyl-1-butanol (Aldrich), al-9 is 2-cyclopentylethanol (Tokyo Kasei Kogyo), al-10 is 2-fluorophenethyl alcohol (Aldrich), and al-11 is 2-(phenylsulfonyl)ethanol.

The amines (am-1) to (am-7) used in Example 30 to 102 are as follows.

am-1 is Intermediate 64, am-2 is Intermediate 65, am-3 is Intermediate 66, am-4 is Intermediate 67, am-5 is Intermediate 68, am-6 is Intermediate 69, and am-7 is Intermediate 70.

Example 103

4-(4-Bromo-5-isoquinolylaminopiperidine hydrochloride (Exemplary Compound No. 2-181)

(Step A) Synthesis of 4-(4-bromo-5-isoquinolyl)amino-1-(tert-butoxycarbonyl)piperidine (Intermediate 71)

A mixture of 4-bromo-5-aminoisoquinoline (3.00 g) obtained in Reference Example 1 and tert-butyl 4-oxo-1-piperidinecarboxylate (5.50 g, Aldrich) was added with titanium tetraisopropoxide (8.20 ml, Aldrich) at room temperature and stirred at room temperature for 15 hours. Subsequently, the reaction mixture was added with methanol (60 ml) and sodium borohydride (2.21 g, Kanto Chemicals) and further stirred at room temperature for 19 hours. The reaction mixture was added with saturated aqueous sodium hydrogencarbonate (100 ml) and ethyl acetate (100 ml), stirred for 0.5 hour and filtered through Celite, and the solvent was evaporated under reduced pressure. The residue was added with ethyl acetate (100 ml) and washed twice with saturated aqueous sodium hydrogencarbonate (50 ml for each time), and the organic layer was dried over anhydrous sodium sulfate. The solvent was evaporated under reduced pressure, and the residue was purified by silica gel column chromatography (n-hexane:acetone:isopropylamine=150:10:2) to obtain the title compound (2.92 g).

(Step B) Synthesis of 4-(4-bromo-5-isoquinolyl)aminopiperidine hydrochloride

According to the method of Example 1, Step C, deprotection was performed (50° C., 2 hours) by using Intermediate 71 (123 mg) and 10% hydrogen chloride/methanol solution (6 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (52 mg) as light yellow powdery solid.

$^1$H-NMR (DMSO-$d_6$) δ (ppm): 1.72–1.85 (2H, m), 2.20–2.24 (2H, m), 3.02–3.13 (2H, m), 3.28–3.33 (2H, m), 3.79–3.86 (1H, m), 7.16 (1H, d, J=7.9 Hz), 7.53 (1H, d, J=7.9 Hz), 7.63 (1H, d, J=7.9 Hz), 8.58 (1H, s), 9.00–9.18 (1H, br.s), 9.26 (1H, s)

MS (m/z): 306 (MH+)

Example 104

4-(4-Fluoro-5-isoquinolyl)aminopiperidine hydrochloride (Exemplary Compound No. 2-103)

(Step A) Synthesis of 4-(4-fluoro-5-isoquinolyl)amino-1-(tert-butoxycarbonyl)piperidine (Intermediate 72)

A solution of Intermediate 71 (104 mg) in dimethyl sulfoxide (2 ml) was added with cesium fluoride (284 mg, Wako Pure Chemical Industries) and stirred at 150° C. for 8 hours. The reaction mixture was cooled to room temperature and then filtered through Celite. The residue was added with water (20 ml), extracted with ethyl acetate (20 ml) and washed twice with saturated brine (10 ml for each time). The organic layer was dried over anhydrous sodium sulfate, and then the solvent was evaporated under reduced pressure. The residue was purified by silica gel column chromatography (n-hexane:ethyl acetate=3:1) to obtain the title compound (21.1 mg).

(Step B) Synthesis of 4-(4-fluoro-5-isoquinolyl)aminopiperidine hydrochloride

According to the method of Example 1, Step C, deprotection was performed (50° C., 2 hours) by using Intermediate 72 (30.2 mg) and 10% hydrogen chloride/methanol solution (3 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (18.1 mg) as light yellow powdery solid.

$^1$H-NMR (DMSO-$d_6$) δ (ppm): 1.70–1.84 (2H, m), 2.16–2.20 (2H, m), 2.98–3.10 (2H, m), 3.29–3.34 (2H, m), 3.80–3.82 (1H, m), 7.12 (1H, d, J=8.0 Hz), 7.51–7.54 (1H, m), 7.65 (1H, d, J=8.0 Hz), 8.43 (1H, d, J=6.1 Hz), 8.90–9.10 (1H, m), 9.20 (1H, s)

MS (m/z): 246 (MH+)

Example 105

4-(4-Methylthio-5-isoquinolyl)aminopiperidine hydrochloride (Step A) Synthesis of 5-amino-4-methylthioisoquinoline (Intermediate 73)

A solution of 4-bromo-5-aminoisoquinoline (1.04 g) obtained in Reference Example 1 in N,N-dimethylformamide (10 ml) was added with methylmercaptan sodium salt (1.38 g, Aldrich) and stirred at 100° C. for 16 hours. The reaction mixture was cooled to room temperature and filtered through Celite. The residue was added with ethyl acetate (100 ml) and washed three times with saturated brine (50 ml for each time). The organic layer was dried over anhydrous sodium sulfate, and then the solvent was evaporated under reduced pressure. The residue was purified by silica gel column chromatography (n-hexane:ethyl acetate=3:1) to obtain the title compound (225 mg).

(Step B) Synthesis of 4-(4-methylthio-5-isoquinolyl)amino-1-(tert-butoxycarbonyl)piperidine (Intermediate 74)

According to the method of Example 103, Step A with the modifications that the reaction was carried out for 72 hours, and the compound was purified by silica gel column chromatography (n-hexane:ethyl acetate=4:1), the title compound (256 mg) was obtained from Intermediate 73 (225 mg), tert-butyl 4-oxo-1-piperidinecarboxylate (484 mg), titanium tetraisopropoxide (720 µl) and sodium borohydride (195 mg).

(Step C) Synthesis of 4-(4-methylthio-5-isoquinolyl)aminopiperidine hydrochloride According to the method of Example 1, Step C, deprotection was performed (50° C., 2 hours) by using Intermediate 74 (214 mg) and 10% hydrogen chloride/methanol solution (5 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (154 mg) as brown powdery solid.

$^1$H-NMR (DMSO-$d_6$) δ (ppm): 1.70–1.85 (2H, m), 2.18–2.24 (2H, m), 2.62 (3H, s), 3.01–3.13 (2H, m), 3.29–3.34 (2H, m), 3.78–3.82 (1H, m), 7.14 (1H, br.s), 7.24 (1H, d, J=7.2 Hz), 7.60–7.72 (2H, m), 8.31 (1H, s), 8.99 (1H, br.s), 9.09 (1H, br.s), 9.34 (1H, s)

MS (m/z): 274 (MH+)

Example 106

4-(4-Methyl-5-isoquinolyl)aminopiperidine hydrochloride (Exemplary Compound No. 2-70)

(Step A) Synthesis of 4-(4-methyl-5-isoquinolyl)amino-1-(tert-butoxycarbonyl)piperidine (Intermediate 75)

A solution of Intermediate 71 (313 mg) in toluene (6 ml) was added with tetrakis(triphenylphosphine)palladium(0) (17.9 mg, Aldrich), tetramethyltin (165 µl, Kanto Chemicals) and 2,6-di-tert-butyl-4-methylphenol (several pellets, Tokyo Kasei Kogyo) and stirred in a sealed tube at 150° C. for 48 hours. The reaction mixture was cooled to room temperature, filtered through Celite and concentrated under reduced pressure. The residue was added with saturated brine (30 ml) and extracted three times with ethyl acetate (30 ml for each time). The organic layers were combined and dried over anhydrous sodium sulfate, and then the solvent was evaporated under reduced pressure. The residue was purified by silica gel column chromatography (hexane:ethyl acetate=2:1) to obtain the title compound (61.7 mg).

(Step B) Synthesis of 4-(4-methyl-5-isoquinolyl)aminopiperidine hydrochloride

According to the method of Example 1, Step C, deprotection was performed (50° C., 2 hours) by using Intermediate 75 (90.7 mg) and 10% hydrogen chloride/methanol solution (2 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (90.4 mg) as light yellow powdery solid.

$^1$H-NMR (DMSO-$d_6$) δ (ppm): 1.80–1.90 (2H, m), 2.16–2.21 (2H, m), 3.04–3.16 (5H, m), 3.27–3.31 (2H, m), 3.73–3.80 (1H, m), 7.37–7.41 (1H, m), 7.74–7.81 (2H, m), 8.30 (1H, s), 9.17–9.20 (1H, m), 9.35–9.39 (1H, m), 9.57 (1H, s)

MS (m/z): 242 (MH+)

Example 107

N-(4-Bromo-5-isoquinolyl)-1,4-cyclohexanediamine hydrochloride (Step A) Synthesis of N-(tert-butoxycarbonyl)-N'-(4-bromo-5-isoquinolyl)-1,4-cyclohexanediamine (Intermediate 76)

According to the method of Example 103, Step A, the title compound (942 mg) was obtained from 4-bromo-5-aminoisoquinoline (1.02 g) obtained in Reference Example 1, tert-butyl 4-oxo-1-aminocyclohexylcarboxylate (1.95 g, Asta Tech), titanium tetraisopropoxide (2.78 ml) and sodium borohydride (752 mg).

(Step B) Synthesis of N-(4-bromo-5-isoquinolyl)-1,4-cyclohexanediamine hydrochloride According to the method of Example 1, Step C, deprotection was performed (50° C., 2 hours) by using Intermediate 76 (124 mg) and 10% hydrogen chloride/methanol solution (3 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (107 mg).

MS (m/z): 320 (MH+)

Example 108

N-(4-Fluoro-5-isoquinolyl)-1,4-cyclohexanediamine hydrochloride (Step A) Synthesis of N-(tert-butoxycarbonyl)-N'-(4-fluoro-5-isoquinolyl)-1,4-cyclohexanediamine (Intermediate 77)

According to Example 104, Step A, the title compound (90.8 mg) was obtained from Intermediate 76 (125 mg) and cesium fluoride (316 mg).

(Step B) Synthesis of N-(4-fluoro-5-isoquinolyl)-1,4-cyclohexanediamine hydrochloride According to the method of Example 1, Step C, deprotection was performed (50° C., 2 hours) by using Intermediate 77 (90.8 mg) and 10% hydrogen chloride/methanol solution (2 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (75.4 mg).

MS (m/z): 260 (MH+)

Example 109

N-(4-Methylthio-5-isoquinolyl)-1,4-cyclohexanediamine hydrochloride (Step A) Synthesis of N-(tert-butoxycarbonyl)-N'-(4-methylthio-5-isoquinolyl)-1,4-cyclohexanediamine (Intermediate 78)

According to the method of Example 103, Step A, the title compound (341 mg) was obtained from Intermediate 73 (270 mg), tert-butyl 4-oxo-1-aminocyclohexylcarboxylate (605 mg), titanium tetraisopropoxide (864 µl) and sodium borohydride (233 mg).

(Step B) Synthesis of N-(4-methylthio-5-isoquinolyl)-1,4-cyclohexanediamine hydrochloride According to the method of Example 1, Step C, deprotection was performed (50° C., 2 hours) by using Intermediate 78 (341 mg) and 10% hydrogen chloride/methanol solution (5 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (279 mg).

MS (m/z): 288 (MH+)

Example 110

4-(4-Methanesulfinyl-5-isoquinolyl)aminopiperidine hydrochloride (Step A) Synthesis of 4-(4-methanesulfinyl-5-isoquinolyl)amino-1-(tert-butoxycarbonyl)piperidine (Intermediate 79)

Intermediate 74 (746 mg) obtained in Example 105, Step B was added with acetic acid (1.5 ml) and 30% aqueous hydrogen peroxide (2 ml) and stirred at room temperature for 17 hours. The reaction mixture was added with ethyl acetate (50 ml) and washed three times with saturated aqueous sodium hydrogencarbonate (25 ml for each time), and the organic layer was dried over anhydrous sodium sulfate. The solvent was evaporated under reduced pressure, and the residue was purified by silica gel column chromatography (n-hexane:acetone=3:1) to obtain the title compound (390 mg).

(Step B) Synthesis of 4-(4-methanesulfinyl-5-isoquinolyl)aminopiperidine hydrochloride According to the method of Example 1, Step C, deprotection was performed (50° C., 2 hours) by using Intermediate 79 (138 mg) and 10% hydrogen chloride/methanol solution (3 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (92.2 mg) as brown powdery solid.

$^1$H-NMR (DMSO-$d_6$) δ (ppm): 1.68–1.83 (2H, m), 2.12–2.24 (2H, m), 2.81 (3H, s), 3.00–3.12 (2H, m), 3.25–3.38 (2H, m), 3.66–3.78 (1H, m), 6.54 (1H, br.s), 7.37–7.40 (1H, m), 7.71–7.75 (2H, m), 8.79 (1H, s), 8.87 (1H, br.s), 9.06 (1H, br.s), 9.54 (1H, s)

MS (m/z): 290 (MH+)

Example 111

4-(4-Methanesulfonyl-5-isoquinolyl)aminopiperidine hydrochloride (Exemplary Compound No. 2-48)

(Step A) Synthesis of 4-(4-methanesulfonyl-5-isoquinolyl)amino-1-(tert-butoxycarbonyl)piperidine (Intermediate 80)

Intermediate 74 (746 mg) obtained in Example 105, Step B was added with acetic acid (1.5 ml) and 30% aqueous hydrogen peroxide (2 ml) and stirred at room temperature for 17 hours. The reaction mixture was added with ethyl acetate (50 ml) and washed three times with saturated aqueous sodium hydrogencarbonate (25 ml for each time), and the organic layer was dried over anhydrous sodium sulfate. The solvent was evaporated under reduced pressure, and the residue was purified by silica gel column chromatography (n-hexane:acetone=4:1) to obtain the title compound (40.9 mg).

(Step B) Synthesis of 4-(4-methanesulfonyl-5-isoquinolyl)aminopiperidine hydrochloride According to the method of Example 1, Step C, deprotection was performed (50° C., 2 hours) by using Intermediate 80 (40.9 mg) and 10% hydrogen chloride/methanol solution (1 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (11.4 mg) as brown powdery solid.

MS (m/z): 306 (MH+)

Example 112

4-(4-Vinyl-5-isoquinolyl)aminopiperidine hydrochloride (Exemplary Compound No. 2-203)

(Step A) Synthesis of 4-(4-vinyl-5-isoquinolyl)amino-1-(tert-butoxycarbonyl)piperidine (Intermediate 81)

According to the method of Example 106, Step A, the title compound (1.55 g) was obtained from Intermediate 71 (2.31 g), tetrakis(triphenylphosphine)palladium(0) (131 mg), tri(n-butyl)vinyltin (2.60 ml, Tokyo Kasei Kogyo) and 2,6-di-tert-butyl-4-methylphenol (several pellets).

(Step B) Synthesis of 4-(4-vinyl-5-isoquinolyl)aminopiperidine hydrochloride

According to the method of Example 1, Step C, deprotection was performed (50° C., 2 hours) by using Intermediate 81 (46.6 mg) and 10% hydrogen chloride/methanol solution (2 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (25.3 mg).

$^1$H-NMR (DMSO-$d_6$) δ (ppm): 1.68–1.81 (2H, m), 2.10–2.21 (2H, m), 2.98–3.10 (2H, m), 3.23–3.30 (2H, m), 3.70–3.81 (1H, m), 5.54 (1H, br.s), 5.70 (1H, m), 5.81 (1H, m), 7.30 (1H, dd, J=2.3, 6.5 Hz), 7.60–7.77 (3H, m), 8.26 (1H, s), 9.00 (1H, br.s), 9.18 (1H, br.s), 9.52 (1H, s)

MS (m/z): 254 (MH+)

Example 113

4-(4-Ethyl-5-isoquinolyl)aminopiperidine hydrochloride (Exemplary Compound No. 2-192)

(Step A) Synthesis of 4-(4-ethyl-5-isoquinolyl)amino-1-(tert-butoxycarbonyl)piperidine (Intermediate 82)

A solution (2 ml) of Intermediate 81 (103 mg) in methanol was vigorously stirred in the presence of 10% palladium carbon catalyst (16.5 mg) at room temperature under hydrogen atmosphere of ordinary pressure. The reaction mixture was filtered through Celite, and the solvent was evaporated under reduced pressure. The residue was purified by silica gel column chromatography (hexane:ethyl acetate=2:1) to obtain the title compound (93.7 mg).

(Step B) Synthesis of 4-(4-ethyl-5-isoquinolyl)aminopiperidine hydrochloride

According to the method of Example 1, Step C, deprotection was performed (50° C., 2 hours) by using Intermediate 82 (93.7 mg) and 10% hydrogen chloride/methanol solution (2 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (63.2 mg) as light yellow powdery solid.

$^1$H-NMR (DMSO-$d_6$) δ (ppm): 1.24 (3H, t, J=7.3 Hz), 1.71–1.86 (2H, m), 2.18–2.22 (2H, m), 3.01–3.17 (2H, m), 3.38–3.42 (2H, m), 3.70–3.78 (1H, m), 5.82 (1H, br.s), 7.36–7.39 (1H, m), 7.74–7.75 (2H, m), 8.28 (1H, s), 8.85 (1H, br.s), 9.05 (1H, br.s), 9.49 (1H, s)

MS (m/z): 256 (MH+)

Example 114

4-(1-Chloro-5-isoquinolyl)aminopiperidine trifluoroacetate (Step A) Synthesis of 1-chloro-5-aminoisoquinoline (Intermediate 83)

A solution (40 ml) of 1-chloro-5-nitroisoquinoline (2.23 g, synthesized according to the method described in J. Med. Chem. 45, 3, 740 (2002)) in ethyl acetate was added with tin(II) chloride dihydrate (12.39 g, Wako Pure Chemical Industries) at room temperature and stirred with heating at 70° C. for 1 hour. The reaction mixture was cooled to room temperature, then added with ice (200 g) and stirred for 0.5 hour. The reaction mixture was filtered through Celite and extracted three times with ethyl acetate (200 ml for each time), and the organic layer was dried over anhydrous sodium sulfate. The solvent was evaporated under reduced pressure, and the residue was purified by silica gel column chromatography (n-hexane:ethyl acetate=3:1) to obtain the title compound (749 mg).

(Step B) Synthesis of 4-(1-chloro-5-isoquinolyl) amino-1-(tert-butoxycarbonyl)piperidine (Intermediate 84)

According to the method of Example 103, Step A, the title compound (846 mg) was obtained from Intermediate 83 (749 mg), tert-butyl 4-oxo-1-piperidinecarboxylate (1.72 g), titanium tetraisopropoxide (2.60 ml) and sodium borohydride (691 mg).

(Step C) Synthesis of 4-(1-chloro-5-isoquinolyl)aminopiperidine trifluoroacetate Deprotection was performed (room temperature, 2 hours) by using Intermediate 84 (81.9 mg) and a mixed solution of trifluoroacetic acid and methylene chloride (1:1, 2 ml). The solvent was evaporated under reduced pressure, and the residue was added with methanol (2 ml) and diethyl ether (6 ml). The deposited precipitates were collected by filtration and washed with diethyl ether to obtain the title compound (64 mg) as yellow powdery crystals.

$^1$H-NMR (DMSO-$d_6$) δ (ppm): 1.68–1.82 (2H, m), 2.09–2.19 (2H, m), 3.02–3.13 (2H, m), 3.37–3.41 (2H, m), 3.70–3.80 (1H, m), 6.40 (1H, br.s), 6.97 (1H, d, J=7.7 Hz), 7.46 (1H, d, J=8.3 Hz), 7.57 (1H, t, J=8.1 Hz), 8.19–8.24 (2H, m), 8.58 (1H, br.s), 8.73 (1H, br.s)

MS (m/z): 262 (MH+)

Example 115

4-(1-Hydroxy-5-isoquinolyl)aminopiperidine hydrochloride (Exemplary Compound No. 2-59)

Intermediate 84 (76.6 mg) was added with concentrated hydrochloric acid (1.5 ml) and stirred with heating at 85° C. for 7 hours. The reaction mixture was cooled to room temperature, and then the residue was added with ethanol (1 ml) and diethyl ether (2 ml). The deposited precipitates were collected by filtration and washed with diethyl ether to obtain the title compound (55.5 mg) as white powdery solid.

$^1$H-NMR (DMSO-$d_6$) δ (ppm): 1.70–1.81 (2H, m), 2.07–2.11 (2H, m), 2.95–3.06 (2H, m), 3.30–3.34 (2H, m), 3.63–3.70 (1H, m), 6.87–6.94 (2H, m), 7.07–7.11 (1H, m), 7.27 (1H, t, J=7.9 Hz), 7.50 (1H, d, J=8.1 Hz), 8.87 (1H, br.s), 9.00 (1H, br.s), 11.20 (1H, br.s), MS (m/z): 244 (MH+)

Example 116

N-(4-Vinyl-5-isoquinolyl)-1,4-cyclohexanediamine hydrochloride (Step A) Synthesis of N-(tert-butoxycarbonyl)-N'-(4-vinyl-5-isoquinolyl)-1,4-cyclohexanediamine (Intermediate 85)

According to the method of Example 106, Step A, the title compound (222 mg) was obtained from Intermediate 76 (302 mg), tetrakis(triphenylphosphine)palladium(0) (16.8 mg), tri(n-butyl)vinyltin (328 μl) and 2,6-di-tert-butyl-4-methylphenol (several pellets).

(Step B) Synthesis of N-(4-vinyl-5-isoquinolyl)-1,4-cyclohexanediamine hydrochloride According to the method of Example 1, Step C, deprotection was performed (50° C., 2 hours) by using Intermediate 85 (85.5 mg) and 10% hydrogen chloride/methanol solution (2 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (52.3 mg).

MS (m/z): 268 (MH+)

Example 117

N-(4-Ethyl-5-isoquinolyl)-1,4-cyclohexanediamine hydrochloride (Step A) Synthesis of N-(tert-butoxycarbonyl)-N'-(4-ethyl-5-isoquinolyl)-1,4-cyclohexanediamine (Intermediate 86)

According to the method of Example 113, Step A, the title compound (133 mg) was obtained from Intermediate 85 (152 mg) and 10% palladium carbon catalyst (14.0 mg).

(Step B) Synthesis of N-(4-ethyl-5-isoquinolyl)-1,4-cyclohexanediamine hydrochloride According to the method of Example 1, Step C, deprotection was performed (50° C., 2 hours) by using Intermediate 86 (133 mg) and 10% hydrogen chloride/methanol solution (2 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (80.9 mg).

MS (m/z): 270 (MH+)

Example 118

4-(4-Chloro-5-isoquinolyl)aminopiperidine hydrochloride (Step A) Synthesis of 4-aminoisoquinoline (Intermediate 87)

A suspension of 4-bromoisoquinoline (25.0 g), copper(II) sulfate pentahydrate (30.4 g, Nacalai Tesque), 28% aqueous ammonia (100 ml) and 1,4-dioxane (100 ml) was stirred in a sealed tube at 165° C. for 21 hours. The reaction mixture was cooled to room temperature, the insoluble matters were removed by filtration through Celite, and the filtrate was extracted twice with ethyl acetate (150 ml for each time). The organic layer was dried over anhydrous sodium sulfate, and then the solvent was evaporated under reduced pressure. The residue was purified by silica gel column chromatography (chloroform:methanol=9:1) to obtain the title compound (13.2 g).

(Step B) Synthesis of 4-chloroisoquinoline (Intermediate 88)

Intermediate 87 (1.27 g) was dissolved in 1 N aqueous hydrochloric acid (36 ml) and added dropwise with an aqueous solution (36 ml) of sodium nitrite (1.21 g, Wako Pure Chemical Industries) with ice cooling. The obtained suspension was added dropwise to a solution of copper(I) chloride (1.83 g, Wako Pure Chemical Industries) in 1 N aqueous hydrochloric acid (20 ml) with ice cooling, then warmed to room temperature and stirred for 15 hours. The reaction mixture was added with 28% aqueous ammonia (50 ml) and extracted twice with ethyl acetate (150 ml for each time). The organic layer was dried over anhydrous sodium sulfate, and then the solvent was evaporated under reduced pressure. The residue was purified by silica gel column chromatography (n-hexane:ethyl acetate=2:1) to obtain the title compound (433 mg).

(Step C) Synthesis of 4-chloro-5-nitroisoquinoline (Intermediate 89)

Intermediate 88 (375 mg) was dissolved in concentrated sulfuric acid (2 ml), then added with potassium nitrate (260 mg) with ice cooling and stirred for 2 hours. The reaction mixture was added with 28% aqueous ammonia (10 ml) and extracted twice with ethyl acetate (15 ml for each time). The organic layer was dried over anhydrous sodium sulfate, and then the solvent was evaporated under reduced pressure. The residue was purified by silica gel column chromatography (n-hexane:ethyl acetate=1:1) to obtain the title compound (332 mg).

(Step D) Synthesis of 4-chloro-5-aminoisoquinoline (Intermediate 90)

Tin(II) chloride dihydrate (1.70 g) was dissolved in concentrated hydrochloric acid (1 ml), added with a mixture of Intermediate 89 (315 mg) and 2 N aqueous hydrochloric acid (2 ml) with ice cooling and refluxed with heating for 2 hours. The reaction mixture was cooled to room temperature, added with 5 N aqueous sodium hydroxide (7 ml) and extracted twice with chloroform (20 ml for each time). The organic layer was dried over anhydrous sodium sulfate, and the solvent was evaporated under reduced pressure to obtain the title compound (182 mg).

(Step E) Synthesis of 4-(4-chloro-5-isoquinolyl)amino-1-(tert-butoxycarbonyl)piperidine (Intermediate 91)

According to the method of Example 103, Step A, a mixture of Intermediate 90 (121 mg), tert-butyl 4-oxo-1-piperidinecarboxylate (274 mg), titanium tetraisopropoxide (0.41 ml) and dichloromethane (7 ml) was stirred at room temperature for 138 hours. The reaction mixture was added with sodium borohydride (114 mg) and methanol (1 ml) and stirred for 1.5 hours with ice cooling. The reaction mixture was added with saturated aqueous sodium hydrogencarbonate (10 ml) with ice cooling and extracted twice with ethyl acetate (15 ml for each time). The organic layer was dried over anhydrous sodium sulfate, and then the solvent was evaporated under reduced pressure. The residue was purified by silica gel column chromatography (n-hexane:ethyl acetate=1:1) to obtain the title compound (53.5 mg).

(Step F) Synthesis of 4-(4-chloro-5-isoquinolyl)aminopiperidine hydrochloride

According to the method of Example 1, Step C, deprotection was performed (room temperature, 2 hours) by using Intermediate 91 (53.5 mg) and 10% hydrogen chloride/methanol solution (2 ml). The solvent was evaporated under reduced pressure, and the residue was added with methanol (1 ml) and diethyl ether (3 ml). The deposited precipitates were collected by filtration and washed with diethyl ether to obtain the title compound (50.8 mg) as light yellow powdery solid.

$^1$H-NMR (DMSO-$d_6$) δ (ppm): 1.72–1.92 (2H, m), 2.18–2.24 (2H, m), 3.01–3.09 (2H, m), 3.27–3.32 (2H, m), 3.78–3.85 (1H, m), 7.20 (1H, d, J=7.9 Hz), 7.58 (1H, d, J=8.1 Hz), 7.67 (1H, t, J=7.9 Hz), 8.48 (1H, s), 9.17 (1H, s), 9.32 (2H, br.s)

MS (m/z): 262 (MH+)

Example 119

N-(4-Chloro-5-isoquinolyl)-1,4-cyclohexanediamine hydrochloride (Step A) Synthesis of N-(tert-butoxycarbonyl)-N'-(4-chloro-5-isoquinolyl)-1,4-cyclohexanediamine (Intermediate 92)

According to the method of Example 103, Step A, a mixture of Intermediate 90 (100 mg), tert-butyl 4-oxo-1-aminocyclohexylcarboxylate (270 mg), titanium tetraisopropoxide (0.34 ml) and dichloromethane (7 ml) was stirred at room temperature for 120 hours. The reaction mixture was added with sodium borohydride (94 mg) and methanol (1 ml) and stirred for 1.5 hours with ice cooling. The reaction mixture was added with saturated aqueous sodium hydrogencarbonate (10 ml) with ice cooling and then extracted twice with ethyl acetate (15 ml for each time). The organic layer was dried over anhydrous sodium sulfate, and then the solvent was evaporated under reduced pressure. The residue was purified by silica gel column chromatography (n-hexane:ethyl acetate=1:1) to obtain the title compound (40.4 mg).

(Step B) Synthesis of N-(4-chloro-5-isoquinolyl)-1,4-cyclohexanediamine hydrochloride According to the method of Example 1, Step C, deprotection was performed (room temperature, 2 hours) by using Intermediate 92 (40.4 mg) and 10% hydrogen chloride/methanol solution (2 ml). The solvent was evaporated under reduced pressure, and the residue was added with methanol (1 ml) and diethyl ether (3 ml). The deposited precipitates were collected by filtration and washed with diethyl ether to obtain the title compound (37.8 mg) as light yellow powdery solid.

MS (m/z): 276 (MH+)

Example 120

Cis-N-(4-methyl-5-isoquinolyl)-1,4-cyclohexanediamine hydrochloride (Exemplary Compound No. 2-71)

(Step A) Synthesis of 5-bromo-4-methylisoquinoline (Intermediate 93)

4-Methylisoquinoline (0.1 ml, synthesized according to the method described in Tetrahedron. Lett. 34, 45, 7239 (1993)) was dissolved in concentrated sulfuric acid (1 ml), then added with N-bromosuccinimide (125 mg) with ice cooling and stirred for 2 hours. The reaction mixture was added with 28% aqueous ammonia (5 ml) and extracted twice with dichloromethane (10 ml for each time). The organic layer was dried over anhydrous sodium sulfate, and then the solvent was evaporated under reduced pressure. The residue was purified by silica gel column chromatography (chloroform:methanol=50:1) to obtain the title compound (108 mg).

(Step B) Synthesis of cis-N-(tert-butoxycarbonyl)-N'-(4-methyl-5-isoquinolyl)-1,4-cyclohexanediamine (Intermediate 94)

According to the method of Example 15, Step A, the title compound was synthesized from Intermediate 93. That is, under nitrogen atmosphere, a suspension of Intermediate 93 (602 mg), tris(dibenzylideneacetone)dipalladium(0) (124 mg), tri(tert-butyl)phosphine (0.5 ml, Kanto Chemicals), cis-N-(tert-butoxycarbonyl)-1,4-cyclohexanediamine (697 mg) and sodium tert-butoxide (390 mg) in toluene was stirred with heating at 120° C. for 16.5 hours. The reaction mixture was cooled to room temperature and added with ethyl acetate (10 ml), and the insoluble matters were removed by filtration through Celite. The solvent was evaporated under reduced pressure, and the residue was purified by silica gel column chromatography (n-hexane:ethyl acetate=1:1) to obtain the title compound (45 mg).

(Step C) Synthesis of cis-N-(4-methyl-5-isoquinolyl)-1,4-cyclohexanediamine hydrochloride According to the method of Example 1, Step C, deprotection was performed (room temperature, 2 hours) by using Intermediate 94 (35.8 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (30.3 mg) as light yellow powdery solid.

$^1$H-NMR (DMSO-$d_6$) δ (ppm): 1.60–1.90 (6H, m), 1.95–2.20 (2H, m), 3.10–3.20 (4H, m), 3.72 (1H, br.s), 7.23 (1H, d, J=7.2 Hz), 7.70–7.80 (2H, m), 8.20–8.50 (4H, m), 9.56 (1H, s)

MS (m/z): 256 (MH+)

Example 121

Trans-N-(4-methyl-5-isoquinolyl)-1,4-cyclohexanediamine hydrochloride (Exemplary Compound No. 2-72)

(Step A) Synthesis of trans-N-(tert-butoxycarbonyl)-N'-(4-methyl-5-isoquinolyl)-1,4-cyclohexanediamine (Intermediate 95)

According to the method of Example 15, Step A, the title compound was synthesized from Intermediate 93. That is, under nitrogen atmosphere, a suspension of Intermediate 93 (1.13 g), tris(dibenzylideneacetone)dipalladium(0) (0.71 g), tri(tert-butyl)phosphine (0.5 ml), trans-N-(tert-butoxycarbonyl)-1,4-cyclohexanediamine (1.04 g) and sodium tert-butoxide (0.73 g) in toluene was stirred with heating at 120° C. for 1 hour. The reaction mixture was cooled to room temperature and added with ethyl acetate (50 ml), and the insoluble matters were removed by filtration through Celite. The solvent was evaporated under reduced pressure, and the residue was purified by silica gel column chromatography (n-hexane:ethyl acetate=1:1) to obtain the title compound (456 mg).

(Step B) Synthesis of trans-N-(4-methyl-5-isoquinolyl)-1,4-cyclohexanediamine hydrochloride According to the method of Example 1, Step C, deprotection was performed (room temperature, 2 hours) by using Intermediate 95 (389 mg) and 10% hydrogen chloride/methanol solution (10 ml). The solvent was evaporated under reduced pressure, and the residue was added with methanol (2 ml) and diethyl ether (6 ml). The deposited precipitates were collected by filtration and washed with diethyl ether to obtain the title compound (355 mg) as light yellow powdery solid.

$^1$H-NMR (DMSO-$d_6$) δ (ppm): 1.30–1.70 (4H, m), 1.95–2.25 (4H, m), 2.87–3.15 (4H, m), 3.35–3.55 (1H, m), 7.32 (1H, d, J=6.9 Hz), 7.65–7.80 (2H, m), 8.20–8.40 (4H, m), 9.53 (1H, s)

MS (m/z): 256 (MH+)

Example 122

4-(4-Methoxy-5-isoquinolyl)aminopiperidine hydrochloride (Exemplary Compound No. 2-37)

(Step A) Synthesis of 4-(4-methoxy-5-isoquinolyl) amino-1-(tert-butoxycarbonyl)piperidine (Intermediate 96)

A suspension of Intermediate 71 (600 mg) and copper(I) iodide (141 mg, Kanto Chemicals) in methanol (5.5 ml) and pyridine (5.5 ml) was added with sodium methoxide (28% methanol solution, 1.7 ml, Wako Pure Chemical Industries) and stirred with heating at 65° C. for 24 hours. The reaction mixture was cooled to room temperature, then added with water (30 ml) and extracted three times with ethyl acetate (20 ml for each time). The combined organic layer was washed twice with saturated brine (30 ml for each time) and dried over anhydrous sodium sulfate. The solvent was evaporated under reduced pressure, and the residue was purified by silica gel column chromatography (n-hexane:ethyl acetate=1:2) to obtain the title compound (364 mg).

(Step B) Synthesis of 4-(4-methoxy-5-isoquinolyl)aminopiperidine hydrochloride

According to the method of Example 1, Step C, deprotection was performed (50° C., 2 hours) by using Intermediate 96 (358 mg) and 10% hydrogen chloride/methanol solution (10 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (336 mg) as light yellow powdery solid.

$^1$H-NMR (DMSO-$d_6$) δ (ppm): 1.67–1.81 (2H, m), 2.16–2.25 (2H, m), 2.97–3.14 (2H, m), 3.22–3.36 (2H, m), 3.75–3.85 (1H, m), 4.14 (3H, s), 6.99 (1H, br.s), 7.16 (1H, d, J=8.1 Hz), 7.55 (1H, d, J=8.1 Hz), 7.71 (1H, t, J=8.1 Hz), 8.10 (1H, s), 9.13 (2H, br.s), 9.22 (1H, s)

MS (m/z): 258 (MH+)

Example 123

N-(4-Methoxy-5-isoquinolyl)-1,4-cyclohexanediamine hydrochloride (Step A) Synthesis of N-(tert-butoxycarbonyl)-N'-(4-methoxy-5-isoquinolyl)-1,4-cyclohexanediamine (Intermediate 97)

According to the method of Example 122, Step A, the title compound (392 mg) was obtained from Intermediate 76 (621 mg), copper(I) iodide (141 mg), methanol (5.5 ml), pyridine (5.5 ml) and sodium methoxide (28% methanol solution, 1.7 ml).

(Step B) Synthesis of N-(4-methoxy-5-isoquinolyl)-1,4-cyclohexanediamine hydrochloride According to the method of Example 1, Step C, deprotection was performed (50° C., 2 hours) by using Intermediate 97 (372 mg) and 10% hydrogen chloride/methanol solution (10 ml). The reaction mixture was cooled to room temperature, and then the solvent was evaporated under reduced pressure. The residue was added with methanol (2 ml) and diethyl ether (6 ml). The deposited precipitates were collected by filtration and washed with diethyl ether to obtain the title compound (348 mg) as light yellow powdery solid.

MS (m/z): 272 (MH+)

Example 124

N-[(5-Isoquinolyl)sulfonyl]-N-[3-(4-methanesulfonyl)phenylpropyl]-1,3-propylenediamine hydrochloride (Exemplary Compound No. 3-50)

(Step A) Synthesis of 3-(4-methanesulfonyl)phenyl-2-propyn-1-ol (Intermediate 98)

A solution of dichlorobis(benzonitrile)palladium(II) (230 mg, Aldrich), copper(I) iodide (76 mg), tri(tert-butyl)phosphine (299 µl), N,N-diisopropylamine (3.4 ml, Tokyo Kasei Kogyo), 4-bromophenylmethylsulfone (4.7 g, Lancaster) and 2-propyn-1-ol (1.4 ml, Tokyo Kasei Kogyo) in 1,4-dioxane (25 ml) was stirred at room temperature for 12 hours. The reaction mixture was added with ethyl acetate (50 ml), and the deposited precipitates were removed by filtration through Celite. The solvent was evaporated under reduced pressure, and the residue was added with ethyl acetate (40 ml) and washed successively with water (30 ml) and saturated brine (30 ml). The organic layer was dried over anhydrous sodium sulfate, and the solvent was evaporated under reduced pressure. The residue was purified by silica gel column chromatography (n-hexane:ethyl acetate=1:1) to obtain the title compound (1.52 g).

(Step B) Synthesis of 3-(4-methanesulfonyl)phenyl-1-propanol (Intermediate 99)

A solution of Intermediate 98 (1.26 g) in methanol (16 ml) was vigorously stirred at room temperature in the presence of 10% palladium carbon catalyst (63 mg, Wako Pure Chemical Industries) under hydrogen atmosphere of ordinary pressure. The reaction mixture was filtered through Celite, and the solvent was evaporated under reduced pressure. The residue was purified by silica gel column chromatography (n-hexane:ethyl acetate=1:1) to obtain the title compound (1.13 g).

(Step C) Synthesis of N-(tert-butoxycarbonyl)-N'-[(5-isoquinolyl)sulfonyl]-N'-[3-(4-methanesulfonyl) phenylpropyl]-1,3-propylenediamine (Intermediate 100)

According to the method of Example 1, Step B with the modifications that the reaction was carried out for 24 hours, and the compound was purified by silica gel column chromatography (n-hexane:ethyl acetate=1:1), the title compound (449 mg) was obtained from Intermediate 1 (365 mg), tri(n-butyl)phosphine (747 μl), Intermediate 99 (429 mg) and 1,1'-azobis(N,N-dimethylformamide) (517 mg).

(Step D) Synthesis of N-[(5-isoquinolyl)sulfonyl]-N-[3-(4-methanesulfonyl)phenylpropyl]-1,3-propylenediamine hydrochloride According to the method of Example 1, Step C, deprotection was performed (50° C., 2 hours) by using Intermediate 100 (281 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (230 mg) as white powdery solid.

$^1$H-NMR (DMSO-$d_6$) δ (ppm): 1.71–1.92 (4H, m), 2.54–2.60 (2H, m), 2.70–2.80 (2H, m), 3.27–3.33 (2H, m), 3.39–3.46 (2H, m), 7.38 (2H, d, J=8.1 Hz), 7.80 (2H, d, J=8.1 Hz), 7.99 (1H, t, J=7.8 Hz), 8.13 (3H, br.s), 8.50 (1H, d, J=7.8 Hz), 8.62 (1H, d, J=6.6 Hz), 8.67 (1H, d, J=8.1 Hz), 8.79 (1H, d, J=6.6 Hz), 9.84 (1H, s)

MS (m/z): 462 (MH+)

Example 125

N-[(5-Isoquinolyl)sulfonyl]-N-[3-(3-methanesulfonyl)phenylpropyl]-1,3-propylenediamine hydrochloride (Exemplary Compound No. 3-49)

(Step A) Synthesis of 3-bromophenylmethylsulfone (Intermediate 101)

Trifluoroacetic acid (15 ml) was added with 3-bromothioanisole (5.17 g, Fluorochem) and added dropwise with 30% aqueous hydrogen peroxide (10 ml, Wako Pure Chemical Industries) at 0° C. The reaction mixture was stirred at room temperature for 3 hours, then cooled to 0° C. and neutralized with 5 N aqueous sodium hydroxide. The reaction mixture was extracted twice with ethyl acetate (50 ml for each), and the combined organic layer was washed twice with saturated brine (100 ml for each time). The organic layer was dried over anhydrous sodium sulfate, and the solvent was evaporated under reduced pressure. The residue was recrystallized (n-hexane/acetone) to obtain the title compound (5.40 g) as white needle-like crystals.

(Step B) Synthesis of 3-(3-methanesulfonyl)phenyl-2-propyn-1-ol (Intermediate 102)

According to the method of Example 124, Step A, the title compound (1.33 g) was obtained from Intermediate 101 (4.7 g), dichlorobis(benzonitrile)palladium(II) (230 mg, Aldrich), copper(I) iodide (76 mg), tri(tert-butyl)phosphine (299 μl), N,N-diisopropylamine (3.4 ml) and 2-propyn-1-ol (1.4 ml).

(Step C) Synthesis of 3-(3-methanesulfonyl)phenyl-1-propanol (Intermediate 103)

According to the method of Example 124, Step B, the title compound (1.19 g) was obtained from Intermediate 102 (1.26 g).

(Step D) Synthesis of N-(tert-butoxycarbonyl)-N'-[(5-isoquinolyl)sulfonyl]-N'-[3-(3-methanesulfonyl)phenylpropyl]-1,3-propylenediamine (Intermediate 104)

According to the method of Example 1, Step B with the modifications that the reaction was carried out for 24 hours, and the compound was purified by silica gel column chromatography (n-hexane:ethyl acetate=1:1), the title compound (462 mg) was obtained from Intermediate 1 (365 mg), tri(n-butyl)phosphine (747 μl), Intermediate 103 (429 mg) and 1,1'-azobis(N,N-dimethylformamide) (517 mg).

(Step E) Synthesis of N-[(5-isoquinolyl)sulfonyl]-N-[3-(3-methanesulfonyl)phenylpropyl]-1,3-propylenediamine hydrochloride According to the method of Example 1, Step C, deprotection was performed (50° C., 2 hours) by using Intermediate 104 (281 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (203 mg) as white powdery solid.

MS (m/z): 462 (MH+)

Example 126

N-[(5-Isoquinolyl)sulfonyl]-N-[3-(2-methanesulfonyl)phenylpropyl]-1,3-propylenediamine hydrochloride (Exemplary Compound No. 3-48)

(Step A) Synthesis of 2-bromophenylmethylsulfone (Intermediate 105)

According to the method of Example 125, Step A, the title compound (5.22 g) was obtained from 2-bromothioanisole (5.17 g, Tokyo Kasei Kogyo) as white needle-like crystals.

(Step B) Synthesis of 3-(3-methanesulfonyl)phenyl-2-propyn-1-ol (Intermediate 106)

According to the method of Example 124, Step A, the title compound (1.01 g) was obtained from Intermediate 105 (4.7 g), dichlorobis(benzonitrile)palladium(II) (230 mg), copper (I) iodide (76 mg), tri(tert-butyl)phosphine (299 μl), N,N-diisopropylamine (3.4 ml) and 2-propyn-1-ol (1.4 ml).

(Step C) Synthesis of 3-(2-methanesulfonyl)phenyl-1-propanol (Intermediate 107)

According to the method of Example 124, Step B, the title compound (580 mg) was obtained from Intermediate 106 (630 mg).

(Step D) Synthesis of N-(tert-butoxycarbonyl)-N'-[(5-isoquinolyl)sulfonyl]-N'-[3-(2-methanesulfonyl)phenylpropyl]-1,3-propylenediamine (Intermediate 108)

According to the method of Example 1, Step B with the modifications that the reaction was carried out for 24 hours, and the compound was purified by silica gel column chromatography (n-hexane:ethyl acetate=1:1), the title compound (440 mg) was obtained from Intermediate 1 (365 mg), tri(n-butyl)phosphine (747 µl), Intermediate 107 (429 mg) and 1,1'-azobis(N,N-dimethylformamide) (517 mg).

(Step E) Synthesis of N-[(5-isoquinolyl)sulfonyl]-N-[3-(2-methanesulfonyl)phenylpropyl]-1,3-propylenediamine hydrochloride According to the method of Example 1, Step C, deprotection was performed (50° C., 2 hours) by using Intermediate 108 (281 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (210 mg) as white powdery solid.
MS (m/z): 462 (MH+)

Example 127

N-[(5-Isoquinolyl)sulfonyl]-N-[3-(4-carboxy)phenylpropyl]-1,3-propylenediamine hydrochloride (Step A) Synthesis of 3-(4-methoxycarbonyl)phenyl-2-propyn-1-ol (Intermediate 109)

According to the method of Example 124, Step A, the title compound (607 mg) was obtained from methyl 4-bromobenzoate (1.72 g, Tokyo Kasei Kogyo), dichlorobis(benzonitrile)palladium(II) (92 mg), copper(I) iodide (31 mg), tri(tert-butyl)phosphine (117 µl), N,N-diisopropylamine (1.35 ml) and 2-propyn-1-ol (559 µl).

(Step B) Synthesis of 3-(4-methoxycarbonyl)phenyl-1-propanol (Intermediate 110)

According to the method of Example 124, Step B, the title compound (545 mg) was obtained from Intermediate 109 (600 mg).

(Step C) Synthesis of N-(tert-butoxycarbonyl)-N'-[(5-isoquinolyl)sulfonyl]-N'-[3-(4-methoxycarbonyl)phenylpropyl]-1,3-propylenediamine (Intermediate 111)

According to the method of Example 1, Step B with the modifications that the reaction was carried out for 24 hours, and the compound was purified by silica gel column chromatography (n-hexane:ethyl acetate=1:1), the title compound (433 mg) was obtained from Intermediate 1 (365 mg), tri(n-butyl)phosphine (747 µl), Intermediate 110 (389 mg) and 1,1'-azobis(N,N-dimethylformamide) (517 mg).

(Step D) Synthesis of N-[(5-isoquinolyl)sulfonyl]-N-[3-(4-carboxy)phenylpropyl]-1,3-propylenediamine hydrochloride Intermediate 111 (271 mg) was added with concentrated hydrochloric acid (5 ml) and stirred with heating at 50° C. for 24 hours. The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (194 mg) as white powdery solid.
MS (m/z): 428 (MH+)

Example 128

N-[(5-Isoquinolyl)sulfonyl]-N-[3-(3-carboxy)phenylpropyl]-1,3-propylenediamine hydrochloride (Step A) Synthesis of 3-(3-methoxycarbonyl)phenyl-2-propyn-1-ol (Intermediate 112)

According to the method of Example 124, Step A, the title compound (610 mg) was obtained from methyl 3-bromobenzoate (1.72 g, Tokyo Kasei Kogyo), dichlorobis(benzonitrile)palladium(II) (92 mg), copper(I) iodide (31 mg), tri(tert-butyl)phosphine (117 µl), N,N-diisopropylamine (1.35 ml) and 2-propyn-1-ol (559 µl).

(Step B) Synthesis of 3-(3-methoxycarbonyl)phenyl-1-propanol (Intermediate 113)

According to the method of Example 124, Step B, the title compound (550 mg) was obtained from Intermediate 112 (600 mg).

(Step C) Synthesis of N-(tert-butoxycarbonyl)-N'-[(5-isoquinolyl)sulfonyl]-N'-[3-(3-methoxycarbonyl)phenylpropyl]-1,3-propylenediamine (Intermediate 114)

According to the method of Example 1, Step B with the modifications that the reaction was carried out for 24 hours, and the compound was purified by silica gel column chromatography (n-hexane:ethyl acetate=1:1), the title compound (420 mg) was obtained from Intermediate 1 (365 mg), tri(n-butyl)phosphine (747 µl), Intermediate 113 (389 mg) and 1,1'-azobis(N,N-dimethylformamide) (517 mg).

(Step D) Synthesis of N-[(5-isoquinolyl)sulfonyl]-N-[3-(3-carboxy)phenylpropyl]-1,3-propylenediamine hydrochloride According to the method of Example 127, Step D, the title compound (201 mg) was obtained from Intermediate 114 (271 mg) as white powdery solid.
MS (m/z): 428 (MH+)

Example 129

N-[(5-Isoquinolyl)sulfonyl]-N-[3-(2-carboxy)phenylpropyl]-1,3-propylenediamine hydrochloride (Step A) Synthesis of 3-(2-methoxycarbonyl)phenyl-2-propyn-1-ol (Intermediate 115)

According to the method of Example 124, Step A, the title compound (600 mg) was obtained from methyl 2-bromobenzoate (1.72 g, Tokyo Kasei Kogyo), dichlorobis(benzonitrile)palladium(II) (92 mg), copper(I) iodide (31 mg), tri(tert-butyl)phosphine (117 µl), N,N-diisopropylamine (1.35 ml) and 2-propyn-1-ol (559 µl).

(Step B) Synthesis of 3-(2-methoxycarbonyl)phenyl-1-propanol (Intermediate 116)

According to the method of Example 124, Step B, the title compound (529 mg) was obtained from Intermediate 115 (600 mg).

(Step C) Synthesis of N-(tert-butoxycarbonyl)-N'-[(5-isoquinolyl)sulfonyl]-N'-[3-(2-methoxycarbonyl)phenylpropyl]-1,3-propylenediamine (Intermediate 117)

According to the method of Example 1, Step B with the modifications that the reaction was carried out for 24 hours, and the compound was purified by silica gel column chromatography (n-hexane:ethyl acetate=1:1), the title compound (423 mg) was obtained from Intermediate 1 (365 mg), tri(n-butyl)phosphine (747 μl), Intermediate 116 (389 mg) and 1,1'-azobis(N,N-dimethylformamide) (517 mg).

(Step D) Synthesis of N-[(5-isoquinolyl)sulfonyl]-N-[3-(2-carboxy)phenylpropyl]-1,3-propylenediamine hydrochloride According to the method of Example 127, Step D, the title compound (211 mg) was obtained from Intermediate 117 (271 mg) as white powdery solid.
MS (m/z): 428 (MH+)

Example 130

N-[(5-Isoquinolyl)sulfonyl]-N-[3-(4-methoxycarbonyl)phenylpropyl]-1,3-propylenediamine hydrochloride According to the method of Example 1, Step C, deprotection was performed (50° C., 2 hours) by using Intermediate 111 (271 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (199 mg) as white powdery solid.
MS (m/z): 442 (MH+)

Example 131

N-[(5-Isoquinolyl)sulfonyl]-N-[3-(3-methoxycarbonyl)phenylpropyl]-1,3-propylenediamine hydrochloride According to the method of Example 1, Step C, deprotection was performed (50° C., 2 hours) by using Intermediate 114 (271 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (180 mg) as white powdery solid.
MS (m/z): 442 (MH+)

Example 132

N-[(5-Isoquinolyl)sulfonyl]-N-[3-(2-methoxycarbonyl)phenylpropyl]-1,3-propylenediamine hydrochloride According to the method of Example 1, Step C, deprotection was performed (50° C., 2 hours) by using Intermediate 117 (271 mg) and 10% hydrogen chloride/methanol solution (5 ml). The reaction mixture was cooled to room temperature, and then the solvent was evaporated under reduced pressure. The residue was added with methanol (1 ml) and diethyl ether (3 ml). The deposited precipitates were collected by filtration and washed with diethyl ether to obtain the title compound (189 mg) as white powdery solid.
MS (m/z): 442 (MH+)

Example 133

Trans-4-[(4-bromo-5-isoquinolyl)oxy]cyclohexylamine hydrochloride (Step A) Synthesis of cis-4-methoxybenzoic acid 4-(tert-butoxycarbonylamino)cyclohexyl ester (Intermediate 118)

A solution of Intermediate 35 (21.06 g), 1,1'-azobis(N,N-dimethylformamide) (64.11 g) and p-anisic acid (23.03 g, Tokyo Kasei Kogyo) in tetrahydrofuran (400 ml) was added with tri(n-butyl)phosphine (35.6 ml) at room temperature and stirred at 50° C. for 2.5 hours. The reaction mixture was cooled to room temperature, then added with ethyl acetate (200 ml) and successively washed with saturated aqueous sodium hydrogencarbonate twice (200 ml each) and 0.1 N aqueous sodium hydroxide (50 ml), and dried over anhydrous sodium sulfate. The solvent was evaporated under reduced pressure, and the residue was purified by silica gel column chromatography (n-hexane:ethyl acetate=5:1) to obtain the title compound (32.92 g).

(Step B) Synthesis of cis-4-(tert-butoxycarbonylamino)cyclohexanol (Intermediate 119)

A solution of Intermediate 118 (32.92 g) in methanol (400 ml) was added with 3 N aqueous sodium hydroxide (163 ml) at room temperature and stirred at 50° C. for 1.5 hours. The reaction mixture was cooled to room temperature, then added with ethyl acetate (400 ml) and washed 4 times with 0.5 N aqueous sodium hydroxide (50 ml each) and dried over anhydrous sodium sulfate. The solvent was evaporated under reduced pressure, and the residue was purified by silica gel column chromatography (n-hexane:ethyl acetate=2:1) to obtain the title compound (7.94 g).

(Step C) Synthesis of 4-bromo-5-hydroxyisoquinoline (Intermediate 120)

A solution of 4-bromo-5-aminoisoquinoline (762 mg) obtained in Reference Example 1 in concentrated sulfuric acid (5 ml) was added with sodium nitrite (235 mg) with ice cooling and stirring and stirred for 1.5 hours. The reaction mixture was added with water (5 ml) and then stirred at 130° C. for 16 hours. The reaction mixture was neutralized with 28% aqueous ammonia solution, and the precipitates were collected by filtration. The obtained solid was purified by silica gel column chromatography (chloroform:methanol=40:1) to obtain the title compound (172 mg).

(Step D) Synthesis of trans-N-(tert-butoxycarbonyl)-4-[(4-bromo-5-isoquinolyl)oxy]cyclohexylamine (Intermediate 121)

According to the method of Example 10, Step A except that the reaction was performed for 27 hours, and the purification of the compound was performed by using silica gel column chromatography (n-hexane:ethyl acetate=2:1), the title compound (166 mg) was obtained from Intermediate 120 (160 mg), Intermediate 119 (466 mg), 1,1'-azobis(N,N-dimethylformamide) (370 mg) and tri(n-butyl)phosphine (531 μl).

(Step E) Synthesis of trans-4-[(4-bromo-5-isoquinolyl)oxy]cyclohexylamine hydrochloride According to the method of Example 1, Step C, deprotection was performed (room temperature, 2 hours) by using Intermediate 121 (49.4 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (44.3 mg).

$^1$H-NMR (DMSO-$d_6$) δ (ppm): 1.45–1.76 (4H, m), 1.99–2.13 (2H, m), 2.18–2.31 (2H, m), 3.06–3.21 (1H, m), 4.51–4.67 (1H, m), 7.58 (1H, d, J=7.2 Hz), 7.70 (1H, t, J=8.1 Hz), 7.79 (1H, d, J=8.1 Hz), 8.10–8.35 (3H, m), 8.65 (1H, s), 9.29 (1H, s)

MS (m/z): 321 (MH+)

Example 134

Trans-4-[(4-cyano-5-isoquinolyl)oxy]cyclohexylamine hydrochloride (Step A) Synthesis of trans-N-(tert-butoxycarbonyl)-4-[(4-cyano-5-isoquinolyl)oxy]cyclohexylamine (Intermediate 122)

A suspension of Intermediate 121 (113.7 mg), zinc cyanide (19.4 mg, Wako Pure Chemical Industries), tris(dibenzylideneacetone)dipalladium(0) (24.0 mg) and 1,1'-bis(diphenylphosphino)ferrocene (35.3 mg, Tokyo Kasei Kogyo) in DMF (2 ml) was stirred at 120° C. for 19 hours. The reaction mixture was concentrated under reduced pressure, and the residue was purified by silica gel column chromatography (n-hexane:ethyl acetate=1:1) to obtain the title compound (34.9 mg).

(Step B) Synthesis of trans-4-[(4-cyano-5-isoquinolyl)oxy]cyclohexylamine hydrochloride According to the method of Example 1, Step C, deprotection was performed (room temperature, 2 hours) by using Intermediate 122 (34.9 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (22.4 mg).

$^1$H-NMR (DMSO-$d_6$) δ (ppm): 1.47–1.74 (4H, m), 2.02–2.16 (2H, m), 2.20–2.33 (2H, m), 3.01–3.21 (1H, m), 4.58–4.75 (1H, m), 7.64 (1H, d, J=7.2 Hz), 7.77 (1H, t, J=7.8 Hz), 7.84 (1H, d, J=8.1 Hz), 8.02–8.35 (3H, m), 8.95 (1H, s), 9.53 (1H, s)

MS (m/z): 268 (MH+)

Example 135

Trans-4-[(5-isoquinolyl)oxy]cyclohexylamine hydrochloride (Exemplary Compound No. 1-4)

(Step A) Synthesis of trans-N-(tert-butoxycarbonyl)-4-[(5-isoquinolyl)oxy]cyclohexylamine (Intermediate 123)

According to the method of Example 10, Step A except that the reaction was performed for 21 hours, and the purification of the compound was performed by using silica gel column chromatography (n-hexane:ethyl acetate=2:1), the title compound (64 mg) was obtained from 5-hydroxyisoquinoline (108 mg), Intermediate 119 (484 mg), 1,1'-azobis(N,N-dimethylformamide) (381 mg) and tri(n-butyl)phosphine (552 μl).

(Step B) Synthesis of trans-4-(5-isoquinolyloxy)cyclohexylamine hydrochloride

According to the method of Example 1, Step C, deprotection was performed (room temperature, 2 hours) by using Intermediate 123 (59.6 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (52.8 mg).

$^1$H-NMR (DMSO-$d_6$) δ (ppm): 1.50–1.74 (4H, m), 2.09 (2H, brs), 2.25 (2H, brs), 3.08–3.21 (1H, m), 4.62–4.72 (1H, m), 7.77 (1H, d, J=7.8 Hz), 7.89 (1H, t, J=7.8 Hz), 8.02 (1H, d, J=8.1 Hz), 8.25–8.37 (3H, m), 8.40 (1H, d, J=6.3 Hz), 8.62 (1H, d, J=6.3 Hz), 9.81 (1H, s)

MS (m/z): 243 (MH+)

Example 136

Trans-4-[(4-vinyl-5-isoquinolyl)oxy]cyclohexylamine hydrochloride (Step A) Synthesis of trans-N-(tert-butoxycarbonyl)-4-[(4-vinyl-5-isoquinolyl)oxy]cyclohexylamine (Intermediate 124)

A solution of Intermediate 121 (500 mg), tri(n-butyl)vinyltin (518 μl, Tokyo Kasei Kogyo), tetrakis(triphenylphosphine)palladium(0) (28.1 mg) and 2,6-di-tert-butyl-p-cresol (3.2 mg, Tokyo Kasei Kogyo) in toluene (10 ml) was stirred at 110° C. for 3 hours. The solvent was evaporated under reduced pressure, and the residue was purified by silica gel column chromatography (n-hexane:ethyl acetate=2:1) to obtain the title compound (409.5 mg).

(Step B) Synthesis of trans-4-[(4-vinyl-5-isoquinolyl)oxy]cyclohexylamine hydrochloride According to the method of Example 1, Step C, deprotection was performed (room temperature, 2 hours) by using Intermediate 124 (83.9 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (63.3 mg).

$^1$H-NMR (DMSO-$d_6$) δ (ppm): 1.47–1.73 (4H, m), 2.01–2.12 (2H, m), 2.18–2.27 (2H, m), 3.05–3.22 (1H, m), 4.57–4.68 (1H, m), 5.47 (1H, dd, J=1.5 Hz, 10.8 Hz), 5.67 (1H, dd, J=1.2 Hz, 11.1 Hz), 7.66–7.77 (2H, m), 7.84 (1H, t, J=8.1 Hz), 7.98 (1H, d, J=7.2 Hz), 8.22–8.32 (3H, m), 8.46 (1H, s), 9.63 (1H, s)

MS (m/z): 269 (MH+)

Example 137

Trans-4-[(4-amino-5-isoquinolyl)oxy]cyclohexylamine hydrochloride (Exemplary Compound No. 1-28)

(Step A) Synthesis of trans-N-(tert-butoxycarbonyl)-4-[(4-amino-5-isoquinolyl)oxy]cyclohexylamine (Intermediate 125)

A suspension of Intermediate 121 (100 mg), tris(dibenzylideneacetone)dipalladium(0) (22.1 mg), 2-(di-tert-butylphosphino)biphenyl (33.9 mg) and sodium tert-butoxide (35.3 mg) in 0.5 N ammonia/dioxane solution (2 ml) was stirred at 70° C. for 22 hours. The reaction mixture was filtered through a Celite layer, and the solvent was evaporated under reduced pressure. Then, the residue was purified by silica gel column chromatography (chloroform:methanol=9:1) to obtain the title compound (36.1 mg).

(Step B) Synthesis of trans-4-[(4-amino-5-isoquinolyl)oxy]cyclohexylamine hydrochloride According to the method of Example 1, Step C, deprotection was performed (room temperature, 8 hours) by using Intermediate 125 (36.1 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (13.3 mg).

$^1$H-NMR (DMSO-$d_6$) δ (ppm): 1.46–1.80 (4H, m), 2.01–2.12 (2H, m), 2.18–2.31 (2H, m), 3.07–3.17 (1H, m), 3.18–3.75 (1.5H, m), 4.60–4.70 (1H, m), 7.12 (1H, brs), 7.60 (1H, d, J=7.2 Hz), 7.71–7.80 (3H, m), 8.10–8.30 (3H, m), 8.74 (1H, s)

MS (m/z): 258 (MH+)

Example 138

Trans-4-[(4-ethyl-5-isoquinolyl)oxy]cyclohexylamine hydrochloride (Step A) Synthesis of trans-N-(tert-butoxycarbonyl)-4-[(4-ethyl-5-isoquinolyl)oxy]cyclohexylamine (Intermediate 126)

A solution of Intermediate 124 (90.5 mg) in methanol (5 ml) was added with platinum oxide (13 mg, Wako Pure Chemical Industries) and stirred for 15 hours under hydrogen atmosphere. The reaction mixture was filtered through a Celite layer, and the solvent was evaporated under reduced pressure. Then, the residue was purified by silica gel column chromatography (chloroform:methanol=20:1) to obtain the title compound (41.1 mg).

(Step B) Synthesis of trans-4-[(4-ethyl-5-isoquinolyl)oxy]cyclohexylamine hydrochloride According to the method of Example 1, Step C, deprotection was performed (room temperature, 2 hours) by using Intermediate 126 (41.1 mg) and 10% hydrogen chloride/methanol solution (2 ml). The solvent was evaporated under reduced pressure, and the residue was added with methanol (0.5 ml) and diethyl ether (1.5 ml). The deposited precipitates were collected by filtration and washed with diethyl ether to obtain the title compound (32.7 mg).

$^1$H-NMR (DMSO-$d_6$) δ (ppm): 1.29 (3H, t, J=7.5 Hz), 1.53–1.73 (4H, m), 2.08 (2H, brs), 2.31 (2H, brs), 3.05–3.19 (1H, m), 3.32 (2H, m), 4.63–4.73 (1H, m), 7.78 (1H, d, J=8.1 Hz), 7.87 (1H, t, J=8.1 Hz), 8.01 (1H, d, J=8.1 Hz), 8.23–8.38 (3H, m), 8.39 (1H, s), 9.64 (1H, s)

MS (m/z): 271 (MH+)

Example 139

4-[(4-Methyl-5-isoquinolyl)oxy]piperidine hydrochloride (Exemplary Compound No. 1-19)

(Step A) Synthesis of 4-methyl-5-hydroxyisoquinoline (Intermediate 127)

A solution of 4-methyl-5-aminoisoquinoline (869 mg) in concentrated sulfuric acid (8 ml) was added with sodium nitrite (379 mg) with ice cooling and stirring and stirred for 0.5 hours. The reaction mixture was added with water (12 ml) and then stirred at 130° C. for 16 hours. The reaction mixture was neutralized with 28% aqueous ammonia solution and extracted with ethyl acetate, and the solvent was evaporated under reduced pressure. The residue was purified by silica gel column chromatography (chloroform:methanol=30:1) to obtain the title compound (559 mg).

(Step B) Synthesis of 4-(4-methyl-5-isoquinolyl)oxy-1-(tert-butoxycarbonyl)piperidine (Intermediate 128)

According to the method of Example 10, Step A except that the reaction was performed for 21 hours, and the purification of the compound was performed by using silica gel column chromatography (n-hexane:ethyl acetate=2:1), the title compound (686 mg) was obtained from Intermediate 127 (530 mg), tert-butyl 4-hydroxy-1-piperidine-carboxylate (2.01 g), 1,1'-azobis(N,N-dimethylformamide) (1.72 g) and tri(n-butyl)phosphine (2.46 ml).

(Step C) Synthesis of 4-[(4-methyl-5-isoquinolyl)oxy]piperidine hydrochloride

According to the method of Example 1, Step C, deprotection was performed (room temperature, 2 hours) by using Intermediate 128 (604 mg) and 10% hydrogen chloride/methanol solution (20 ml). The solvent was evaporated under reduced pressure, and the residue was added with methanol (5 ml) and diethyl ether (15 ml). The deposited precipitates were collected by filtration and washed with diethyl ether to obtain the title compound (513 mg).

$^1$H-NMR (DMSO-$d_6$) δ (ppm): 1.95–2.13 (2H, m), 2.20–2.33 (2H, m), 2.91 (3H, s), 3.05–3.35 (4H, m), 4.92–5.05 (1H, m), 7.65 (1H, d, J=7.5 Hz), 7.84 (1H, t, J=8.1 Hz), 7.97 (1H, d, J=7.5 Hz), 8.41 (1H, s), 8.85–9.15 (0.5H, m), 9.56 (1H, s)

MS (m/z): 243 (MH+)

Example 140

Trans-4-[(4-methyl-5-isoquinolyl)oxy]cyclohexylamine hydrochloride (Exemplary Compound No. 1-21)

(Step A) Synthesis of trans-N-(tert-butoxycarbonyl)-4-[(4-methyl-5-isoquinolyl)oxy]cyclohexylamine (Intermediate 129)

According to the method of Example 10, Step A except that the reaction was performed for 18 hours, and the purification of the compound was performed by using silica gel column chromatography (n-hexane:ethyl acetate=2:1), the title compound (194 mg) was obtained from Intermediate 127 (473 mg), Intermediate 119 (1918 mg), 1,1'-azobis(N,N-dimethylformamide) (1534 mg) and tri(n-butyl)phosphine (2.2 ml).

(Step B) Synthesis of trans-4-[(4-methyl-5-isoquinolyl)oxy]cyclohexylamine hydrochloride According to the method of Example 1, Step C, deprotection was performed (room temperature, 2 hours) by using Intermediate 129 (194 mg) and 10% hydrogen chloride/methanol solution (3.5 ml). The solvent was evaporated under reduced pressure, and the residue was added with methanol (1 ml) and diethyl ether (3 ml). The deposited precipitates were collected by filtration and washed with diethyl ether to obtain the title compound (172 mg).

$^1$H-NMR (DMSO-d$_6$) δ (ppm): 1.50–1.74 (4H, m), 2.08 (2H, brs), 2.27 (2H, brs), 2.88 (3H, s), 3.07–3.17 (1H, m), 4.57–4.68 (1H, m), 7.76 (1H, d, J=7.5 Hz), 7.86 (1H, t, J=7.8 Hz), 8.00 (1H, d, J=8.1 Hz), 8.27–8.44 (4H, m), 9.65 (1H, s)

MS (m/z): 257 (MH+)

Example 141

Cis-4-[(1-amino-5-isoquinolyl)oxy]cyclohexylamine hydrochloride (Exemplary Compound No. 1-13)

(Step A) Synthesis of cis-N-(tert-butoxycarbonyl)-4-[(1-chloro-5-isoquinolyl)oxy]cyclohexylamine (Intermediate 130)

According to the method of Example 10, Step A except that the reaction was performed for 18 hours, and the purification of the compound was performed by using silica gel column chromatography (n-hexane:ethyl acetate=2:1), the title compound (1.93 g) was obtained from 1-chloro-5-hydroxyisoquinoline (2.06 g), Intermediate 35 (7.41 g), 1,1'-azobis(N,N-dimethylformamide) (5.93 g) and tri(n-butyl)phosphine (8.50 ml).

(Step B) Synthesis of cis-N-(tert-butoxycarbonyl)-4-[(1-amino-5-isoquinolyl)oxy]cyclohexylamine (Intermediate 131)

A solution of Intermediate 130 (500 mg) in dioxane (2.5 ml) was added with 28% aqueous ammonia solution (2.5 ml) and stirred at 150° C. for 20 hours in a sealed tube. The reaction mixture was cooled to room temperature, and then the solvent was evaporated under reduced pressure. The residue was added with dioxane (6 ml), 2 N aqueous sodium hydroxide (2 ml) and di-t-butyl dicarbonate (655 mg) and stirred at room temperature for 1 hour. The solvent was evaporated under reduced pressure, and the residue was purified by silica gel column chromatography (ethyl acetate:methanol=30:1) to obtain the title compound (95.0 mg).

(Step C) Synthesis of cis-4-[(1-amino-5-isoquinolyl)oxy]cyclohexylamine hydrochloride According to the method of Example 1, Step C, deprotection was performed (room temperature, 2 hours) by using Intermediate 131 (76 mg) and 10% hydrogen chloride/methanol solution (2 ml). The solvent was evaporated under reduced pressure, and the residue was added with methanol (1 ml) and diethyl ether (3 ml). The deposited precipitates were collected by filtration and washed with diethyl ether to obtain the title compound (52 mg).

$^1$H-NMR (DMSO-d$_6$) δ (ppm): 1.64–1.90 (6H, m), 1.97–2.11 (2H, m), 3.15 (1H, brs), 4.92 (1H, brs), 7.48 (1H, d, J=7.2 Hz) 7.56 (1H, d, J=8.1 Hz), 7.65–7.73 (2H, m), 8.12 (1H, d, J=8.4 Hz), 8.20 (3H, brs), 9.14 (1.5H, brs), 13.56 (0.5H, brs)

MS (m/z): 258 (MH+)

Example 142

4-(1-Amino-5-isoquinolyl)aminopiperidine hydrochloride (Exemplary Compound No. 2-12)

(Step A) Synthesis of 4-[1-(4-methoxybenzyl)amino-5-isoquinolyl]amino-1-(tert-butoxycarbonyl)piperidine (Intermediate 132)

A suspension of Intermediate 84 (235 mg), 4-methoxybenzylamine (110 μl), tris(dibenzylideneacetone)dipalladium(0) (30.4 mg), 2-(di-tert-butylphosphino)biphenyl (41.0 mg) and sodium tert-butoxide (93.6 mg) in toluene (4.5 ml) was stirred at 70° C. for 1 hour. The reaction mixture was filtered through a Celite layer, and the solvent was evaporated under reduced pressure. Then, the residue was purified by silica gel column chromatography (n-hexane:ethyl acetate=3:1) to obtain the title compound (270 mg).

(Step B) Synthesis of 4-(1-amino-5-isoquinolyl)amino-1-(tert-butoxycarbonyl)piperidine (Intermediate 133)

A solution of Intermediate 132 (270 mg) in 95% trifluoroacetic acid (5 ml) was stirred at 50° C. for 16 hours, and the solvent was evaporated under reduced pressure. The residue was added with dioxane (3 ml), 2 N aqueous sodium hydroxide (1 ml) and 2 di-t-butyl dicarbonate (393 mg) and stirred at room temperature for 1 hour. The solvent was evaporated under reduced pressure, and then the residue was purified by silica gel column chromatography (n-hexane:ethyl acetate:isopropylamine=5:5:1) to obtain the title compound (199 mg).

(Step C) Synthesis of 4-(1-amino-5-isoquinolyl)aminopiperidine

According to the method of Example 1, Step C, deprotection was performed (room temperature, 2 hours) by using Intermediate 133 (199 mg) and 10% hydrogen chloride/methanol solution (3 ml). The solvent was evaporated under reduced pressure, and the residue was added with methanol (1 ml) and diethyl ether (3 ml). The deposited precipitates were collected by filtration and washed with diethyl ether to obtain the title compound (101 mg).

$^1$H-NMR (DMSO-d$_6$) δ (ppm): 1.70–1.85 (2H, m), 2.07–2.11 (2H, m), 2.96–3.08 (2H, m), 3.30–3.40 (2H, m), 3.70–3.80 (1H, m), 6.36 (1H, d, J=7.2 Hz) 7.11 (1H, d, J=8.3 Hz), 7.54 (1H, t, J=8.1 Hz), 7.58–7.64 (2H, m), 7.72 (1H, d, J=8.3 Hz), 8.91 (2H, brs), 9.05 (2H, brs)

MS (m/z): 243 (MH+)

Example 143

4-(4-Cyano-5-isoquinolyl)aminopiperidine hydrochloride

(Step A) Synthesis of 4-(4-bromo-5-isoquinolyl)oxy-1-(tert-butoxycarbonyl)piperidine (Intermediate 134)

According to the method of Example 10, Step A (room temperature, 72 hours) except that the purification of the compound was performed by using silica gel column chromatography (n-hexane:ethyl acetate=3:1), the title compound (175 mg) was obtained from Intermediate 120 (162 mg), tert-butyl 4-hydroxy-1-piperidinecarboxylate (437 mg), 1,1'-azobis(N,N-dimethylformamide) (374 mg) and tri(n-butyl)phosphine (540 μl).

(Step B) Synthesis of 4-(4-cyano-5-isoquinolyl)oxy-1-(tert-butoxycarbonyl)piperidine (Intermediate 135)

According to the method of Example 134, Step A (120° C., 12 hours) except that the purification of the compound was performed by silica gel column chromatography (n-hexane:ethyl acetate=3:2), the title compound (596 mg) was obtained from Intermediate 134 (666 mg), zinc cyanide (138 mg), tris(dibenzylideneacetone)dipalladium(0) (150 mg) and 1,1'-bis(diphenylphosphino)ferrocene (186 mg).

(Step C) Synthesis of 4-(4-cyano-5-isoquinolyl)aminopiperidine hydrochloride

According to the method of Example 1, Step C, deprotection was performed (50° C., 30 minutes) by using Intermediate 135 (596 mg) and 10% hydrogen chloride/methanol solution (8 ml). The solvent was evaporated under reduced pressure, and the residue was added with methanol (10 ml) and diethyl ether (30 ml). The deposited precipitates were collected by filtration and washed with diethyl ether to obtain the title compound (286 mg).

$^1$H-NMR (CDCl$_3$) δ (ppm): 2.06–2.14 (2H, m), 2.21–2.29 (2H, m), 3.10–3.21 (2H, m), 3.33–3.45 (2H, m), 5.06–5.10 (1H, m), 7.60 (1H, d, J=8.0 Hz), 7.79 (1H, t, J=8.0 Hz), 7.88 (1H, d, J=8.0 Hz), 8.90 (1H, br.s), 9.00 (1H, s), 9.16 (1H, br.s), 9.56 (1H, s)

MS (m/z): 254 (MH+)

Example 144

1-(2-Hydroxyethyl)-4-(5-isoquinolyl)aminopiperidine hydrochloride

(Step A) Synthesis of 1-[2-(tetrahydro-2H-pyranyloxy)ethyl]-4-(5-isoquinolyl)aminopiperidine (Intermediate 136)

A suspension of the compound of Example 20 (70 mg) and potassium carbonate (142 mg, Kokusan Chemical) in N,N-dimethylformamide (1.5 ml) was added with 2-(2-bromoethoxy)tetrahydro-2H-pyran (254 μl, Aldrich) and stirred at room temperature for 48 hours. The reaction mixture was added with acetone (10 ml), and insoluble matters were separated by filtration. Then, the solvent was evaporated under reduced pressure. The residue was purified by silica gel column chromatography (chloroform:methanol=6:1) to obtain the title compound (40 mg).

(Step B) Trans-1-[(4-cyano-5-isoquinolyl)oxy]-4-[(2-hydroxyethyl)amino]cyclohexane hydrochloride According to the method of Example 1, Step C, deprotection was performed (room temperature, 12 hours) by using Intermediate 136 (40 mg) and 10% hydrogen chloride/methanol solution (1.5 ml). The solvent was evaporated under reduced pressure, and the residue was added with methanol (1 ml) and diethyl ether (3 ml). The deposited precipitates were collected by filtration and washed with diethyl ether to obtain the title compound (35 mg).

$^1$H-NMR (DMSO-d$_6$) δ (ppm): 1.91–2.20 (4H, m), 3.10–3.99 (9H, m), 7.23–7.27 (1H, m), 7.65–7.84 (2H, m), 8.59–8.65 (1H, m), 8.88–9.02 (1H, m), 9.73–9.76 (1H, m), 10.30–10.70 (1H, m)

MS (m/z): 272 (MH+)

Example 145

1-(3-Hydroxypropyl)-4-(5-isoquinolyl)aminopiperidine hydrochloride

According to the method of Example 144, an alkylation reaction with 2-(3-bromopropoxy)tetrahydro-2H-pyran (Aldrich) and a deprotection reaction were performed by using the compound of Example 20 to obtain the title compound.

MS (m/z): 286 (MH+)

Example 146

1-(2-Hydroxyethyl)-4-(4-methyl-5-isoquinolyl)aminopiperidine hydrochloride

According to the method of Example 144, an alkylation reaction with 2-(2-bromoethoxy)tetrahydro-2H-pyran and a deprotection reaction were performed by using the compound of Example 106 to obtain the title compound.

$^1$H-NMR (DMSO-d$_6$) δ (ppm): 1.87–2.28 (4H, m), 3.00–3.90 (12H, m), 5.80 (1H, brs), 7.29–7.37 (1H, m), 7.72–7.80 (2H, m), 8.26–8.33 (1H, m), 9.50–9.73 (1H, m), 10.47 (1H, brs)

MS (m/z): 286 (MH+)

Example 147

1-(3-Hydroxypropyl)-4-(4-methyl-5-isoquinolyl)aminopiperidine hydrochloride

According to the method of Example 144, an alkylation reaction with 2-(3-bromopropoxy)tetrahydro-2H-pyran and a deprotection reaction were performed by using the compound of Example 106 to obtain the title compound.

MS (m/z): 300 (MH+)

Example 148

Trans-N-(5-isoquinolyl)-N'-(2-hydroxyethyl)-1,4-cyclohexanediamine hydrochloride

According to the method of Example 144, an alkylation reaction with 2-(2-bromoethoxy)tetrahydro-2H-pyran and a deprotection reaction were performed by using the compound of Example 24 to obtain the title compound.

MS (m/z): 286 (MH+)

Example 149

Trans-N-(5-isoquinolyl)-N'-(3-hydroxypropyl)-1,4-cyclohexanediamine hydrochloride According to the method of Example 144, an alkylation reaction with 2-(3-bromopropoxy)tetrahydro-2H-pyran and a deprotection reaction were performed by using the compound of Example 24 to obtain the title compound.
MS (m/z): 300 (MH+)

Example 150

Trans-N-(4-methyl-5-isoquinolyl)-N'-(2-hydroxyethyl)-1,4-cyclohexanediamine hydrochloride According to the method of Example 144, an alkylation reaction with 2-(2-bromoethoxy)tetrahydro-2H-pyran and a deprotection reaction were performed by using the compound of Example 121 to obtain the title compound.
MS (m/z): 300 (MH+)

Example 151

Trans-N-(4-methyl-5-isoquinolyl)-N'-(3-hydroxypropyl)-1,4-cyclohexanediamine hydrochloride According to the method of Example 144, an alkylation reaction with 2-(3-bromopropoxy)tetrahydro-2H-pyran and a deprotection reaction were performed by using the compound of Example 121 to obtain the title compound.
MS (m/z): 314 (MH+)

Example 152

Cis-N-(5-isoquinolyl)-N'-(2-hydroxyethyl)-1,4-cyclohexanediamine hydrochloride

According to the method of Example 144, an alkylation reaction with 2-(2-bromoethoxy)tetrahydro-2H-pyran and a deprotection reaction were performed by using the compound of Example 23 to obtain the title compound.
MS (m/z): 286 (MH+)

Example 153

Cis-N-(5-isoquinolyl)-N'-(3-hydroxypropyl)-1,4-cyclohexanediamine hydrochloride

According to the method of Example 144, an alkylation reaction with 2-(3-bromopropoxy)tetrahydro-2H-pyran and a deprotection reaction were performed by using the compound of Example 23 to obtain the title compound.
MS (m/z): 299 (MH+)

Example 154

Cis-N-(4-methyl-5-isoquinolyl)-N'-(2-hydroxyethyl)-1,4-cyclohexanediamine hydrochloride According to the method of Example 144, an alkylation reaction with 2-(2-bromoethoxy)tetrahydro-2H-pyran and a deprotection reaction were performed by using the compound of Example 120 to obtain the title compound.
MS (m/z): 299 (MH+)

Example 155

Cis-N-(4-methyl-5-isoquinolyl)-N'-(3-hydroxypropyl)-1,4-cyclohexanediamine hydrochloride According to the method of Example 144, an alkylation reaction with 2-(3-bromopropoxy)tetrahydro-2H-pyran and a deprotection reaction were performed by using the compound of Example 120 to obtain the title compound.
MS (m/z): 314 (MH+)

Example 156

Trans-1-[(4-cyano-5-isoquinolyl)oxy]-4-[(2-hydroxyethyl)amino]cyclohexane hydrochloride According to the method of Example 144, an alkylation reaction with 2-(2-bromoethoxy)tetrahydro-2H-pyran and a deprotection reaction were performed by using the compound of Example 134 to obtain the title compound.
$^1$H-NMR (DMSO-$d_6$) δ (ppm): 1.57–1.71 (4H, m), 2.16–2.35 (4H, m), 2.96–3.08 (2H, m), 3.09–3.23 (1H, m), 4.60–4.72 (1H, m), 6.72 (1H, brs), 7.65 (1H, d, J=7.2 Hz), 7.70 (1H, t, J=7.5 Hz), 7.85 (1H, d, J=7.2 Hz), 9.53 (1H, s)
MS (m/z): 312 (MH+)

Example 157

Trans-1-[(4-cyano-5-isoquinolyl)oxy]-4-[(3-hydroxypropyl)amino]cyclohexane hydrochloride According to the method of Example 144, an alkylation reaction with 2-(3-bromopropoxy)tetrahydro-2H-pyran and a deprotection reaction were performed by using the compound of Example 134 to obtain the title compound.
MS (m/z): 326 (MH+)

Example 158

1-(2-Hydroxyethyl)-4-[(4-cyano-5-isoquinolyl)oxy]piperidine hydrochloride

According to the method of Example 144, an alkylation reaction with 2-(2-bromoethoxy)tetrahydro-2H-pyran and a deprotection reaction were performed by using the compound of Example 143 to obtain the title compound.
$^1$H-NMR (DMSO-$d_6$) δ (ppm): 2.10–2.45 (4H, m), 3.10–3.60 (4H, m), 3.60–3.72 (2H, m), 3.75–3.83 (2H, m), 4.89–4.96 (1H, m), 7.59–7.65 (1H, m), 7.77–7.82 (1H, m), 7.87–7.90 (1H, m), 8.57 (1H, br.s), 9.02 (1H, s), 9.57 (1H, s), 9.93 (1H, br.s), 10.29 (1H, br.s)
MS (m/z): 298 (MH+)

Example 159

1-(3-Hydroxypropyl)-4-[(4-cyano-5-isoquinolyl)oxy]piperidine hydrochloride

According to the method of Example 144, an alkylation reaction with 2-(3-bromopropoxy)tetrahydro-2H-pyran and a deprotection reaction were performed by using the compound of Example 143 to obtain the title compound.
$^1$H-NMR (DMSO-$d_6$) δ (ppm): 1.80–2.00 (2H, m), 2.10–2.48 (4H, m), 3.05–3.20 (2H, m), 3.20–3.75 (6H, m), 4.85–4.96 (1H, m), 7.59–7.63 (1H, m), 7.79 (1H, t, J=7.9 Hz), 7.88 (1H, d, J=8.1 Hz), 9.01 (1H, s), 9.55 (1H, s), 10.23 (1H, br.s), 10.88 (1H, br.s)
MS (m/z): 312 (MH+)

Example 160

Trans-N-(1-hydroxy-4-methyl-5-isoquinolyl)-4-cyclohexanediamine hydrochloride (Step A) Synthesis of
1-hydroxy-4-bromo-5-nitroisoquinoline
(Intermediate 137)

According to the method of Example 12, Step B, a hydrolysis reaction with concentrated hydrochloric acid was performed by using a known compound, 1-chloro-4-bromo-5-nitroisoquinoline (Indian. J. Chem., 224, 1967), to obtain the title compound.

(Step B) Synthesis of
1-hydroxy-4-bromo-5-aminoisoquinoline
(Intermediate 138)

According to the method of Example 114, Step A, a reduction reaction with tin(II) chloride dihydrate was performed by using Intermediate 137 to obtain the title compound.

(Step C) Synthesis of
1-hydroxy-4-methyl-5-aminoisoquinoline
(Intermediate 139)

According to the method of Example 106, Step A, a methylation reaction with tetramethyltin was performed by using Intermediate 138 to obtain the title compound.

(Step D) Synthesis of trans-N-(1-hydroxy-4-methyl-5-isoquinolyl)-N'-(tert-butoxycarbonyl)-1,4-cyclohexanediamine (Intermediate 140)

According to the method of Example 107, Step A, a reductive alkylation reaction with tert-butyl 4-oxo-1-aminocyclohexylcarboxylate was performed by using Intermediate 139, and fractionation recrystallization was performed from ethyl acetate to separate the cis-compound to obtain the title compound.

(Step E) Synthesis of trans-N-(1-hydroxy-4-methyl-5-isoquinolyl)-1,4-cyclohexanediamine hydrochloride According to the method of Step A of this example, deprotection with concentrated hydrochloric acid was performed by using Intermediate 140 to obtain the title compound.

$^1$H-NMR (DMSO-$d_6$) δ (ppm): 1.39–1.56 (4H, m), 2.00–2.12 (2H, m), 2.51 (3H, s), 2.94–3.04 (1H, m), 3.22–3.32 (1H, m), 6.80 (1H, s), 7.12 (1H, d, J=6.9 Hz), 7.31 (1H, t, J=7.8 Hz), 7.69 (1H, d, J=7.5 Hz), 8.18 (3H, brs), 11.10 (1H, brs)

MS (m/z): 272 (MH+)

Reference Example 1

4-Bromo-5-aminoisoquinoline (Step A) Synthesis of 4-bromo-5-nitroisoquinoline

With vigorous stirring, concentrated sulfuric acid (36 ml) was added with 4-bromoisoquinoline (10.0 g, Tokyo Kasei Kogyo) to such an extent that the temperature should not exceed 10° C. and stirred for a while to attain complete dissolution. Potassium nitrate (4.9 g, Kanto Chemicals) was dissolved in concentrated sulfuric acid (20 ml), added dropwise to the aforementioned solution at a temperature below −5° C. and further stirred for 2 hours while maintaining that temperature. Disappearance of 4-bromoisoquinoline was confirmed by thin layer chromatography (n-hexane:ethyl acetate=1:1), and then the reaction mixture was slowly poured into cold aqueous ammonia (200 ml, Wako Pure Chemical Industries) with vigorous stirring. The reaction mixture was stirred for 15 minutes and then extracted three times with ethyl acetate (150 ml for each time), and the combined organic layer was washed successively with water (250 ml) and saturated brine (250 ml) and dried over anhydrous sodium sulfate. The solvent was evaporated under reduced pressure, and the residue was recrystallized with ethyl acetate to obtain the title compound (5.9 g) as thick yellow needle-like crystals.

(Step B) Synthesis of 4-bromo-5-aminoisoquinoline

4-Bromo-5-nitroisoquinoline (1.0 g) synthesized as described above and stannous chloride dihydrate (4.5 g, Wako Pure Chemical Industries) were suspended in ethanol (30 ml), added with concentrated hydrochloric acid (2.3 ml) and stirred at 80° C. for 30 minutes and at room temperature for further 12 hours. The reaction mixture was adjusted to pH 12 with addition of 2 N aqueous sodium hydroxide. The target compound was extracted three times with ethyl acetate (100 ml for each time), and the combined organic layer was washed with water (200 ml) and saturated brine (200 ml) and dried over anhydrous sodium sulfate. The solvent was evaporated under reduced pressure, and then the residue was purified by silica gel column chromatography (n-hexane:ethyl acetate=3:1) to obtain the title compound (493 mg) as yellow powdery crystals.

$^1$H-NMR(CDCl$_3$) δ (ppm): 5.23 (2H, br.s), 6.92 (1H, dd, J=1.6, 7.3 Hz), 7.38 (2H, m), 8.50 (1H, s), 8.98 (1H, s)

Reference Example 2

Synthesis of
N-[(5-isoquinolyl)sulfonyl]ethylenediamine
(Intermediate 49)

Isoquinoline-5-sulfonyl chloride hydrochloride (33 g, prepared according to the method described in Japanese Patent Unexamined Publication (Kokai) No. 57-200366) was added to dichloromethane (300 ml) and water (300 ml), added with sodium hydrogencarbonate with vigorous stirring until pH of the aqueous layer became 5 to 6. The reaction mixture was further extracted three times with dichloromethane, and the organic layer was dried over anhydrous magnesium sulfate. This solution was added dropwise to a solution of ethylenediamine (30 g) in dichloromethane (600 ml) over 2 hours with ice cooling and stirred at room temperature for 30 minutes. After completion of the reaction, the reaction mixture was added with diluted hydrochloric acid with vigorous stirring to adjust pH of the aqueous layer to about 8. The organic layer and the aqueous layer were separated, and then the aqueous layer was collected and added with potassium carbonate to obtain a saturated solution, which was extracted with dichloromethane (600 ml). The organic layer was dried over anhydrous magnesium sulfate, and then the solvent was evaporated under reduced pressure to obtain the title compound (22.9 g).

Reference Example 3

Synthesis of
N-[(5-isoquinolyl)sulfonyl]-1,3-propylenediamine
(Intermediate 50)

According to the method of Reference Example 2, a reaction was performed by using isoquinoline-5-sulfonyl chloride hydrochloride (20 g) and 1,3-propylenediamine (22.2 g) to obtain the title compound (16.3 g).

Reference Example 4

Synthesis of
N-[(5-isoquinolyl)sulfonyl]-1,4-butylenediamine
(Intermediate 51)

According to the method of Reference Example 2, a reaction was performed by using isoquinoline-5-sulfonyl chloride hydrochloride (18.8 g) and 1,4-butylenediamine (25 g) to obtain the title compound (12.3 g).

Reference Example 5

Synthesis of
N-[(5-isoquinolyl)sulfonyl]-1,3-cyclohexanediamine
(Intermediate 52)

(Step A) Synthesis of
3-(N-tert-butoxycarbonylamino)cyclohexylamine
(Intermediate 53)

3-Diaminocyclohexanediamine (25 g) was dissolved in chloroform (500 ml), added with di-t-butyl dicarbonate (23.9 g) with stirring and ice cooling and stirred at room temperature for 16 hours. The solvent of the reaction mixture was evaporated under reduced pressure, and the residue was added with dichloromethane and saturated aqueous sodium carbonate for extraction. The organic layer was dried over anhydrous magnesium sulfate, and the solvent was evaporated under reduced pressure. The residue was purified by flash column chromatography (chloroform:methanol:triethylamine=100:10:1) to obtain the title compound (16 g).

(Step B) Synthesis of N-(tert-butoxycarbonyl)-N'-[(5-isoquinolyl)sulfonyl]-1,3-cyclohexanediamine
(Intermediate 54)

Dichloromethane (80 ml) and water (80 ml) were added with isoquinoline-5-sulfonyl chloride hydrochloride (8 g) and added with sodium hydrogencarbonate with vigorous stirring until pH of the aqueous layer became 5 to 6, and further, the reaction mixture was extracted three times with dichloromethane. The organic layer was dried over anhydrous magnesium sulfate. This solution was added dropwise to a solution containing Intermediate 53 (6.5 g) mentioned above and triethylamine (4.3 ml) in dichloromethane (50 ml) with ice cooling and stirred at room temperature for 4 hours. The reaction mixture was washed successively with water and saturated brine. The organic layer was dried over anhydrous magnesium sulfate, and the solvent was evaporated under reduced pressure. The residue was purified by flash column chromatography (chloroform:methanol=40:1) to obtain the title compound (6 g).

(Step C) Synthesis of
N-[(5-isoquinolyl)sulfonyl]-1,3-cyclohexanediamine

Intermediate 54 (6 g) obtained above was added to a 10% hydrogen chloride solution in methanol (50 ml) and stirred under reflux by heating for 1.5 hours. The solvent was evaporated under reduced pressure, and the residue was dissolved in a mixed solvent of dichloromethane and ethanol, added with saturated aqueous potassium carbonate and vigorously shaken. The organic layer was dried over anhydrous sodium sulfate, and the solvent was evaporated under reduced pressure to obtain the title compound (4.9 g).

Reference Example 6

Synthesis of N-[(5-isoquinolyl)sulfonyl]-2,2-dimethyl-1,3-propylenediamine (Intermediate 55)

(Step A) Synthesis of 3-(N-tert-butoxycarbonylamino)-2,2-dimethylpropylamine (Intermediate 56)

Water (340 ml) and t-butyl alcohol (200 ml) were added with 2,2-dimethyl-1,3-propylenediamine (25 g), added successively with 4 N aqueous sodium hydroxide (20.5 ml) and a solution of di-t-butyl dicarbonate (21.4 g) in t-butyl alcohol with ice cooling and stirred at room temperature for 16 hours. The solvent (t-butyl alcohol) was evaporated under reduced pressure, and the residue was extracted with ethyl acetate. The organic layer was washed successively with water and saturated brine and dried over anhydrous sodium sulfate, and the solvent was evaporated under reduced pressure. The residue was purified by flash column chromatography (ethyl acetate:methanol=10:1) to obtain the title compound (6 g).

(Step B) Synthesis of N-(tert-butoxycarbonyl)-N'-[(5-isoquinolyl)sulfonyl]-2,2-dimethyl-1,3-propylenediamine (Intermediate 57)

According to Reference Example 5, Step B, a reaction was performed by using isoquinoline-5-sulfonyl chloride hydrochloride (7.8 g) and Intermediate 56 (5.97 g) to obtain the title compound (11.36 g).

(Step C) Synthesis of N-[(5-isoquinolyl)sulfonyl]-2,2-dimethyl-1,3-propylenediamine According to Reference Example 5, Step C, a reaction was performed by using Intermediate 57 (11 g) and 10% hydrogen chloride in methanol (80 ml) to obtain the title compound (7.58 g).

Reference Example 7

Synthesis of
N-[(5-Isoquinolyl)sulfonyl]-1,4-xylylenediamine
(Intermediate 58)

(Step A) Synthesis of
4-(N-tert-butoxycarbonylaminomethyl)benzylamine
(Intermediate 59)

According to Reference Example 6, Step A, a reaction was performed by using p-xylylenediamine (25 g) to obtain the title compound (9 g).

(Step B) Synthesis of N-(tert-butoxycarbonyl)-N'-[(5-isoquinolyl)sulfonyl]-1,4-xylylenediamine (Intermediate 60)

According to Reference Example 5, Step B, a reaction was performed by using isoquinoline-5-sulfonyl chloride hydrochloride (10 g) and Intermediate 59 (8.96 g) to obtain the title compound (13.39 g).

(Step C) Synthesis of N-[(5-isoquinolyl)sulfonyl]-1,4-xylylenediamine

According to Reference Example 5, Step C, a reaction was performed by using Intermediate 60 (6 g) and 10% hydrogen chloride in methanol (20 ml) to obtain the title compound (3.7 g).

Reference Example 8

Synthesis of N-[(5-isoquinolyl)sulfonyl]-1,3-xylylenediamine (Intermediate 61)

(Step A) Synthesis of 3-(N-tert-butoxycarbonylaminomethyl)benzylamine (Intermediate 62)

According to Reference Example 6, Step A, a reaction was performed by using m-xylylenediamine (25 g) to obtain the title compound (8 g).

(Step B) Synthesis of N-(tert-butoxycarbonyl)-N'-[(5-isoquinolyl)sulfonyl]-1,3-xylylenediamine (Intermediate 63)

According to Reference Example 5, Step B, a reaction was performed by using isoquinoline-5-sulfonyl chloride hydrochloride (9 g) and Intermediate 62 (8 g) to obtain the title compound (11.3 g).

(Step C) Synthesis of N-[(5-isoquinolyl)sulfonyl]-1,3-xylylenediamine

According to Reference Example 5, Step C, a reaction was performed by using Intermediate 63 (5 g) and 10% hydrogen chloride in methanol (20 ml) to obtain the title compound (3.1 g).

Reference Example 9

Synthesis of N-[(5-isoquinolyl)sulfonyl]ethylenediamine carried by crown via trityl linker (Intermediate 64)

Hydroxyl groups of SynPhase Crown (I Series, 8.3 µmol/crown) having a trityl linker produced by Chiron Technologies (currently Mitocore) were chlorinated by allowing a mixed solvent of dichloromethane and acetyl chloride to act on the crown for 18 hours, and washing the crown twice with dichloromethane. Then, a solution of Intermediate 49 of Reference Example 2 and N-methylmorpholine in dimethylformamide was allowed to act on the obtained trityl chloride crown for 21 hours, and the obtained crown was washed with dimethylformamide, methanol and dichloromethane three times for each to obtain the title compound.

Reference Example 10

Synthesis of N-[(5-isoquinolyl)sulfonyl]-1,3-propylenediamine carried by crown via trityl linker (Intermediate 65)

According to the method of Reference Example 9, a reaction was performed by using Intermediate 50 of Reference Example 3 instead of Intermediate 49 to obtain the title compound.

Reference Example 11

Synthesis of N-[(5-isoquinolyl)sulfonyl]-1,4-butylenediamine carried by crown via trityl linker (Intermediate 66)

According to the method of Reference Example 9, a reaction was performed by using Intermediate 51 of Reference Example 4 instead of Intermediate 49 to obtain the title compound.

Reference Example 12

Synthesis of N-[(5-isoquinolyl)sulfonyl]-1,3-cyclohexanediamine carried by crown via trityl linker (Intermediate 67)

According to the method of Reference Example 9, a reaction was performed by using Intermediate 52 of Reference Example 5 instead of Intermediate 49 to obtain the title compound.

Reference Example 13

Synthesis of N-[(5-isoquinolyl)sulfonyl]-2,2-dimethyl-1,3-propylenediamine carried by crown via trityl linker (Intermediate 68)

According to the method of Reference Example 9, a reaction was performed by using Intermediate 55 of Reference Example 6 instead of Intermediate 49 to obtain the title compound.

Reference Example 14

Synthesis of N-[(5-isoquinolyl)sulfonyl]-1,4-xylylenediamine carried by crown via trityl linker (Intermediate 69)

According to the method of Reference Example 9, a reaction was performed by using Intermediate 58 of Reference Example 7 instead of Intermediate 49 to obtain the title compound.

Reference Example 15

Synthesis of N-[(5-isoquinolyl)sulfonyl]-1,3-xylylenediamine carried by crown via trityl linker (Intermediate 70)

According to the method of Reference Example 9, a reaction was performed by using Intermediate 61 of Reference Example 8 instead of Intermediate 49 to obtain the title compound.

Test Example 1

Action on Amount of Phosphorylated Myosin Regulatory Light Chain in the Cells A volume of 50 to 100 ml of peripheral blood collected from healthy volunteers was centrifuged by using Mono-Poly separator solution (Dainippon Pharmaceutical) to prepare a neutrophil containing fraction. The neutrophils were washed with PBS(−) and resuspended in Hanks' Balanced Salt Solution (HBSS+, Gibco) to prepare a cell suspension ($8 \times 10^6$/ml). The cell suspension was diluted to $5 \times 10^6$/ml, introduced into Eppendorf tubes in a volume of 0.4 ml each, then 0.1 ml each of solutions of a test compound at various concentrations were added to the suspension and allowed to react at 25° C. for 5 minutes. After the reaction, 0.1 ml of trichloroacetic acid solution was added to each reaction, the reaction mixture was gently shaken and centrifuged at 12,000 rpm (4° C., 5 minutes), and the supernatant was removed. Subsequently, 3 µl of 1 M Tris solution was added to the residue, the mixture was further mixed with 50 µl of extraction buffer (8 M urea, 0.02% 2-mercaptoethanol, 0.002% bromophenol blue) and left stand at room temperature for 1 hour. Then, the reaction mixture was loaded on a spin column (0.45 µm, Millipore) to remove the insoluble solids and a sample buffer for SDS polyacrylamide gel electrophoresis (25 mM, Tris-HCl pH 6.8, 2.5% 2-mercaptoethanol, 2% sodium dodecylsulfate, 5% sucrose, 0.002% bromophenol blue as final concentrations) was added, and 10 µl of each sample was subjected to electrophoresis.

The gel after the electrophoresis was blotted on a nitrocellulose membrane (BioRad), blocked with 5% skim milk, and reacted successively with antibodies pLC1 (Sakurada K. et al, Am. J. Physiol., 274, C1563–C1572 (1998)), which specifically recognize the phosphorylated myosin regulatory light chain, and donkey anti-mouse IgG (Chemicon) conjugated with horseradish peroxidase (HRP-labeled). The band of the phosphorylated myosin regulatory light chain was detected on a film by using ECL Plus Kit (Amersham Pharmacia Biotech). This band was subjected to quantification using a densitometer. By using this value, the inhibitory ratio (%) for phosphorylation of the myosin regulatory light chain was calculated by using the following equation.

Phosphorylation inhibition ratio (%)=1−(Band intensity of phosphorylated myosin regulatory light chain with addition of the test compound/Band intensity of phosphorylated myosin regulatory light chain without addition of the test compound)×100

Further, the phosphorylation inhibition ratio was calculated with changing the concentrations of the test compound, and a compound concentration providing an inhibition ratio of 50% was obtained as $IC_{50}$.

The results are shown in Table 5 mentioned below. It was revealed that the compounds of the present invention inhibited phosphorylation of the myosin regulatory light chain.

TABLE 5

| Test compound | Inhibition of myosin regulatory light chain phosphorylation ($IC_{50}$: µM) |
|---|---|
| H-7 | 80.0 |
| Example 1 | 0.8 |
| Example 2 | 0.8 |
| Example 4 | 30.0 |
| Example 5 | 0.8 |
| Example 6 | 20.0 |
| Example 7 | 30.0 |
| Example 8 | 0.3 |
| Example 9 | 15.0 |
| Example 10 | 10.0 |
| Example 11 | $20 \geq IC_{50} > 1$ |
| Example 12 | 20.0 |
| Example 13 | 20.0 |
| Example 14 | $40 \geq IC_{50} > 20$ |
| Example 16 | $40 \geq IC_{50} > 20$ |
| Example 18 | $40 \geq IC_{50} > 20$ |
| Example 20 | 1.8 |
| Example 23 | $20 \geq IC_{50} > 1$ |
| Example 24 | $20 \geq IC_{50} > 1$ |
| Example 25 | $40 \geq IC_{50} > 20$ |
| Example 26 | $40 \geq IC_{50} > 20$ |
| Example 27 | $20 \geq IC_{50} > 1$ |
| Example 30 | $40 \geq IC_{50} > 20$ |
| Example 32 | $40 \geq IC_{50} > 20$ |
| Example 33 | $40 \geq IC_{50} > 20$ |
| Example 34 | $40 \geq IC_{50} > 20$ |
| Example 38 | $40 \geq IC_{50} > 20$ |
| Example 39 | $40 \geq IC_{50} > 20$ |
| Example 40 | $40 \geq IC_{50} > 20$ |
| Example 41 | $40 \geq IC_{50} > 20$ |
| Example 42 | $20 \geq IC_{50} > 1$ |
| Example 43 | $40 \geq IC_{50} > 20$ |
| Example 44 | $40 \geq IC_{50} > 20$ |
| Example 45 | $40 \geq IC_{50} > 20$ |
| Example 48 | $40 \geq IC_{50} > 20$ |
| Example 51 | $40 \geq IC_{50} > 20$ |
| Example 57 | $40 \geq IC_{50} > 20$ |
| Example 71 | $40 \geq IC_{50} > 20$ |

In addition to the compounds mentioned in the table, each of the compounds of Examples 21, 22, 29, 103, 104, 105, 106, 107, 112, 113, 118, 120, 121, 124, 128, 130, 131, 133, 134, 135, 136, 137, 138, 139, 140, 142, 143, 144, 145, 146, 156 and 160, which falls within the compounds of the present invention, gave an $IC_{50}$ of 40 µM or less, and each of the compounds of Examples 21, 29, 103, 104, 106, 107, 112, 113, 118, 120, 121, 124, 128, 130, 131, 133, 134, 135, 136, 137, 138, 139, 140, 142, 145, 146, 156 and 160 gave an $IC_{50}$ of 20 µM or less.

Test Example 2

Vasoconstriction Inhibitory Action

Rats (Wistar, 11-week old) were bleeded to death and laparotomized to take out the thoracic aorta. That aorta was cut into a ring of a length of about 3 mm in a conventional manner (Asano, T., et al., J. Pharmacol. Exp. Ther., 241, pp. 1033–1040 (1987)) and hung in 10-ml organ bath filled with Krebs-Hensright nutrient solution bubbled with a mixed gas of 95% $O_2$ and 5% $CO_2$. One end of the blood vessel was connected to an isometric transducer (FD Pickup TB-912T, Nihon Kohden) and applied with 2.5 g of resting tension, and constriction and relaxation reactions of the aorta were recorded. The aorta was constricted with phenylephrine (1 µM, Sigma) and then added with a test compound (1 µM), and the vasoconstriction inhibitory action thereof was observed. The vasoconstriction inhibitory actions of the test compounds are shown in Table 6 mentioned below as the relaxation ratios, which are based on the vasoconstriction with phenylephrine immediately before the addition of the test compound taken as 100%.

H-7: 1-(5-Isoquinolinesulfonyl)-2-methylpiperazine (Seikagaku Corporation)

TABLE 6

| Test compound (1 μM) | Vasoconstriction inhibitory action (relaxation ratio) (%) |
|---|---|
| Physiological saline | 0 |
| H-7 | 22.0 |
| Example 1 | 73.8 |
| Example 7 | 64.3 |
| Example 20 | 82.8 |

In addition to the compounds shown in the table, each of the compounds of Examples 2, 5, 8, 12, 13, 105, 106, 112, 113, 120, 121, 134, 136, 139, 140 and 146, which falls within the compounds of the present invention, also gave significant vasoconstriction inhibitory action.

Thus, it was confirmed that the compounds of the present invention were useful as medicaments for prophylactic and/or therapeutic treatment of diseases relating to cell contraction.

Test Example 3

Respiratory Tract Constriction Suppression Action

Four-week old Hartley guinea pigs (male) were immunized by intraperitoneal administration of ovalbumin (Sigma, Grade V) in amounts of 1 mg for each animal on the day on which the experiment was started, 3 mg for each animal after 2 days, and 10 mg for each animal after 4 days.

Twelve to fourteen days after the final immunization, the ovalbumin-immunized guinea pigs were anesthetized by intraperitoneal administration of about 40 mg/kg of pentobarbital (Somnopentyl), and the tracheas were taken out. Subsequently, a cannula (SP-110, Natsume) was inserted into each trachea, and one end of the cannula was connected to an artificial respirator (Model-b83, Harvard). The aeration conditions were set at 6 ml per kilogram and 60 times per 1 minute. Further, a cannula for medicament administration (JMS wing needle 23G 3/4) was inserted into a hind leg vein. Myoblock (Organon Technica) was administered in an amount of 0.5 mg/kg from the cannula inserted into the hind leg vein to stop the spontaneous breathing, and after 2 or 3 minutes, 0.3 mg/kg of ovalbumin was administered to induce constriction of respiratory tract. The increase of airway resistance value 2 minutes after the induction (measurement apparatuses: pressure transducer TR-603T, respiratory amplifier AR-601G, and recorder RTA-3100, Nihon Kohden Corp.) was confirmed to be above 80 cm $H_2O$ or higher, and then, a solution of a test medicament was administered from the cannula inserted into the hind leg vein, and the airway resistance value was continuously measured for 15 minutes after the administration to determine the effect.

As a result, each of the compounds of Examples 2, 11, 12, 20, 29, 106, 118, 121, 133, 140, 144 and 146, which falls within the compounds of the present invention, significantly improved the constriction of respiratory tract. Therefore, it was confirmed that the compounds of the present invention were useful as medicaments for prophylactic and/or therapeutic treatment of bronchial asthma and/or chronic obstructive pulmonary disease (COPD).

Test Example 4

Intraocular Pressure Reducing Action

A Japanese white rabbit having a body weight of about 2 kg was placed in a positioner and naturalized for one week before the experiment. An ophthalmologic local anesthesant (Benoxil) was administered to the left eye, and then intraocular pressure was measured by using a tonometer (Classic 30, Solan). The initial value of the intraocular pressure was measured, then 50 μl of a test compound (1% aqueous solution) was dropped to the left eye, and after 2 hours, the intraocular pressure was measured. The intraocular pressure reducing action of the test compounds is shown in Table 7 mentioned below as ratios (%) of reduction of intraocular pressure based on the initial value of the intraocular pressure.

TABLE 7

| Test compound (1%) | Intraocular pressure reducing action (reduction ratio) (%) |
|---|---|
| Physiological saline | 0 |
| Example 7 | 30.1 |
| Example 12 | 13.3 |
| Example 20 | 35.7 |
| Example 24 | 35.7 |
| Example 27 | 12.5 |
| Example 29 | 18.8 |
| Example 103 | 31.3 |
| Example 104 | 18.8 |
| Example 105 | 18.8 |
| Example 106 | 31.3 |
| Example 112 | 25.0 |
| Example 118 | 25.0 |
| Example 121 | 31.3 |
| Example 124 | 12.5 |

In addition to the compounds shown in the table, each of the compounds of Examples 107, 113, 115, 120, 133, 134, 135, 136, 139, 140, 144, 145 and 146, which falls within the compounds of the present invention, also gave significant intraocular pressure reducing activity.

Thus, it was confirmed that the compounds of the present invention were useful as medicaments for prophylactic and/or therapeutic treatment of, in particular, glaucoma.

Test Example 5

Neutrophil Migration Inhibitory Action

Neutrophils were isolated from 50 to 100 ml of peripheral blood collected from healthy donors by the method described in Test Example 1 to obtain a cell suspension ($8\times10^6$/ml). Subsequently, solutions of a test compound at various concentrations were introduced into wells of a 96-well plate in a volume of 125 μl per well, the cell suspension of an equivalent volume was added to it and the plate was preincubated at room temperature for 5 minutes. During the preincubation, FMLP (1 μM, Sigma) solution was added to the lower chamber to set Boyden Chamber, the preincubated cell suspension was added to the upper chamber in a volume of 200 μl per well, and the cells were allowed to migrate at 37° C. under 5% carbon dioxide for 30 minutes. The filter after the migration was collected, and the non-migrated cells adhered to the surface that faced the upper chamber were carefully wiped off. Then, the migrated cells on the back surface were stained with DifQuick dye solution (International Reagents), washed with water and dried, and then absorbance was measured at 595 nm. The inhibition ratio against migration (%) of a test compound was calculated by using the following equation:

Migration inhibition ratio (%)=(1−Absorbance of the group with addition of test compound/Absorbance of the group without addition of test compound)×100

Further, the migration inhibitory ratio was calculated with changing the test compound concentration, and a compound concentration providing an inhibition ratio of 50% was obtained as $IC_{50}$. The results are shown in Table 8 mentioned below. The compounds of the present invention had stronger activity than that of H-7 as being a prior art compound.

TABLE 8

H-7 > 40 µM
Compounds for which 40 µM > $IC_{50}$ > 10 µM
Example 16, Example 18, Example 21, Example 25,
Example 26, Example 31, Example 35, Example 37,
Example 38, Example 39, Example 46, Example 47,
Example 48, Example 50, Example 51, Example 57,
Example 59, Example 70, Example 71, Example 73,
Example 79, Example 106, Example 118
Compounds for which 10 µM ≧ $IC_{50}$ > 1 µM
Example 2, Example 4, Example 6, Example 9, Example 10,
Example 11, Example 12, Example 13, Example 14,
Example 20, Example 23, Example 24, Example 30,
Example 32, Example 33, Example 34, Example 40,
Example 41, Example 42, Example 43, Example 44,
Example 45, Example 103, Example 121
Compounds for which 1 µM ≧ $IC_{50}$
Example 1, Example 5, Example 8

In addition to the compounds mentioned above, each of the compounds of Examples 27, 29, 104, 107, 112, 113, 118, 120, 128, 130, 131, 133, 134, 135, 136, 137, 138, 139, 140, 145, 146, 156 and 160, which falls within the compounds of the present invention, gave an $IC_{50}$ of 40 µM or less, and each of the compounds of Examples 107, 120, 130, 133, 134, 135, 138, 139, 140 and 156 gave an $IC_{50}$ of 10 µM or less.

Thus, it was confirmed that the compounds of the present invention were useful as medicaments for prophylactic and/or therapeutic treatment of diseases relating to cell migration.

Test Example 6

Respiratory Tract Inflammation Suppressing Action

According to the method described in Henderson, W. R., et al., Am. J. Respir. Cric. Care Med., 165(1), 108–116 (2002), suppressing action on bronchial inflammation was confirmed. BALB/c female mice (7-week old) were used for the test, each group consisting of 7 mice, and the control group consisting of 11 or 12 mice. The mice were intraperitoneally administered with ovalbumin (OVA, 100 ng, Sigma) and 1 mg of aluminum hydroxide for initial immunization, and after 2 weeks, they are subcutaneously administered with 10 ng of OVA as additional immunization. After further 1 week, a test compound was dissolved in water containing 0.5% carboxymethylcellulose and orally administered (30 mg/kg) to the test animals once a day for 5 days. The control group was similarly given only with water containing 0.5% carboxymethylcellulose. After 1 hour, the mice were orally inhaled with 2% OVA for 10 minutes to induce a respiratory tract inflammation. Further, the control group, in which the mice were not given with the test compound, was divided into a positive control group (n=7), in which the mice were inhaled with 2% OVA to induce the reaction, and a negative control group (n=4 or 5), in which the mice were similarly inhaled with physiological saline. After 24 hours, alveoli in the lungs of the test animals were washed with physiological saline, and the total infiltrated white blood cells (WBC) were counted.

TABLE 9

| Test compound | Total WBC count × 10E5/ml/mouse |
|---|---|
| Without immunization | 100 |
| Physiological saline | 400 |
| Example 1 | 300 |
| Example 2 | 200 |
| Example 7 | 400 |
| Example 10 | 150 |
| Example 12 | 100 |

In addition to the compounds mentioned in the table, decrease of infiltrated white blood cell number was also observed when the compound of Example 106 was used, which falls within the compound of the present invention.

Thus, it was confirmed that the compounds of the present invention were useful as medicaments for prophylactic and/or therapeutic treatment of diseases relating to cell migration.

Further, no abnormality was observed in the test animals (mice) after oral administration of 30 mg/kg of the compounds for 5 consecutive days, which revealed that they were safe compounds.

Test Example 7

Action on Increase of Intracellular Calcium Concentration

According to the method described in Test Example 1, a neutrophil containing fraction was prepared. Fura2-AM (Sigma) at a final concentration of 3 µM was added to the human neutrophil fraction and the mixture was incubated at 37° C. for 1 hour. After centrifugation (250 g for 5 minutes), the supernatant was discarded, and the neutrophils were resuspended in Hanks' Balanced Salt Solution (HBSS, Gibco) to prepare a cell suspension ($8 \times 10^6$/ml) for measurement of intracellular calcium concentration. The cell suspension for measurement of intracellular calcium concentration was left stand at room temperature for 30 minutes. Then, 490 µl of the cell suspension for measurement of intracellular calcium concentration was placed in a cuvette, 10 µl of calcium chloride solution at a final concentration of 1 µM was added to it and the cuvette was set in an intracellular calcium concentration analyzer (CAF110, Nippon Bunko). fMLP (Sigma) solution at a final concentration of 1 µM was added to the cell suspension, and F340 and F380, which are fluorescence intensity at 340 nm and 380 nm, respectively, were measured to obtain an R value (F340/F380) as an index of the intracellular calcium concentration. A test compound (1 µM) was added 3 minutes before the addition of fMLP, and the action on the intracellular calcium concentration was observed. The ratios of the maximum R value obtained with addition of each test compound, based on the maximum R value obtained without addition of test compound and taken as 100%, are shown in Table 10 mentioned below.

It was revealed that the compounds of the present invention had almost no effect on the increase of the intracellular calcium concentration caused by the fMLP stimulation.

TABLE 10

| Test compound | Maximum R value (%) |
|---|---|
| None | 100 |
| Example 1 | 98 |
| Example 2 | 99 |
| Example 5 | 98 |
| Example 7 | 101 |
| Example 10 | 99 |
| Example 8 | 99 |
| Example 20 | 100 |

Test Example 7

Action on Myosin Light Chain Phosphorylation Enzyme (MLCK) Activity

A myosin light chain phosphorylation enzyme (MLCK) was purified from chicken gizzard smooth muscle by a conventional method (Yoshida, M., et al., J. Biochem., 99, 1027–1036 (1986)). The myosin regulatory light chain as a substrate was purified from the chicken gizzard smooth muscle by a conventional method (Grand, R. J., et al., Biochem. J., 211, 267–272 (1983)). The MLCK activity was measured by ELISA using pLC1 described in Test Example 1 (Sakurada, K., et al., J. Biochem., 115, 18–21 (1994)). The myosin regulatory light chain was diluted in phosphate-buffered saline (PBS, Sigma) to a concentration of 5.0 g/ml, added to 96-well Immunoplate (Nunc) in a volume of 100 μl per well and left stand overnight at 4° C. Each well was washed with PBS, and 25 mM Tris/HCl buffer containing 100 μM ATP, 3 mM MgCl$_2$, 1 mM CaCl$_2$, 100 ng/ml of calmodulin (Sigma) and 100 ng/ml of MLCK (pH 7.4, Buffer A) was added to each well and incubated at 30° C. for 10 minutes. In a volume of 100 μl each of 20% aqueous phosphoric acid solution was added to each well to terminate the enzymatic reaction. Each well was washed with 25 mM Tris/HCl buffer (TTBS) containing 0.1% Tween 20, and then 100 μl each of pLC1 described in Test Example 1 was added to each well and incubated at room temperature for 90 minutes.

Each well was washed with TTBS, and then 100 μl of the HRP-labeled rabbit anti-mouse IgG antibodies (Bio-Rad) were added to each well and incubated at room temperature for 90 minutes. Each well was washed with TTBS, and then 25 mM citrate buffer (pH 5.0) containing orthophenylenediamine (Sigma) as a substrate of HRP and aqueous hydrogen peroxide (0.03%) was added in a volume of 100 μl per well and incubated at room temperature for 5 minutes. 50 μl of 4 N sulfuric acid was added to each well to terminate the reaction, and then absorbance was measured by using an immunoplate reader (Bio-Rad). The MLCK activity inhibition ratio was calculated by adding the test compound to Buffer A at various concentrations to obtain a compound concentration providing an inhibition ratio of 50% as IC$_{50}$. The results are as shown in Table 11 mentioned below.

It was revealed that the compounds of the present invention had almost no inhibitory effect on MLCK.

TABLE 11

| Test compound | Myosin light chain phosphorylation enzyme inhibitory action IC$_{50}$(μM) |
|---|---|
| Example 1 | >50 |
| Example 2 | >50 |
| Example 7 | >50 |
| Example 10 | >30 |
| Example 8 | >50 |
| Example 20 | >100 |

In addition to the compounds mentioned in the table, each of the compounds of Examples 27, 29, 104, 106, 112, 120, 128, 130, 141 and 144 also did not inhibit MLCK.

INDUSTRIAL APPLICABILITY

The compounds of the present invention represented by the formula (1) have an inhibitory action on phosphorylation of myosin regulatory light chain, and are useful as active ingredients of medicaments for prophylactic and/or therapeutic treatment of, for example, diseases relating to contraction of various cells, diseases relating to morphological change of various cells, diseases relating to migration of various cells, diseases relating to release of various cells, diseases relating to aggregation of various cells, diseases relating to apoptosis of various cells, and/or diseases relating to abnormality of gene expression in various cells.

What is claimed is:

1. A compound represented by the following formula (1) or a salt thereof:

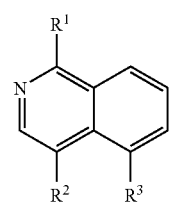

(1)

wherein R$^1$ represents hydrogen atom, a halogen atom, hydroxyl group, amino group, or a C$_{1-6}$ alkoxyl group;

R$^2$ represents hydrogen atom, a halogen atom, a C$_{1-6}$ alkyl group, —(C$_{2-3}$ alkylene)O(G$^1$), —(C$_{2-3}$ alkylene)CO$_2$ (G$^1$), —N(G$^2$)(G$^3$), —O(C$_{2-3}$ alkylene)O(G$^1$), —NH (C$_{2-3}$ alkylene)O(G$^1$), —NH(C$_{2-3}$ alkylene)N(G$^2$)(G$^3$), a C$_{2-3}$ alkenyl group, a C$_{2-3}$ alkynyl group, a C$_{1-6}$ alkoxyl group, —(C$_{2-3}$ alkylene)SO$_2$(C$_{1-6}$ alkyl), —S(O)$_p$(C$_{1-6}$ alkyl), —O(C$_{2-3}$ alkylene)SO$_2$(C$_{1-6}$ alkyl), or cyano group;

G$^1$, G$^2$, and G$^3$ independently represent hydrogen atom, or a C$_{1-6}$ alkyl group;

p represents an integer of from 0 to 2;

R$^3$ represents a group represented by the following formula (1-1), formula (1-2), or formula (1-3);

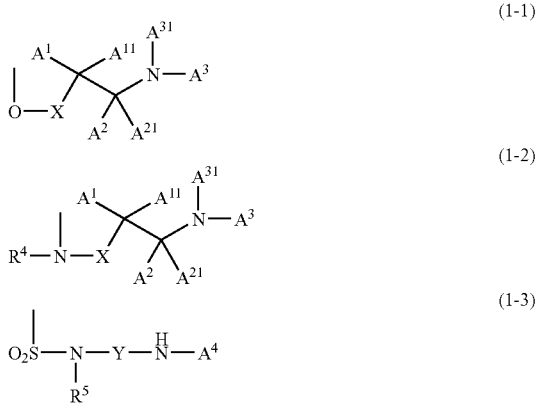

wherein
(i) when $R^3$ represents a group represented by the formula (1-1):
$R^1$ is hydrogen atom, hydroxyl group, or amino group;
$R^2$ is a $C_{1-6}$ alkyl group, —($C_{2-8}$ alkylene )O($G^1$), a $C_{2-8}$ alkenyl group, —S(O)$_p$($C_{1-6}$ alkyl), or cyano group;
X represents propylene group, butylene group, —C($A^5$)($A^{51}$)-, —C($A^5$)($A^{51}$)-C($A^6$)($A^{61}$)-, or a single bond;
$A^{11}$, $A^{21}$, $A^{51}$, and $A^{61}$ independently represent hydrogen atom, or a $C_{1-6}$ alkyl group;
$A^{31}$ represents a $C_{1-6}$ alkyl group substituted with hydroxyl group, or hydrogen atom; and
groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a 5- or 6-membered ring, provided that a group or groups among $A^1$, $A^2$, $A^3$, $A^5$, and $A^6$ not involved in the ring formation independently represent hydrogen atom, or a $C_{1-6}$ alkyl group;
(ii) when $R^3$ represents a group represented by the formula (1-2):
X represents propylene group, butylene group, —C($A^5$)($A^{51}$)-, —C($A^5$)($A^{51}$)-C($A^6$)($A^{61}$)-, or a single bond;
$A^{11}$, $A^{21}$, $A^{51}$, and $A^{61}$ independently represent hydrogen atom, or a $C_{1-6}$ alkyl group;
$A^{31}$ represents a $C_{1-6}$ alkyl group substituted with hydroxyl group, or hydrogen atom;
$R^4$ represents hydrogen atom, or a $C_{1-6}$ alkyl group; and
$A^1$, $A^2$, $A^3$, $A^5$, and $A^6$ independently represent hydrogen atom, or a $C_{1-6}$ alkyl group; or
groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring; and
(iii) when $R^3$ represents a group represented by the formula (1-3):
Y represents a $C_{2-6}$ alkylene group, a $C_{2-6}$ alkylene group substituted with a $C_{1-6}$ alkyl group, a $C_{2-6}$ alkylene group substituted with phenyl group, a $C_{2-6}$ alkylene group substituted with benzyl group, —($C_{1-6}$ alkylene) phenylene($C_{1-6}$ alkylene)-, 1,2-cyclohexylene group, or 1,3-cyclohexylene group;
$A^4$ represents hydrogen atom, or a $C_{1-6}$ alkyl group, or may binds to any one of carbon atoms of the alkylene moiety of Y to form a 4- to 7-membered ring;

$R^5$ represents —($C_{2-6}$ alkylene)(cycloalkyl), —($C_{2-6}$ alkylene)(aryl), —($C_{2-6}$ alkylene)(heteroaryl), —($C_{2-6}$ alkylene)S(O)$_q$(cycloalkyl), —($C_{2-6}$ alkylene)S(O)$_q$(aryl), —($C_{2-6}$ alkylene)S(O)$_q$(heteroaryl), —($C_{2-6}$ alkylene)N($G^6$)(cycloalkyl), —($C_{2-6}$ alkylene)N($G^6$)(aryl), —($C_{2-6}$ alkylene)N($G^6$)(heteroaryl), —($C_{2-6}$alkylene)CON($G^6$)(cycloalkyl), —($C_{2-6}$ alkylene)CON($G^6$)(aryl), or —($C_{2-6}$ alkylene)CON($G^6$)(heteroaryl);
$G^6$ represents hydrogen atom, or a $C_{1-6}$ alkyl group;
q represents an integer of from 0 to 2;
wherein aryl is a phenyl group which may be substituted with one or more substituents selected from the group consisting of a halogen atom, a $C_{1-6}$ alkyl group, $CF_3$ group, a $C_{1-6}$ alkoxyl group, cyano group, —N($G^7$)($G^8$), —CO$_2$($G^9$), —S(O)$_r$($G^9$), and —N($G^9$)SO$_2$($C_{1-6}$ alkyl);
$G^9$ represents hydrogen atom, or a $C_{1-6}$ alkyl group;
$G^7$ and $G^8$ independently represents hydrogen atom, or a $C_{1-6}$ alkyl group, or —N($G^7$)($G^8$) in said "aryl" as a whole may form a 4- to 7-membered ring which may contain oxygen atom, sulfur atom, or an N($G^{10}$) group, besides said nitrogen atom;
$G^{10}$ represents hydrogen atom, or a $C_{1-6}$ alkyl group;
wherein heteroaryl is selected from pyranyl, pyrazinyl, dioxolyl, furyl, thienyl, pyridyl, pyrimidyl, pyridazinyl, tetrazolyl, pyrrolyl, oxazolyl, thiazolyl, isoxazolyl, isothiazolyl, imidazolyl, pyrazolyl, oxadiazolyl, thiadiazolyl, and triazolyl, and these groups may optionally be substituted with one or more substituents selected from the group consisting of a $C_{1-6}$ alkyl group which may be substituted with a halogen atom, and a halogen atom; and
r represents an integer of from 0 to 2.

2. The compound or salt thereof according to claim 1, wherein $R^3$ is a group represented by the formula (1-1).

3. The compound or salt thereof according to claim 1, wherein $R^3$ is a group represented by a formula (1-2).

4. The compound or salt thereof according to claim 3, wherein $R^3$ is a group represented by a formula (1-2);
X represents propylene group, butylene group, —C($A^5$)($A^{51}$)-, —C($A^5$)($A^{51}$)-C($A^6$)($A^{61}$)-, or a single bond;
$A^{11}$, $A^{21}$, $A^{51}$, and $A^{61}$ independently represent hydrogen atom, or a $C_{1-6}$ alkyl group;
$A^{31}$ is a $C_{1-6}$ alkyl group substituted with hydroxyl group, or hydrogen atom;
$R^4$ is hydrogen atom, or a $C_{1-6}$ alkyl group; and
groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a 5- or 6-membered ring provided that among $A^1$, $A^2$, $A^3$, $A^5$, and $A^6$, the group or groups not involved in the ring formation independently represent hydrogen atom, or a $C_{1-6}$ alkyl group.

5. The compound or salt thereof according to claim 1, wherein the ring formed by groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ binding to each other is (i) a 6-membered ring, (ii) a ring consisting of carbon atoms, or when the ring contains a nitrogen atom to which $A^3$ binds, a ring consisting of carbon atoms except for the nitrogen atom, or (iii) a saturated ring.

6. The compound or salt thereof according to claim 1, wherein X is —C($A^5$)($A^{51}$)-, or —C($A^5$)($A^{51}$)-C($A^6$)($A^{61}$)-.

7. The compound or salt thereof according to claim 2, wherein $R^3$ is a group represented by the following formula (1-1-4) or formula (1-1-7)

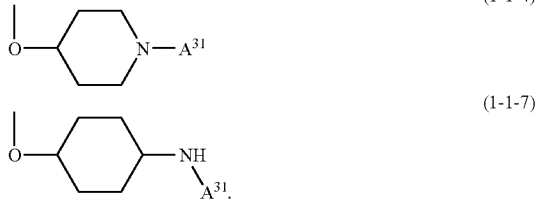

(1-1-4)

(1-1-7)

8. The compound or salt thereof according to claim 3, wherein $R^3$ is a group represented by the following formula (1-2-4) or formula (1-2-7)

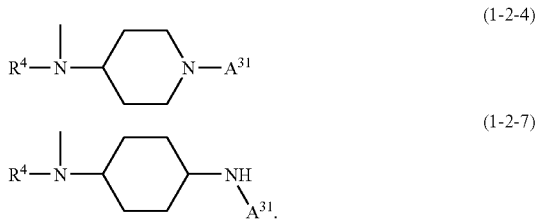

(1-2-4)

(1-2-7)

9. The compound or salt thereof according to claim 1, wherein $A^{31}$ is hydrogen atom.

10. The compound or salt thereof according to claim 1, wherein $A^{31}$ is a $C_{1-6}$ alkyl group substituted with hydroxyl group.

11. The compound or salt thereof according to claim 3, wherein $R^4$ hydrogen atom.

12. The compound or salt thereof according to claim 1, wherein $R^3$ is a group represented by a formula (1-3).

13. The compound or salt thereof according to claim 12, wherein Y is a $C_{2-4}$ alkylene.

14. The compound or salt thereof according to claim 12, wherein $R^5$ is —($C_{2-4}$ alkylene)(aryl), —($C_{2-4}$ alkylene)(thienyl), —($C_{2-4}$ alkylene)$SO_2$(aryl), or —($C_{2-4}$ alkylene)$SO_2$(thienyl), where the aryl is a phenyl group which may be substituted with one or more substituents selected from the group consisting a halogen atom, a $C_{1-6}$ alkyl group, $CF_3$ group, a $C_{1-6}$ alkoxyl group, cyano group, —N($G^7$)($G^8$), —$CO_2$($G^9$), —S(O)$_r$($G^9$), and —N($G^9$)$SO_2$($C_{1-6}$ alkyl), where $G^9$ is hydrogen atom, or a $C_{1-6}$ alkyl group, $G^7$ and $G^8$ independently represent hydrogen atom, or a $C_{1-6}$ alkyl group, and r is an integer of 0 to 2.

15. The compound or salt thereof according to claim 1, wherein $R^1$ is hydrogen atom, hydroxyl group, or amino group.

16. The compound or salt thereof according to claim 1, wherein $R^2$ is hydrogen atom, a $C_{1-6}$ alkyl group, a $C_{2-3}$ alkenyl group, a halogen atom, a —($C_{2-3}$ alkylene)O($G^1$)-, —S(O)$_p$($C_{1-6}$ alkyl), or cyano group.

17. The compound or salt thereof according to claim 1, wherein $R^2$ is a $C_{1-6}$ alkyl group, or cyano group.

18. The compound or salt thereof according to claim 1, wherein $R^1$ is hydrogen atom, hydroxyl group, or amino group, and $R^2$ is a $C_{1-6}$ alkyl group, —($C_{2-3}$ alkylene)O($G^1$), a $C_{2-3}$ alkenyl group, —S(O)$_p$($C_{1-6}$ alkyl), or cyano group.

19. The compound or salt thereof according to claim 7, wherein $R^1$ is hydrogen atom, hydroxyl group, or amino group, $R^2$ is a $C_{1-6}$ alkyl group, a $C_{2-3}$ alkenyl group, or cyano group, and $R^3$ is a group represented by the formula (1-1-4) or formula (1-1-7).

20. The compound or salt thereof according to claim 8, wherein $R^1$ is hydrogen atom, hydroxyl group, or amino group, $R^2$ is a $C_{1-6}$ alkyl group, —($C_{2-3}$ alkylene)O($G^1$), a $C_{2-3}$ alkenyl group, or —S(O)$_p$($C_{1-6}$ alkyl), $R^3$ is a group represented by the formula (1-2-4) or formula (1-2-7), and $R^4$ is hydrogen atom.

21. The compound or salt thereof according to claim 8, wherein $R^1$ is hydrogen atom, hydroxyl group, or amino group, $R^2$ is a $C_{1-6}$ alkyl group, or a $C_{2-3}$ alkenyl group, $R^3$ is a group represented by the formula (1-2-4) or formula (1-2-7), and $R^4$ is hydrogen atom.

22. The compound or salt thereof according to claim 12, wherein $R^3$ is a group represented by the formula (1-3), $R^1$ is hydrogen atom, hydroxyl group, or amino group, $R^2$ is hydrogen atom, or a $C_{1-6}$ alkyl group, and $R^5$ is 3-phenylpropyl, 2-(2-thienyl)ethyl, 2-(3-thienyl)ethyl, or 2-(phenylsulfonyl).

23. The compound or salt thereof according to claim 1, wherein the compound of the formula (1) is selected from the group consisting of 4-[(4-methyl-5-isoquinolyl)oxy]piperidine; 4-[(4-ethyl-5-isoquinolyl)oxy]piperidine; 4-[(4-cyano-5-isoquinolyl)-oxy]piperidine; trans-4-[(4-methyl-5-isoquinolyl)oxy]cyclohexyl-amine; trans-4-[(4-ethyl-5-isoquinolyl)oxy]cyclohexylamine; trans-4-[(4-cyano-5-isoquinolyl)oxy]cyclohexylamine; cis-4-[(4-methyl-5-isoquinolyl)oxy]cyclohexylamine; cis-4-[(4-ethyl-5-isoquinolyl)-oxy]cyclohexylamine; and cis-4-[(4-cyano-5-isoquinolyl)oxy]cyclohexylamine.

24. The compound or salt thereof according to claim 1, wherein the compound of the formula (1) is selected from the group consisting of 1-(2-hydroxyethyl)-4-[(4-methyl-5-isoquin-olyl)oxy]piperidine; 1-(2-hydroxyethyl)-4-[(4-ethyl-5-isoquinolyl)-oxy]piperidine; 1-(2-hydroxyethyl)-4-[(4-cyano-5-isoquinolyl)oxy]-piperidine; trans-1-[(4-methyl-5-isoquinolyl)oxy]-4-[(2-hydroxy-ethyl)amino]cyclohexane; trans-1-[(4-ethyl-5-isoquinolyl)oxy]-4-[(2-hydroxyethyl)amino]cyclohexane; trans-1-[(4-cyano-5-isoquin-olyl)oxy]-4-[(2-hydroxyethyl)amino]cyclohexane; cis-1-[(4-methyl-5-isoquinolyl)oxy]-4-[(2-hydroxyethyl)amino]cyclohexane; cis-1-[(4-ethyl-5-isoquinolyl)oxy]-4-[(2-hydroxyethyl)amino]cyclohexane; and cis-1-[(4-cyano-5-isoquinolyl)oxy]-4-[(2-hydroxyethyl)amino]cyclohexane.

25. The compound or salt thereof according to claim 1, wherein the compound of the formula (1) is selected from the group consisting of 1-(3-hydroxypropyl)-4-[(4-methyl-5-isoquin-olyl)oxy]piperidine; 1-(3-hydroxypropyl)-4-[(4-ethyl-5-isoquinol-yl)oxy]piperidine; 1-(3-hydroxypropyl)-4-[(4-cyano-5-isoquinolyl)-oxy]piperidine; trans-1-[(4-methyl-5-isoquinolyl)oxy]-4-[(3-hydroxypropyl)amino]cyclohexane; trans-1-[(4-ethyl-5-isoquinolyl)-oxy]-4-[(3-hydroxypropyl)amino]cyclohexane; trans-1-[(4-cyano-5-isoquinolyl)oxy]-4-[(3-hydroxypropyl)amino]cyclohexane; cis-1-[(4-methyl-5-isoquinolyl)oxy]-4-[(3-hydroxypropyl)amino]cyclohexane; cis-1-[(4-ethyl-5-isoquinolyl)oxy]-4-[(3-hydroxypropyl)amino]cyclo-hexane; and cis-1-[(4-cyano-5-isoquinolyl)oxy]-4-[(3-hydroxy-propyl)amino]cyclohexane.

26. The compound or salt thereof according to claim 1, wherein the compound of the formula (1) is selected from the group consisting of 4-[(1-hydroxy-4-methyl-5-iso-quinolyl)-oxy]piperidine; 4-[(1-hydroxy-4-ethyl-5-iso-quinolyl)oxy]piperidine; trans-4-[(1-hydroxy-4-methyl-5-isoquinolyl)oxy]cyclohexylamine; trans-4-[(1-hydroxy-4- ethyl-5-isoquinolyl)oxy]cyclohexylamine; cis-4-[(1-hydroxy-4-methyl-5-isoquinolyl)oxy]cyclohexylamine; and cis-4-[(1-hydroxy-4-ethyl-5-isoquinolyl)oxy]cyclohexylamine.

27. The compound or salt thereof according to claim 1, wherein the compound of the formula (1) is selected from the group consisting of 4-[(4-methyl-5-isoquinolyl)amino]piperidine; 4-[(4-ethyl-5-isoquinolyl)amino]piperidine; 4-[(4-vinyl-5-isoquin-olyl)amino]piperidine; trans-N-(4-methyl-5-isoquinolyl)-1,4-cyclo-hexanediamine; trans-N-(4-ethyl-5-isoquinolyl)-1,4-cyclohexane-diamine; trans-N-(4-vinyl-5-isoquinolyl)-1,4-cyclohexanediamine; cis-N-(4-methyl-5-isoquinolyl)-1,4-cyclohexanediamine; cis-N-(4-ethyl-5-isoquinolyl)-1,4-cyclohexanediamine; and cis-N-(4-vinyl-5-isoquinolyl)-1,4-cyclohexanediamine.

28. The compound or salt thereof according to claim 1, wherein the compound of the formula (1) is selected from the group consisting of 1-(2-hydroxyethyl)-4-(4-methyl-5-isoquin-olyl)aminopiperidine; 1-(2-hydroxyethyl)-4-(4-ethyl-5-isoquinolyl)-aminopiperidine; 1-(2-hydroxyethyl)-4-(4-vinyl-5-isoquinolyl)amino-piperidine; 1-(3-hydroxypropyl)-4-(4-methyl-5-isoquinolyl)amino-piperidine; 1-(3-hydroxypropyl)-4-(4-ethyl-5-isoquinolyl)amino-piperidine; 1-(3-hydroxypropyl)-4-(4-vinyl-5-isoquinolyl)amino-piperidine; trans-N-(4-methyl-5-isoquinolyl)-N'-(2-hydroxyethyl)-1,4-cyclohexanediamine; trans-N-(4-ethyl-5-isoquinolyl)-N'-(2-hydroxyethyl)-1,4-cyclohexanediamine; trans-N-(4-vinyl-5-isoquin-olyl)-N'-(2-hydroxyethyl)-1,4-cyclohexanediamine; trans-N-(4-methyl-5-isoquinolyl)-N'-(3-hydroxypropyl)-1,4-cyclohexanediamine; trans-N-(4-ethyl-5-isoquinolyl)-N'-(3-hydroxypropyl)-1,4-cyclo-hexanediamine; trans-N-(4-vinyl-5-isoquinolyl)-N'-(3-hydroxy-propyl)-1,4-cyclohexanediamine; cis-N-(4-methyl-5-isoquinolyl)-N'-(2-hydroxyethyl)-1,4-cyclohexanediamine; cis-N-(4-ethyl-5-isoquin-olyl)-N'-(2-hydroxyethyl)-1,4-cyclohexanediamine; cis-N-(4-vinyl-5-isoquinolyl)-N'-(2-hydroxyethyl)-1,4-cyclohexanediamine; cis-N-(4-methyl-5-isoquinolyl)-N'-(3-hydroxypropyl)-1,4-cyclohexanediamine; cis-N-(4-ethyl-5-isoquinolyl)-N'-(3-hydroxypropyl)-1,4-cyclohexane-diamine; and cis-N-(4-vinyl-5-isoquinolyl)-N'-(3-hydroxypropyl)-1,4-cyclohexanediamine.

29. The compound or salt thereof according to claim 1, wherein the compound of the formula (1) is selected from the group consisting of 4-(1-hydroxy-4-methyl-5-isoquinolyl)amino-piperidine; 4-(1-hydroxy-4-ethyl-5-isoquinolyl)aminopiperidine; trans-N-(1-hydroxy-4-methyl-5-isoquinolyl)-1,4-cyclohexanediamine; trans-N-(1-hydroxy-4-ethyl-5-isoquinolyl)-1,4-cyclohexanediamine; cis-N-(1-hydroxy-4-methyl-5-isoquinolyl)-1,4-cyclohexanediamine; and cis-N-(1-hydroxy-4-ethyl-5-isoquinolyl)-1,4-cyclohexanediamine.

30. The compound or salt thereof according to claim 1, wherein the compound of the formula (1) is selected from the group consisting of N-[(5-isoquinolyl)sulfonyl]-N-(3-phenylpropyl)-1,3-propylenediamine; N-[(5-isoquinolyl)sulfonyl]-N-[3-(3-carboxy-phenyl)propyl]-1,3-propylenediamine; N-[(5-isoquinolyl)sulfonyl]-N-[2-(2-thienyl)ethyl]-1,3-propylenediamine; N-[(5-isoquinolyl)-sulfonyl]-N-[2-(phenylsulfonyl)ethyl]-1,3-propylenediamine; N-[(5-isoquinolyl)sulfonyl]-N-(3-phenylpropyl)ethylenediamine; N-[(5-isoquinolyl)sulfonyl]-N-[3-(3-carboxyphenyl)propyl]ethylenediamine; N-[(5-isoquinolyl)sulfonyl]-N-[2-(2-thienyl)ethyl]ethylenediamine; N-[(5-isoquinolyl)sulfonyl]-N-[2-(phenylsulfonyl)ethyl]ethylene-diamine; N-[(4-methyl-5-isoquinolyl)sulfonyl]-N-(3-phenylpropyl)-1,3-propylenediamine; N-[(4-methyl-5-isoquinolyl)sulfonyl]-N-[3-(3-carboxyphenyl)propyl]-1,3-propylenediamine; N-[(4-methyl-5-isoquin-olyl)sulfonyl]-N-[2-(2-thienyl)ethyl]-1,3-propylenediamine; N-[(4-methyl-5-isoquinolyl)sulfonyl]-N-[2-(phenylsulfonyl)ethyl]-1,3-propylenedi-amine; N-[(4-methyl-5-isoquinolyl)sulfonyl]-N-(3-phenylpropyl)ethylenediamine; N-[(4-methyl-5-isoquinolyl)sulfonyl]-N-[3-(3-carboxyphenyl)propyl]ethylenediamine; N-[(4-methyl-5-isoquin-olyl)sulfonyl]-N-[2-(2-thienyl)ethyl]ethylenediamine; and N-[(4-methyl-5-isoquinolyl)sulfonyl]-N-[2-(phenylsulfonyl)ethyl]ethylene-diamine.

31. The compound or salt thereof according to claim 1, wherein the compound of the formula (1) is selected from the group consisting of N-[(1-hydroxy-5-isoquinolyl)sulfonyl]-N-(3-phenylpropyl)-1,3-propylenediamine; N-[(1-hydroxy-5-isoquinolyl)-sulfonyl]-N-[3-(3-carboxyphenyl)propyl]-1,3-propylenediamine; N-[(1-hydroxy-5-isoquinolyl)sulfonyl]-N-[2-(2-thienyl)ethyl]-1,3-propylenediamine; N-[(1-hydroxy-5-isoquinolyl)sulfonyl]-N-[2-(phenylsulfonyl)ethyl]-1,3-propylenediamine; N-[(1-hydroxy-5-isoquinolyl)sulfonyl]-N-(3-phenylpropyl)ethylenediamine; N-[(1-hydroxy-5-isoquinolyl)sulfonyl]-N-[3-(3-carboxyphenyl)propyl]ethyl-enediamine; N-[(1-hydroxy-5-isoquinolyl)sulfonyl]-N-[2-(2-thienyl)-ethyl]ethylenediamine; N-[(1-hydroxy-5-isoquinolyl)sulfonyl]-N-[2-(phenylsulfonyl)ethyl]ethylenediamine; N-[(1-amino-5-isoquinolyl)-sulfonyl]-N-(3-phenylpropyl)-1,3-propylenediamine; N-[(1-amino-5-isoquinolyl)sulfonyl]-N-[3-(3-carboxyphenyl)propyl]-1,3-propyl-enediamine; N-[(1-amino-5-isoquinolyl)sulfonyl]-N-[2-(2-thienyl)-ethyl]-1,3-propylenediamine; N-[(1-amino-5-isoquinolyl)sulfonyl]-N-[2-(phenylsulfonyl)ethyl]-1,3-propylenediamine; N-[(1-amino-5-isoquinolyl)sulfonyl]-N-(3-phenylpropyl)ethylenediamine; N-[(1-amino-5-isoquinolyl)sulfonyl]-N-[3-(3-carboxyphenyl)propyl]ethyl-enediamine; N-[(1-amino-5-isoquinolyl)sulfonyl]-N-[2-(2-thienyl)-ethyl]ethylenediamine; and N-[(1-amino-5-isoquinolyl)sulfonyl]-N-[2-(phenylsulfonyl)ethyl]ethylenediamine.

32. The compound or salt thereof according to claim 1, wherein the compound of the formula (1) is selected from the group consisting of N-[(1-hydroxy-4-methyl-5-isoquinolyl)sulfonyl]-N-(3-phenylpropyl)-1,3-propylenedi-amine; N-[(1-hydroxy-4-methyl-5-isoquinolyl)sulfonyl]-N-[3-(3-carboxyphenyl)propyl]-1,3-propyl-enediamine; N-[(1-hydroxy-4-methyl-5-isoquinolyl)sulfonyl]-N-[2-(2-thienyl)ethyl]-1,3-propylenediamine; N-[(1-hydroxy-4-methyl-5-iso-quinolyl)sulfonyl]-N-[2-(phenylsulfonyl)ethyl]-1,3-propylenedi-amine; N-[(1-hydroxy-4-methyl-5-isoquinolyl)sulfonyl]-N-(3-phenyl-propyl)ethylenediamine; N-[(1-hydroxy-4-methyl-5-isoquinolyl)sul-fonyl]-N-[3-(3-carboxyphenyl)propyl]ethylenediamine; N-[(1-hydroxy-4-methyl-5-isoquinolyl)sulfonyl]-N-[2-(2-thienyl)ethyl]ethyl-ene-diamine; N-[(1-hydroxy-4-methyl-5-isoquinolyl)sulfonyl]-N-[2-(phenylsulfonyl)ethyl]ethylenediamine; N-[(1-amino-4-methyl-5-isoquinolyl)sulfonyl]-N-(3-phenylpropyl)-1,3-propylenediamine; N-[(1-amino-4-methyl-5-isoquinolyl)sulfonyl]-N-[3-(3-carboxyphenyl)-propyl]-1,3-propylenediamine; N-[(1-amino-4-methyl-5-isoquinolyl)-sulfonyl]-N-[2-(2-thienyl)ethyl]-1,3-propylenediamine; N-[(1-amino-4-methyl-5-isoquinolyl)sulfonyl]-N-[2-(phenylsulfonyl)ethyl]-1,3-propylenediamine; N-[(1-amino-4-methyl-5-isoquinolyl)sulfonyl]-N-(3-phenylpropyl)ethylenediamine; N-[(1-amino-4-methyl-5-isoquin-olyl)sulfonyl]-N-[3-(3-carboxyphenyl)propyl]ethylenediamine; N-[(1-amino-4-methyl-5-isoquinolyl)sulfonyl]-N-[2-(2-thienyl)ethyl]ethyl-enediamine; and N-[(1-amino-4-methyl-5-isoquinolyl)sulfonyl]-N-[2-(phenylsulfonyl)ethyl]ethyl-enediamine.

33. The compound or salt thereof according to claim 1 wherein $R^2$ is a $C_{1-6}$ alkyl group, —($C_{2-3}$ alkylene)O($G^1$), —($C_{2-3}$ alkylene)CO$_2$($G^1$), —N($G^2$)($G^3$), —O($C_{2-3}$ alkylene)O($G^1$), —NH($C_{2-3}$ alkylene)O($G^1$), —NH($C_{2-3}$ alkylene)N($G^2$)($G^3$), a $C_{2-3}$ alkenyl group, a $C_{2-3}$ alkynyl group, a $C_{1-6}$ alkoxyl group, —($C_{2-3}$ alkylene)SO$_2$($C_{1-6}$ alkyl), —S(O)$_p$($C_{1-6}$ alkyl), —O($C_{2-3}$ alkylene)SO$_2$($C_{1-6}$ alkyl), or cyano group; and $R^3$ represents a group represented by the formula (1-1) wherein X represents propylene group, butylene group, —C($A^5$)($A^{51}$)-, —C($A^5$)($A^{51}$)-C($A^6$)($A^{61}$)-, or a single bond; and $A^{11}$, $A^{21}$, $A^{51}$, and $A^{61}$ independently represent hydrogen atom, or a $C_{1-6}$ alkyl group; $A^{31}$ represents a $C_{1-6}$ alkyl group substituted with hydroxyl group, or hydrogen atom; and groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a saturated 6-membered ring, provided that a group or groups among $A^1$, $A^2$, $A^3$, $A^5$, and $A^6$ not involved in the ring formation independently represent hydrogen atom, or a $C_{1-6}$ alkyl group.

34. The compound or salt thereof according to claim 1 wherein the groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ are groups in each of one or more combinations selected from the group consisting of combinations of $A^3$ and $A^2$, $A^3$ and $A^1$, $A^3$ and $A^5$, and $A^2$ and $A^5$.

35. The compound or salt thereof according to claim 1 wherein the groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ are groups in each of one or more combinations selected from the group consisting of combinations of, $A^3$ and $A^5$, and $A^2$ and $A^5$.

36. The compound or salt thereof according to claim 33 wherein $R^2$ is a $C_{1-6}$ alkyl group, a $C_{2-3}$ alkenyl group, or cyano group.

37. The compound or salt thereof according to claim 34 wherein $R^2$ is a $C_{1-6}$ alkyl group, a $C_{2-3}$ alkenyl group, or cyano group.

38. The compound or salt thereof according to claim 35 wherein $R^2$ is a $C_{1-6}$ alkyl group, a $C_{2-3}$ alkenyl group, or cyano group.

39. The compound or salt thereof according to claim 1 wherein $R^2$ is a $C_{1-6}$ alkyl group, —($C_{2-3}$ alkylene)O($G^1$), —($C_{2-3}$ alkylene)CO$_2$($G^1$), —N($G^2$)($G^3$), —O($C_{2-3}$ alkylene)O($G^1$), —NH($C_{2-3}$ alkylene)O($G^1$), —NH($C_{2-3}$ alkylene)N($G^2$)($G^3$), a $C_{2-3}$ alkenyl group, a $C_{2-3}$ alkynyl group, a $C_{1-6}$ alkoxyl group, —($C_{2-3}$ alkylene)SO$_2$($C_{1-6}$ alkyl), —S(O)$_p$($C_{1-6}$ alkyl), —O($C_{2-3}$ alkylene)SO$_2$($C_{1-6}$ alkyl), or cyano group; and $R^3$ represents a group represented by the formula (1-2), wherein X represents propylene group, butylene group, —C($A^5$)($A^{51}$)-, —C($A^5$)($A^{51}$)-C($A^6$)($A^{61}$)-, or a single bond;

$A^{11}$, $A^{21}$, $A^{51}$, and $A^{61}$ independently represent hydrogen atom, or a $C_{1-6}$ alkyl group;

$A^{31}$ represents a $C_{1-6}$ alkyl group substituted with hydroxyl group, or hydrogen atom;

$R^4$ represents hydrogen atom, or a $C_{1-6}$ alkyl group; and $A^1$, $A^2$, $A^3$, $A^5$, and $A^6$ independently represent hydrogen atom, or a $C_{1-6}$ alkyl group; or groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ may bind to each other to form a 5- or 6-membered ring.

40. The compound or salt thereof according to claim 1 wherein groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ bind to each other to form a 5- or 6-membered ring, provided that a group or groups among $A^1$, $A^2$, $A^3$, $A^5$, and $A^6$ not involved in the ring formation independently represent hydrogen atom, or a $C_{1-6}$ alkyl group.

41. The compound or salt thereof according to claim 1 wherein the 5- or 6-membered ring is a saturated 6-membered ring.

42. The compound or salt thereof according to claim 1 wherein the groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ are groups in each of one or more combinations selected from the group consisting of combinations of $A^3$ and $A^2$, $A^3$ and $A^1$, $A^3$ and $A^5$, and $A^2$ and $A^5$.

43. The compound or salt thereof according to claim 1 wherein the groups in each of one or more combinations selected from the group consisting of combinations of $A^3$ and $A^2$, $A^3$ and $A^1$, $A^3$ and $A^5$, $A^3$ and $A^6$, $A^2$ and $A^1$, $A^2$ and $A^5$, $A^2$ and $A^6$, $A^1$ and $A^5$, $A^1$ and $A^6$, and $A^5$ and $A^6$ are groups in each of one or more combinations selected from the group consisting of combinations of $A^3$ and $A^5$, and $A^2$ and $A^5$.

44. The compound or salt thereof according to claim 1 wherein $R^2$ is a $C_{1-6}$ alkyl group, —($C_{2-3}$ alkylene)CO$_2$($G^1$), a $C_{2-3}$ alkenyl group, or —S(O)$_p$($C_{1-6}$ alkyl).

45. The compound or salt thereof according to claim 1 wherein $R^2$ is a $C_{1-6}$ alkyl group, —($C_{2-3}$ alkylene)CO$_2$($G^1$), a $C_{2-3}$ alkenyl group, or —S(O)$_p$($C_{1-6}$ alkyl).

46. The compound or salt thereof according to claim 1 wherein $R^2$ is a halogen atom.

47. The compound or salt thereof according to claim 1 wherein $R^2$ is a halogen atom.

48. The compound or salt thereof according to claim 1 wherein $R^2$ is a halogen atom.

49. The compound or salt thereof according to claim 1 wherein $R^8$ is a group represented by the formula (1-2) or the formula (1-3).

50. A pharmaceutical composition comprising a compound represented by the formula (1) according to claim 1 or a physiologically acceptable salt thereof.

* * * * *